(12) United States Patent
Kawamura et al.

(10) Patent No.: US 8,822,041 B2
(45) Date of Patent: Sep. 2, 2014

(54) ANTHRACENE DERIVATIVES, LUMINESCENT MATERIALS AND ORGANIC ELECTROLUMINESCENT DEVICES

(75) Inventors: Masahiro Kawamura, Chiba (JP); Mitsunori Ito, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 412 days.

(21) Appl. No.: 12/933,434

(22) PCT Filed: Mar. 19, 2009

(86) PCT No.: PCT/JP2009/055454
§ 371 (c)(1),
(2), (4) Date: Dec. 6, 2010

(87) PCT Pub. No.: WO2009/116628
PCT Pub. Date: Sep. 24, 2009

(65) Prior Publication Data
US 2011/0068683 A1 Mar. 24, 2011

(30) Foreign Application Priority Data

Mar. 19, 2008 (JP) .................. 2008-072437
Apr. 30, 2008 (JP) .................. 2008-118945
Apr. 30, 2008 (JP) .................. 2008-118948

(51) Int. Cl.
| | | |
|---|---|---|
| H01L 51/54 | (2006.01) | |
| H01J 1/62 | (2006.01) | |
| C07D 307/91 | (2006.01) | |
| C07D 209/86 | (2006.01) | |
| C07C 15/28 | (2006.01) | |

(52) U.S. Cl.
USPC .......... 428/690; 428/917; 549/460; 548/445; 313/504; 313/506; 585/26

(58) Field of Classification Search
None
See application file for complete search history.

(56) References Cited

U.S. PATENT DOCUMENTS

| | | | |
|---|---|---|---|
| 2004/0076853 A1* | 4/2004 | Jarikov .................. | 428/690 |
| 2004/0137270 A1* | 7/2004 | Seo et al. .............. | 428/690 |
| 2005/0089715 A1* | 4/2005 | Cosimbescu et al. ..... | 428/690 |
| 2005/0089717 A1 | 4/2005 | Cosimbescu et al. | |
| 2007/0055085 A1* | 3/2007 | Kubota et al. ......... | 585/26 |
| 2007/0072002 A1* | 3/2007 | Kim et al. ............. | 428/690 |
| 2007/0237984 A1 | 10/2007 | Matsuura et al. | |
| 2008/0079356 A1* | 4/2008 | Park et al. ............ | 313/504 |
| 2008/0182129 A1 | 7/2008 | Klubek et al. | |
| 2009/0026919 A1 | 1/2009 | Stossel et al. | |
| 2009/0230852 A1 | 9/2009 | Lee et al. | |

FOREIGN PATENT DOCUMENTS

| | | | |
|---|---|---|---|
| EP | 1333018 | * | 8/2003 |
| EP | 1009044 | * | 6/2004 |
| JP | 2006 151844 | | 6/2006 |
| JP | 2006-253445 | | 9/2006 |
| JP | 2007 511067 | | 4/2007 |
| JP | 2007-227717 | | 9/2007 |
| JP | 2007 238500 | | 9/2007 |
| JP | 2009-123976 | | 6/2009 |
| JP | 2009-203203 | | 9/2009 |
| KR | 10 0877344 | | 12/2008 |
| KR | 10 2009 0016048 | | 2/2009 |
| WO | 2004 018588 | | 3/2004 |
| WO | WO 2004/044088 | * | 5/2004 |
| WO | 2006 039982 | | 4/2006 |
| WO | 2008 094399 | | 8/2008 |
| WO | 2009/102026 | | 8/2009 |

OTHER PUBLICATIONS

International Search Report issued May 12, 2009 in PCT/JP09/055454 filed Mar. 19, 2009.
U.S. Appl. No. 12/667,777, filed Jan. 5, 2010, Kawamura, et al.
U.S. Appl. No. 12/668,105, filed Jan. 7, 2010, Kawamura, et al.
Japanese Office Action issued Jun. 11, 2013 in connection with corresponding Japanese Patent Application No. 2010-503928.

* cited by examiner

*Primary Examiner* — Dawn Garrett

(74) *Attorney, Agent, or Firm* — Oblon, Spivak, McClelland, Maier & Neustadt, L.L.P.

(57) ABSTRACT

Anthracene derivatives each having a structure including an anthracene skeleton, a phenanthrene skeleton selected from among various phenanthrene skeletons different in bonding site which is bonded to the 9-position of the anthracene skeleton and a group selected from among various aryl groups and so on which is bonded to the 10-position of the anthracene skeleton. Organic EL devices made by using the derivatives exhibit high light emission efficiency and a long life.

21 Claims, No Drawings

ANTHRACENE DERIVATIVES, LUMINESCENT MATERIALS AND ORGANIC ELECTROLUMINESCENT DEVICES

TECHNICAL FIELD

The present invention relates to an anthracene derivative and an organic electroluminescence device, in particular, a light emitting material formed of an anthracene derivative having a specific partial structure, and an organic EL device having high luminous efficiency and a long lifetime as a result of the use of the material.

BACKGROUND ART

An organic electroluminescence device (hereinafter, being occasionally abbreviated as EL) is a spontaneous light emitting device which utilizes such a principle that a fluorescent substance emits light by virtue of recombination energy of holes injected from an anode and electrons injected from a cathode by an application of an electric field.

The organic EL devices are each one display form for a display or the like, and are promising new-generation displays because of such characteristics as described below. Each of the organic EL devices has a wide view angle, can be thinned, and shows good motion picture responsiveness. Since the rollout of the organic EL devices by Tang et al. in 1987, assorted materials for the organic EL devices have been disclosed. Of those, light emitting materials that contribute to light emission each directly affect durability (hereinafter, being occasionally referred to as "lifetime") and luminous efficiency, and hence the development of a material that realizes along-lifetime, high-efficiency organic EL device has been requested.

Devices each using a fused polycyclic compound in an electron transporting layer or light emitting layer have been disclosed in recent years. A fused polycyclic compound obtained by introducing a 4-(9-phenanthryl)phenyl group, a biphenylyl group, a terphenyl group, a dibenzofuryl group, a dibenzothiophenyl group, a dibenzodioxynyl group, a dibenzodithiinyl group, a dibenzoxythiinyl group, a benzophenonyl group, or the like to the 10-position of the anthracenylene group of a substituted or unsubstituted 9-(9-phenanthryl) anthracene has been proposed as a compound having an anthracene skeleton (Patent Document 1).

A fused polycyclic compound in which the 9-position of a substituted or unsubstituted phenanthryl group and the 9-position of an anthracenylene group are directly bonded to each other has been proposed (Patent Document 2).

In addition, a fused polycyclic compound in which a 9-phenanthryl group is bonded to the 9-position of an anthracenylene group through a phenylene group has been proposed (Patent Document 3).

Further, a fused polycyclic compound in which the 9-position of a substituted or unsubstituted phenanthryl group and the 9-position of an anthracenylene group are bonded to each other through a naphthylene group has been proposed (Patent Document 4).

A compound in which the 9- and 10-positions of an anthracenylene group are each substituted with a 2-phenanthryl group (Patent Document 5), a compound in which the 2- and 7-positions of phenanthrene are each substituted with an anthracenylene group (Patent Document 6), and a compound in which the 9-position of an anthracenylene group is substituted with a 9-phenanthryl group (Patent Document 7) have been disclosed.

Further, tris[10-(9-phenanthryl)anthracen-9-yl]benzene as a starburst fused polycyclic compound (Patent Document 8) has been disclosed.

In addition, a fused polycyclic compound obtained by introducing a 4-(9-phenanthryl)phenyl group, a biphenylyl group, a terphenyl group, a dibenzofuryl group, a dibenzothiophenyl group, a dibenzodioxynyl group, a dibenzodithiinyl group, a dibenzoxythiinyl group, a benzophenonyl group, or the like to the 10-position of the anthracene nucleus of a substituted or unsubstituted 9-(9-phenanthryl) anthracene has been investigated (Patent Document 9).

In addition, a 3-phenanthrylanthracene derivative containing carbazole (Patent Document 10) has been disclosed.

An improvement in material performance has been observed in any one of those material systems. At present, however, none of the systems has achieved performance sufficient for commercialization because an optical output with additionally high luminance or additionally high conversion efficiency is needed. In addition, the systems each still involve a large number of problems in terms of durability such as a change over time due to long-term use and deterioration due to, for example, an atmospheric gas containing oxygen or moisture. Therefore, durability as well as additionally high luminous efficiency has been requested at present.

Patent Document 1: WO 2004/018587
Patent Document 2: JP-A-2005-041843
Patent Document 3: WO 2005/054162
Patent Document 4: WO 2005/061656
Patent Document 5: U.S. Pat. No. 5,935,721
Patent Document 6: WO 2006/039982
Patent Document 7: US 2005/089717
Patent Document 8: JP-A-2002-329580
Patent Document 9: JP-A-2005-314239
Patent Document 10: WO 2005/113531

DISCLOSURE OF THE INVENTION

Problems to be solved by the Invention

An object of the present invention is to obtain a light emitting material having specifically high luminous efficiency and a specifically long lifetime as compared with those of such conventional materials as described above, and an organic EL device using the material.

Means for solving the Problems

The inventors of the present invention have made extensive studies. As a result, the inventors have found that a light emitting material having specifically high efficiency and a specifically long lifetime as compared with those of a conventional material can be obtained by using an anthracene derivative in which a phenanthryl group any one of the 1- to 4-positions of which is substituted is bonded to the 9-position of an anthracenylene skeleton through an arylene group as a blue host material. Thus, the inventors have completed the present invention.

That is, the present invention provides the following.
(1) An anthracene derivative including a phenanthryl group, the anthracene derivative being represented by the following general formula (1-1):

[Chem. 1]

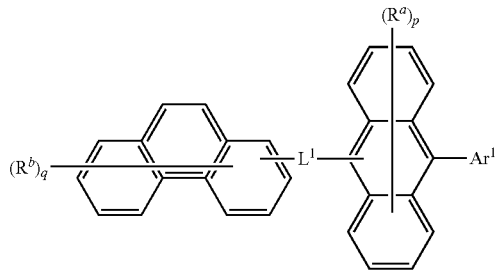

(1-1)

in the general formula (1-1),
L¹ represents a single bond, a substituted or unsubstituted arylene group having 6 to 50 ring forming carbon atoms, or a substituted or unsubstituted, divalent heterocyclic group having 5 to 50 ring forming atoms;
when L¹ represents a group except a single bond, Ar¹ represents a substituted or unsubstituted aryl group having 6 to 50 ring forming carbon atoms, or a substituted or unsubstituted heterocyclic group having 5 to 50 ring forming atoms;
when L¹ represents a single bond, Ar¹ represents a group represented by the following general formula (2),

[Chem. 2]

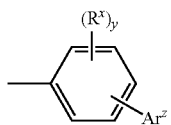

(2)

a substituted or unsubstituted fused aromatic ring group having 10 to 50 ring forming carbon atoms, a substituted or unsubstituted fluorenyl group, a substituted or unsubstituted indenyl group, or a substituted or unsubstituted heterocyclic group having 5 to 50 ring forming atoms, provided that
when L¹ represents a single bond, Ar¹ represents a group except a group represented by the above-mentioned general formula (2), and the 1-position of the phenanthryl group is bonded to an anthracene skeleton, Ar¹ represents a group except an unsubstituted 1-phenanthryl group,
when L¹ represents a single bond, Ar¹ represents a group except a group represented by the above-mentioned general formula (2), and the 2-position of the phenanthryl group is bonded to the anthracene skeleton, Ar¹ represents a group except a substituted or unsubstituted 2-phenanthryl group, and
when L¹ represents a single bond, Ar¹ represents a group except a group represented by the above-mentioned general formula (2), and the 3-position of the phenanthryl group is bonded to the anthracene skeleton, Ar¹ represents a group except an unsubstituted 3-phenanthryl group;
substituents $R^x$, $R^a$, and $R^b$ each independently represent a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring forming carbon atoms, a substituted or unsubstituted aryl group having 6 to 50 ring forming carbon atoms, a substituted or unsubstituted heteroaryl group having 5 to 50 ring forming atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms, provided that when L¹ represents a group except a single bond, the substituent $R^b$ represents a group except a substituted or unsubstituted anthracenyl group;
"p" represents an integer of 0 to 8, "q" represents an integer of 0 to 9, and "y" represents an integer of 0 to 4, and when "p" represents 2 to 8, "q" represents 2 to 9, or "y" represents 2 to 4, a plurality of $R^x$'s, a plurality of $R^a$'s, or a plurality of $R^b$'s may be identical to or different from each other, provided that when L represents a single bond, a case where all Rx, $R^a$, and $R^b$ each represent an anthracenyl group is excluded; and
Ar² represents a substituent selected from a substituted or unsubstituted phenyl group, a substituted or unsubstituted indenyl group, a substituted or unsubstituted fluorenyl group, a substituted or unsubstituted benzofluorenyl group, a substituted or unsubstituted dibenzofluorenyl group, a substituted or unsubstituted naphthyl group, a substituted or unsubstituted phenanthryl group, a substituted or unsubstituted anthracenyl group, a substituted or unsubstituted benzanthracenyl group, a substituted or unsubstituted naphthacenyl group, a substituted or unsubstituted fluoranthenyl group, a substituted or unsubstituted benzofluoranthenyl group, a substituted or unsubstituted triphenylenyl group, a substituted or unsubstituted chrysenyl group, a substituted or unsubstituted pyrenyl group, a substituted or unsubstituted benzophenanthryl group, a substituted or unsubstituted benzochrysenyl group, and a substituted or unsubstituted heterocycle-containing group having 3 to 50 nucleus forming atoms, when Ar² has a plurality of substituents, a plurality of adjacent substituents may be bonded to each other to form a saturated or unsaturated, divalent group that completes a ring, when a phenanthrene skeleton is bonded at its 1- or 2-position to the anthracene skeleton, Ar² represents a group except an unsubstituted phenyl group, and when the phenanthrene skeleton is bonded at its 3-position to the anthracene skeleton, $R^x$ and Ar² each represent a group except an unsubstituted carbazolyl group,
provided that
when L¹ and $R^b$ are bonded to the 2- and 7-positions of the phenanthryl group, respectively in the general formula (1-1), L and $R^b$ may each represent a group except a substituted or unsubstituted aromatic hydrocarbon group, a substituted or unsubstituted fused aromatic hydrocarbon group, and a substituted or unsubstituted aromatic heterocyclic group, and
when L¹ and $R^b$ are bonded to the 2- and 7-positions of the phenanthryl group, respectively in the formula, L¹ may represent a group except a phenyl group and $R^b$ may represent a group except a phenyl group having a substituent at a para position or a 2-phenanthryl group.
(2) An anthracene derivative including a phenanthryl group, the anthracene derivative being represented by the following general formula (1-2):

[Chem. 3]

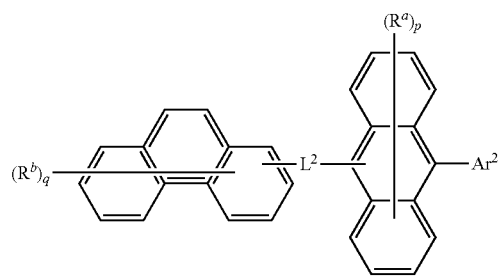

(1-2)

in the general formula (1-2),
L² represents a substituted or unsubstituted arylene group having 6 to 50 ring forming carbon atoms, or a divalent heterocyclic group having 5 to 50 ring forming atoms;

Ar² represents a substituted or unsubstituted aryl group having 6 to 50 ring forming carbon atoms, or a heterocyclic group having 5 to 50 ring forming atoms;

substituents R$^a$ and R$^b$ each independently represent a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring forming carbon atoms, a substituted or unsubstituted aryl group having 6 to 50 ring forming carbon atoms, a substituted or unsubstituted heteroaryl group having 5 to 50 ring forming atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms, and the substituent R$^b$ represents a group except a substituted or unsubstituted anthracenyl group; and p represents an integer of 0 to 8, q represents an integer of 0 to 9, and when p represents 2 to 8 or q represents 2 to 9, a plurality of R$^a$'s or a plurality of R$^b$'s may be identical to or different from each other, provided that when L² and R$^b$ are bonded to the 2- and 7-positions of the phenanthryl group, respectively in the general formula (1-2), L² and R$^b$ may each represent a group except a substituted or unsubstituted aromatic hydrocarbon group, a substituted or unsubstituted fused aromatic hydrocarbon group, and a substituted or unsubstituted aromatic heterocyclic group, and when L² and R$^b$ are bonded to the 2- and 7-positions of the phenanthryl group, respectively in the formula, L² may represent a group except a phenyl group and R$^b$ may represent a group except a phenyl group having a substituent at a para position or a 2-phenanthryl group.

(3) The anthracene derivative described in the above (1) or (2), in which L or L² is represented by the following general formula (3):

[Chem. 4]

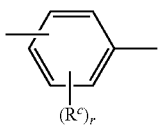

(3)

where:

a substituent R$^c$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring forming carbon atoms, a substituted or unsubstituted aryl group having 5 to 50 ring forming carbon atoms, a substituted or unsubstituted heteroaryl group having 5 to 50 ring forming atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms; and "r" represents an integer of 0 to 4, and when "r" represents 2 to 4, a plurality of R$^c$'s may be identical to or different from each other.

(4) The anthracene derivative described in the above (1) to (3), in which L¹ or L² represents a substituted or unsubstituted fused aromatic ring group having 10 to 50 ring forming carbon atoms.

(5) The anthracene derivative described in any one of the above (1) to (4), in which L¹ represents a group except a single bond, and Ar¹ or Ar² represents a substituted or unsubstituted fused aromatic ring having 10 to 50 ring forming carbon atoms.

(6) The anthracene derivative described in any one of the above (1) to (5), in which L¹ or L² is represented by the following general formula (3), and Ar¹ or Ar² is represented by the following general formula (4):

[Chem. 5]

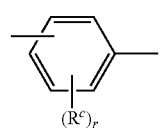

(3)

[Chem. 6]

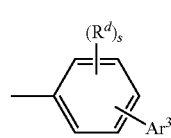

(4)

in the general formula (3) or (4),

Ar³ represents a substituted or unsubstituted aryl group having 6 to 50 ring forming carbon atoms, or a heterocyclic group having 5 to 50 ring forming atoms;

a substituent R$^c$ or R$^d$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring forming carbon atoms, a substituted or unsubstituted aryl group having 6 to 50 ring forming carbon atoms, a substituted or unsubstituted heteroaryl group having 5 to 50 ring forming atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms; and r and s each represent an integer of 0 to 4, and when r and/or s each represent/represents 2 to 4, a plurality of R$^c$'s and/or a plurality of R$^d$'s may be identical to or different from each other.

(7) The anthracene derivative described in any one of the above (1) to (6), in which $L^1$ represents a group except a single bond, and the phenanthryl group includes one of a substituted or unsubstituted 1-phenanthryl group, a substituted or unsubstituted 2-phenanthryl group, a substituted or unsubstituted 3-phenanthryl group, and a substituted or unsubstituted 4-phenanthryl group.
(8) The anthracene derivative described in any one of the above (1) to (7), in which $L^1$ represents a group except a single bond, and q represents 0.
(9) The anthracene derivative described in the above (1), in which $L^1$ represents a single bond, and $Ar^1$ represents a group except a group represented by the general formula (2).
(10) The anthracene derivative described in the above (9), in which $L^1$ represents a single bond, and $Ar^1$ represents a substituted or unsubstituted naphthyl group.
(11) The anthracene derivative described in the above (9) or (10), in which $L^1$ represents a single bond, and one of the 1-, 2-, and 3-positions of the phenanthryl group is bonded to the anthracene skeleton.
(12) The anthracene derivative described in any one of the above (9) to (11), in which $L^1$ represents a single bond, and q represents 0.
(13) The anthracene derivative described in the above (1), in which $Ar^1$ represents a group represented by the general formula (2).
(14) The anthracene derivative described in the above (13), in which the 2-position of the phenanthryl group is bonded to the anthracene skeleton.
(15) The anthracene derivative described in the above (13), in which the 3-position of the phenanthryl group is bonded to the anthracene skeleton.
(16) The anthracene derivative described in the above (13), in which the 1-position of the phenanthryl group is bonded to the anthracene skeleton.
(17) The anthracene derivative described in any one of the above (13) to (16), in which q represents 0.
(18) The anthracene derivative described in any one of the above (1) to (17), in which the anthracene derivative includes a material for an organic electroluminescence device.
(19) The anthracene derivative described in any one of the above (1) to (17), in which the anthracene derivative includes a light emitting material for an organic electroluminescence device.
(20) An organic electroluminescence device including one or more organic thin film layers including a light emitting layer between a cathode and an anode, in which at least one layer of the organic thin film layers contains the anthracene derivative described in any one of the above (1) to (17).
(21) The organic electroluminescence device described in the above (20), in which the light emitting layer contains the anthracene derivative.
(22) The organic electroluminescence device described in the above (20), in which the anthracene derivative includes a host material.
(23) The organic electroluminescence device described in any one of the above (20) to (22), in which the light emitting layer further contains at least one of a fluorescent dopant and a phosphorescent dopant.
(24) The organic electroluminescence device described in the above (23), in which the fluorescent dopant includes an arylamine compound.
(25) The organic electroluminescence device described in the above (23), in which the fluorescent dopant includes a styrylamine compound.
(26) The organic electroluminescence device described in the above (23), in which the fluorescent dopant includes a fused ring amine derivative represented by the following general formula (5):

[Chem. 7]

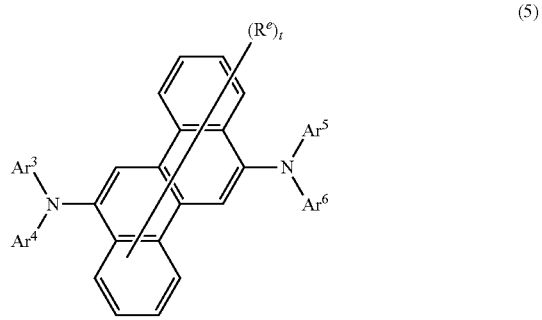

(5)

in the general formula (5),
a substituent $R^e$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxy group having 1 to 20 carbon atoms, a substituted or unsubstituted aryloxy group having 6 to 20 ring forming carbon atoms, a substituted or unsubstituted aryl group having 6 to 50 ring forming carbon atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms; "t" represents an integer of 0 to 10; and
$Ar^3$ to $Ar^6$ each represent a substituted or unsubstituted aryl group having 6 to 20 ring forming carbon atoms, or a substituted or unsubstituted heteroaryl group having 5 to 20 ring forming atoms.
(27) The organic electroluminescence device described in the above (23), in which the fluorescent dopant includes a fused ring amine derivative represented by the following general formula (6):

[Chem. 8]

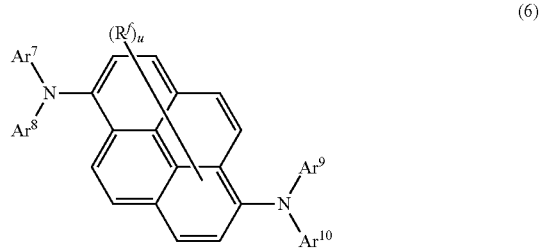

(6)

in the general formula (6),
a substituent $R^f$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxy group having 1 to 20 carbon atoms, a substituted or unsubstituted aryloxy group having 6 to 20 ring forming carbon atoms, a substituted or unsubstituted aryl group having 6 to 50 ring forming carbon atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms; "u" represents an integer of 0 to 8; and $Ar^7$ to $Ar^{10}$ each represent a substituted or unsubstituted aryl group having 6 to 20 ring forming carbon atoms, or a substituted or unsubstituted heteroaryl group having 5 to 20 ring forming atoms.

Effects by the Invention

An organic EL device using the anthracene derivative having a phenanthryl group of the present invention as an organic EL material in which one or more organic thin film layers including at least a light emitting layer are interposed between a cathode and an anode has high luminous efficiency and a long lifetime. Further, the device emits blue light with high luminous efficiency and high color purity, and is excellent in film formability.

BEST MODE FOR CARRYING OUT THE INVENTION

Hereinafter, the anthracene derivative having a phenanthryl group, light emitting material, and organic EL device of the present invention are described in detail.

In order that a high-efficiency, long-lifetime light emitting material may be obtained, the phenanthryl group in the general formula (I-1) or (1-2) is one of a substituted or unsubstituted 11-phenanthryl group, a substituted or unsubstituted 2-phenanthryl group, a substituted or unsubstituted 3-phenanthryl group, and a substituted or unsubstituted 4-phenanthryl group. Of those, a substituted or unsubstituted 1-phenanthryl group, a substituted or unsubstituted 2-phenanthryl group, or a substituted or unsubstituted 3-phenanthryl group is preferred.

$L^1$ in the general formula (1-1) represents a single bond, a substituted or unsubstituted arylene group having 6 to 50, or preferably 6 to 30 ring forming carbon atoms, or a substituted or unsubstituted, divalent heterocyclic group having 5 to 50, or preferably 5 to 30 ring forming atoms. $L^2$ in the general formula (1-2) represents a substituted or unsubstituted arylene group having 6 to 50, or preferably 6 to 30 ring forming carbon atoms, or a substituted or unsubstituted, divalent heterocyclic group having 5 to 50, or preferably 5 to 30 ring forming atoms.

$Ar^1$ when $L^1$ in the general formula (1-1) does not represent a single bond, or $Ar^2$ in the general formula (1-2) represents a substituted or unsubstituted aryl group having 6 to 50, or preferably 6 to 30 ring forming carbon atoms, or a substituted or unsubstituted heteroaryl group having 5 to 50, or preferably 5 to 30 ring forming atoms.

Specific examples of the substituted or unsubstituted arylene group having 6 to 50 ring forming carbon atoms represented by each of $L^1$ and $L^2$ include a phenylene group, a naphthylene group, a biphenylene group, a terphenylene group, an anthranylene group, a pentacenylene group, a perylenylene group, a picenylene group, a pyrenylene group, and a pentaphenylene group. Of those, a naphthylene group and a phenylene group represented by the general formula (3) are preferred. Specific examples of the substituent $R^c$ in the general formula (3) include the same specific examples as those of the substituents $R^a$ and $R^b$ to be described later. The number r of the substituents $R^c$'s is an integer of 0 to 4, or preferably 0 or 1.

Specific examples of the divalent heterocyclic group having 5 to 50 ring forming atoms represented by each of $L^1$ and $L^2$ include a pyridinylene group, a pyrazinylene group, a pyrimidinylene group, a pyridazinylene group, a triazinylene group, an indolinylene group, a quinolinylene group, an acridinylene group, a pyrrolidinylene group, a dioxanylene group, a piperidinylene group, a morpholidinylene group, a piperazinylene group, a triathinylene group, a carbazolylene group, a furanylene group, a thiophenylene group, an oxazolylene group, an oxadiazolylene group, a benzoxazolylene group, a thiazolylene group, a thiadiazolylene group, a benzothiazolylene group, a triazolylene group, an imidazolylene group, a benzimidazolylene group, a furanylene group, and a dibenzofuranylene group. Of those, a dibenzofuranylene group and a benzofuranylene group are preferred.

Specific examples of the substituted or unsubstituted aryl group having 6 to 50 ring forming carbon atoms represented by $Ar^1$ in the case where L in the general formula (1-1) does not represent a single bond, or by $Ar^2$ in the general formula (1-2) include a phenyl group, a naphthyl group, a phenanthryl group, a chrysenyl group, a benzophenanthryl group, a triphenylenyl group, a benzanthranyl group, a benzochrysenyl group, a biphenyl group, a naphthacenyl group, a terphenyl group, an anthranyl group, a pentacenyl group, a picenyl group, and a pentaphenyl group.

Of those, a naphthyl group, a biphenyl group, and an aryl group represented by the general formula (4) are preferred.

Specific examples of the substituent $R^d$ in the general formula (4) include the same specific examples as those of the substituents $R^a$ and $R^b$ to be described later. The number s of the substituents $R^d$'s is an integer of 0 to 4, or preferably 0 or 1.

Specific examples of $Ar^3$ include the same specific examples as those of $Ar^1$ described above.

Divalent heterocyclic groups each having 5 to 50 ring forming atoms as specific examples of $Ar^1$ or $Ar^2$ include the same heterocyclic groups as specific examples of $L^1$ or $L^2$ described above. Of those, a dibenzofuranyl group or a benzofuranyl group is preferred.

When $L^1$ represents a single bond, $Ar^1$ represents a group represented by the general formula (2), a substituted or unsubstituted fused aromatic ring group having 10 to 50 ring forming carbon atoms, a substituted or unsubstituted fluorenyl group, a substituted or unsubstituted indenyl group, or a substituted or unsubstituted heterocyclic group having 5 to 50 ring forming atoms, provided that in the case where $L^1$ represents a single bond and $Ar^1$ does not represent a group represented by the general formula (2): when the 1-position of the phenanthryl group is bonded to the anthracene skeleton, $Ar^1$ does not represent an unsubstituted 1-phenanthryl group; when the 2-position of the phenanthryl group is bonded to the anthracene skeleton, $Ar^1$ does not represent a substituted or unsubstituted 2-phenanthryl group; or when the 3-position of the phenanthryl group is bonded to the anthracene skeleton, $Ar^1$ does not represent an unsubstituted 3-phenanthryl group.

Specific examples of the substituted or unsubstituted, fused aromatic ring group having 10 to 50 ring forming carbon atoms represented by $Ar^1$ in the case where $L^1$ represents a single bond and $Ar^1$ does not represent the group represented by the general formula (2) include a naphthyl group, a naphthacenyl group, an anthranyl group, a phenanthryl group, a pentacenyl group, a picenyl group, chrysenyl group, a benzophenanthryl group, a triphenylenyl group, a benzanthranyl group, a benzochrysenyl group, a fluoranthenyl group, a benzofluoranthenyl group, a benzofluorenyl group, and a dibenzofluorenyl group (It should be noted that, in the general formula (1-1), $Ar^1$ does not represent an unsubstituted 1-phenanthryl group in the case where the 1-position of the phenanthryl group is bonded to the anthracene skeleton. In addition, $Ar^1$ does not represent a substituted or unsubstituted 2-phenanthryl group in the case where the 2-position of the phenanthryl group is bonded to the anthracene skeleton. Further, $Ar^1$ does not represent an unsubstituted 3-phenanthryl group in the case where the 3-position of the phenanthryl group is bonded to the anthracene skeleton). Of those, a naphthyl group is preferred.

Specific examples of the substituted or unsubstituted heterocyclic group having 5 to 50 ring forming atoms represented by $Ar^1$ include a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholyl group, a piperazinyl group, a triazinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzimidazolyl group, a benzofuranyl group, and a dibenzofuranyl group.

When $Ar^1$ represents a group except the fused aromatic ring group and the heterocyclic group, $Ar^1$ may represent the fluorenyl group, or the substituted or unsubstituted indenyl group.

When $Ar^1$ in the general formula (1-1) represents a group represented by the general formula (2), $Ar^2$ represents a substituent selected from a substituted or unsubstituted phenyl group, a substituted or unsubstituted indenyl group, a substituted or unsubstituted fluorenyl group, a substituted or unsubstituted benzofluorenyl group, a substituted or unsubstituted dibenzofluorenyl group, a substituted or unsubstituted naphthyl group, a substituted or unsubstituted phenanthryl group, a substituted or unsubstituted anthracenyl group, a substituted or unsubstituted benzanthracenyl group, a substituted or unsubstituted naphthacenyl group, a substituted or unsubstituted fluoranthenyl group, a substituted or unsubstituted benzofluoranthenyl group, a substituted or unsubstituted triphenylenyl group, a substituted or unsubstituted chrysenyl group, a substituted or unsubstituted pyrenyl group, a substituted or unsubstituted benzophenanthryl group, a substituted or unsubstituted benzochrysenyl group, and a substituted or unsubstituted heterocycle-containing group having 3 to 50, or preferably 5 to 30 nucleus forming atoms. When $Ar^2$ has a plurality of substituents, a plurality of adjacent substituents may be bonded to each other to form a saturated or unsaturated, divalent group that completes a ring. When the phenanthrene skeleton is bonded at its 1- or 2-position to the anthracene skeleton, $Ar^2$ does not represent an unsubstituted phenyl group. In addition, when the phenanthrene skeleton is bonded at its 3-position to the anthracene skeleton, none of $R^x$ and $Ar^2$ represents an unsubstituted carbazolyl group.

The substituents $R^x$, $R^a$, and $R^b$ in the respective general formulae each independently represent a substituted or unsubstituted alkyl group having 1 to 20, preferably 1 to 12, or more preferably 1 to 8 carbon atoms, a substituted or unsubstituted alkenyl group having 2 to 50, preferably 2 to 12, or more preferably 2 to 8 carbon atoms, a substituted or unsubstituted alkynyl group having 2 to 50, preferably 2 to 20, more preferably 2 to 12, or particularly preferably 2 to 8 carbon atoms, a substituted or unsubstituted aralkyl group having 7 to 20, or preferably 9 to 20 carbon atoms, a substituted or unsubstituted cycloalkyl group having 3 to 20, or preferably 5 to 12 carbon atoms, a substituted or unsubstituted alkoxy group having 1 to 20, preferably 1 to 12, or more preferably 1 to 8 carbon atoms, a substituted or unsubstituted aryloxy group having 6 to 20, preferably 6 to 16, or more preferably 6 to 12 ring forming carbon atoms, a substituted or unsubstituted aryl group having 6 to 50, or preferably 6 to 20 ring forming carbon atoms, a substituted or unsubstituted heteroaryl group having 5 to 50 ring forming carbon atoms, a substituted or unsubstituted alkylsilyl group having 1 to 30, or preferably . . . carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms. When $L^1$ in the general formula (1-1) does not represent a single bond, and in the general formula (1-2), the substituent $R^b$ does not represent a substituted or unsubstituted anthracenyl group. When $L^1$ represents a single bond, not all $R^x$, $R^a$, and $R^b$ represent anthranyl groups.

Specific examples of the substituted or unsubstituted alkyl group having 1 to 20 carbon atoms represented by each of $R^x$, $R^a$, and $R^b$ as substituents in each general formula include an ethyl group, a methyl group, an i-propyl group, an n-propyl group, an s-butyl group, a t-butyl group, a pentyl group, a hexyl group, a cyclopentyl group, and a cyclohexyl group. Of those, a methyl group, an i-propyl group, a t-butyl group, and a cyclohexyl group are preferred.

Specific examples of the substituted or unsubstituted alkenyl group having 2 to 50 carbon atoms represented by each of $R^z$, $R^a$, and $R^b$ as substituents in each general formula include a vinyl group, an allyl group, a 1-butenyl group, a 2-butenyl group, a 3-butenyl group, a 1,3-butadienyl group, a 1-methylvinyl group, a styryl group, a 2,2-diphenylvinyl group, a 1,2-diphenylvinyl group, a 1-methylallyl group, α1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group. Of those, a styryl group, a 2,2-diphenylvinyl group, and a 1,2-diphenylvinyl group are preferred, for example.

Specific examples of the alkynyl group having 2 to 50 carbon atoms represented by each of $R^z$, $R^a$, and $R^b$ as substituents in each general formula include a propargyl group and a 3-pentynyl group. Examples of the substituted or unsubstituted aralkyl group having 7 to 20 carbon atoms include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Examples of the cycloalkyl group having 3 to 20 carbon atoms include a cyclopropyl group, a cyclobutyl group, a cyclopentyl group, a cyclohexyl group, a 4-methylcyclohexyl group, an adamantane-1,1-diyl group, and an adamantane-1,3-diyl group.

The alkoxyl group having 1 to 20 carbon atoms is a group represented by —$OY_1$, and examples of $Y_1$ include the same examples as those of the alkyl group.

The substituted or unsubstituted aryl group having 6 to 50 ring forming carbon atoms is the same as that described above for $Ar^1$. The substituted or unsubstituted aryloxy group having 6 to 20 ring forming carbon atoms is a group represented by —OAr. Ar represents an aryl group, and is the same as that described above for $Ar^1$.

Examples of the heteroaryl group having 5 to 50 ring forming atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 11-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 11-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, and divalent groups thereof.

Examples of the alkylsilyl group having 1 to 30 carbon atoms include a trimethylsilyl group, a triethylsilyl group, a t-butyldimethylsilyl group, a vinyldimethylsilyl group, and a propyldimethylsilyl group.

Examples of the arylsilyl group having 6 to 50 ring forming carbon atoms include a triphenylsilyl group, a phenyldimethylsilyl group, a t-butyldiphenylsilyl group, a tritolylsilyl group, a trixylylsilyl group, and a trinaphthylsilyl group.

Examples of the alkylgermanium group having 1 to 50 carbon atoms include a methylhydrogermyl group, a trimethylgermyl group, a triethylgermyl group, a tripropylgermyl group, and a dimethyl-t-butylgermyl group.

Examples of the arylgermanium group having 6 to 50 ring forming carbon atoms include a phenyldihydrogermyl group, a diphenylhydrogermyl group, a triphenylgermyl group, a tritolylgermyl group, and a trinaphthylgermyl group.

The number y of the substituents $R^x$'s is an integer of 0 to 4, preferably 0 or 1, or more preferably 0. The number p of the substituents $R^a$'s is an integer of 0 to 8, preferably 0 to 2, or more preferably 0. The number q of the substituents $R^b$'s is an integer of 0 to 9, preferably 0 to 2, or more preferably 0. The number r of the substituents $R^c$'s is an integer of 0 to 4, preferably 0 or 1, or more preferably 0. The number s of the substituents $R^d$'s is an integer of 0 to 4, preferably 0 or 1, or more preferably 0. When y represents 2 to 4, p represents 2 to 8, q represents 2 to 9, r represents 2 to 4, or s represents 2 to 4, a plurality of $R^x$'s, a plurality of $R^a$'s, a plurality of $R^b$'s, a plurality of $R^c$'s, or a plurality of $R^d$'s may be identical to or different from each other.

Representative examples of the anthracene derivative having a phenanthryl group of the present invention represented by the general formula (1-1) when $L^1$ does not represent a single bond or by the general formula (1-2) are given below. However, the present invention is not limited to the representative examples.

[Chem. 9]
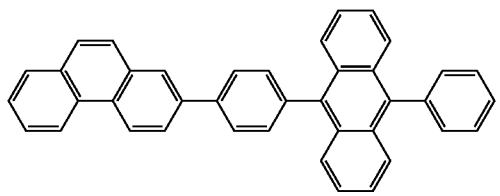

-continued
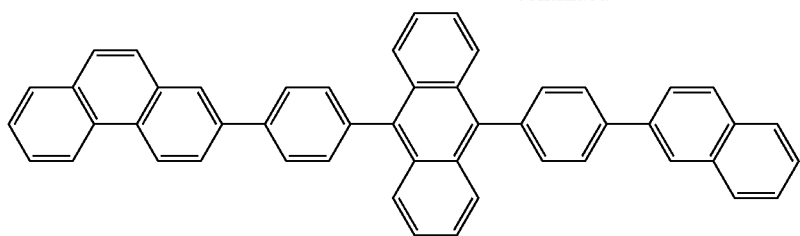
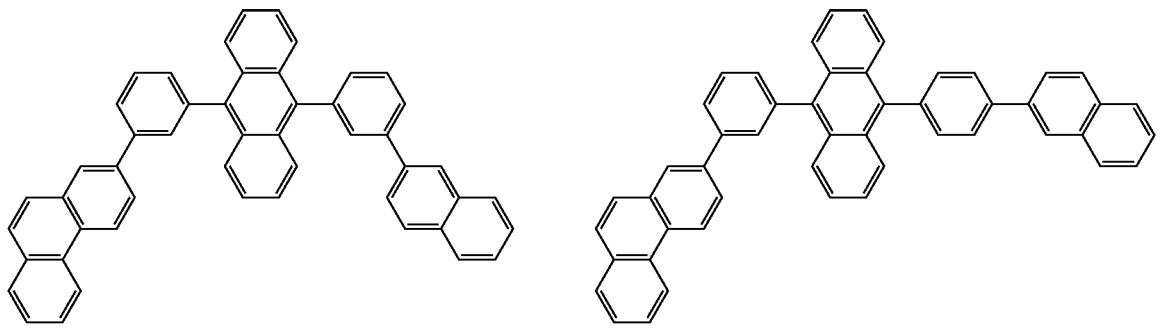
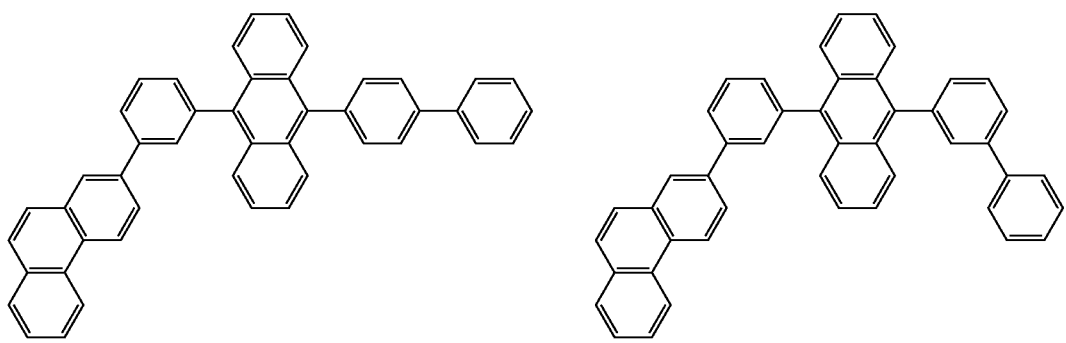
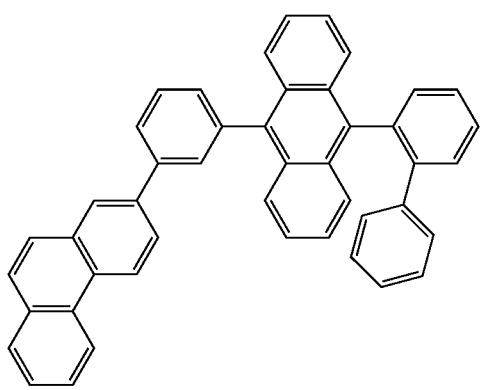
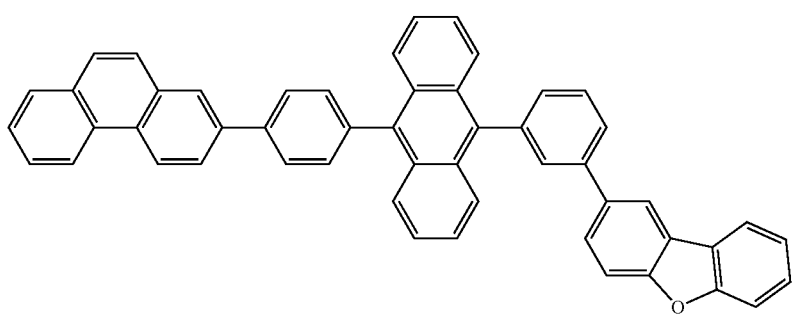

-continued
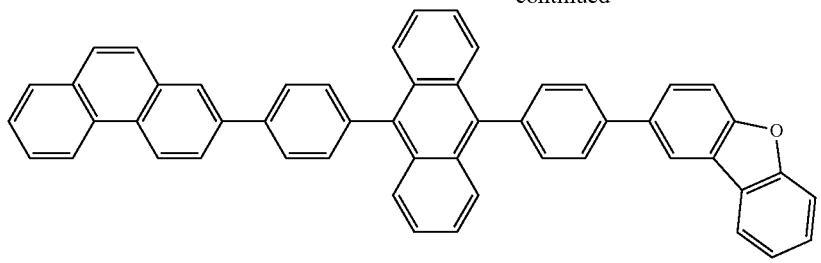
[Chem. 10]
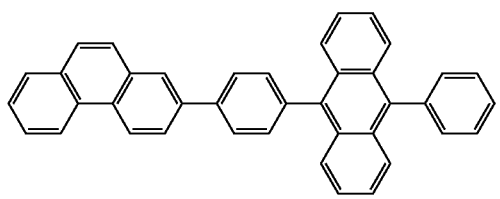 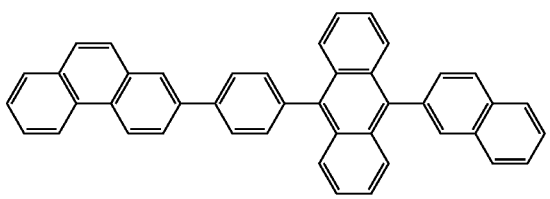
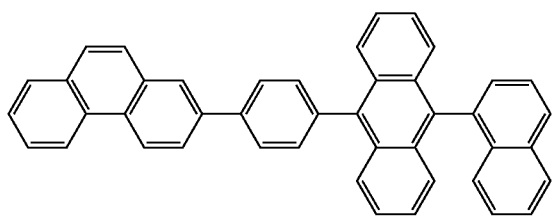 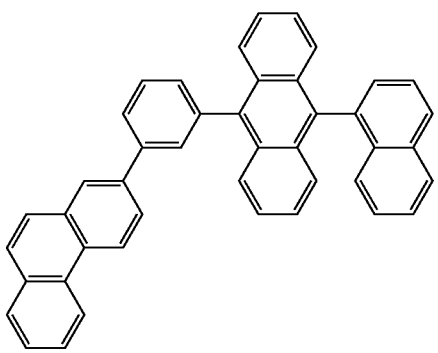
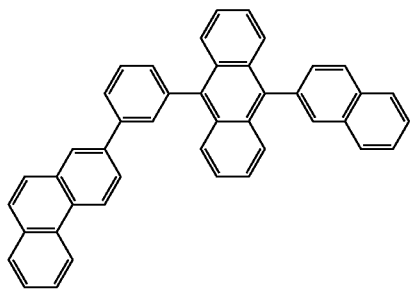 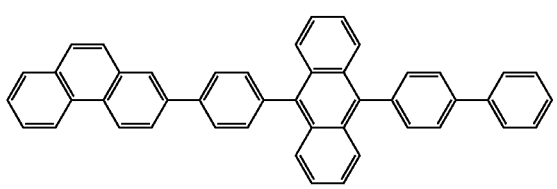
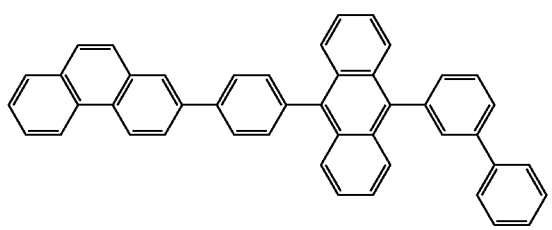 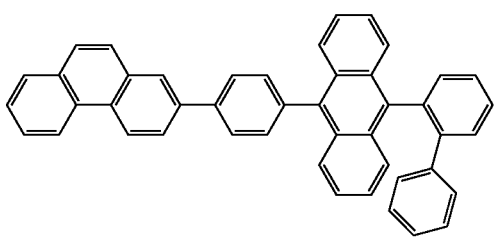
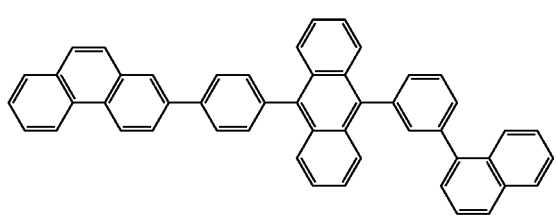 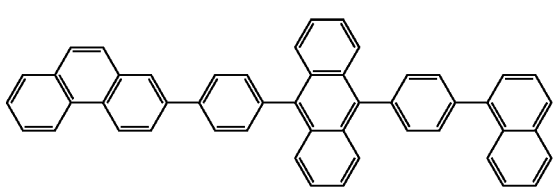

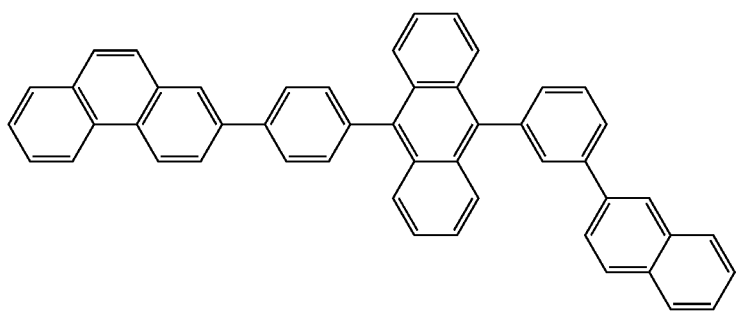
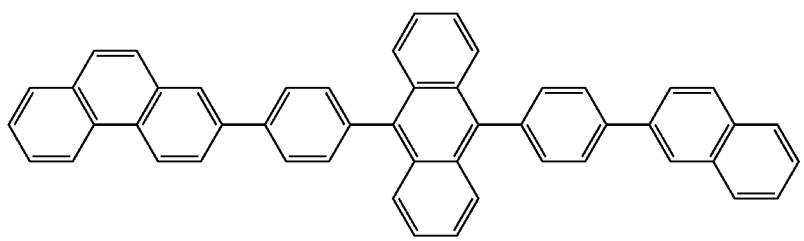
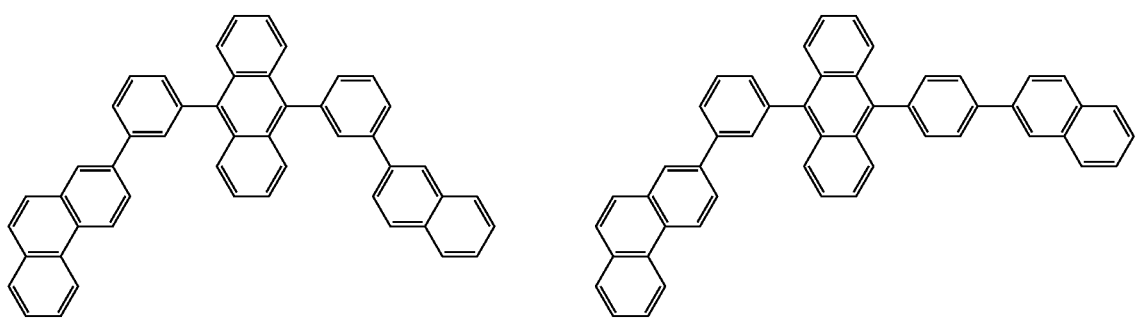
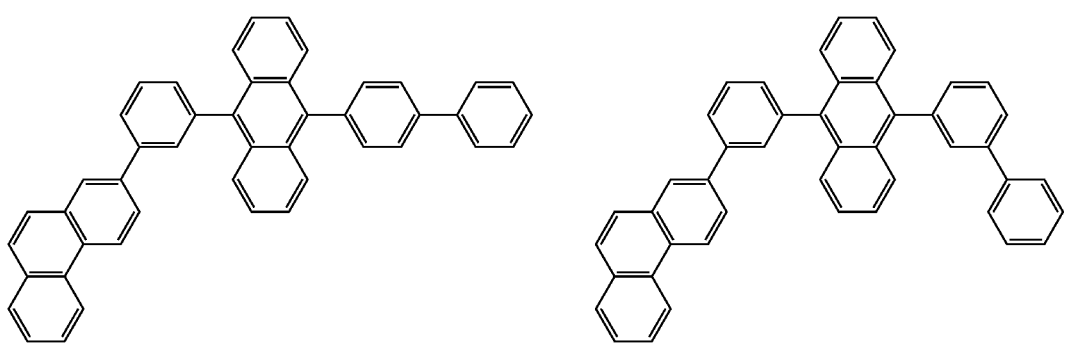
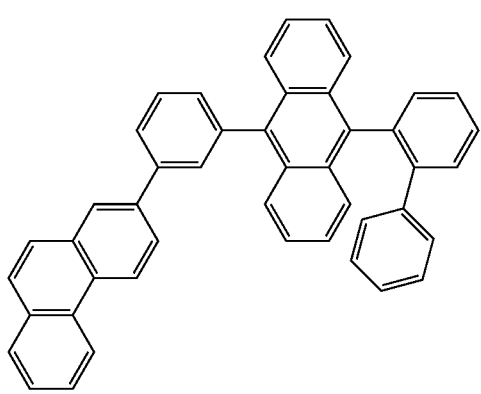

-continued
[Chem. 11]
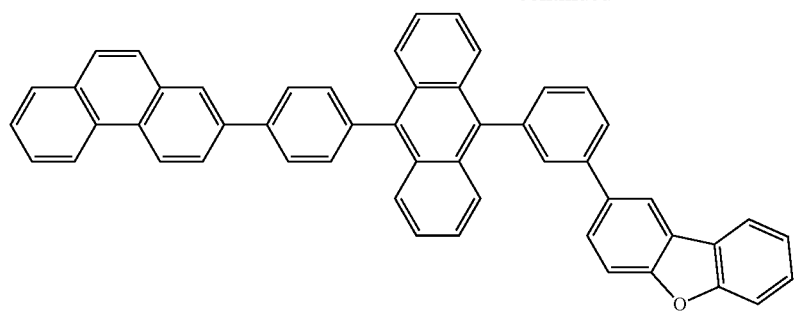

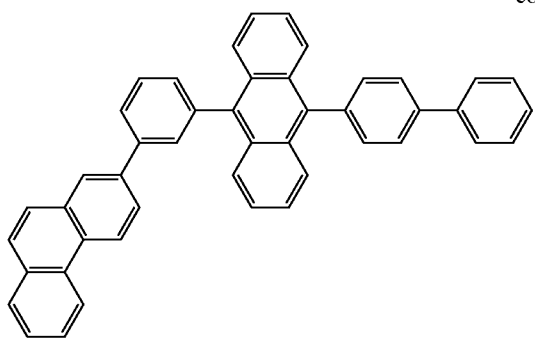
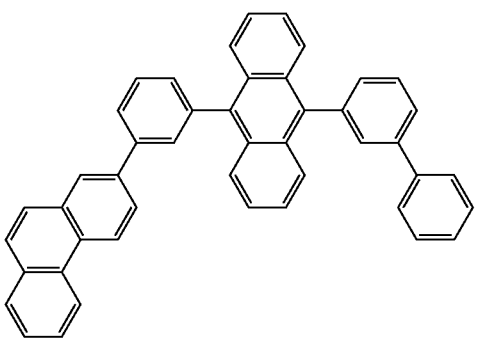
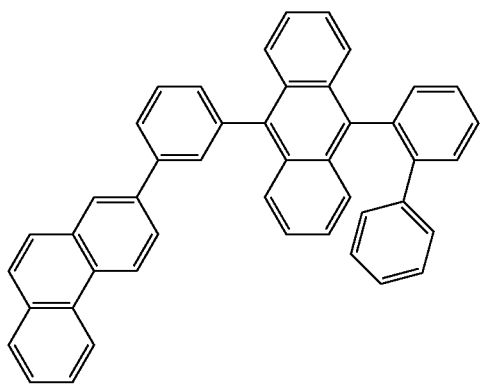
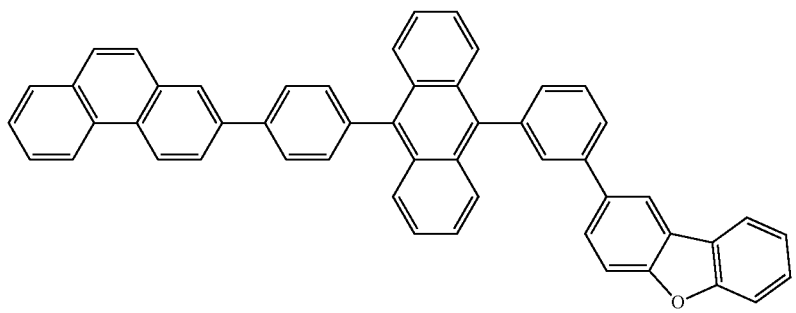
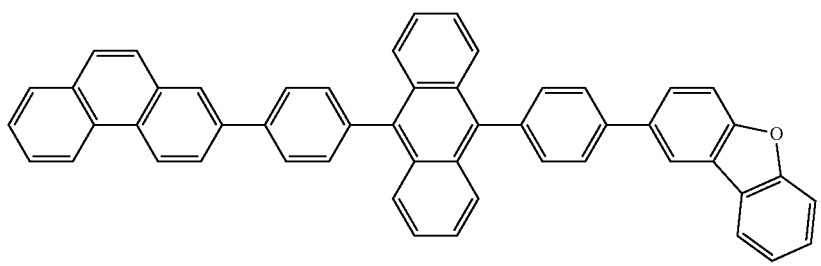
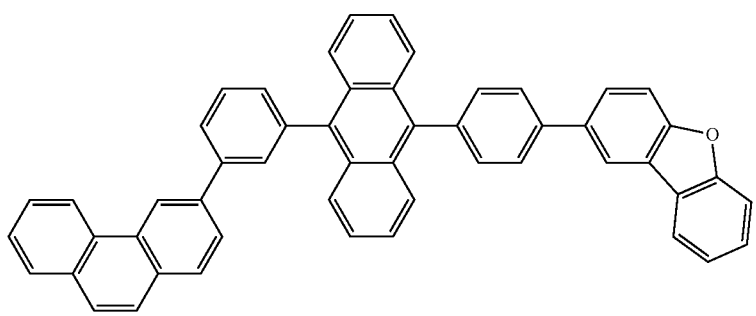

-continued
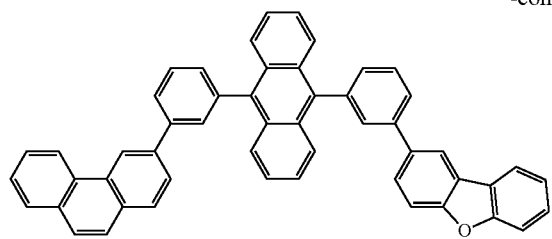
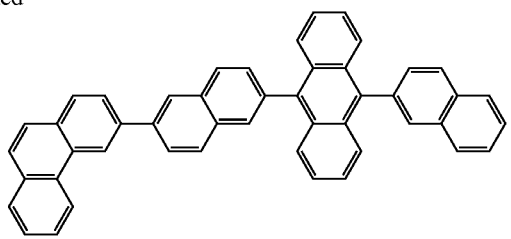
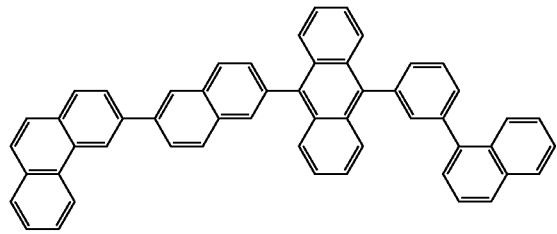
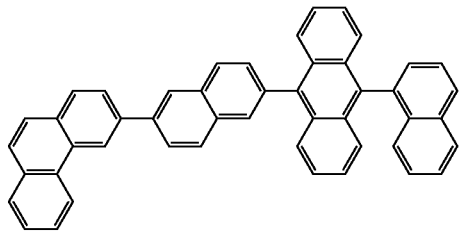
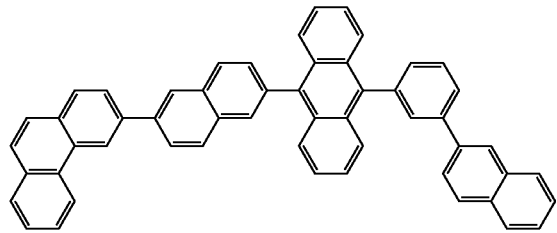
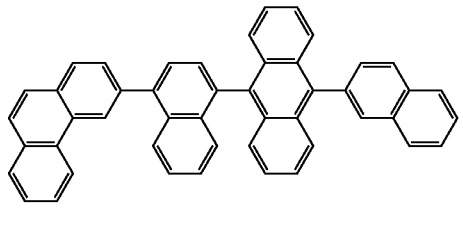
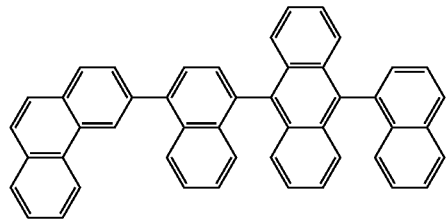
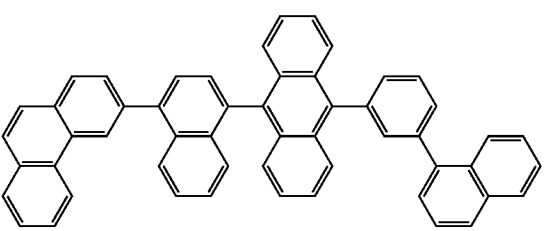
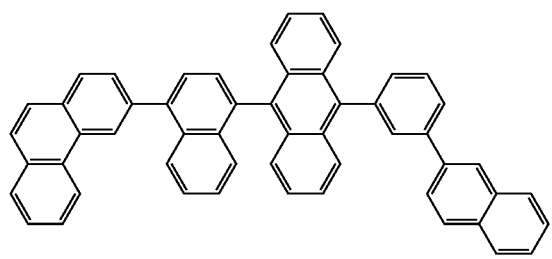
[Chem. 12]
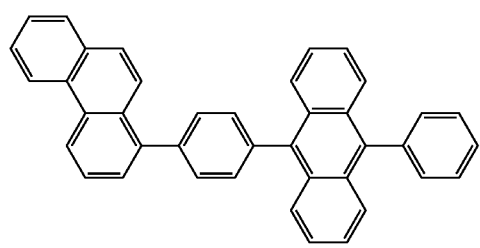
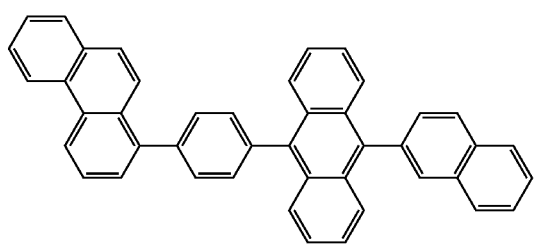
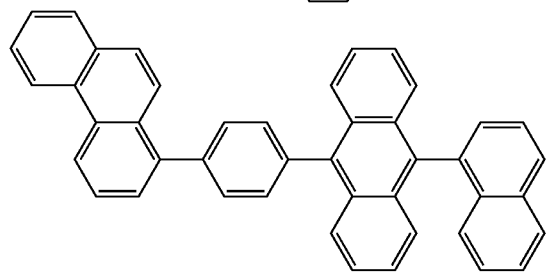
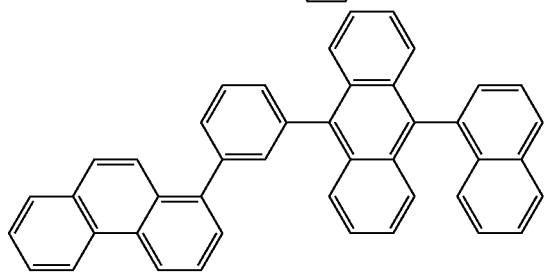

-continued
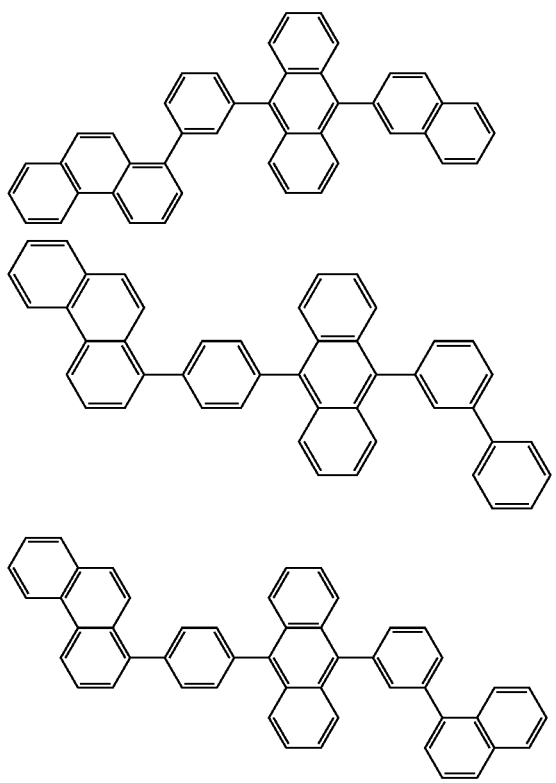
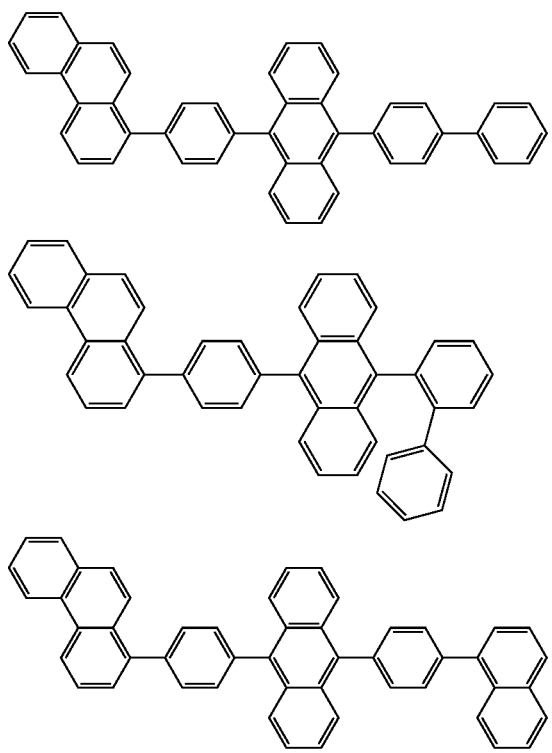
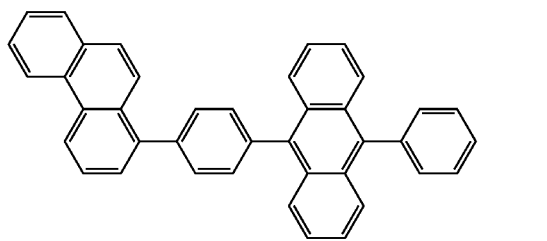
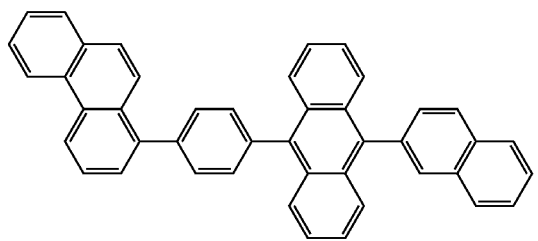
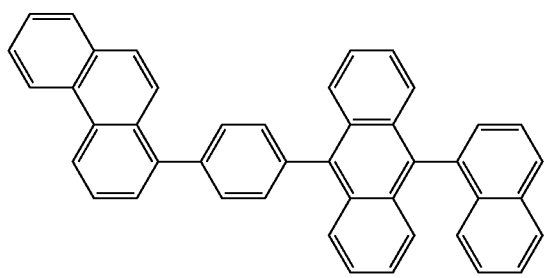
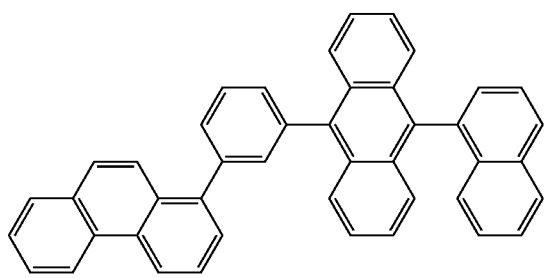
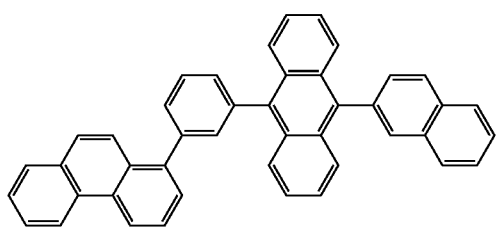
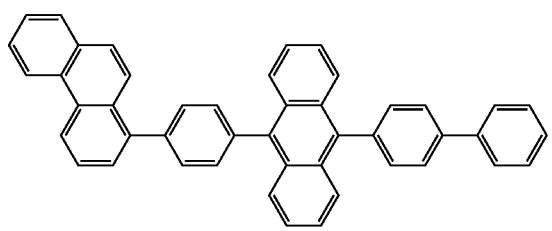

-continued
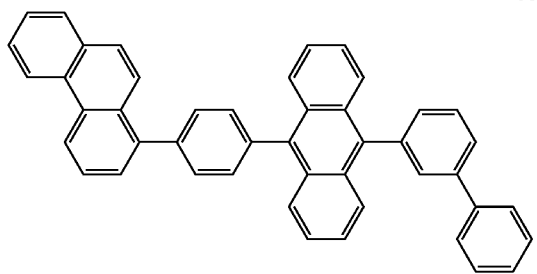
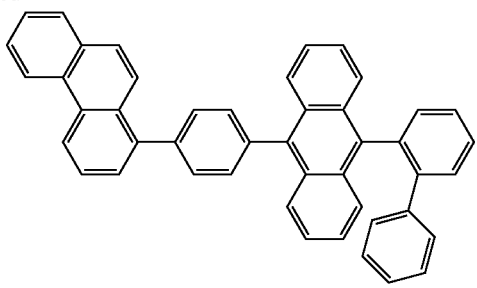
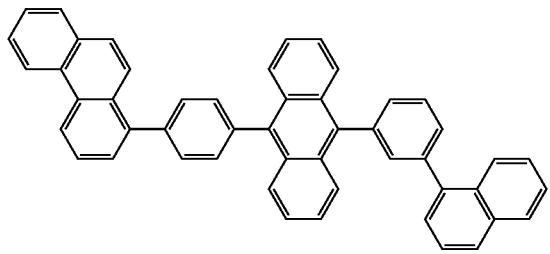
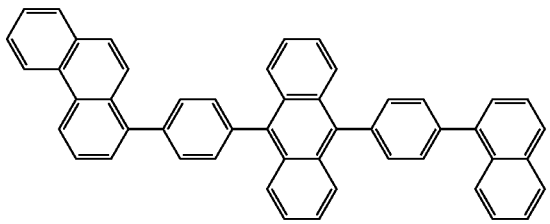
[Chem. 13]
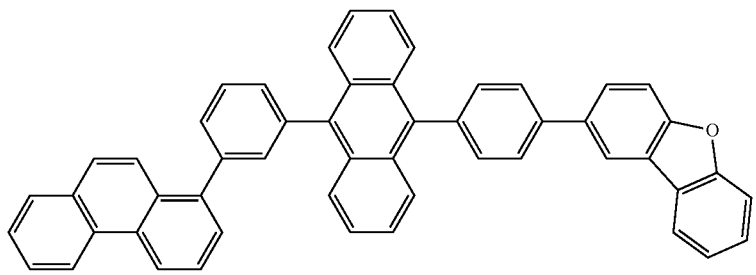
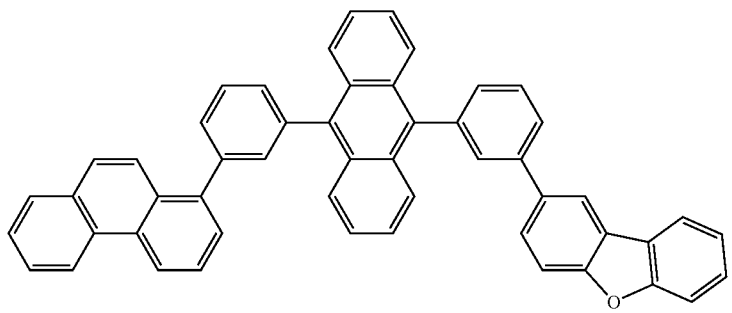
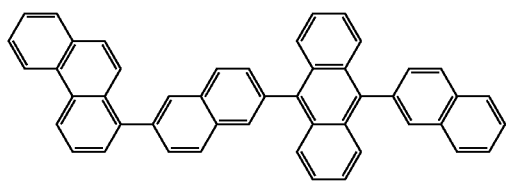
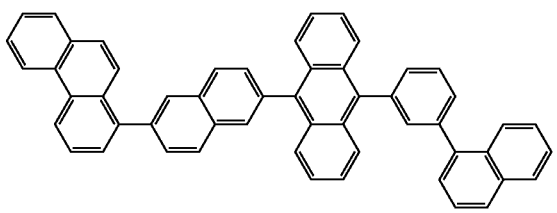
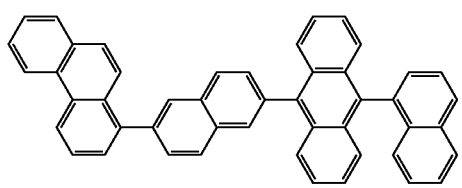
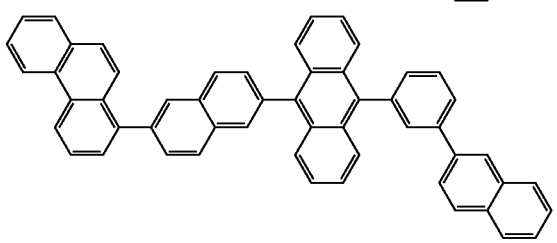

-continued
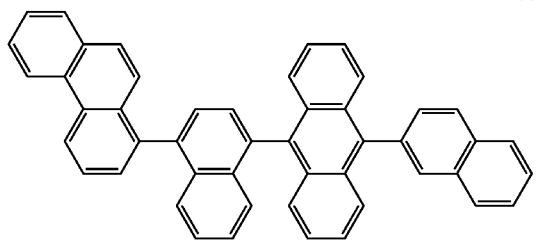
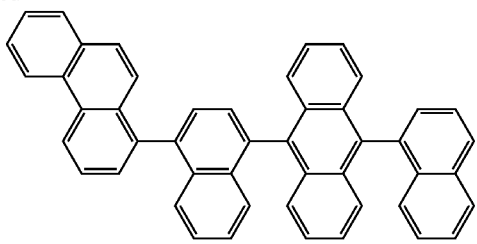
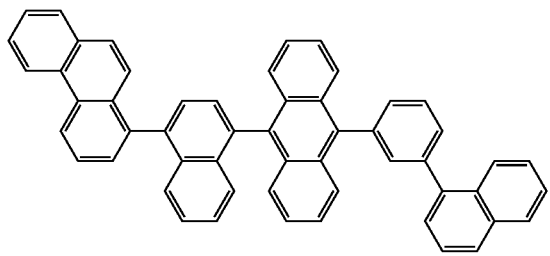
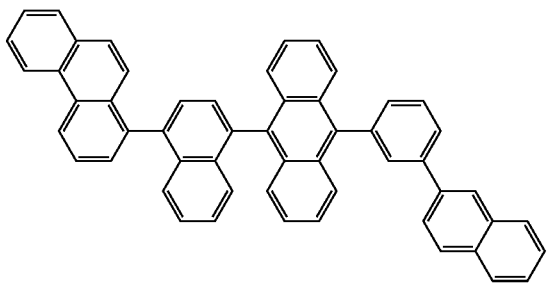
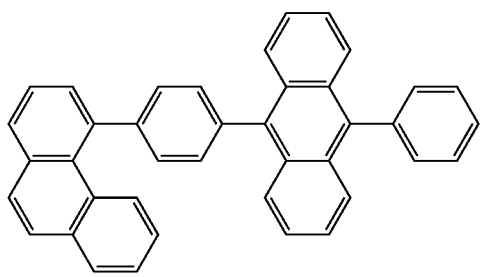
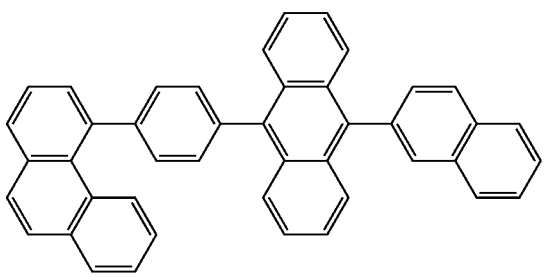
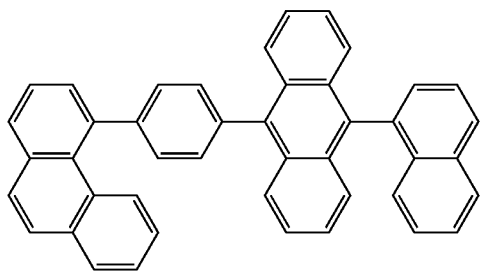
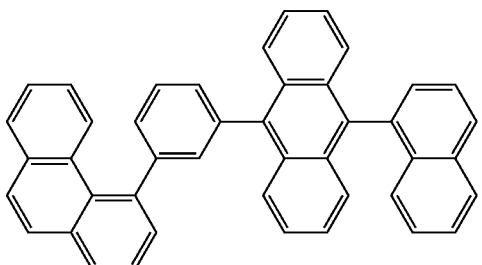
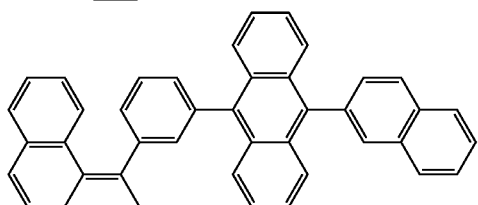
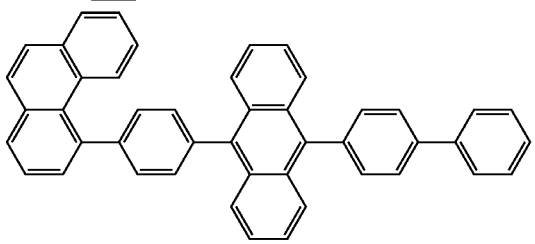
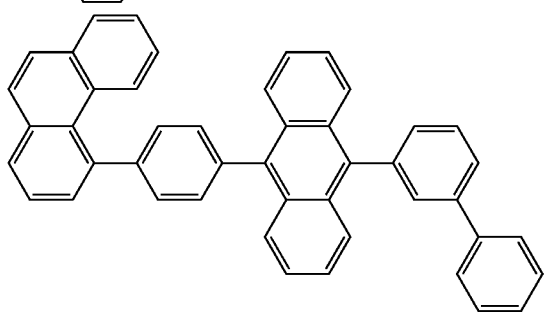
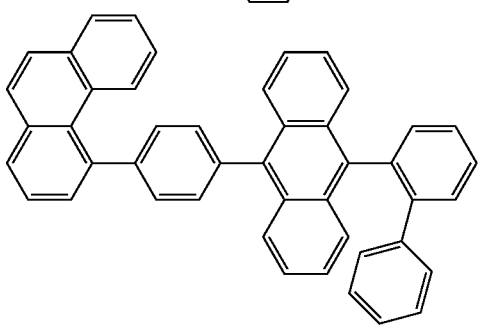

-continued
[Chem. 14]
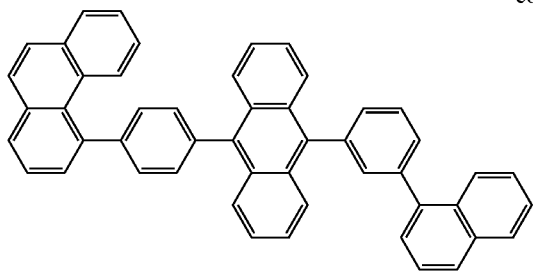

-continued
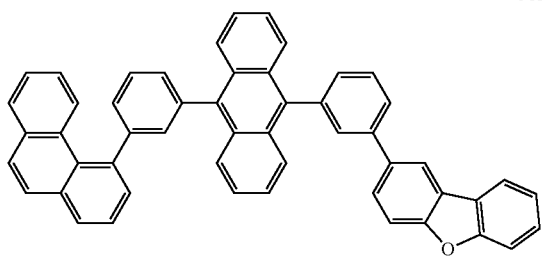
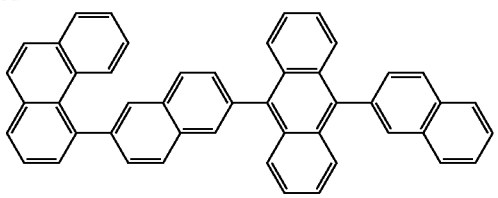
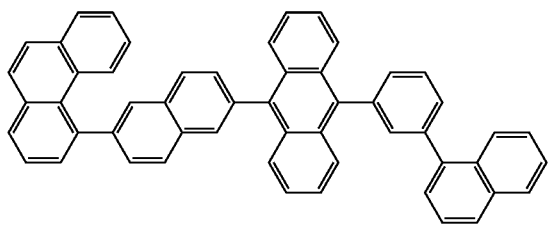
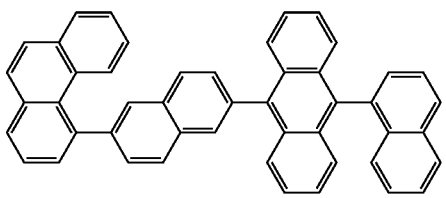
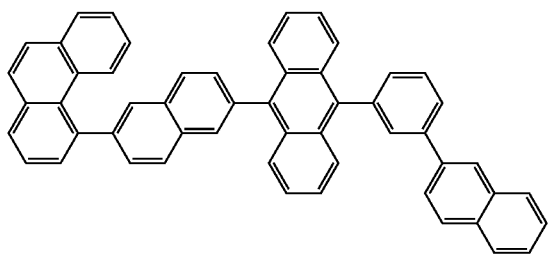
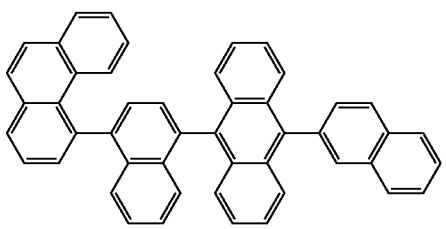
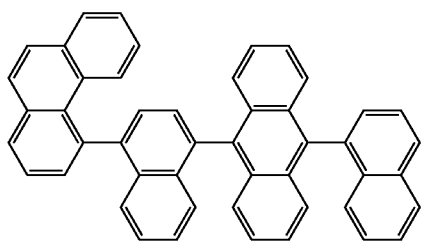
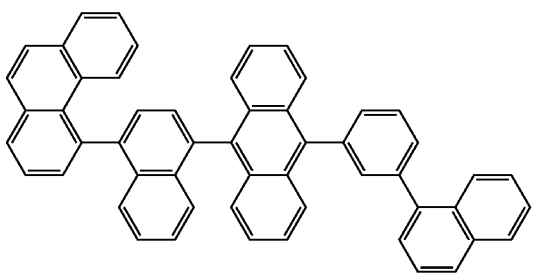
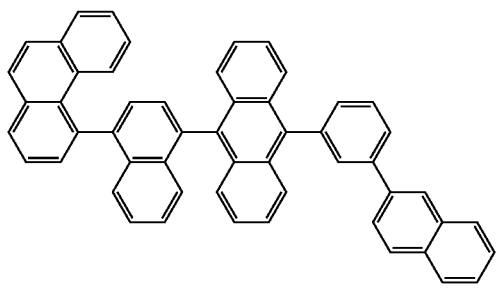
[Chem. 15]
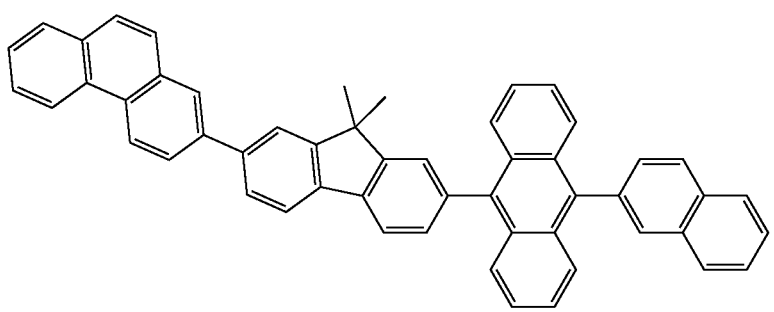

-continued
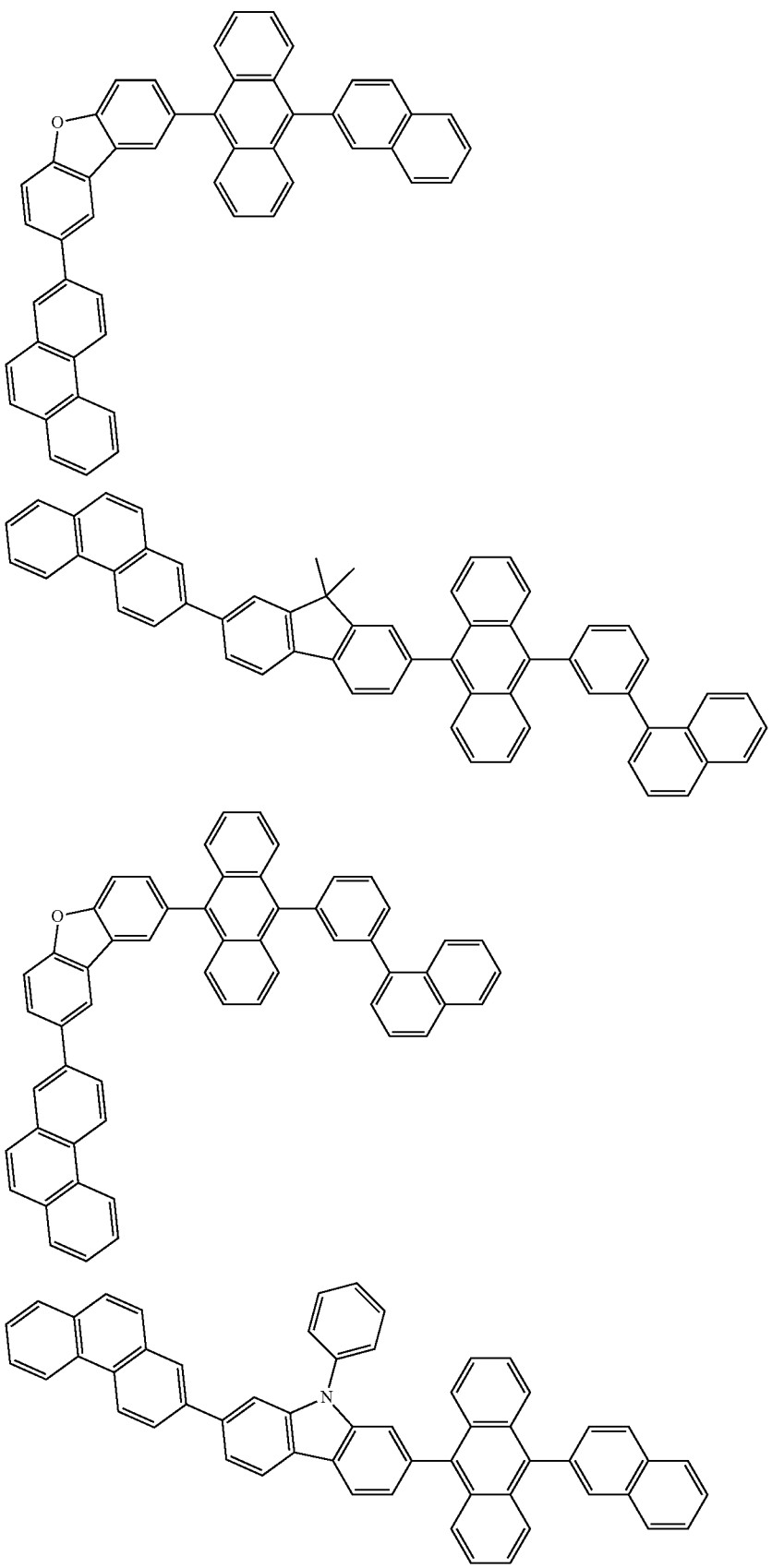

-continued
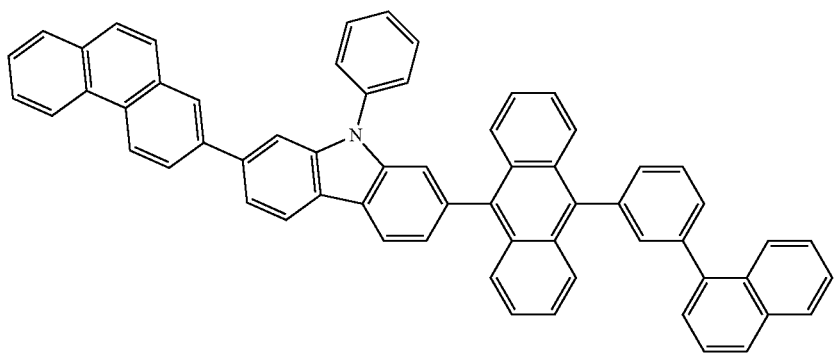
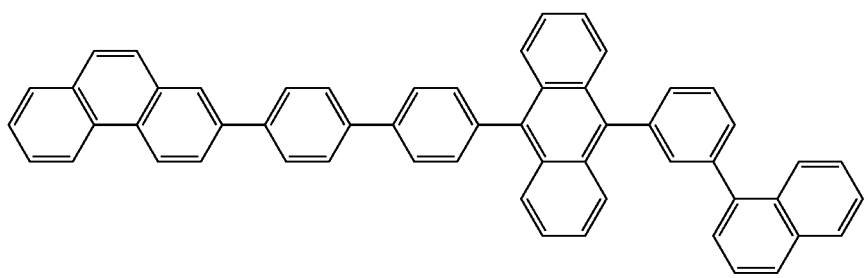
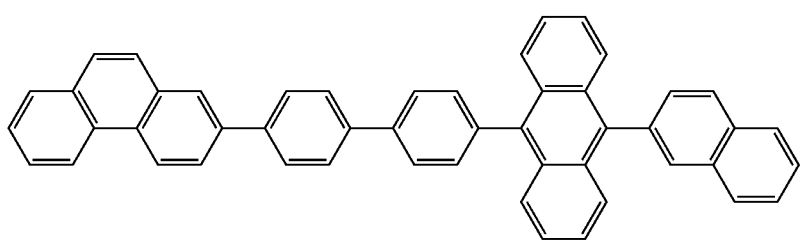
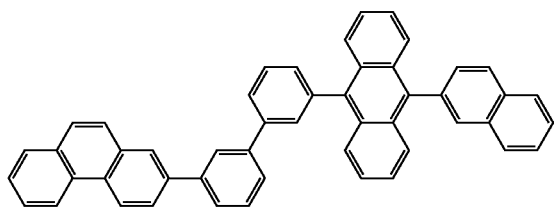
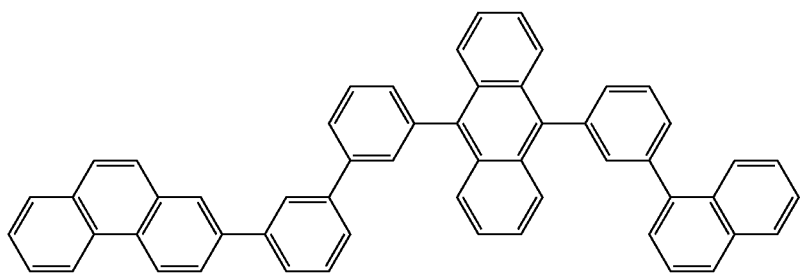
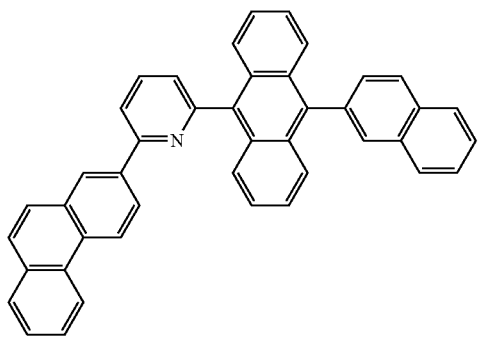
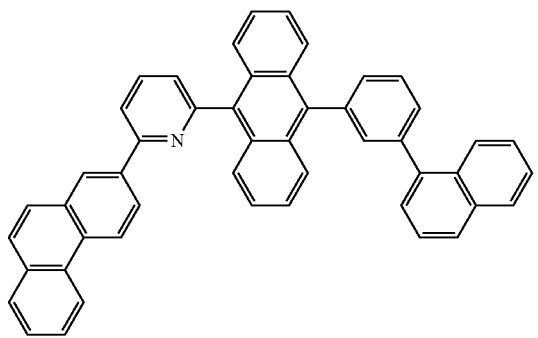

-continued
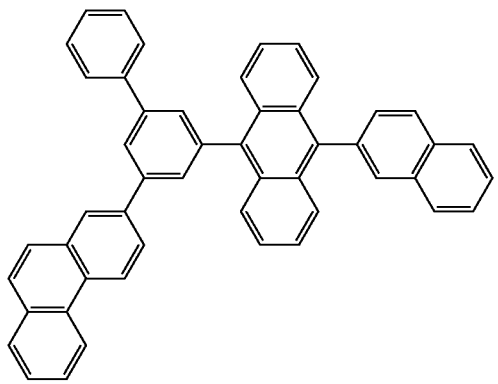
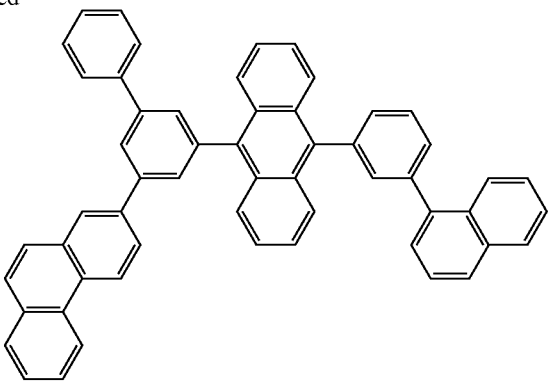
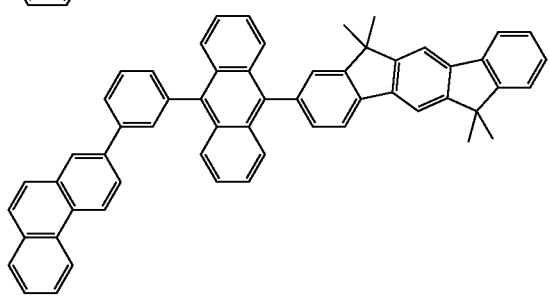
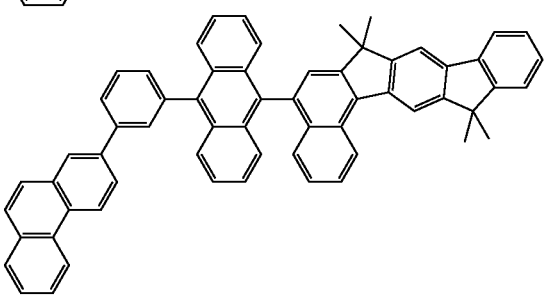
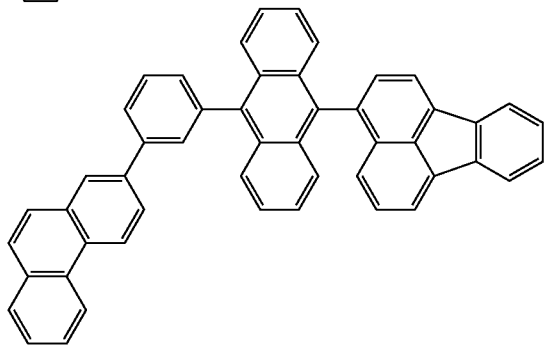
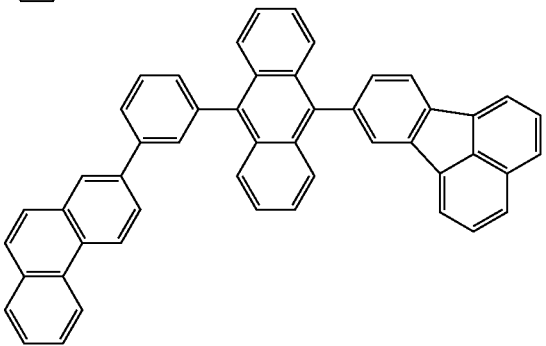
[Chem. 16]
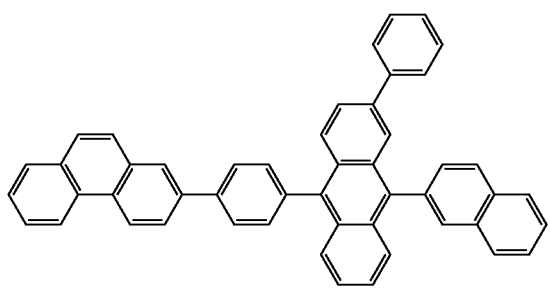
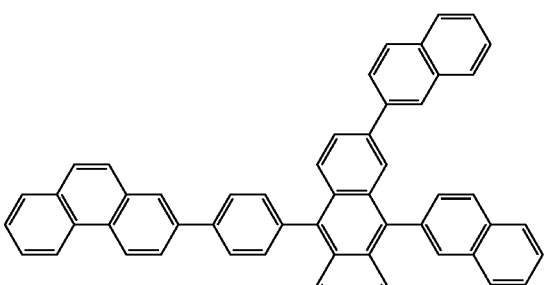
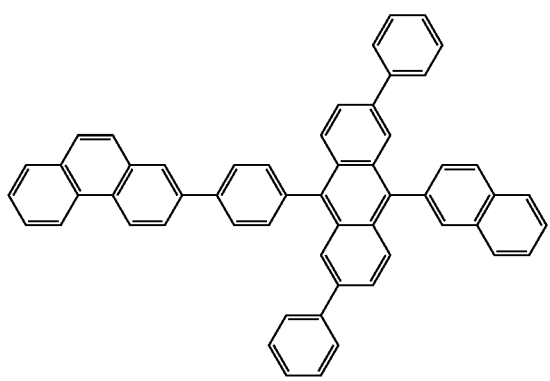
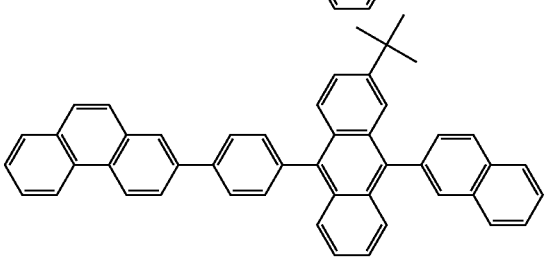

-continued
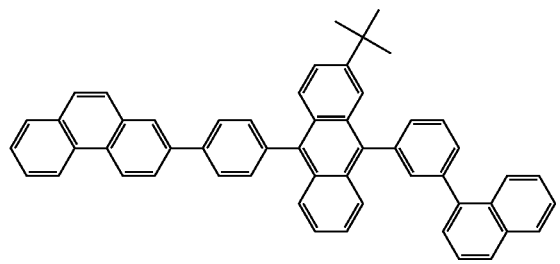
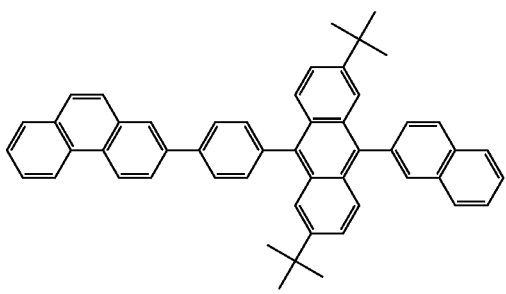
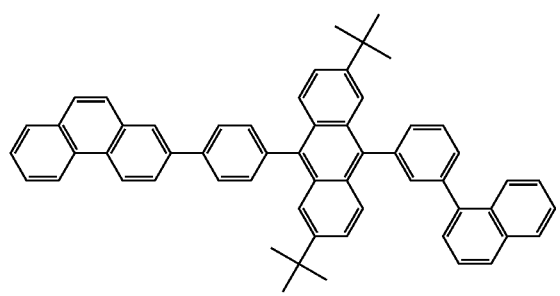
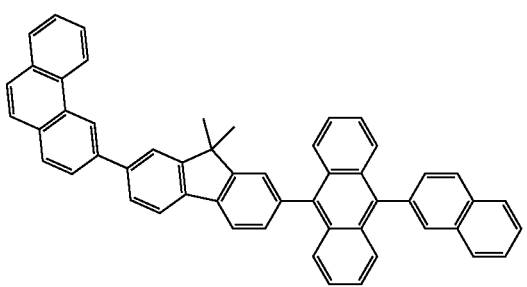
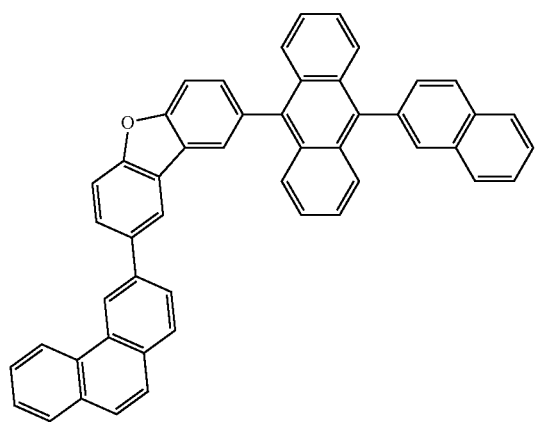
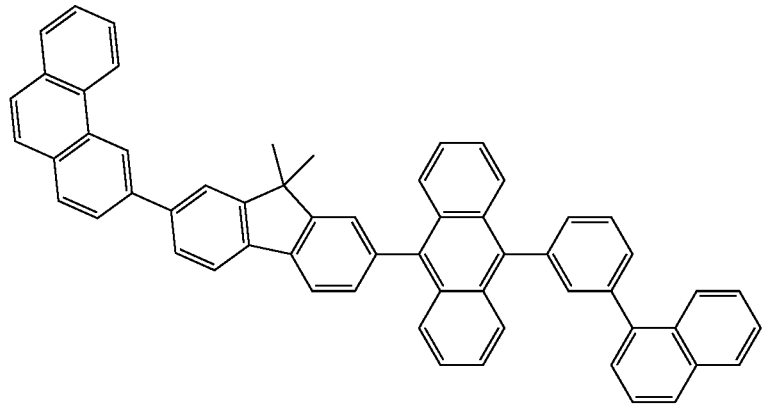

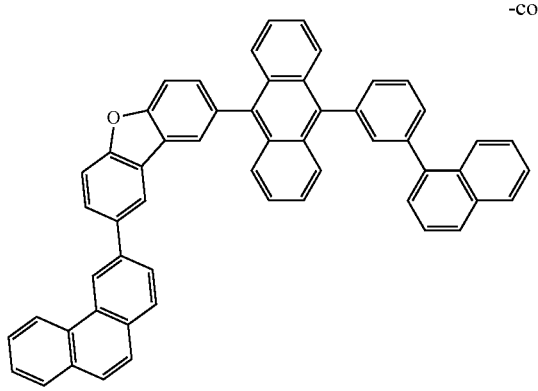
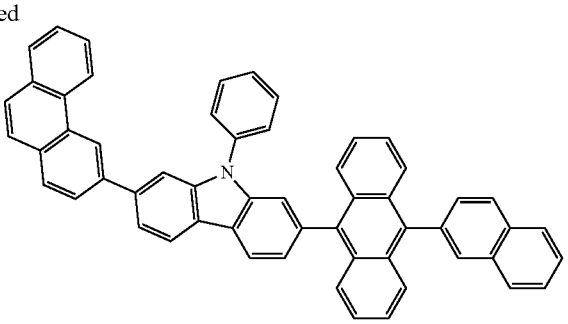
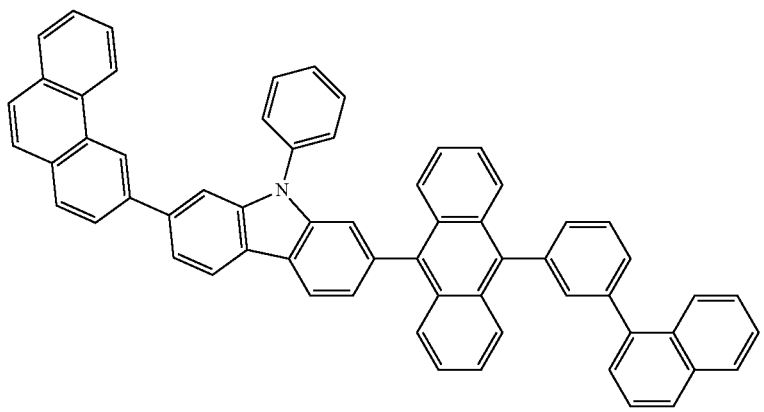
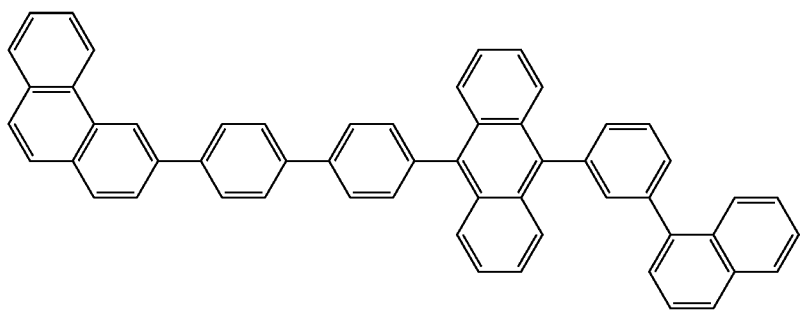
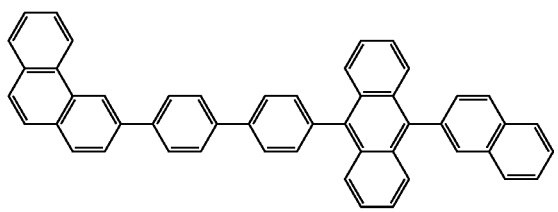
[Chem. 17]
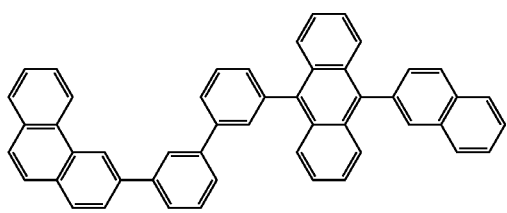
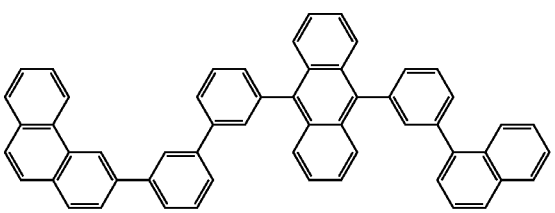

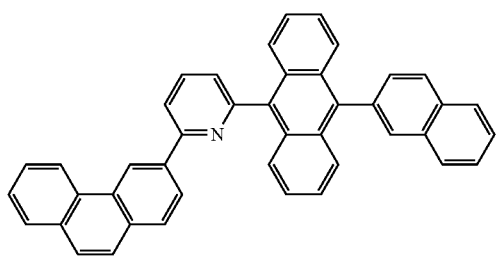
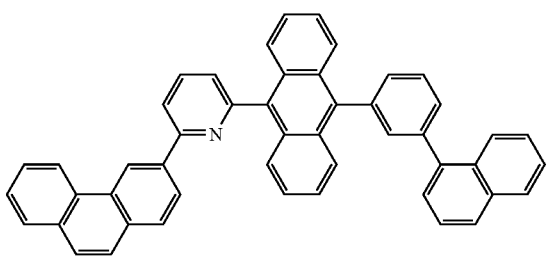
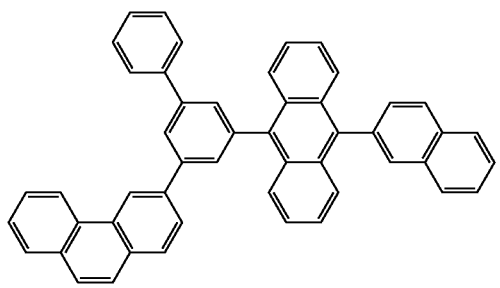
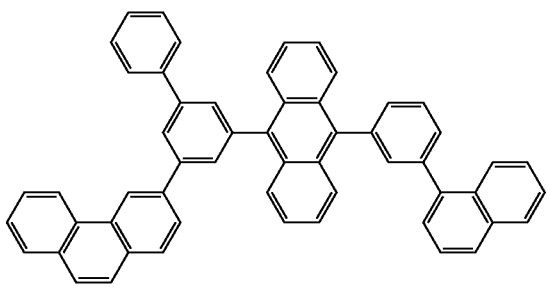
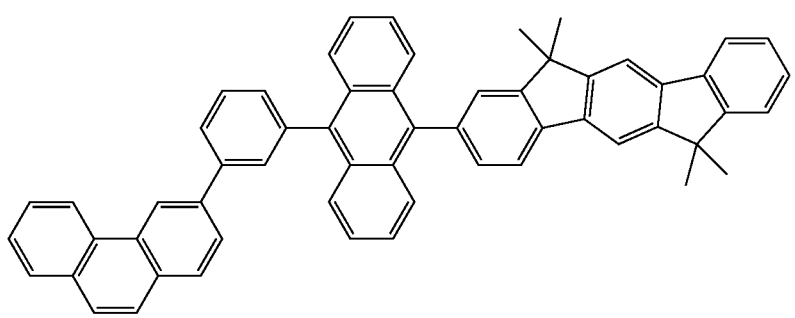
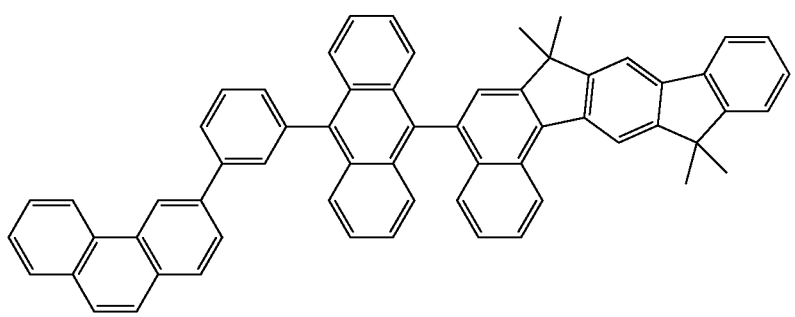
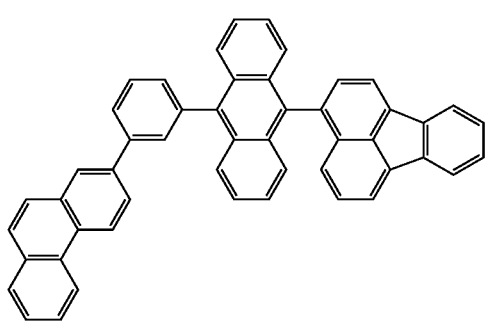
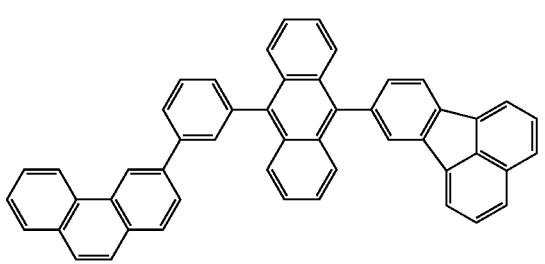

-continued
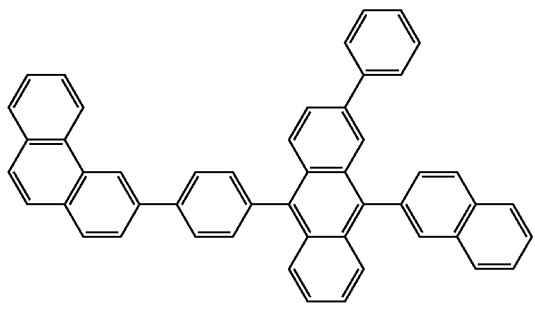
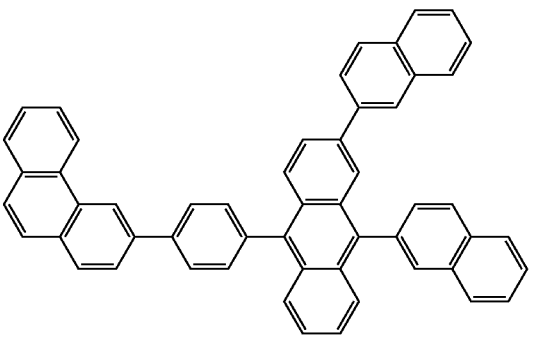
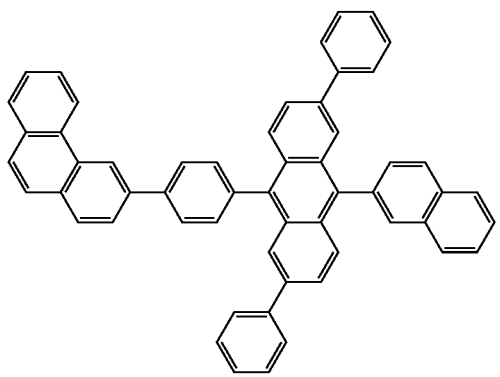
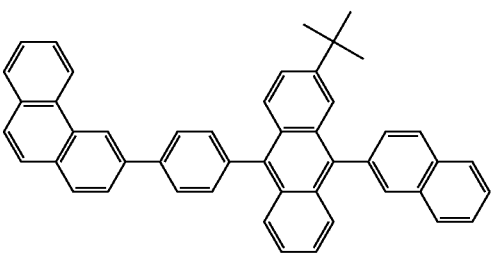
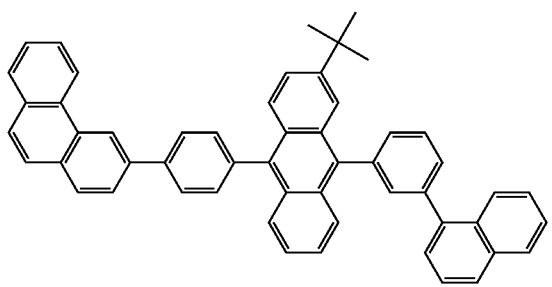
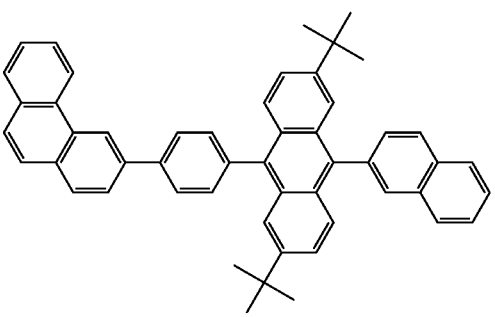
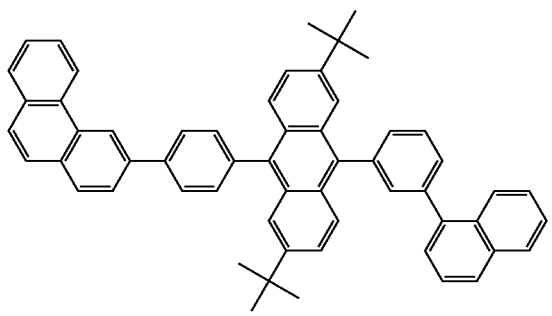

-continued
[Chem. 18]
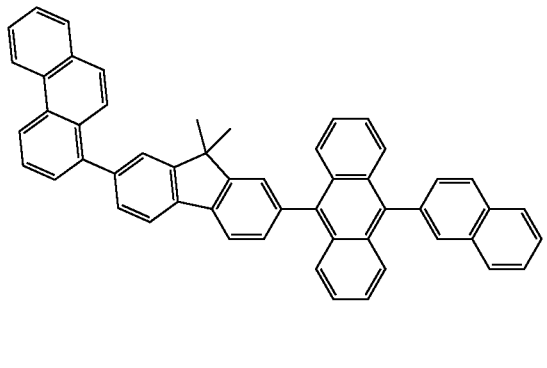
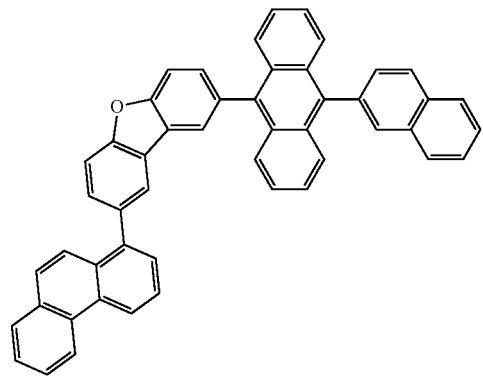
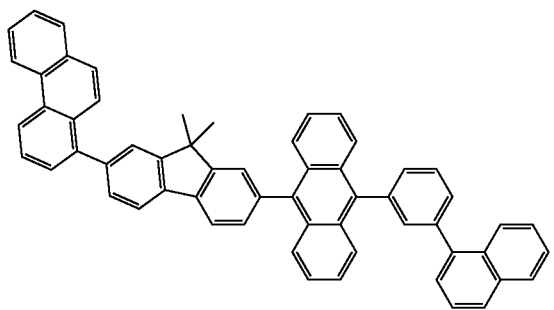
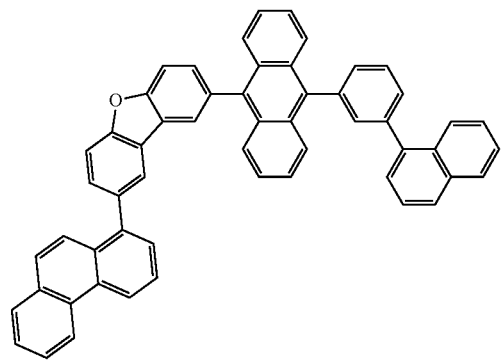
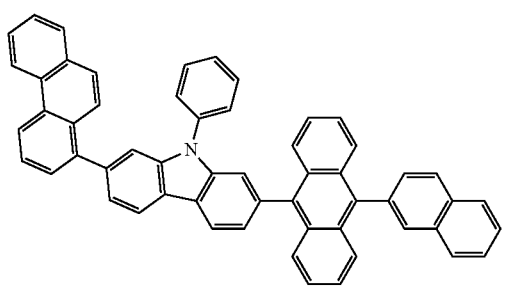
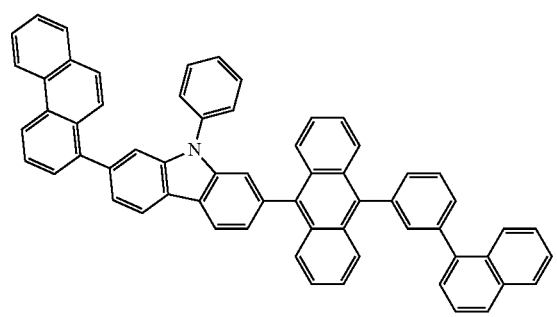
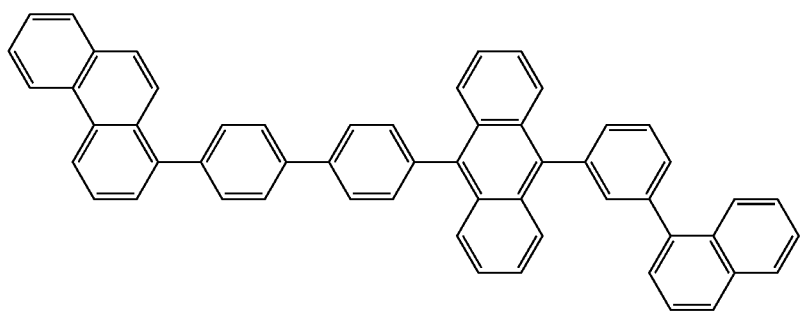
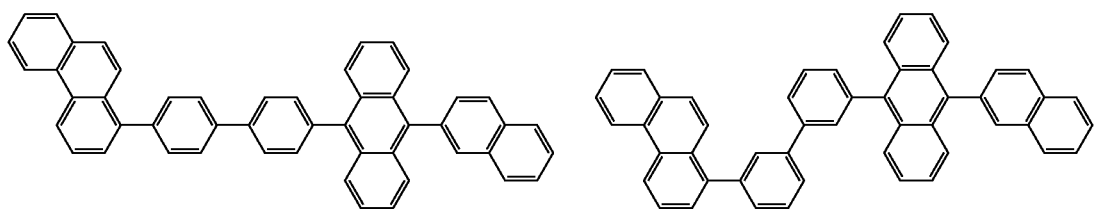

-continued
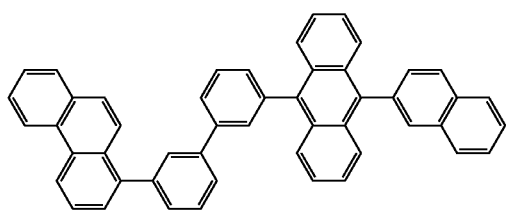
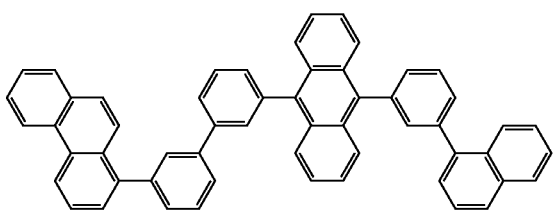
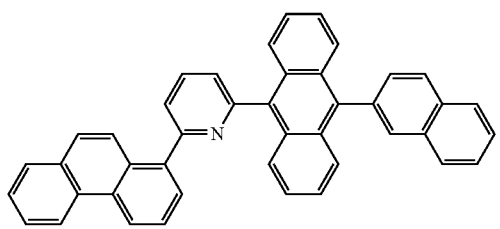
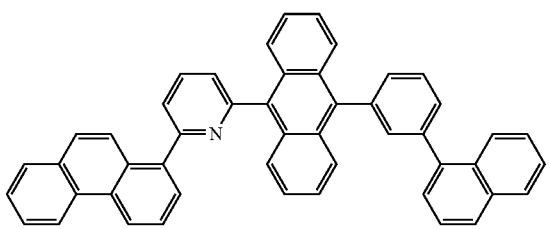
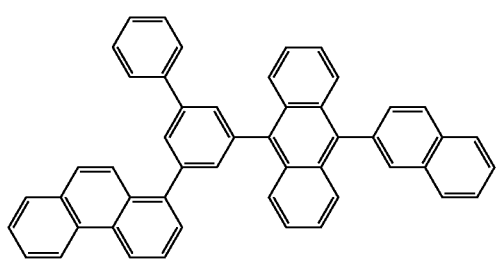
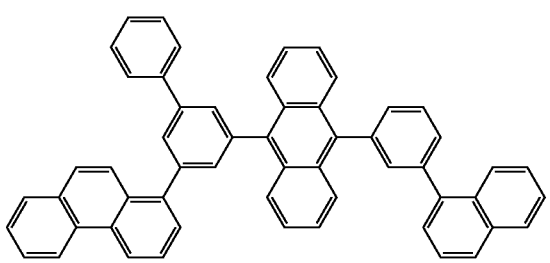
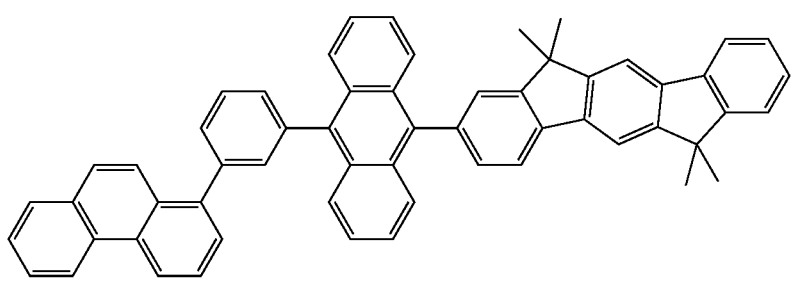
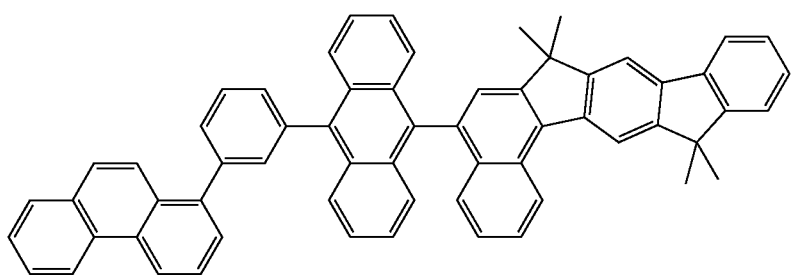
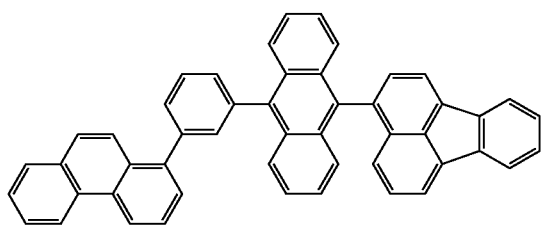
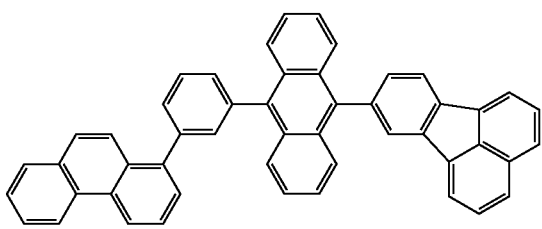

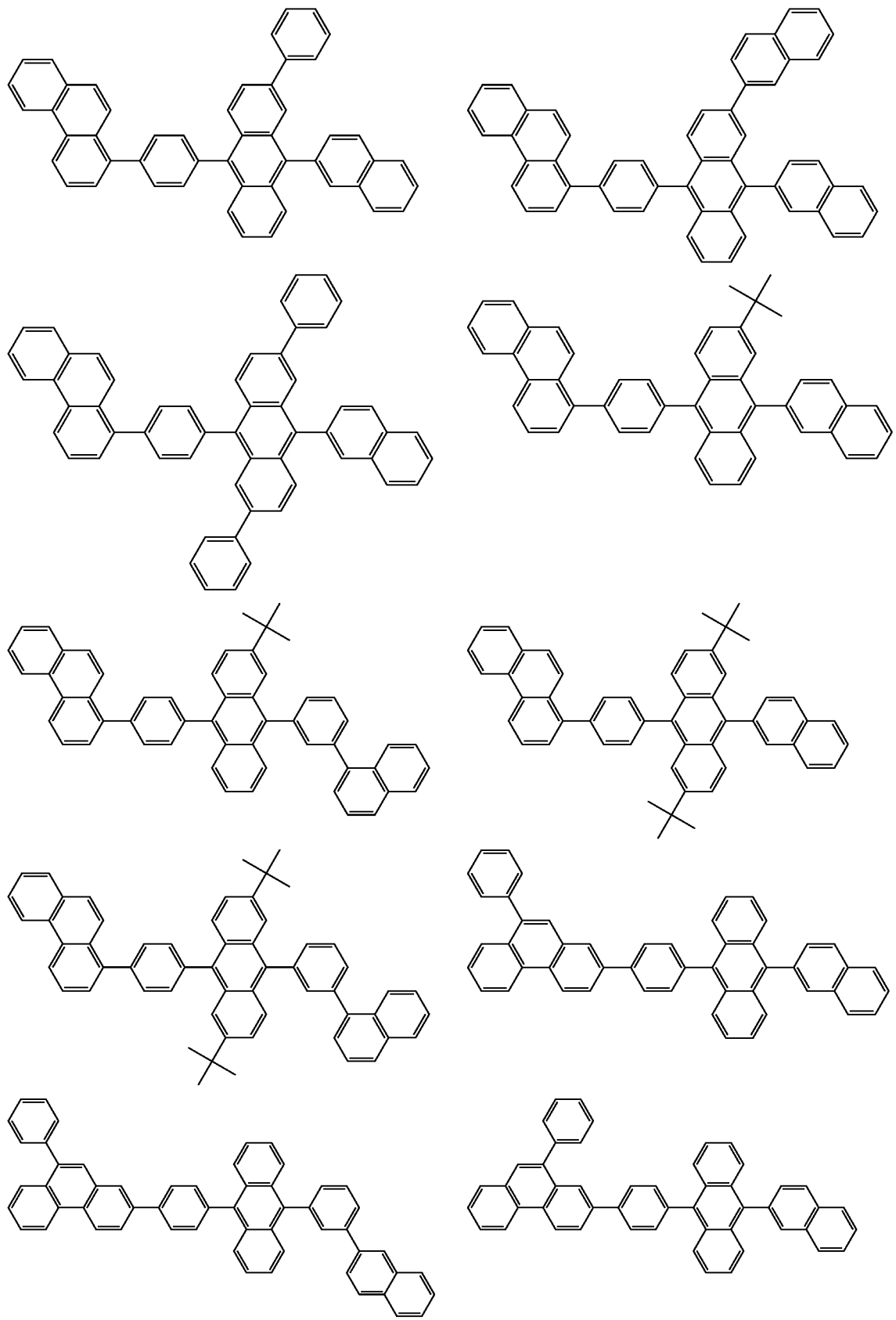
[Chem. 19]

-continued
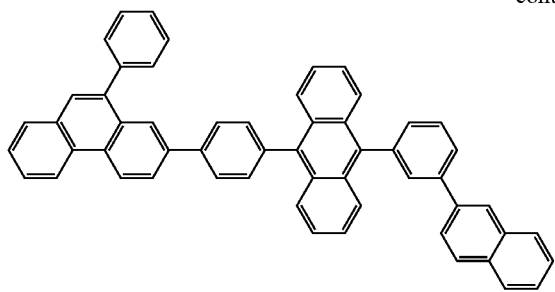
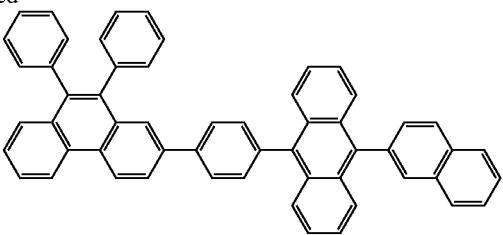
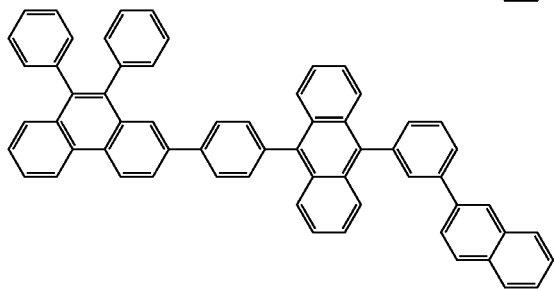
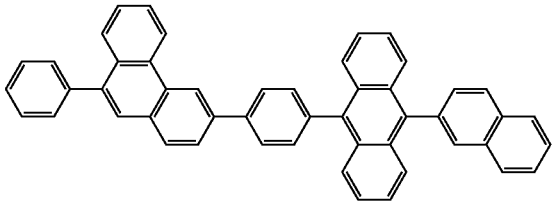
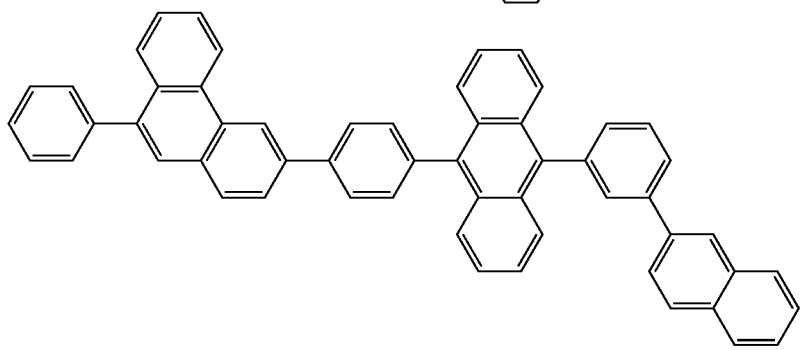
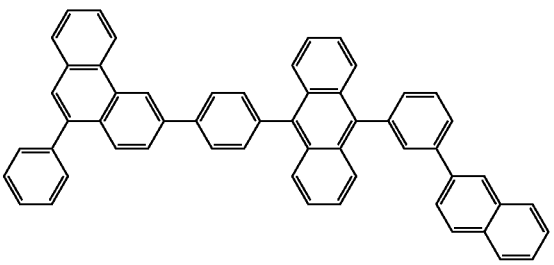
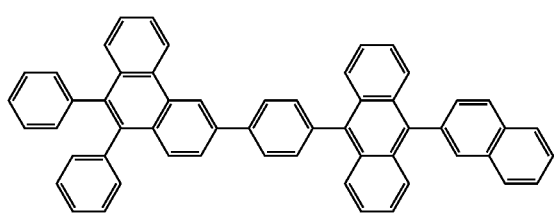
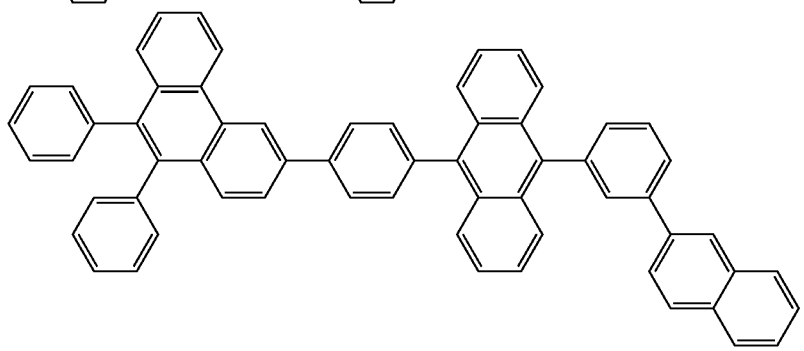

[Chem. 20]
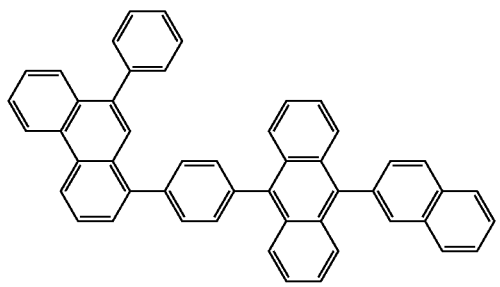
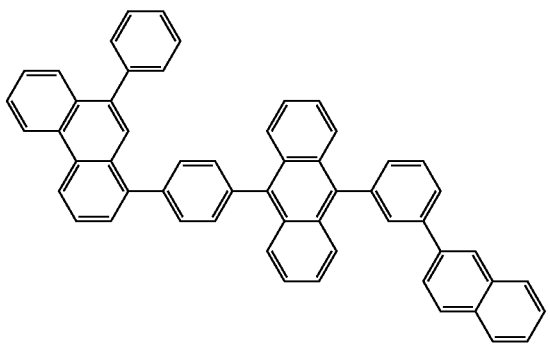
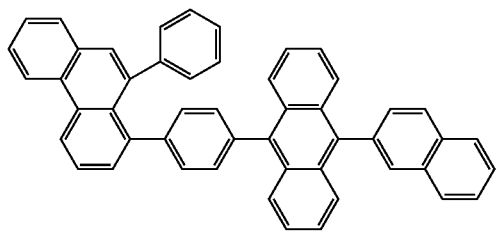
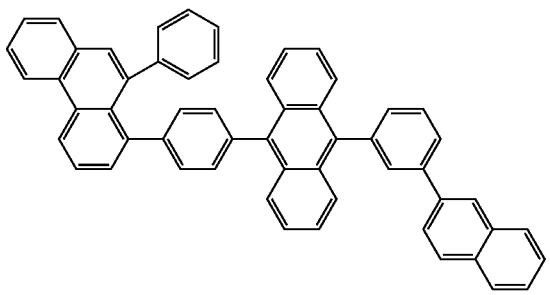
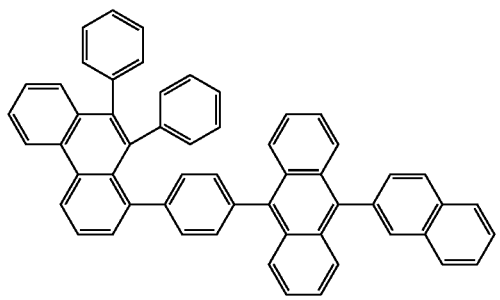
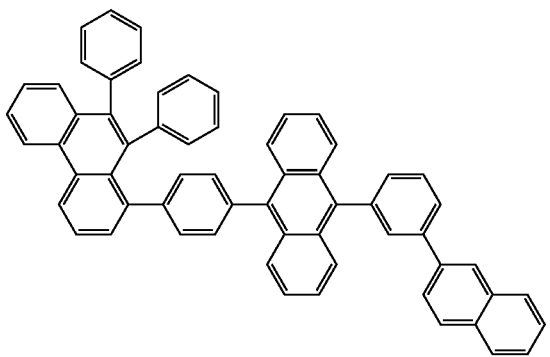
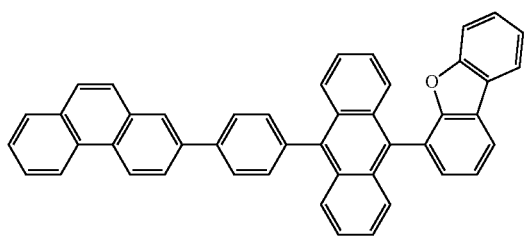
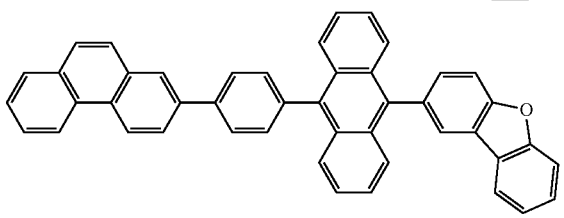
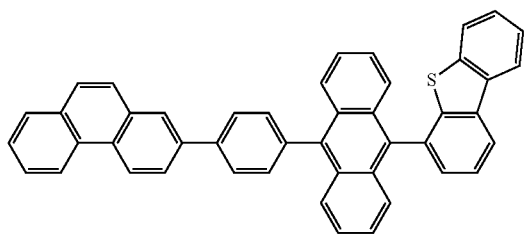
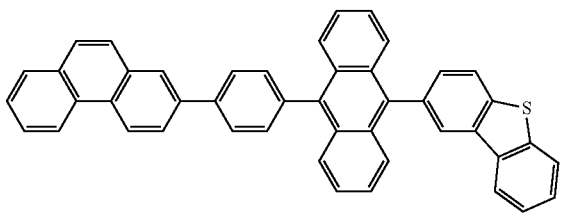

-continued
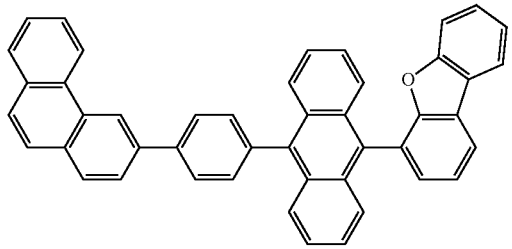
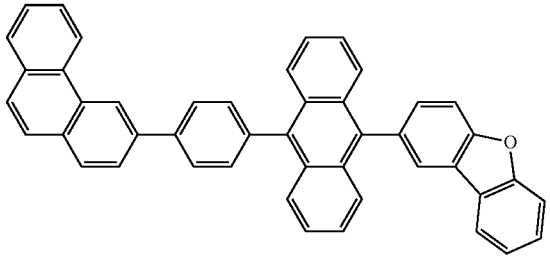
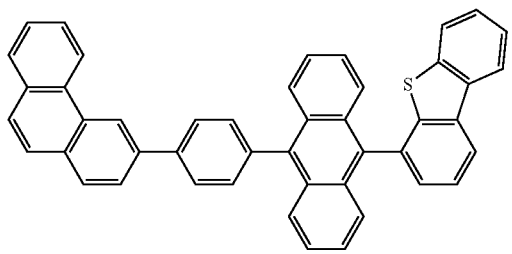
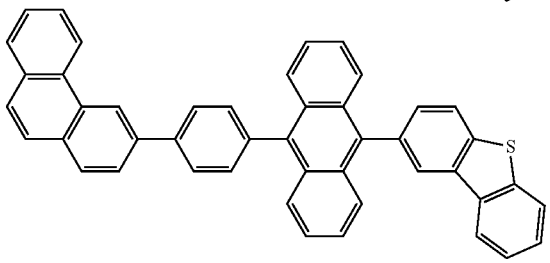
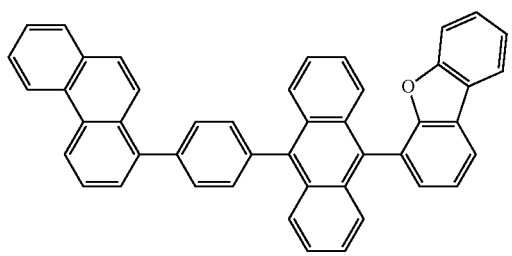
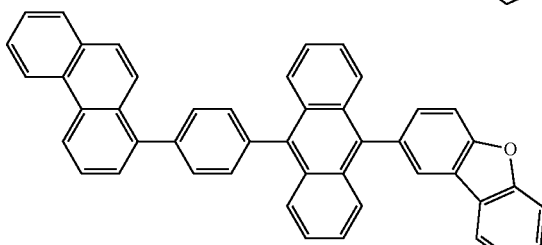
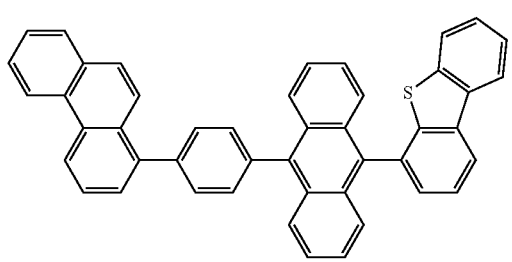
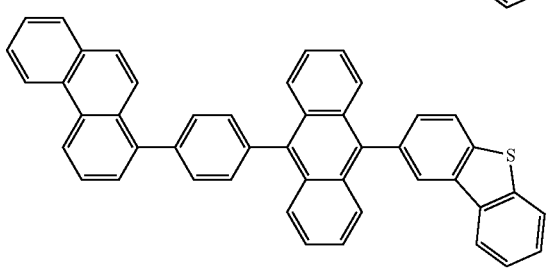
Representative examples of the anthracene derivative having a phenanthryl group of the present invention represented by the general formula (1-1) when $L^1$ represents a single bond and $Ar^1$ is not represented by the general formula (2) are given below. However, the present invention is not limited to the representative examples.
[Chem. 21]
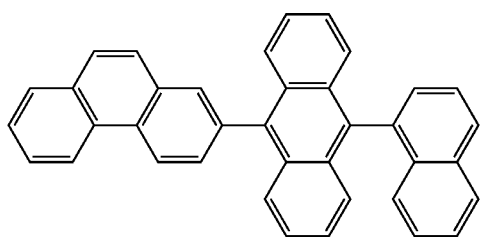
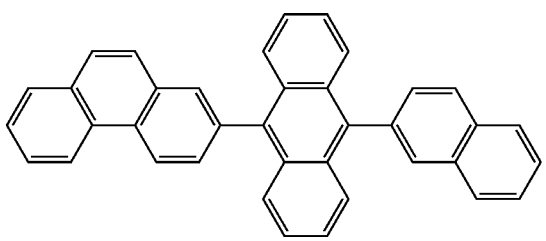
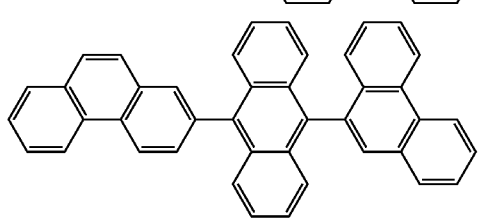
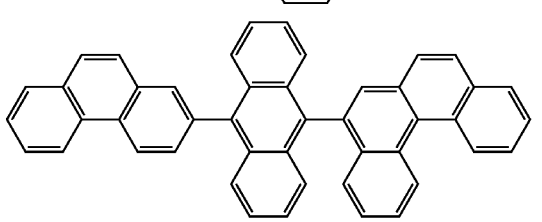

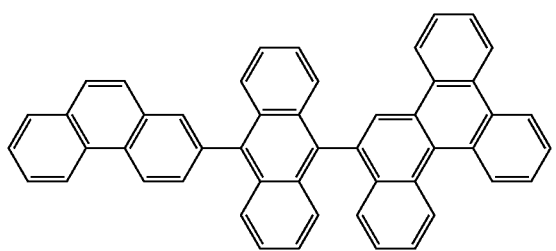
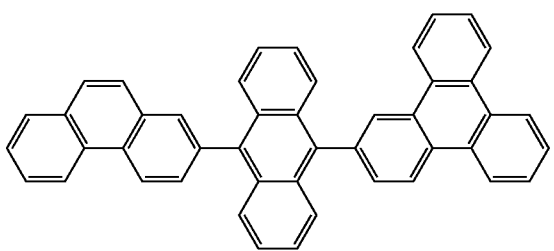
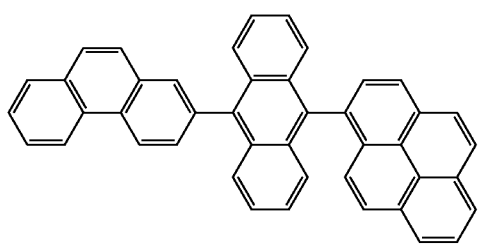
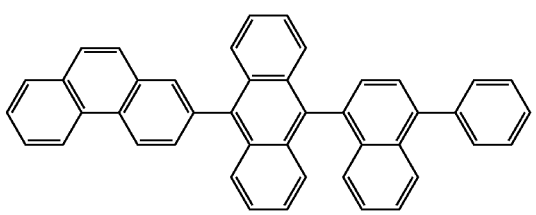
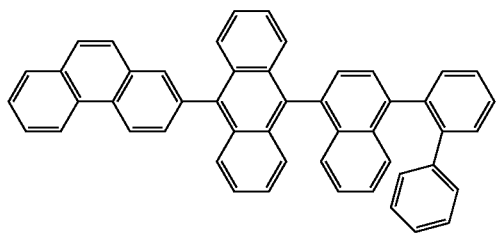
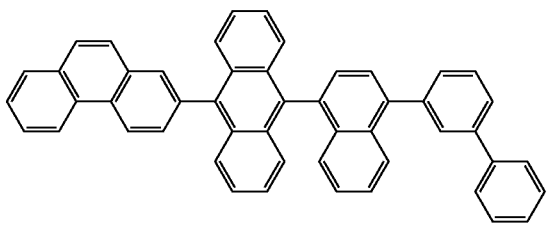
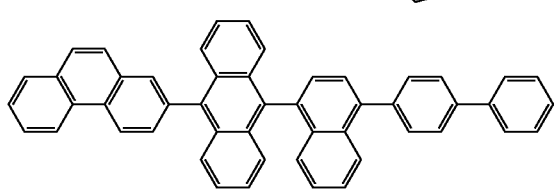
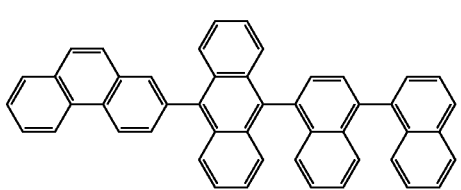
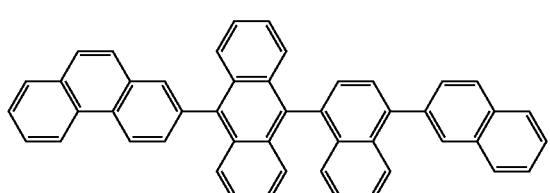
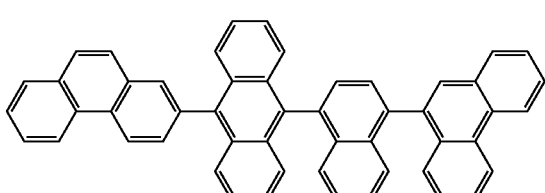
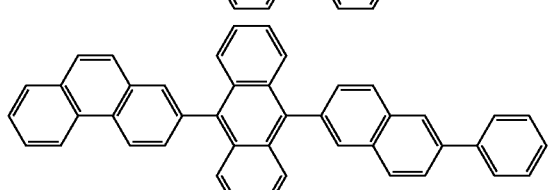
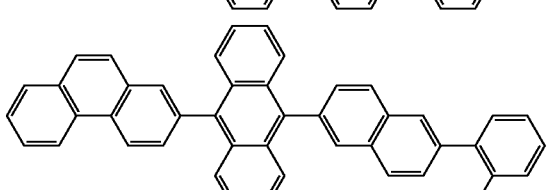
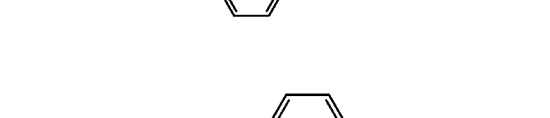
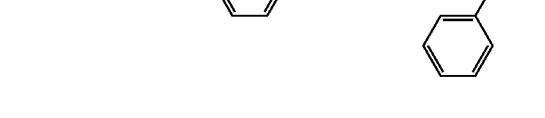
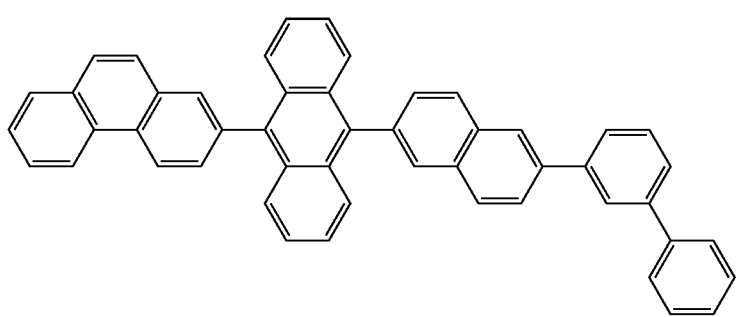

-continued
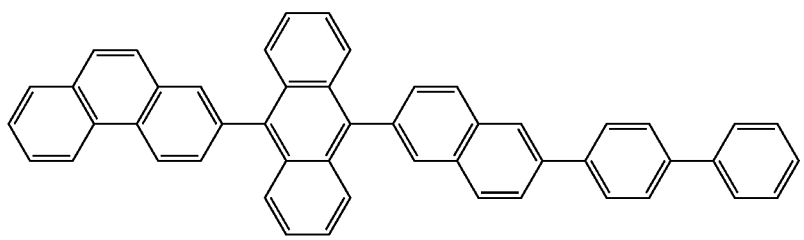

[Chem. 22]
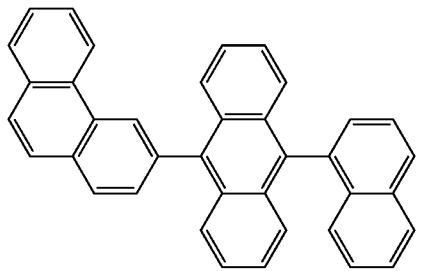
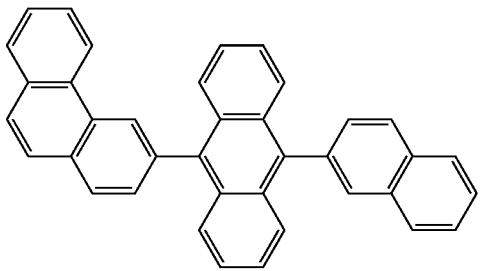
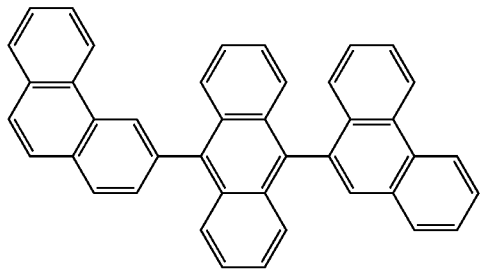
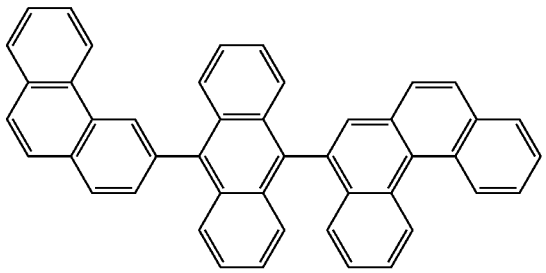
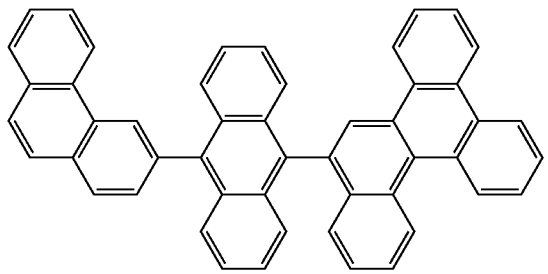
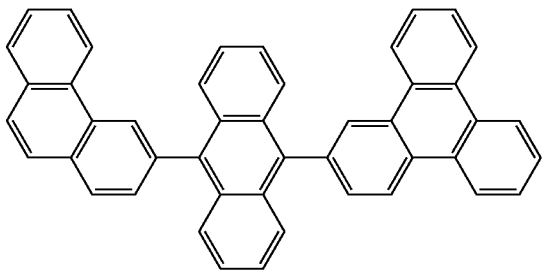
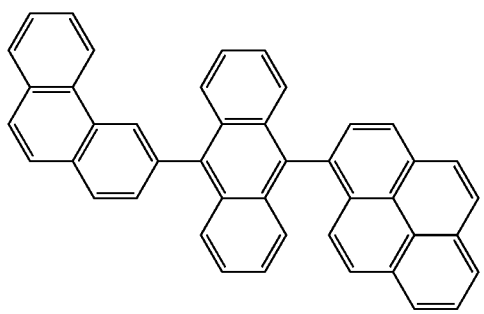
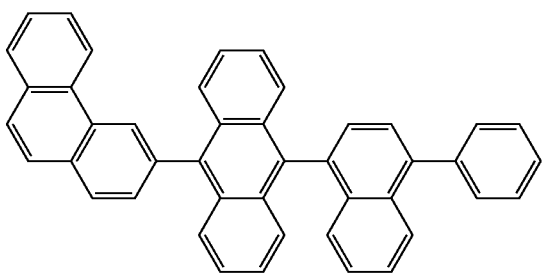
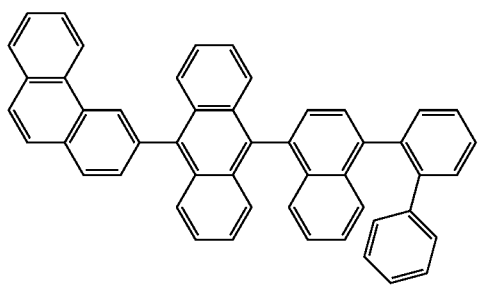
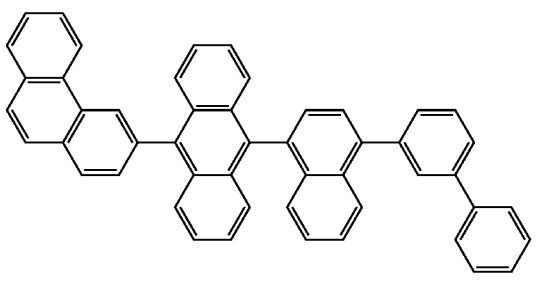
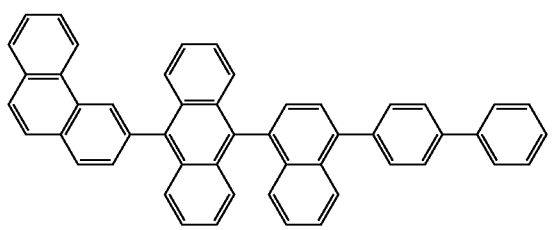
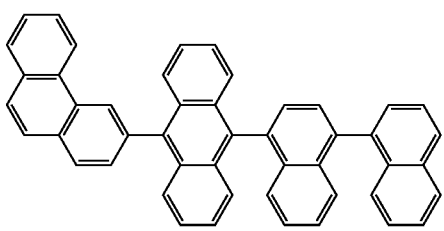

71 72
-continued
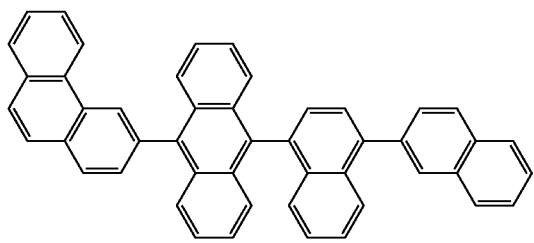 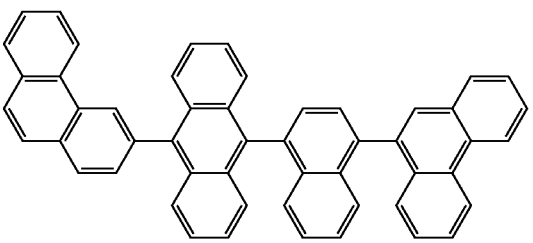
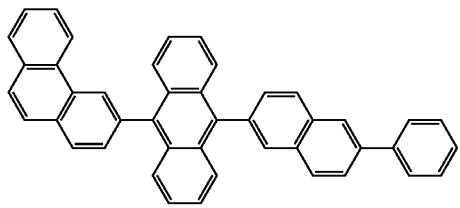 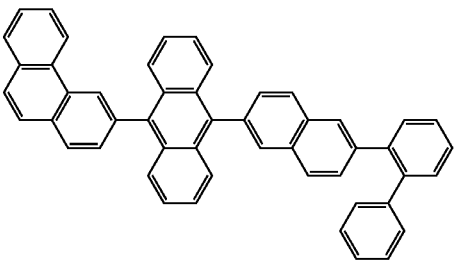
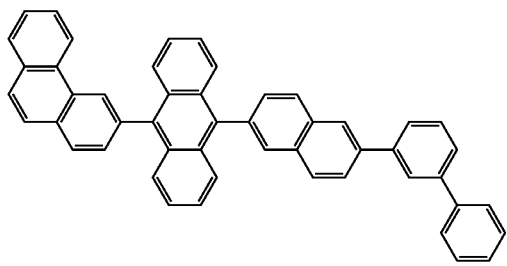 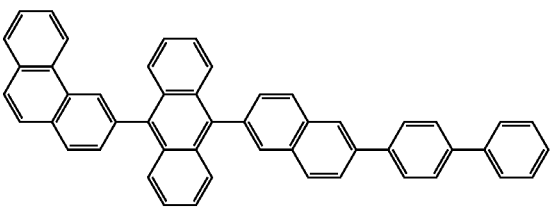
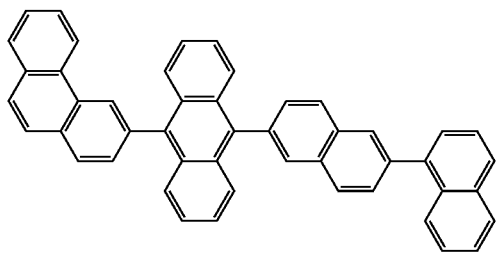 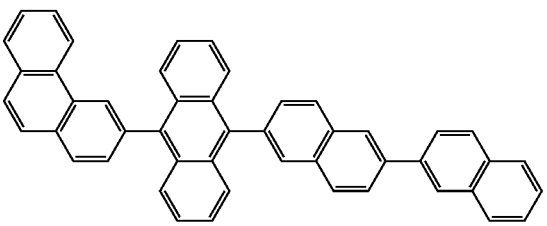
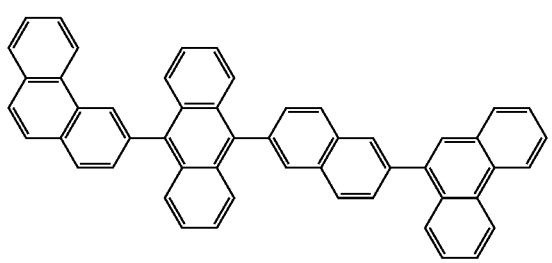 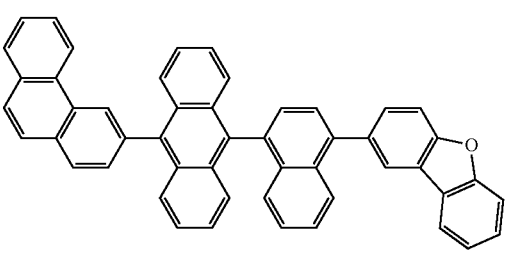
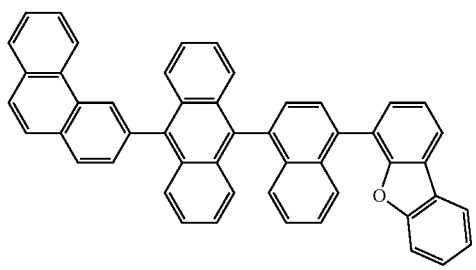 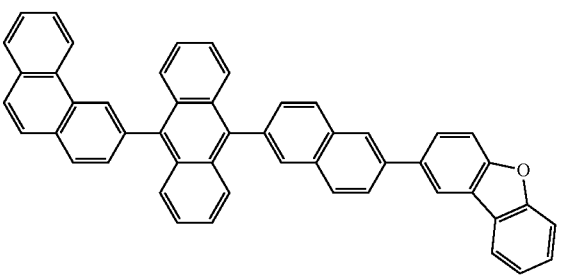

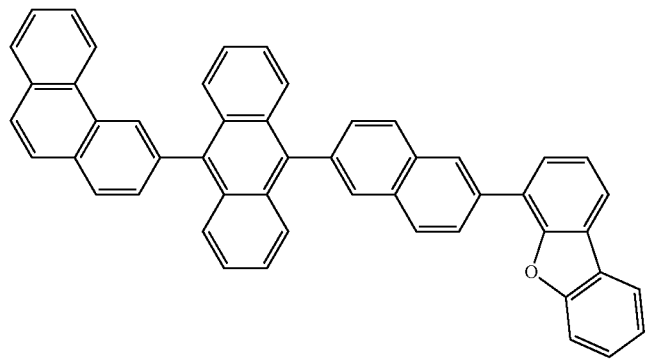 [SMILES: c1ccc2c(c1)ccc1ccc(-c3c4ccccc4c(-c4ccc5cc(-c6cccc7c6oc6ccccc67)ccc5c4)c4ccccc34)cc12]
[Chem. 23]
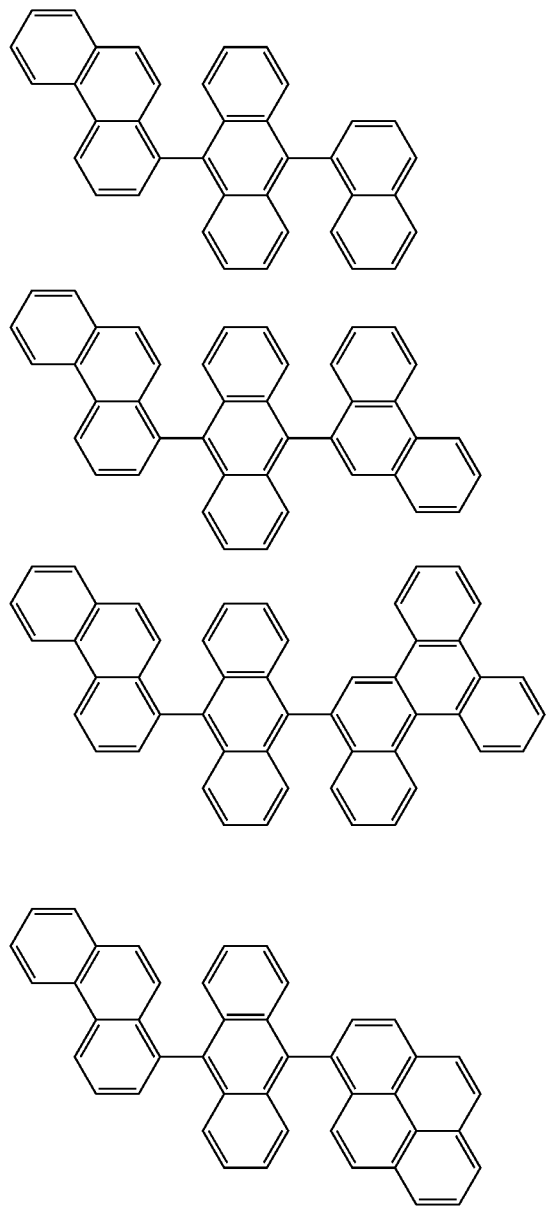
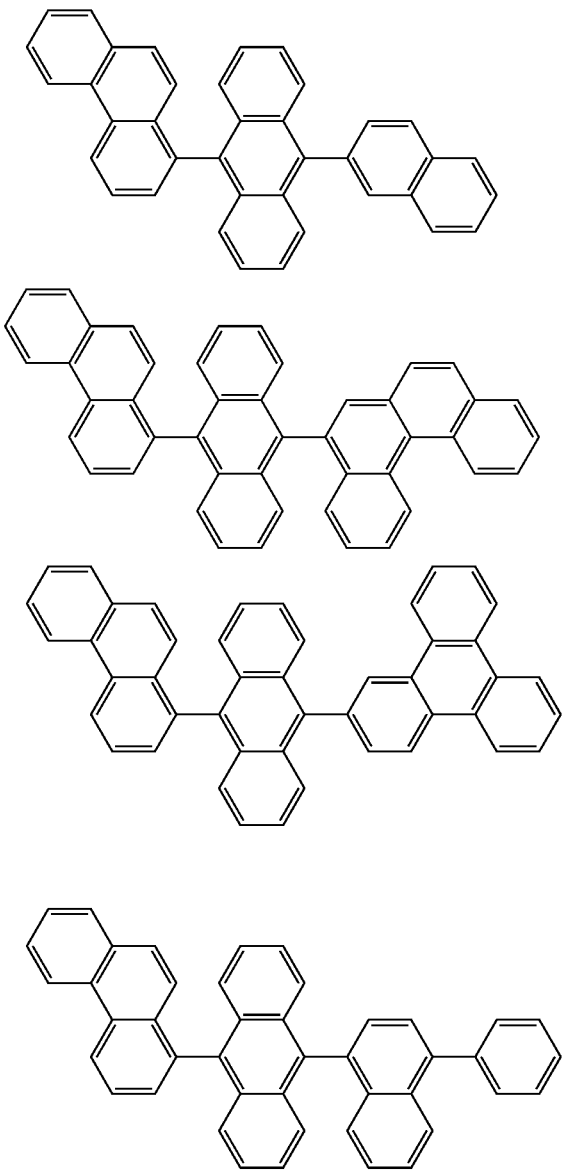

-continued
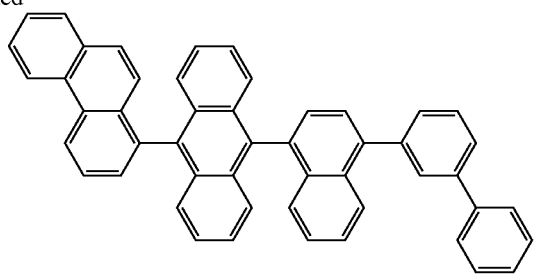
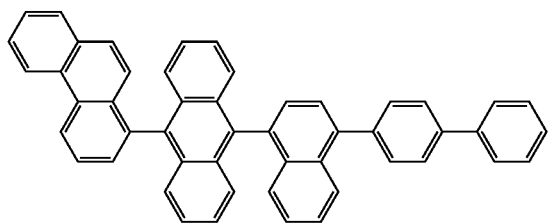
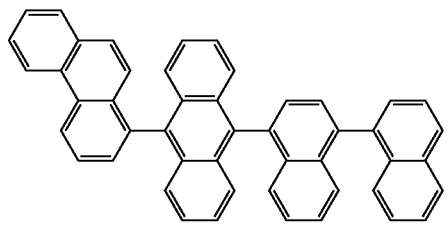
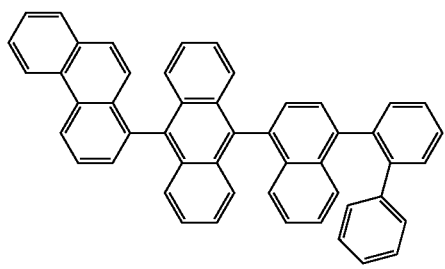
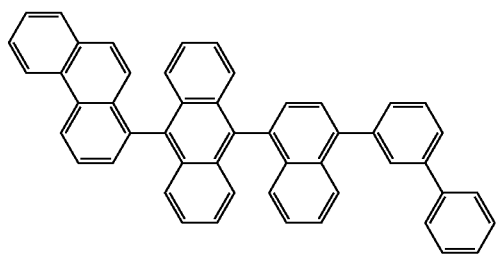
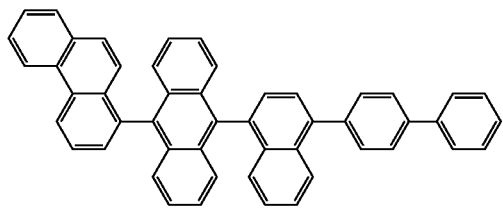
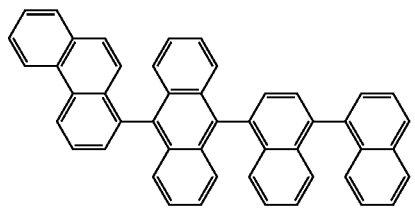
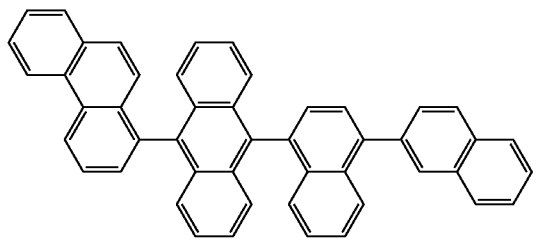
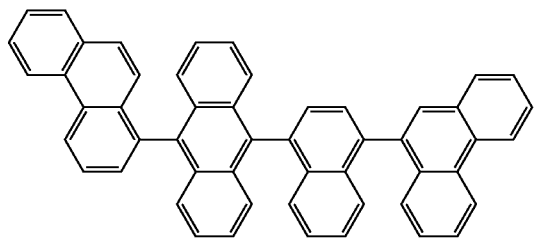
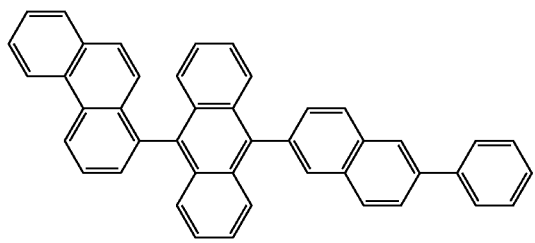
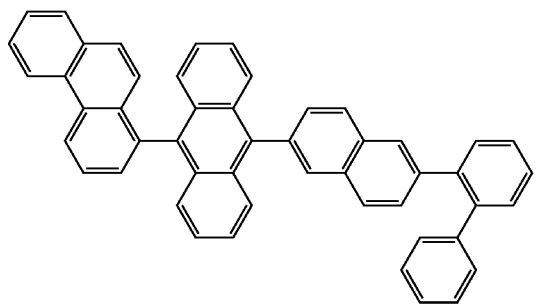

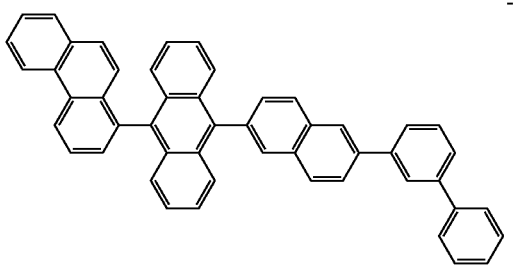
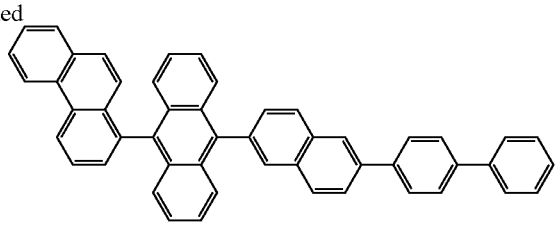
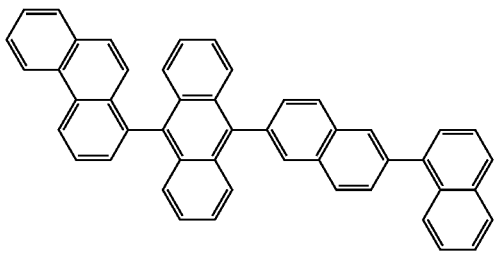
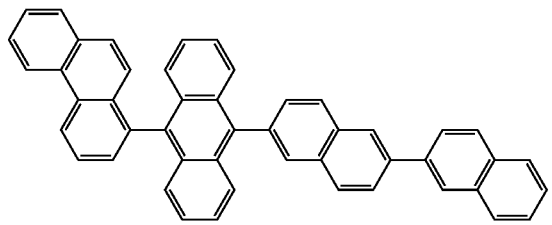
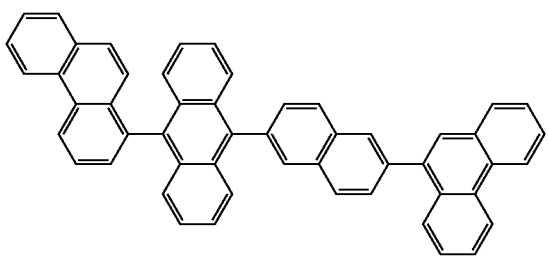
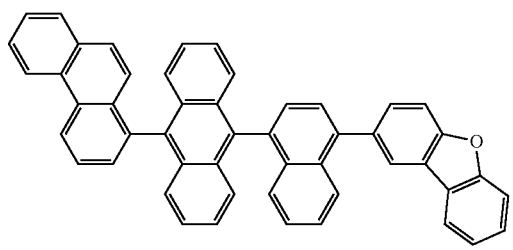
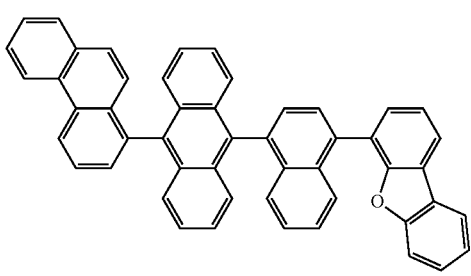
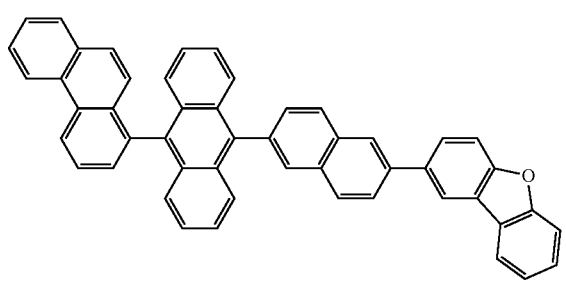
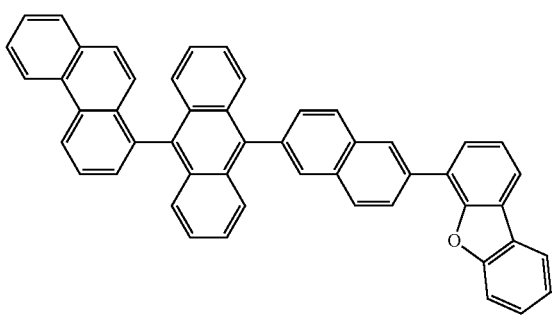
[Chem. 24]
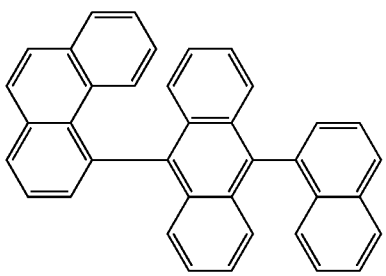
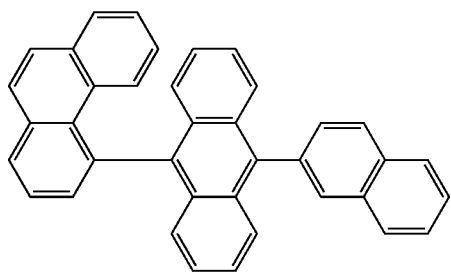

-continued
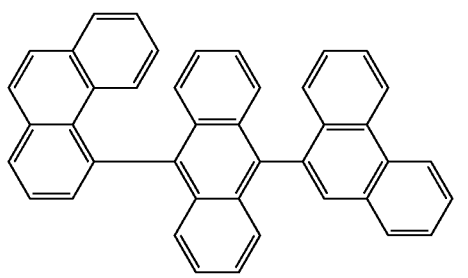
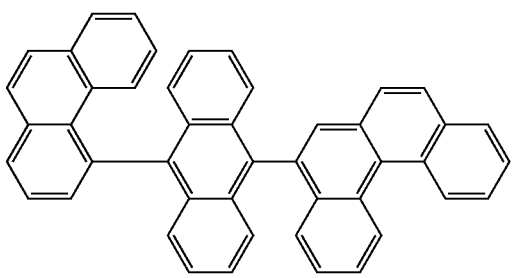
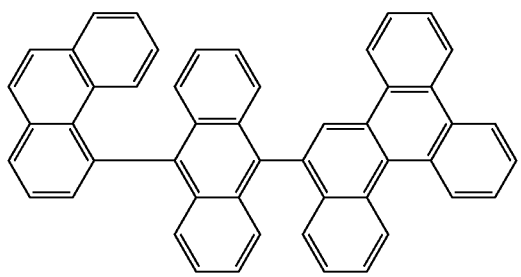
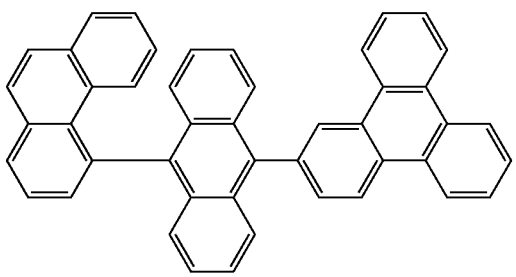
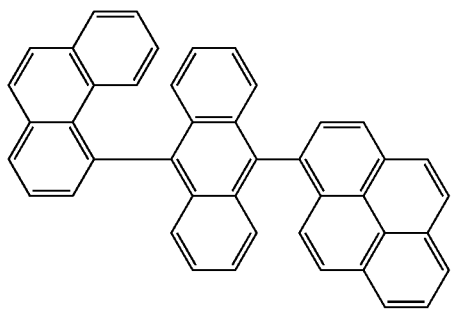
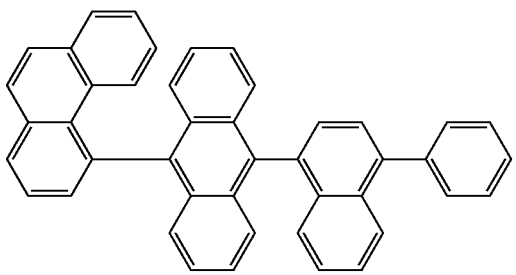
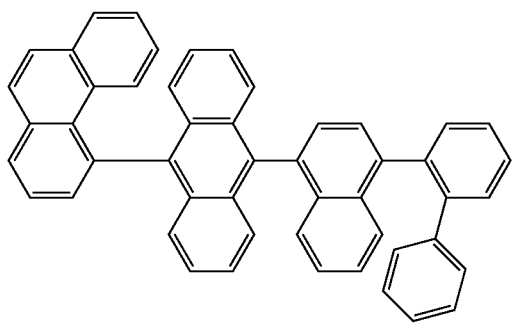
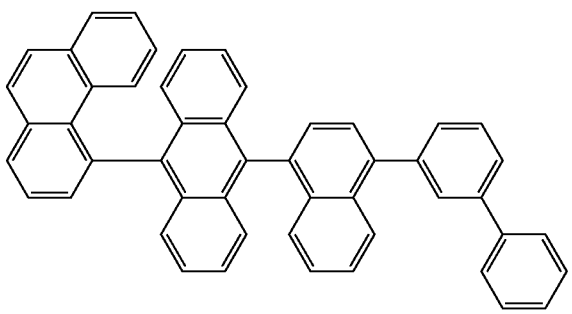
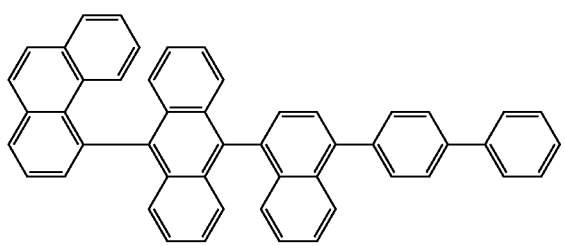
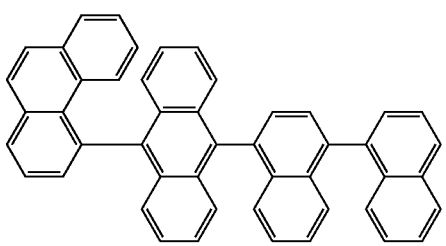
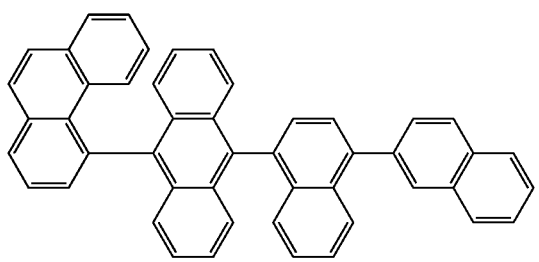
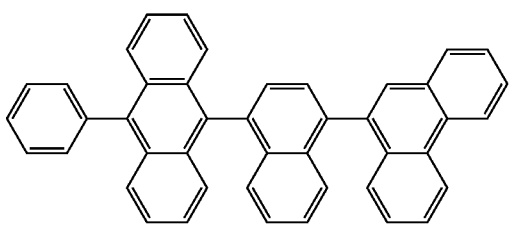

-continued
81
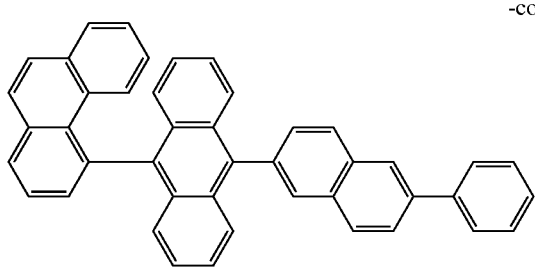
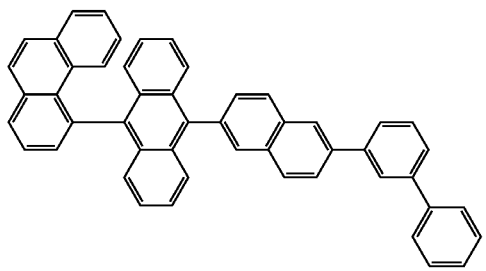
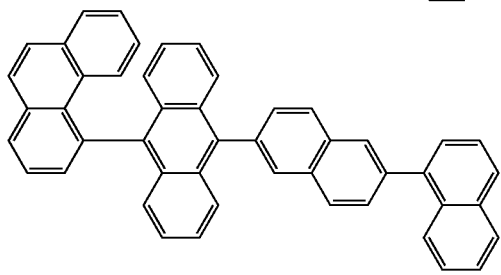
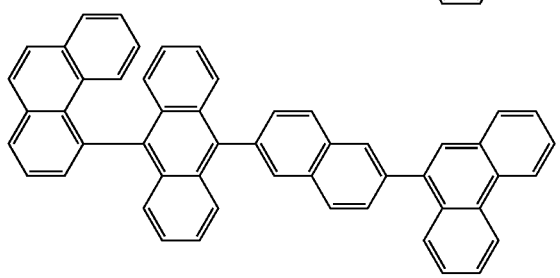
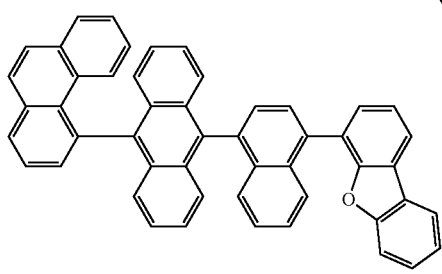
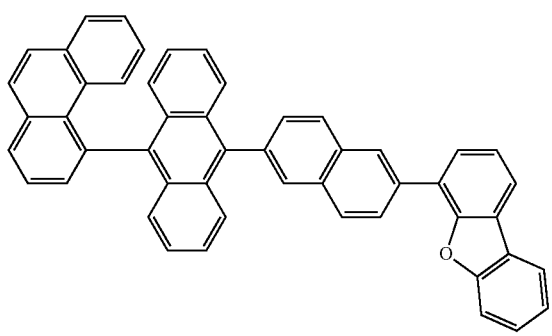
82
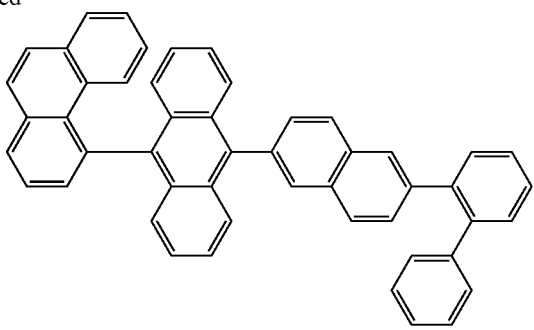
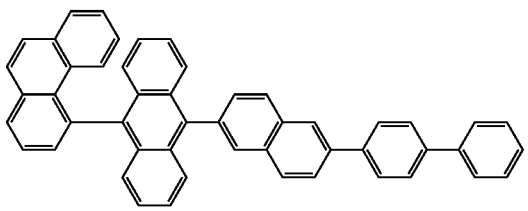
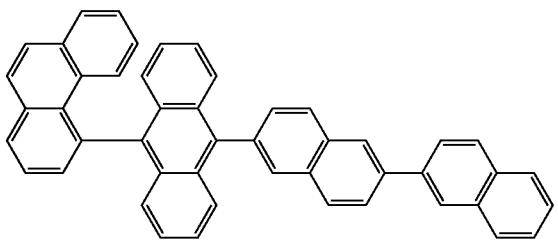
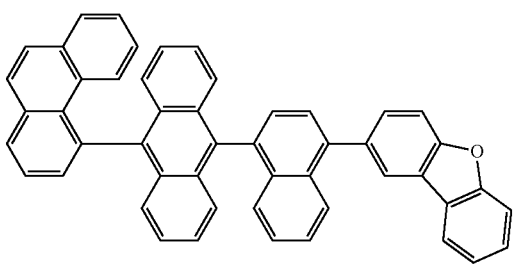
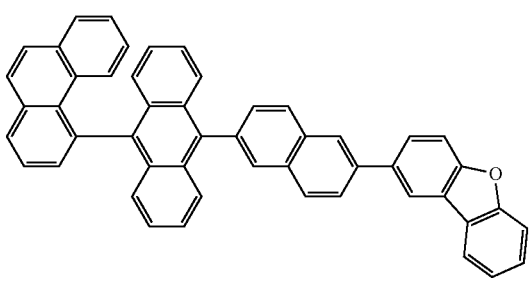

-continued
[Chem. 25]
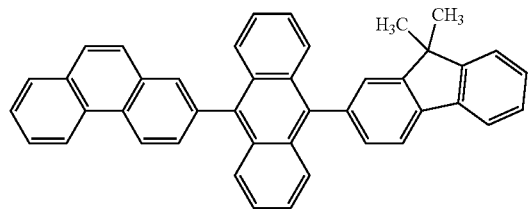
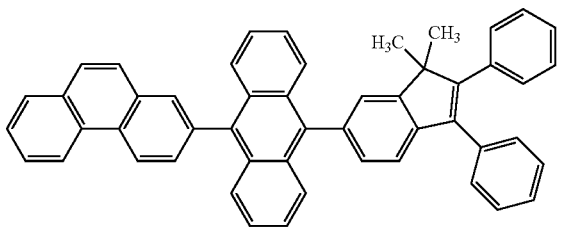
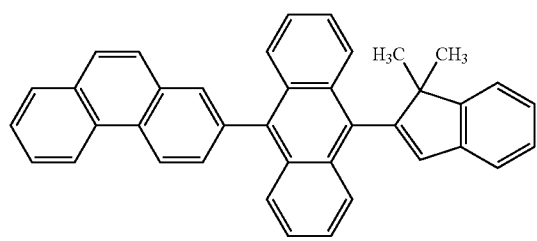
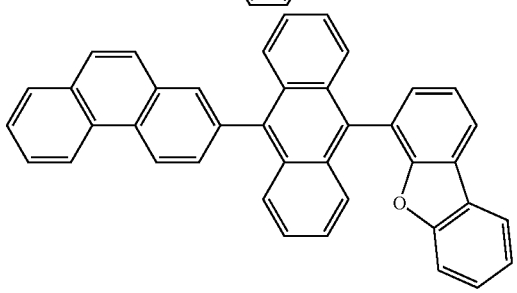
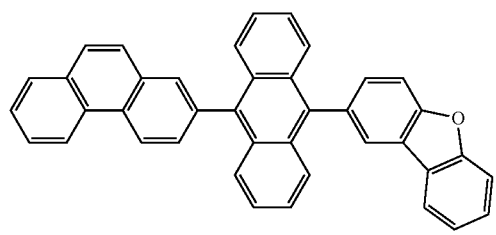
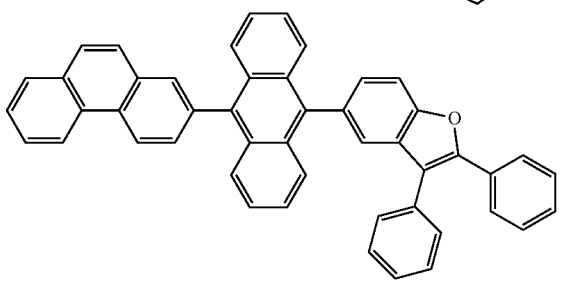
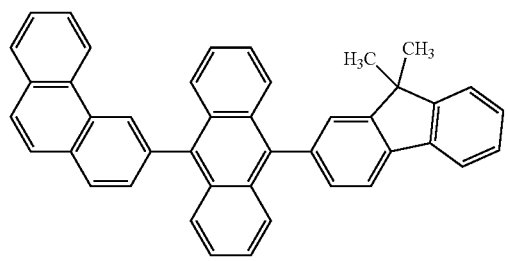
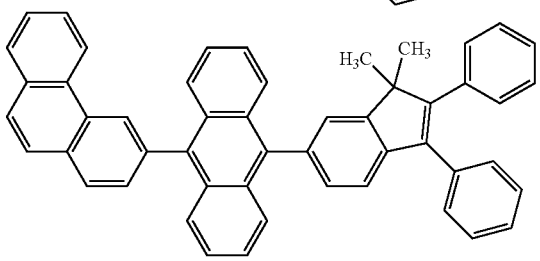
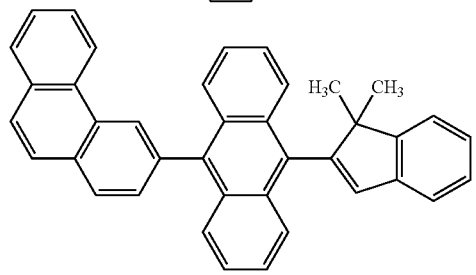
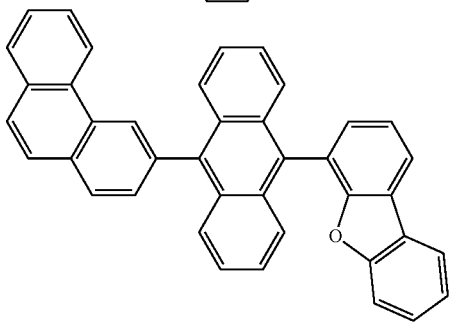
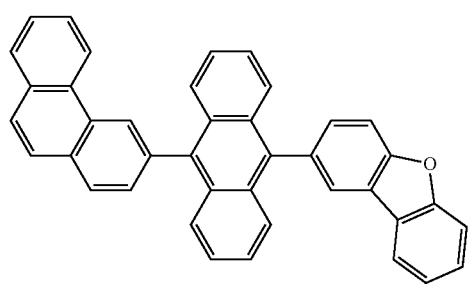
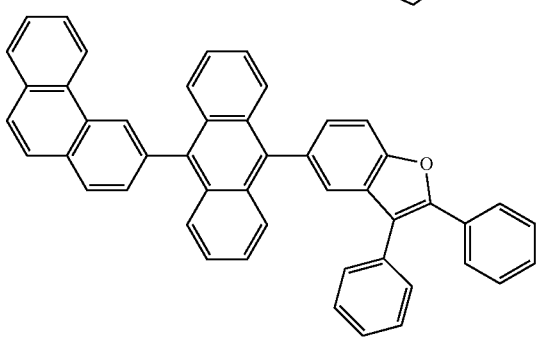

85 86
-continued
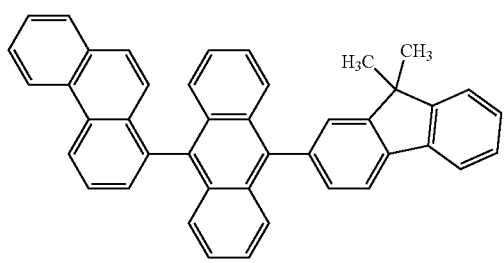
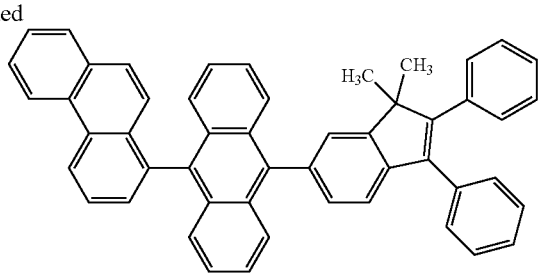
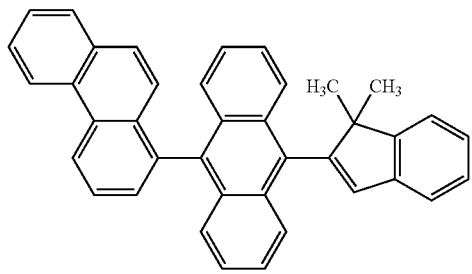
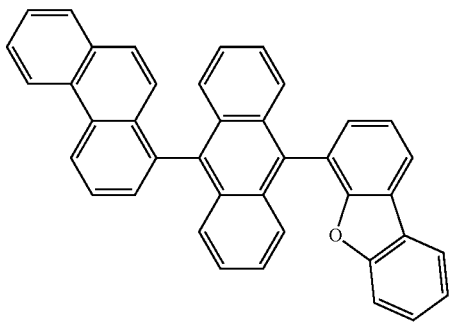
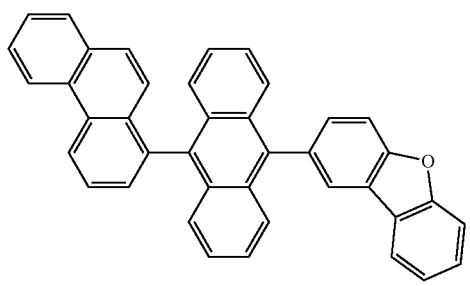
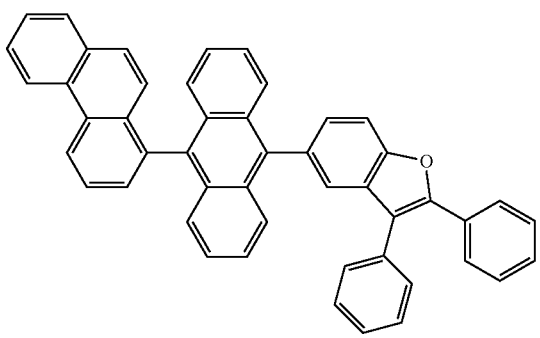
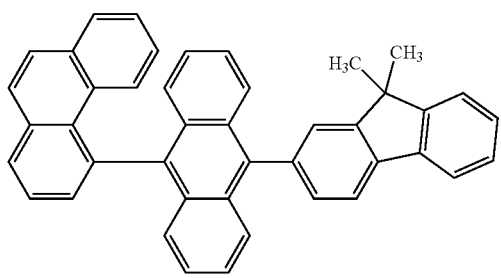
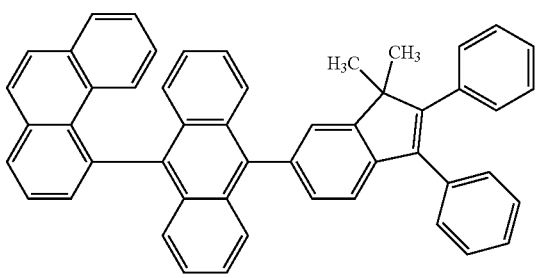
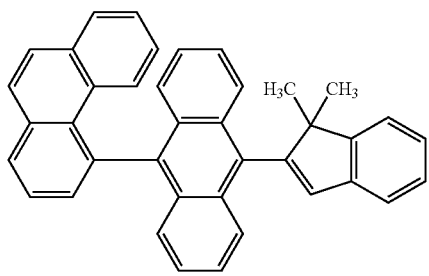
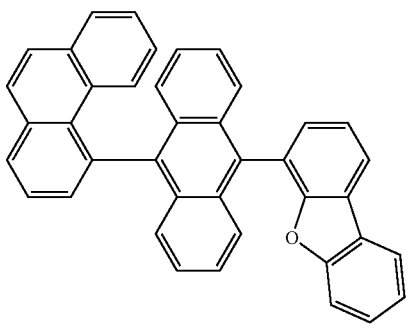

87
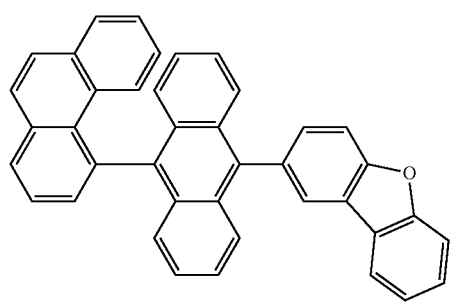
88
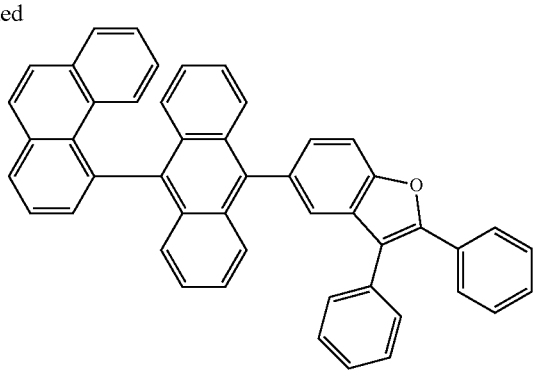
[Chem. 26]
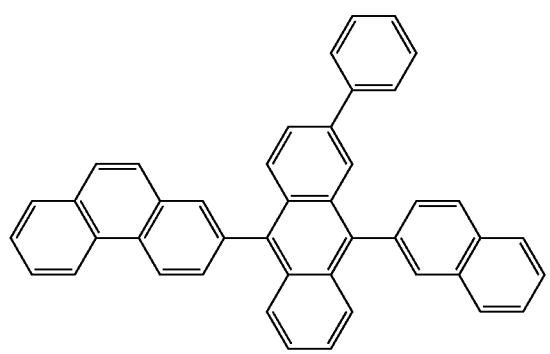
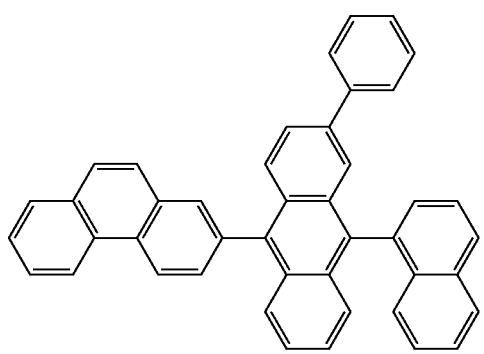
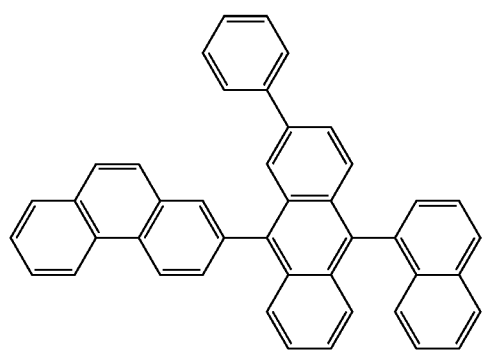
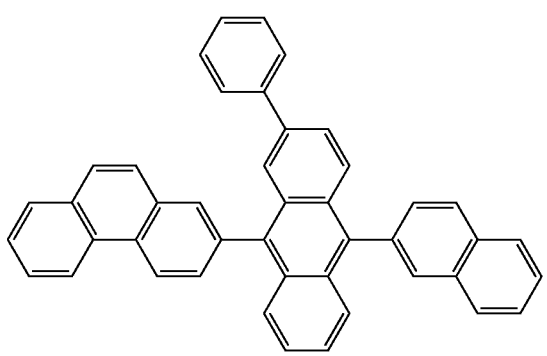
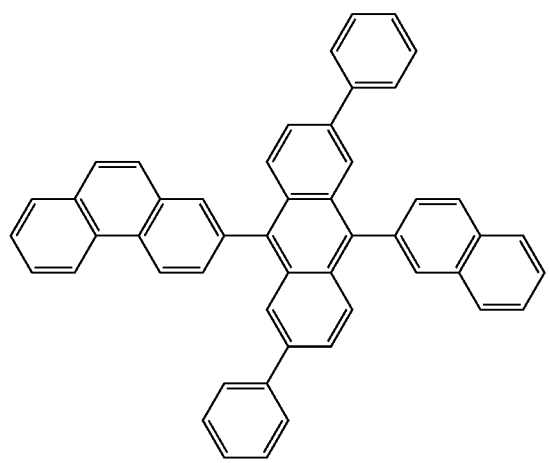
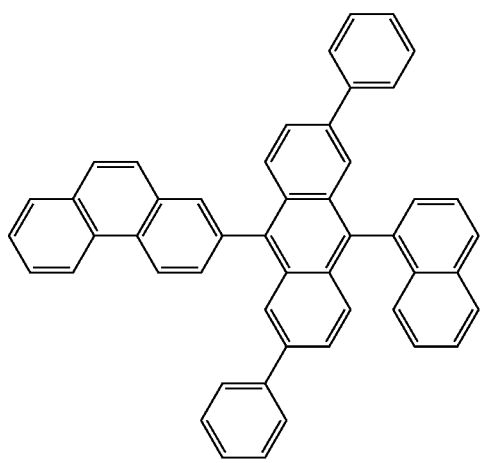

-continued
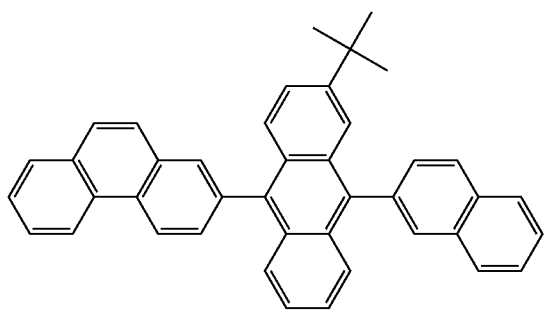
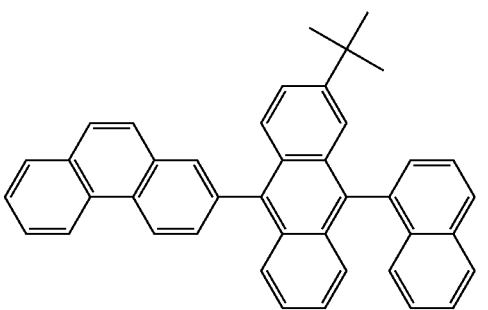
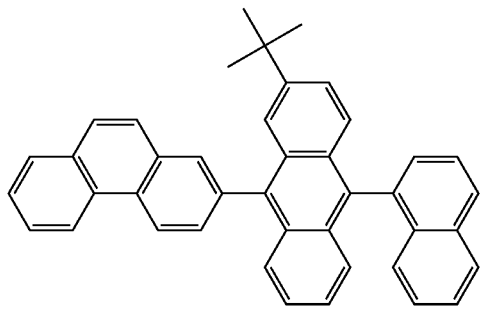
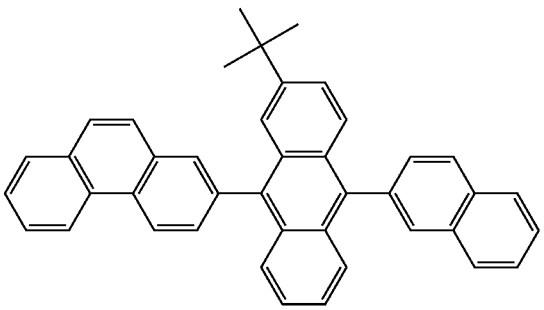
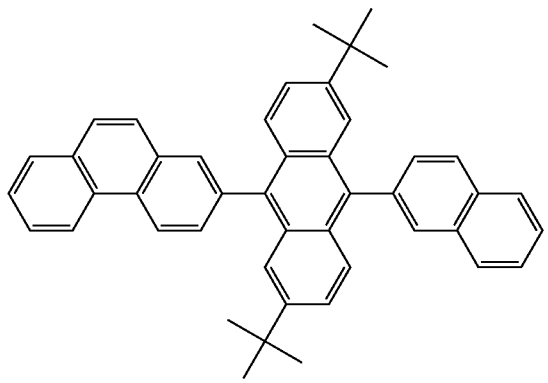
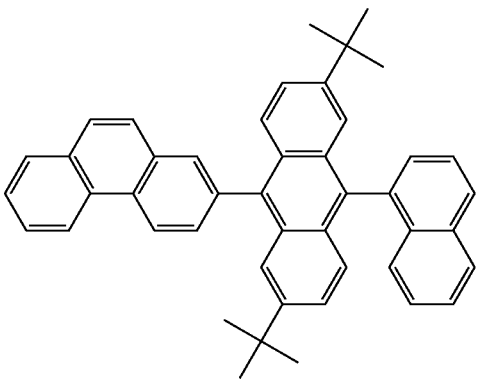
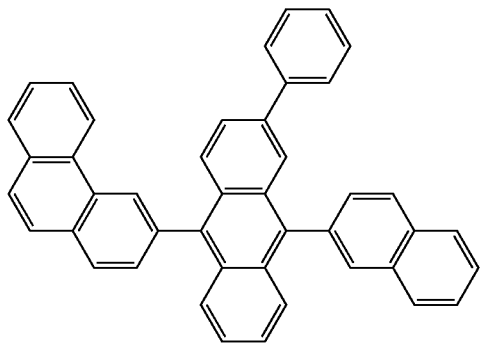
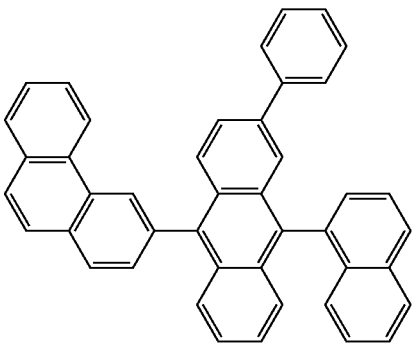
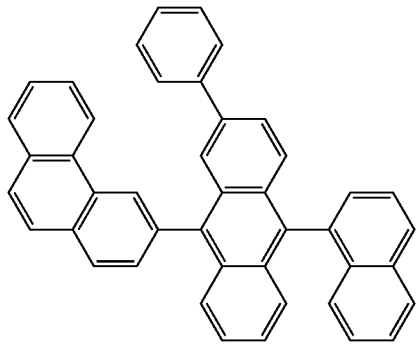
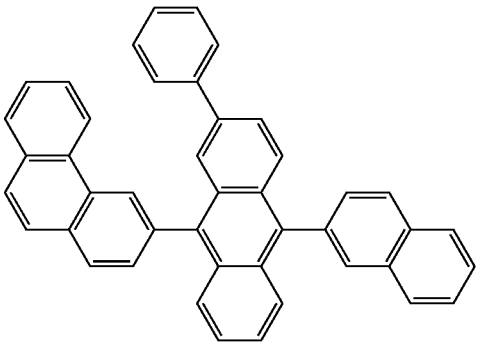

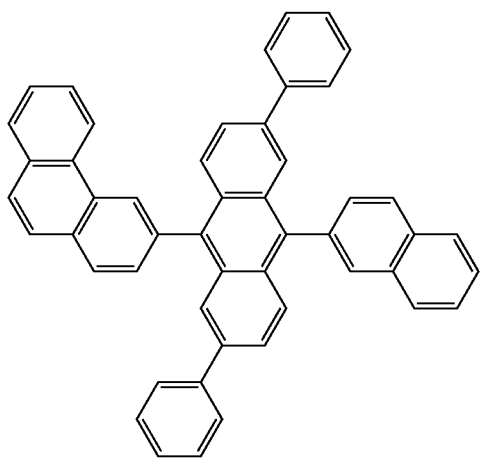
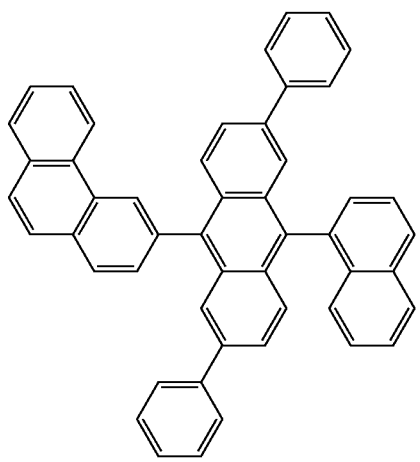
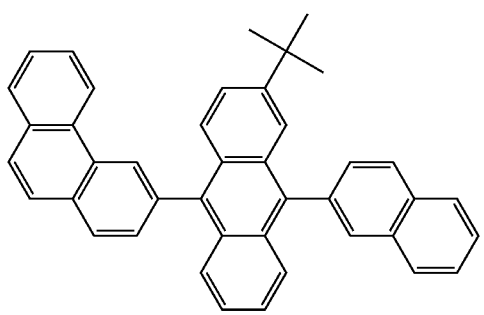
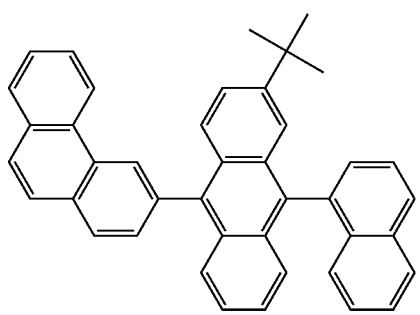
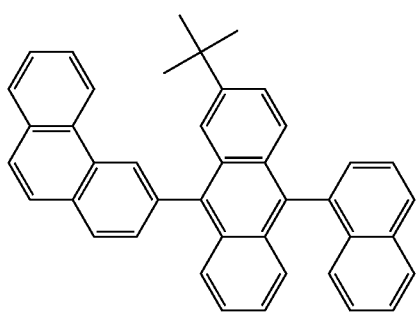
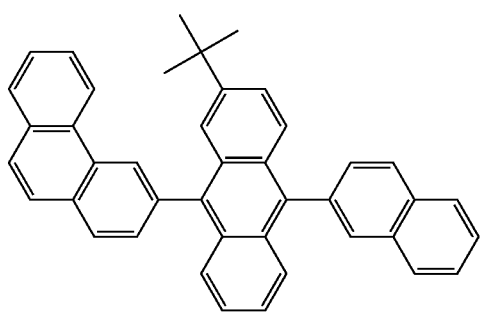
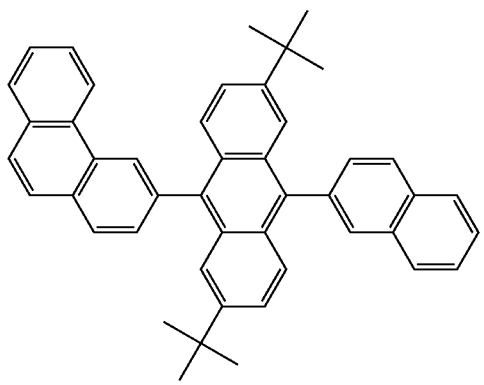
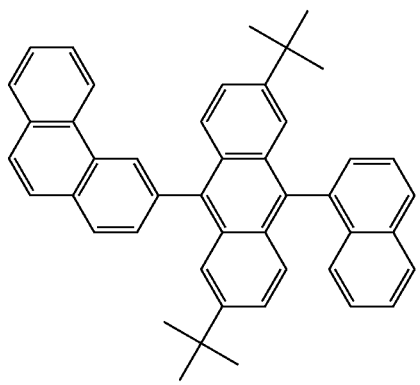

[Chem. 27]
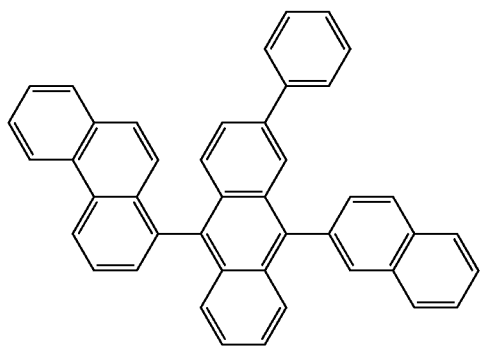
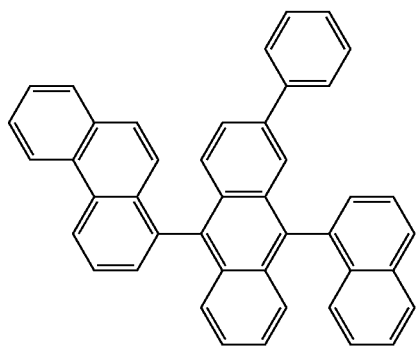
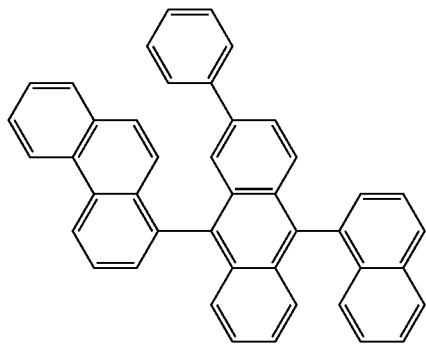
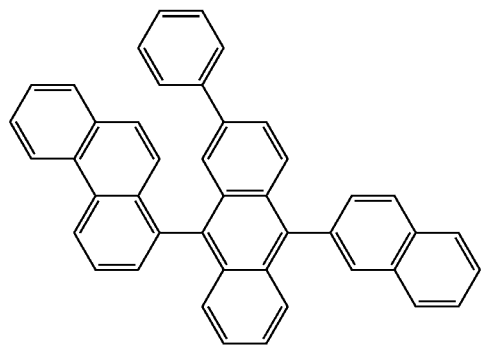
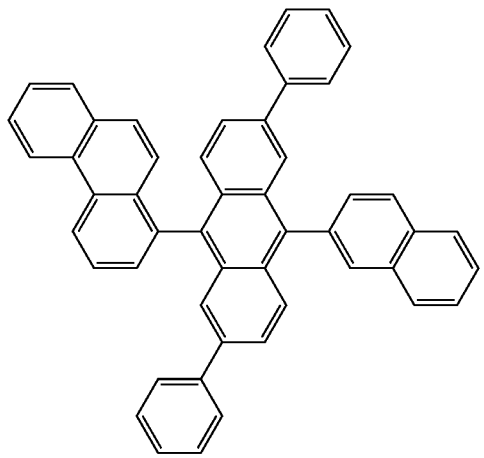
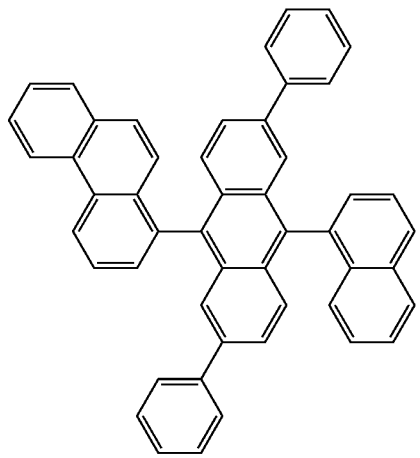
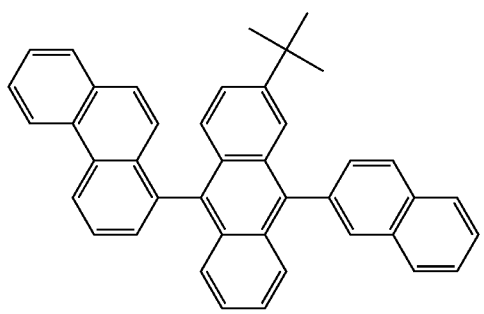
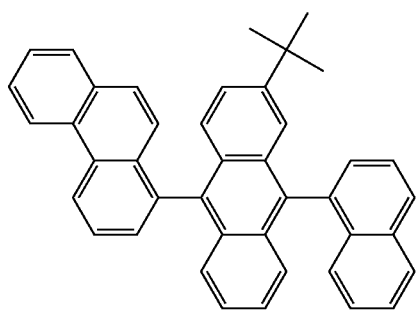

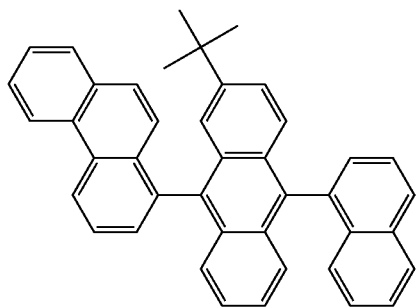
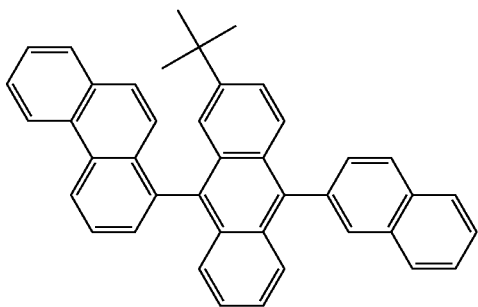
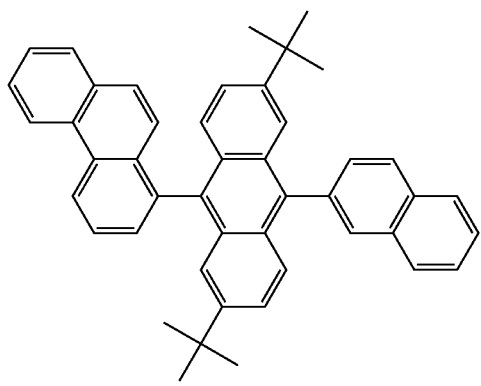
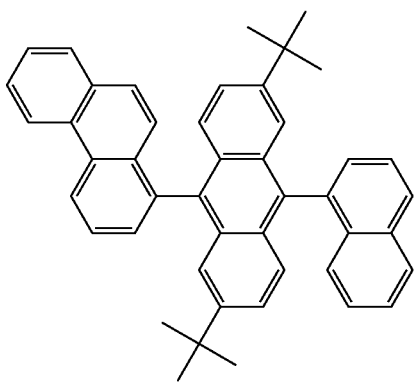
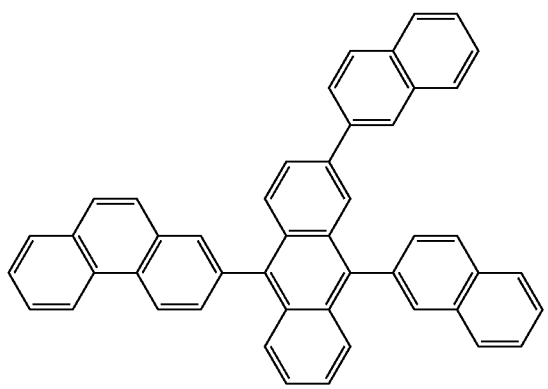
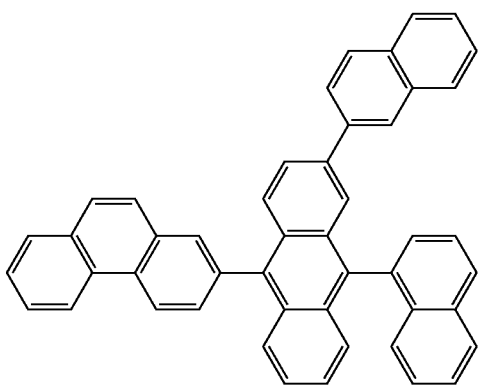
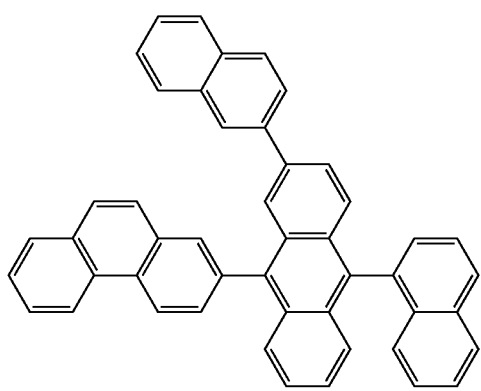
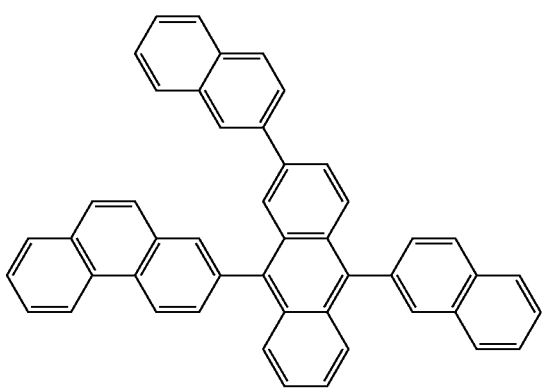

-continued
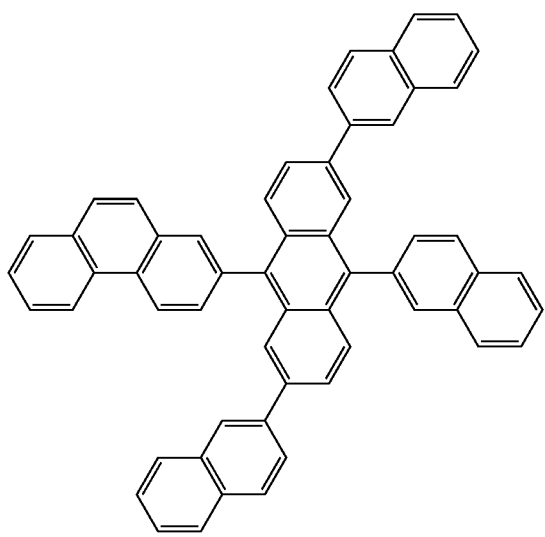 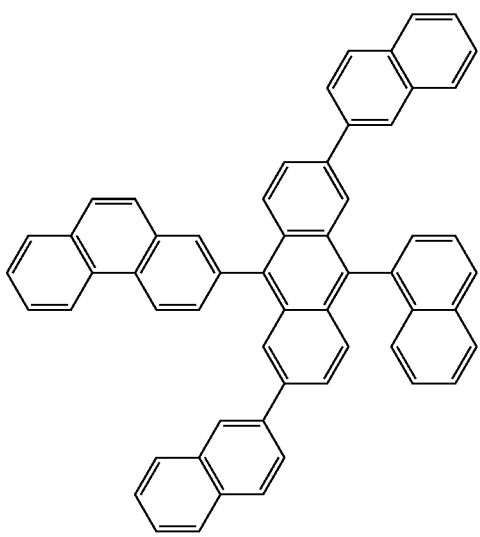
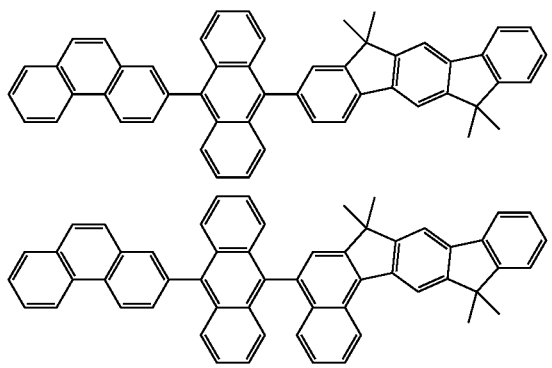 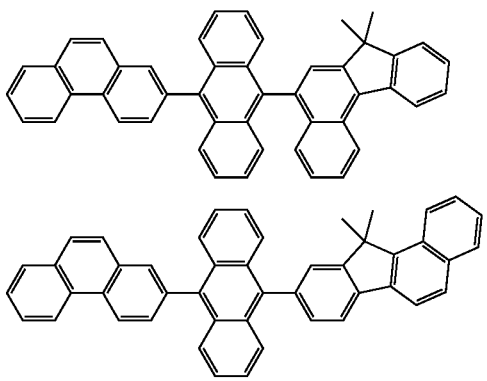
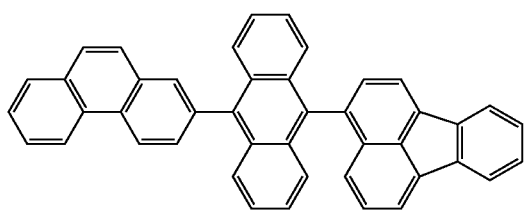 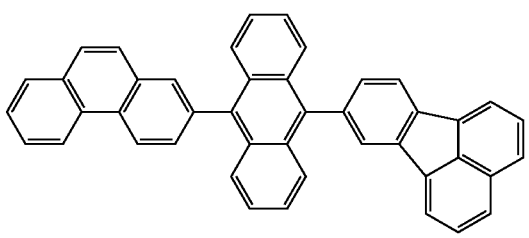
[Chem. 28]
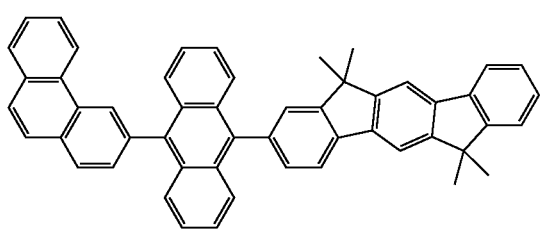 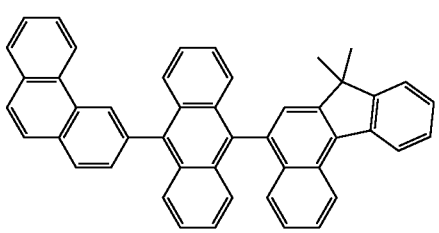
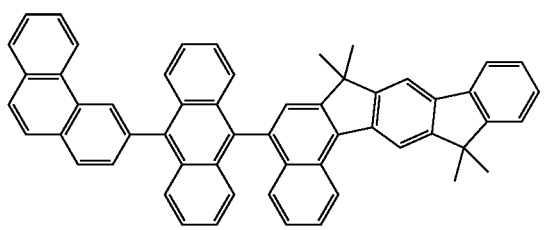 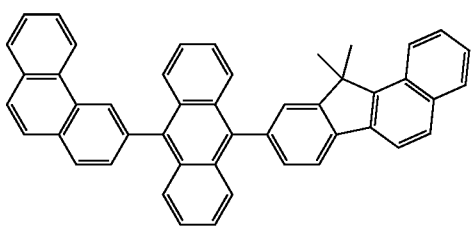

-continued
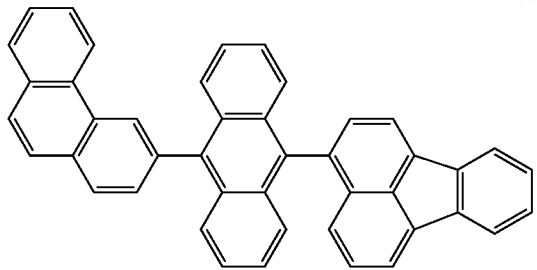

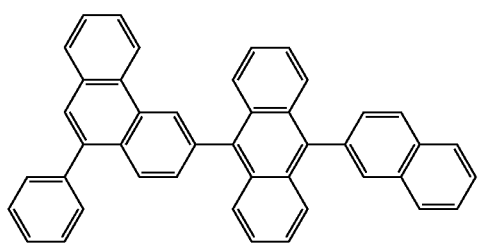
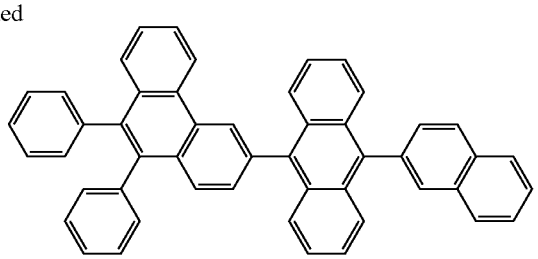
-continued
Representative examples of the anthracene derivative of the present invention represented by the general formula (1-1) when Ar¹ is represented by the general formula (2) are given below. However, the present invention is not limited to the representative examples.
[Chem. 29]
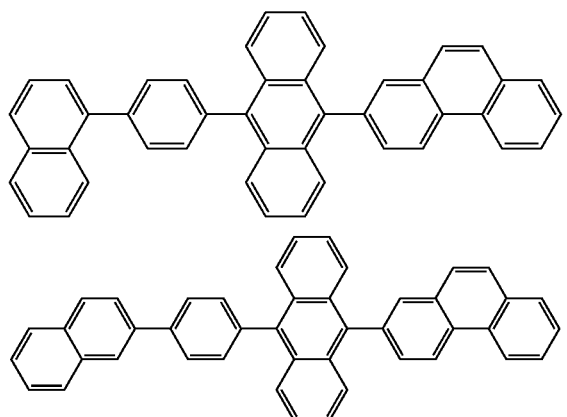
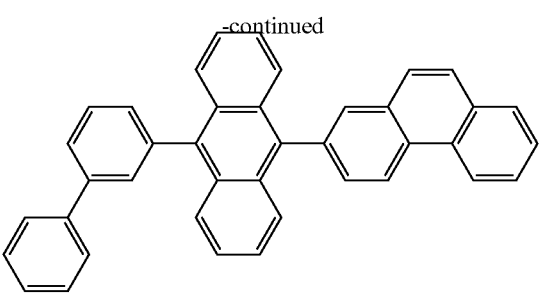
[Chem. 30]
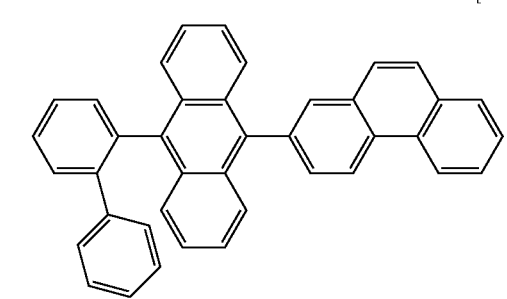
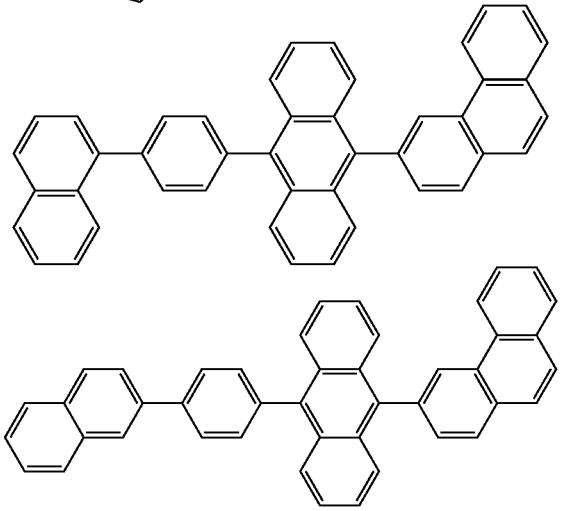
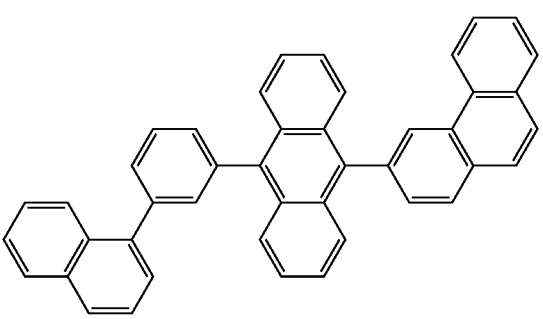

103
-continued
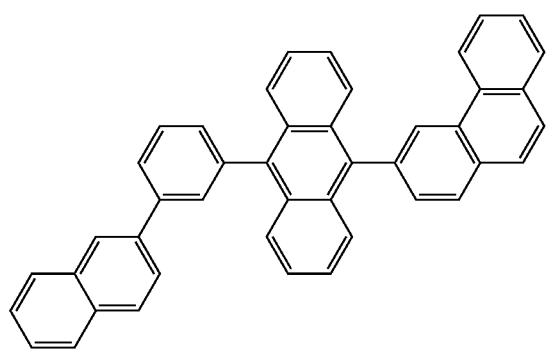
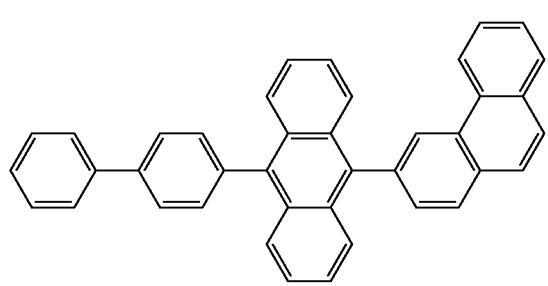
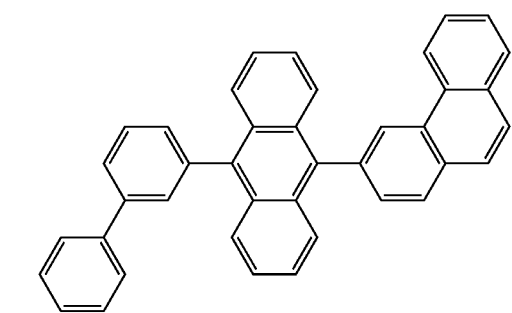
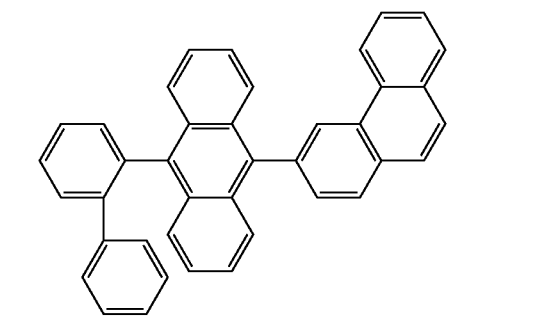
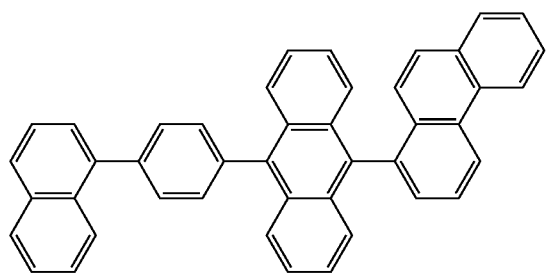
104
-continued
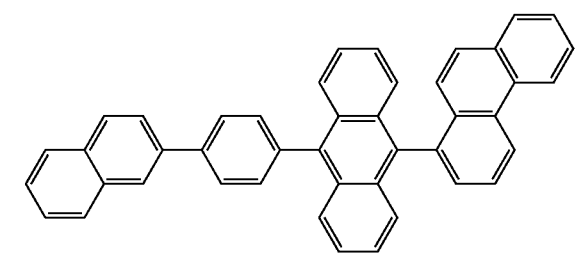
[Chem. 31]
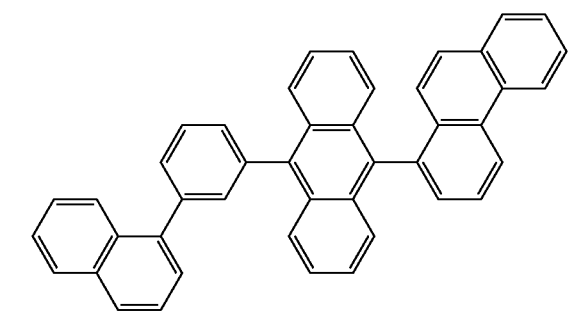
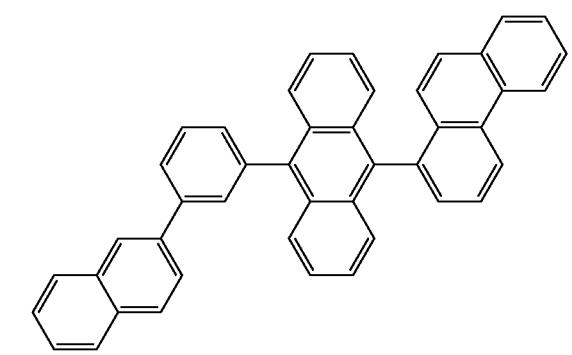
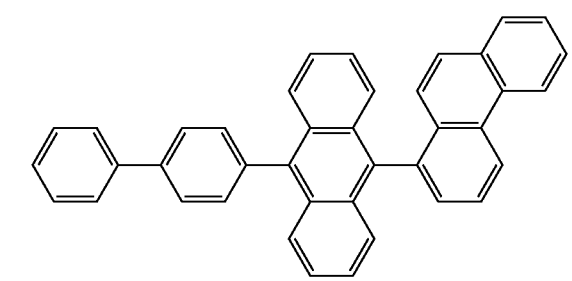
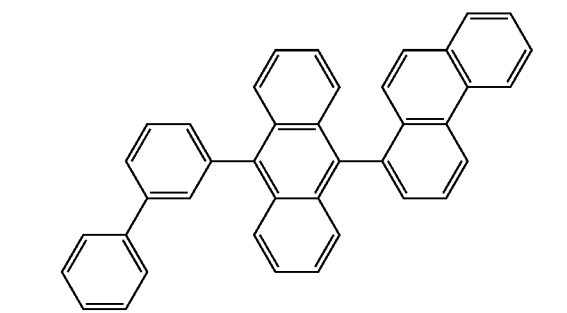

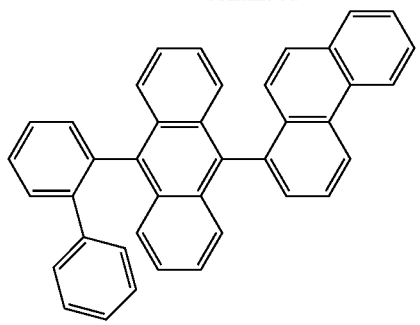
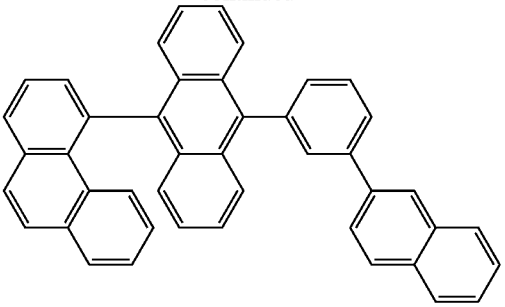
[Chem. 32]
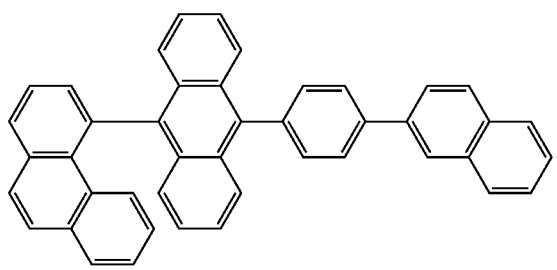
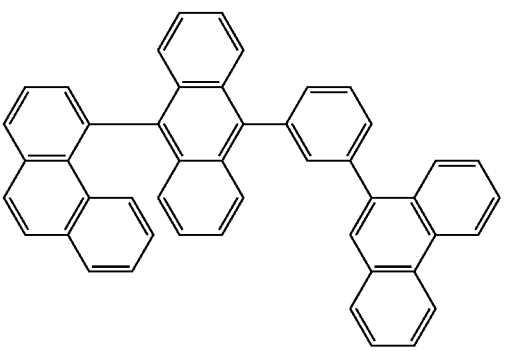
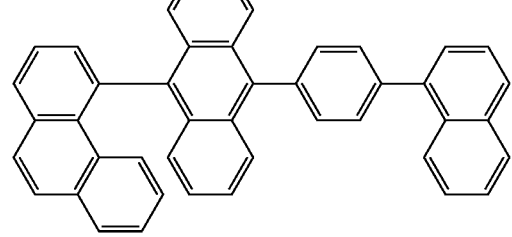
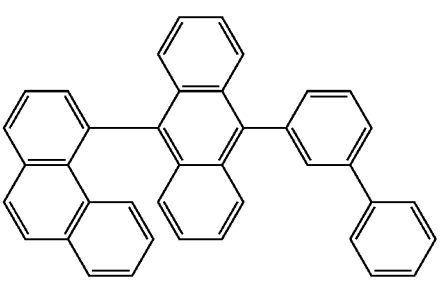
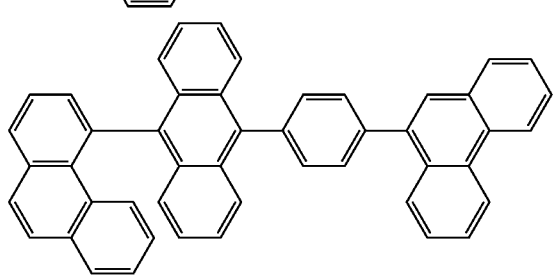
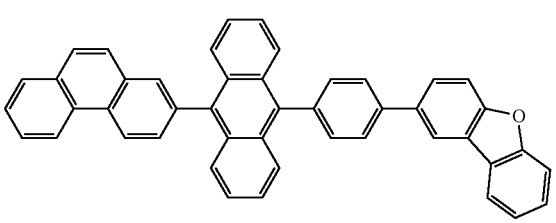
[Chem. 33]
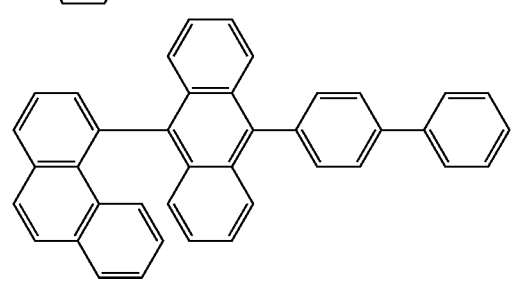
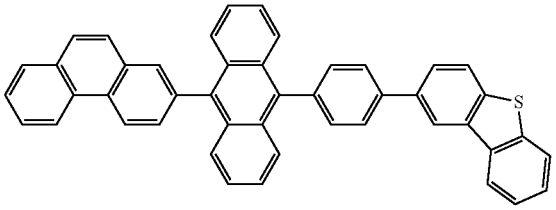
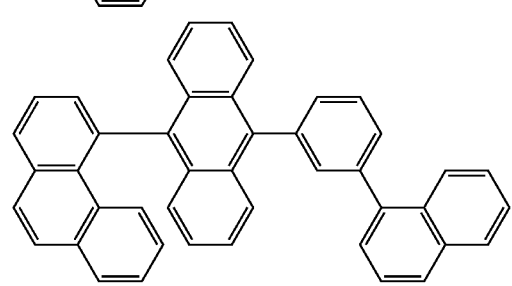
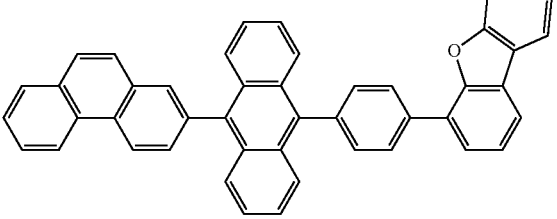

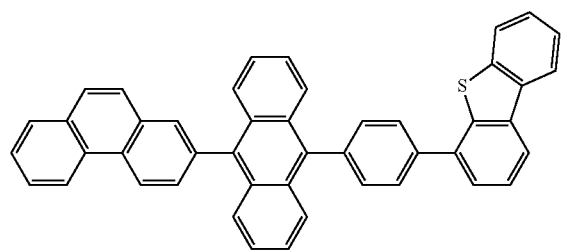
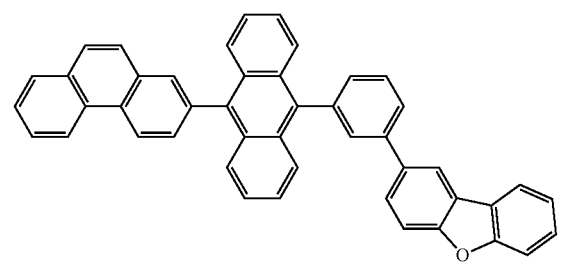
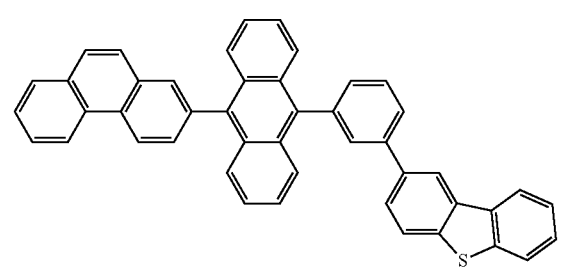
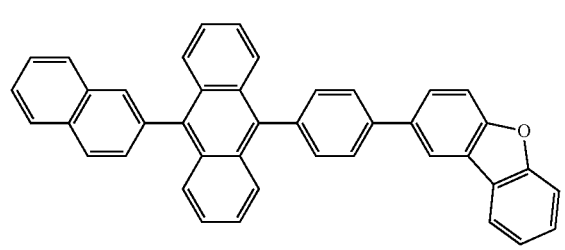
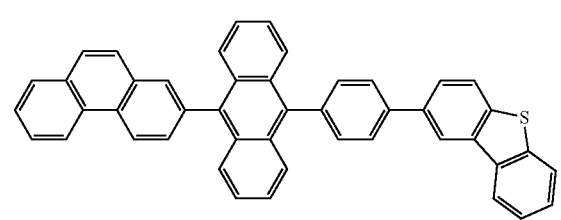
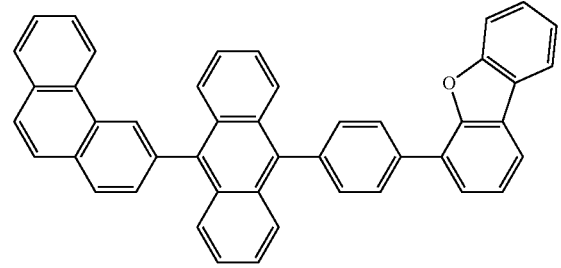
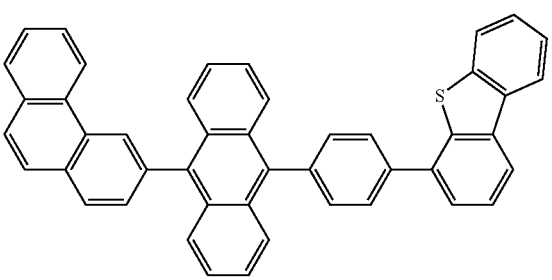
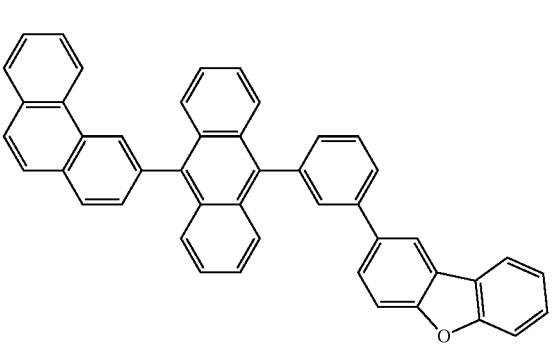
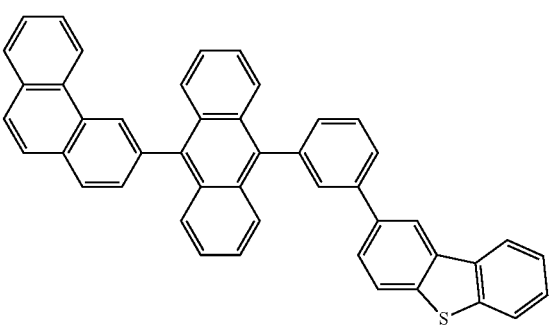
[Chem. 34]
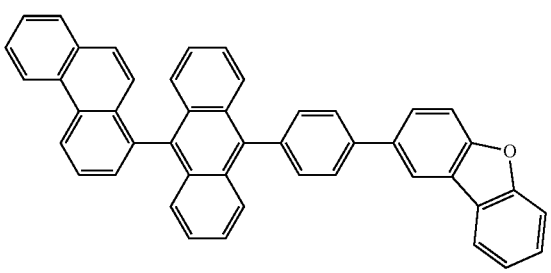
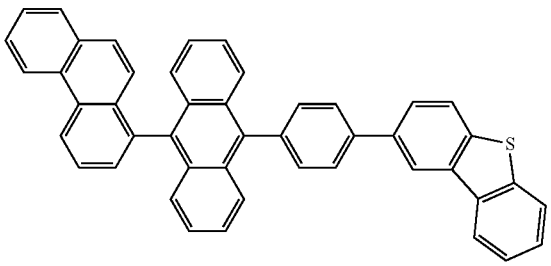

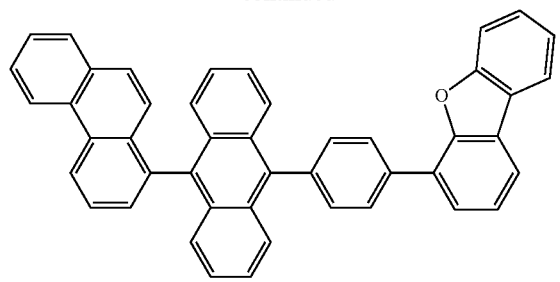
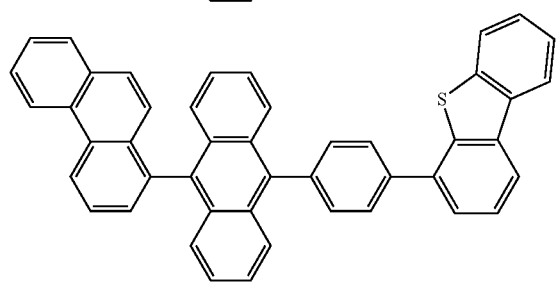
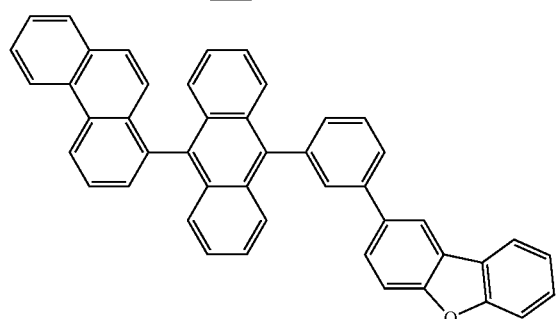
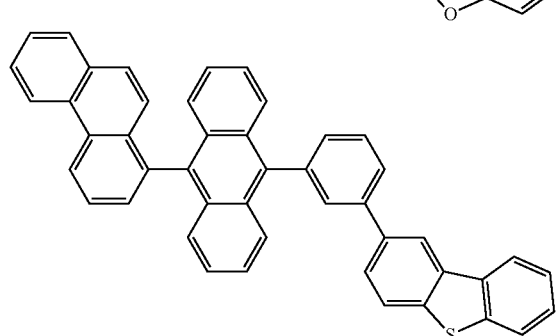
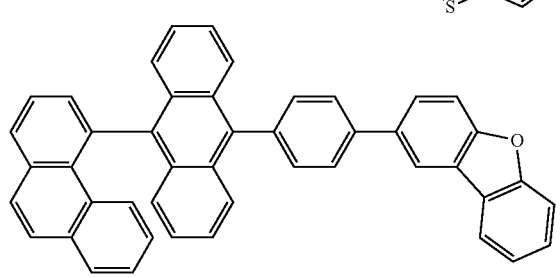
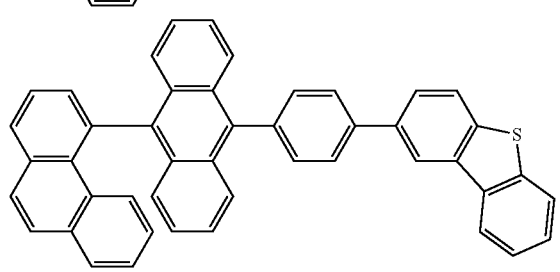
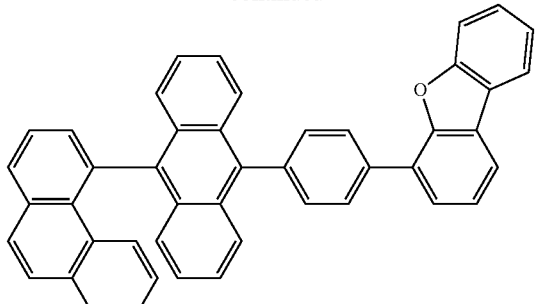
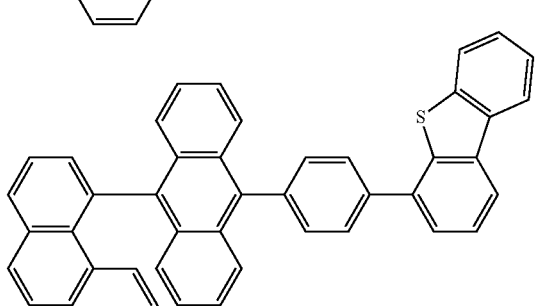
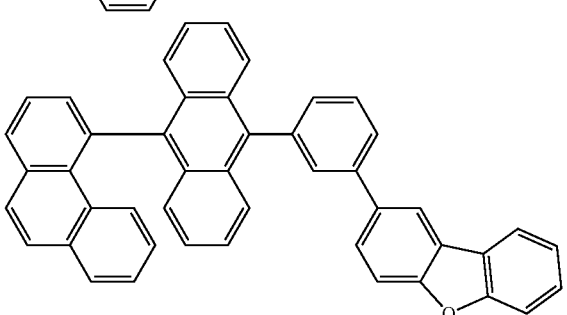
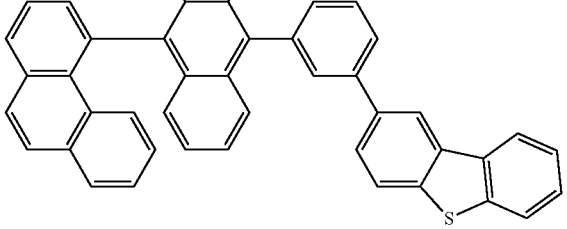
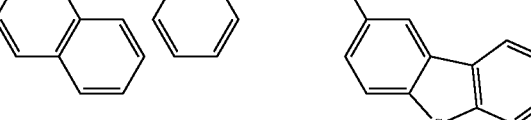
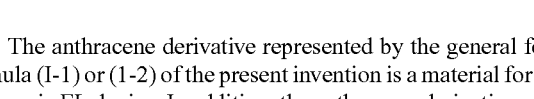
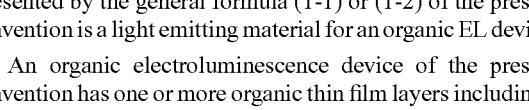
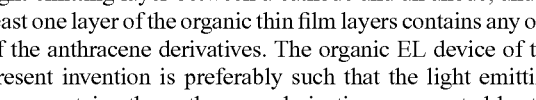
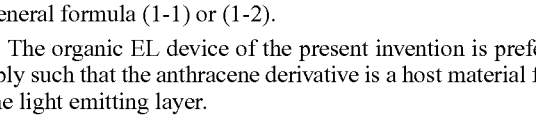

The anthracene derivative represented by the general formula (1-1) or (1-2) of the present invention is a material for an organic EL device. In addition, the anthracene derivative represented by the general formula (1-1) or (1-2) of the present invention is a light emitting material for an organic EL device.

An organic electroluminescence device of the present invention has one or more organic thin film layers including a light emitting layer between a cathode and an anode, and at least one layer of the organic thin film layers contains any one of the anthracene derivatives. The organic EL device of the present invention is preferably such that the light emitting layer contains the anthracene derivative represented by the general formula (1-1) or (1-2).

The organic EL device of the present invention is preferably such that the anthracene derivative is a host material for the light emitting layer.

The anthracene derivative having a phenanthryl group of the present invention described above is utilized mainly in an organic EL device, or specifically as a light emitting material in the organic EL device.

Hereinafter, the constitution of the organic EL device of the present invention is described.

Typical examples of the device structure of the organic EL device of the present invention include the following:
(1) an anode/light emitting layer/cathode;
(2) an anode/hole injecting layer/light emitting layer/cathode;
(3) an anode/light emitting layer/electron injecting layer/cathode;
(4) an anode/hole injecting layer/light emitting layer/electron injecting layer/cathode;
(5) an anode/organic semiconductor layer/light emitting layer/cathode;
(6) an anode/organic semiconductor layer/electron blocking layer/light emitting layer/cathode;
(7) an anode/organic semiconductor layer/light emitting layer/adhesion improving layer/cathode;
(8) an anode/hole injecting layer/hole transporting layer/light emitting layer/electron injecting layer/cathode;
(9) an anode/insulating layer/light emitting layer/insulating layer/cathode;
(10) an anode/inorganic semiconductor layer/insulating layer/light emitting layer/insulating layer/cathode;
(11) an anode/organic semiconductor layer/insulating layer/light emitting layer/insulating layer/cathode;
(12) an anode/insulating layer/hole injecting layer/hole transporting layer/light emitting layer/insulating layer/cathode; and
(13) an anode/insulating layer/hole injecting layer/hole transporting layer/light emitting layer/electron injecting layer/cathode.

Of those, the structure (8) is preferably used in ordinary cases. However, the structure is not limited to the foregoing.

In addition, in the organic EL device of the present invention, the anthracene derivative having a phenanthryl group of the present invention represented by the general formula (1-1) or the general formula (1-2) may be used in any one of the above-mentioned organic layers. However, the derivative is incorporated into preferably a light emitting zone in the structural elements, or into particularly preferably the light emitting layer. The content at which the derivative is incorporated is selected from the range of 30 to 100 mol %.

The organic EL device is generally prepared on a light-transmissive substrate. The light-transmissive substrate is the substrate which supports the organic EL device. As for the light transmittance, the light-transmissive substrate desirably has a transmittance of light of 50% or more in the visible light region where the wavelength is 400 to 700 nm. Further, the light-transmissive substrate is preferably flat and smooth. As the light-transmissive substrate, for example, a glass plate or a synthetic resin plate is suitably used. Examples of the glass plate include plates formed of, in particular, soda-lime glass, glass containing barium and strontium, lead glass, alumino-silicate glass, borosilicate glass, barium borosilicate glass, and quartz. In addition, examples of the synthetic resin plate include plates formed of a polycarbonate resin, an acrylic resin, a polyethylene terephthalate resin, a polyether sulfide resin, and a polysulfone resin.

Subsequently, the anode bears the role of injecting a hole to the hole transporting layer or the light emitting layer. It is effective that the anode has a work function of 4.5 eV or more. Specific examples of a material for the anode used in the present invention include indium tin oxide (ITO), a mixture of indium oxide and zinc oxide, a mixture of ITO and cerium oxide (ITCO), a mixture of the mixture of indium oxide and zinc oxide and cerium oxide (IZCO), a mixture of indium oxide and cerium oxide (ICO), a mixture of zinc oxide and aluminum oxide (AZO), tin oxide (NESA), gold, silver, platinum, and copper.

The anode may be produced by forming a thin film with one of the above-mentioned materials for electrodes by, for example, a vapor deposition method or a sputtering method. When the light emitted from the light emitting layer is obtained through the anode as described above, it is preferred that the anode have a transmittance of more than 10% with respect to the emitted light. It is also preferred that the sheet resistance of the anode be several hundred Q/O or less. The thickness of the anode is, in general, selected in the range of 10 nm to 1 μm or preferably in the range of 10 to 200 nm although the preferred range may be different depending on the used material.

In the organic EL device of the present invention, the light emitting layer has the following functions.
(i) The injecting function: the function of injecting holes from the anode or the hole injecting layer and injecting electrons from the cathode or the electron injecting layer when an electric field is applied.
(ii) The transporting function: the function of transporting injected charges (i.e., electrons and holes) by the force of the electric field.
(iii) The light emitting function: the function of providing the field for recombination of electrons and holes and leading the recombination to the emission of light.

For example, a known method such as a vapor deposition method, a spin coating method, or an LB method is applicable to the formation of the light emitting layer. The light emitting layer is particularly preferably a molecular deposit film. The term "molecular deposit film" as used herein refers to a thin film formed by the deposition of a material compound in a vapor phase state, or a film formed by the solidification of a material compound in a solution state or a liquid phase state. The molecular deposit film can be typically distinguished from a thin film formed by the LB method (molecular accumulation film) on the basis of differences between the films in aggregation structure and higher order structure, and functional differences between the films caused by the foregoing differences. In addition, as disclosed in JP 57-51781 A, the light emitting layer can also be formed by preparing a solution of a binder such as a resin and a material compound dissolved in a solvent, and then forming the solution into a thin film by the spin coating method or the like. In the present invention, any known metal complex compound other than light emitting materials formed of pyrene-based derivatives and amine compounds may be incorporated into the light emitting layer as desired to such an extent that the object of the present invention is not impaired. In addition, a light emitting layer containing any other known metal complex compound may be laminated on the light emitting layer containing the compound according to the present invention.

The metal complex compound is preferably a metal complex compound containing at least one metal selected from Ir, Ru, Pd, Pt, Os, and Re, and its ligands preferably have at least one skeleton selected from a phenylpyridine skeleton, a bipyridyl skeleton, and a phenanthroline skeleton. Specific examples of such metal complex include, but not limited to, tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethyl platinum porphyrin, octaphenyl platinum porphyrin, octaethyl palladium porphyrin, and octaphenyl palladium porphyrin. An appropriate complex is selected depending on a requested luminescent color, device performance, and a relationship with a host compound.

The phosphorescent dopant is a compound capable of emitting light from a triplet exciton. The dopant, which is not particularly limited as long as light is emitted from a triplet exciton, is preferably a metal complex containing at least one metal selected from the group consisting of Ir, Ru, Pd, Pt, Os, and Re, and is preferably a porphyrin metal complex or an orthometalated metal complex. A porphyrin platinum complex is preferred as the porphyrin metal complex. One kind of a phosphorescent compound may be used alone, or two or more kinds of phosphorescent compounds may be used in combination.

There are various ligands which can be used for forming an orthometalated metal complex. Preferred examples of the ligands include 2-phenylpyridine derivatives, 7,8-benzoquinoline derivatives, 2-(2-thienyl)pyridine derivatives, 2-(1-naphthyl)pyridine derivatives, and 2-phenylquinoline derivatives. Each of those derivatives may have a substituent as required. A metal complex having a ligand into which a fluorine atom or a trifluoromethyl group is introduced is particularly preferred as a blue-based dopant. The metal complex may further include a ligand other than the above-mentioned ligands such as acetylacetonato or picric acid as an auxiliary ligand.

The content of the phosphorescent dopant in the light emitting layer is not particularly limited, and can be appropriately selected in accordance with the purpose. The content is, for example, 0.1 to 70 mass %, or preferably 1 to 30 mass %. When the content of the phosphorescent compound is less than 0.1 mass %, the intensity of emitted light is weak, and an effect of the incorporation of the compound is not sufficiently exerted. When the content exceeds 70 mass %, a phenomenon called concentration quenching becomes remarkable, and device performance reduces.

In addition, the light emitting layer may contain a hole transporting material, an electron transporting material, or a polymer binder as required.

Further, the thickness of the light emitting layer is preferably 5 to 50 nm, more preferably 7 to 50 nm, or most preferably 10 to 50 nm. When the thickness is less than 5 nm, it becomes difficult to form the light emitting layer, so the adjustment of chromaticity may be difficult. When the thickness exceeds 50 nm, the driving voltage may increase.

The fluorescent dopant is preferably a compound selected from, for example, an amine-based compound, an aromatic compound, a chelate complex such as a tris(8-quinolinolato) aluminum complex, a coumarin derivative, a tetraphenylbutadiene derivative, a bisstyrylarylene derivative, and an oxadiazole derivative in accordance with a requested luminescent color. An arylamine compound and an aryldiamine compound are particularly preferred examples of such compound. Of those, a styrylamine compound, a styryldiamine compound, an aromatic amine compound, or an aromatic diamine compound is more preferred, and a fused polycyclic amine derivative is still more preferred. One kind of those fluorescent dopants may be used alone, or two or more kinds thereof may be used in combination. Such fused polycyclic amine derivative is preferably any one of those represented by the following general formulae (5) and (6).

[Chem. 35]

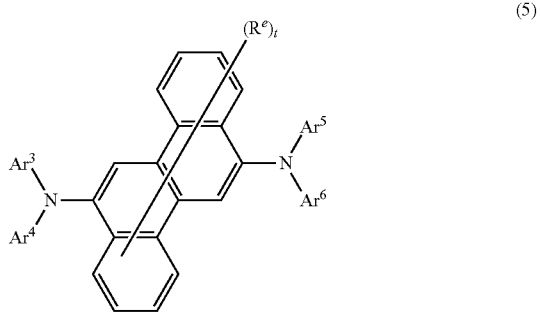

(5)

[Chem. 36]

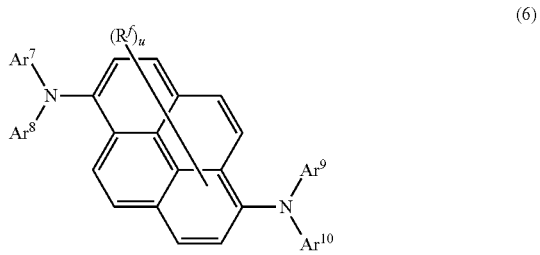

(6)

In the general formulae (5) and (6):

substituents $R^e$ and $R^f$ each represent a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 ring forming carbon atoms, a substituted or unsubstituted alkoxy group having 1 to 20 carbon atoms, a substituted or unsubstituted aryloxy group having 6 to 20 ring forming carbon atoms, a substituted or unsubstituted aryl group having 6 to 50 ring forming carbon atoms, a substituted or unsubstituted alkylsilyl group having 1 to 30 carbon atoms, a substituted or unsubstituted arylsilyl group having 6 to 50 ring forming carbon atoms, a substituted or unsubstituted alkylgermanium group having 1 to 50 carbon atoms, or a substituted or unsubstituted arylgermanium group having 6 to 50 ring forming carbon atoms;

"t" represents an integer of 0 to 10;

"u" represents an integer of 0 to 8; and $Ar^3$ to $Ar^6$ and $Ar^7$ to $Ar^{10}$ each represent a substituted or unsubstituted aryl group having 6 to 20 ring forming carbon atoms, or a substituted or unsubstituted heteroaryl group having 5 to 20 ring forming atoms. Specific examples of the substituents $R^e$ and $R^f$ in the general formulae (5) and (6) are the same as the specific examples of the substituents $R^a$ and $R^b$, and specific examples of $Ar^3$ to $Ar^6$ and $Ar^7$ to $Ar^{10}$ in the formulae are the same as the specific examples of $Ar^1$.

The styrylamine compound and the styryldiamine compound are preferably those represented by the following general formulae (7) and (8).

[Chem. 37]

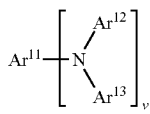
(7)

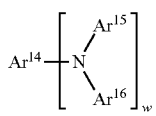
(8)

In the general formula (7), $Ar^{11}$ represents a group selected from a phenyl group, a naphthyl group, a biphenyl group, a terphenyl group, a stilbene group, and a distyrylaryl group, $Ar^{12}$ and $Ar^{13}$ each represent an aromatic hydrocarbon group having 6 to 20 ring forming carbon atoms, and $Ar^{11}$, $Ar^{12}$, and $Ar^{13}$ may each be substituted, "v" represents an integer of 1 to 4, or "v" preferably represents an integer of 1 or 2, one of $Ar^{11}$ to $Ar^{13}$ preferably represents a group containing a styryl group, and at least one of $Ar^{12}$ and $Ar^{13}$ is more preferably substituted with a styryl group.

Herein, examples of the aromatic hydrocarbon group having 6 to 20 ring forming carbon atoms include a phenyl group, a naphthyl group, an anthranyl group, a phenanthryl group, and a terphenyl group. In the general formula (8), $Ar^{14}$ to $Ar^{16}$ each represent a substituted or unsubstituted aromatic group having 6 to 40 ring forming carbon atoms, and "w" represents an integer of 1 to 4, or "w" preferably represents an integer of 1 or 2.

Herein, examples of the aromatic group having 6 to 40 ring forming carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzoanthracenyl group, a phenylanthranyl group, a bisanthracenyl group, and an aromatic group represented by the following general formulae (9) or (10). Preferred are a naphthyl group, an anthranyl group, a chrysenyl group, a pyrenyl group, and an aromatic represented by the general formula (10).

[Chem. 38]

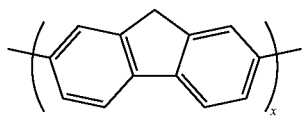
(9)

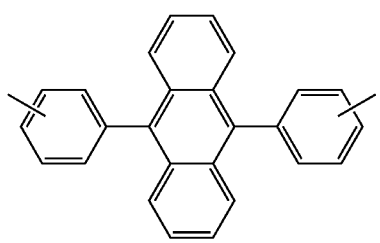
(10)

In the above-mentioned general formula (9), "x" represents an integer of 1 to 3.

It should be noted that examples of the substituent which preferably substitutes the aromatic group include alkyl groups each having 1 to 6 carbon atoms (such as an ethyl group, a methyl group, an i-propyl group, an n-propyl group, an s-butyl group, a t-butyl group, a pentyl group, a hexyl group, a cyclopentyl group, and a cyclohexyl group), alkoxy groups each having 1 to 6 carbon atoms (such as an ethoxy group, a methoxy group, an i-propoxy group, an n-propoxy group, an s-butoxy group, a t-butoxy group, a pentoxy group, a hexyloxy group, a cyclopentoxy group, and a cyclohexyloxy group), aromatic groups each having 5 to 40 ring forming carbon atoms, amino groups each substituted by an aromatic group having 5 to 40 ring forming carbon atoms, ester groups each containing an aromatic group having 5 to 40 ring forming carbon atoms, ester groups each containing an alkyl group having 1 to 6 carbon atoms, a cyano group, a nitro group, and halogen atoms.

Subsequently, the hole injecting/transporting layer is a layer which: aids the injection of a hole into the light emitting layer; and transports the hole to a light emitting region. The hole injecting/transporting layer has a large hole mobility, and its ionization energy is typically as small as 5.5 eV or less. Such hole injecting/transporting layer is preferably formed of a material that transports a hole to the light emitting layer at an additionally low electric field intensity. Further, the hole mobility is preferably at least $10^{-4}$ cm$^2$/V-sec at the time of the application of, for example, an electric field of $10^4$ to $10^6$ V/cm.

A material of which the hole injecting/transporting layer is formed is not particularly limited as long as the material has the preferred nature. An arbitrary material selected from those conventionally used as hole charge transporting materials in photoconductive materials and known materials used in the hole injecting layers of organic EL devices can be used. Potential examples of the aromatic amine derivative include compounds represented by the following general formulae (11) to (15).

[Chem. 39]

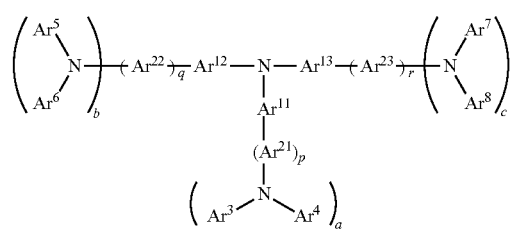
(11)

In the general formula (11), $Ar^{11}$ to $Ar^{13}$, $Ar^{21}$ to $Ar^{23}$, and $Ar^3$ to $Ar^8$ each represent a substituted or unsubstituted aromatic hydrocarbon group having 6 to 50 ring forming carbon atoms, or a substituted or unsubstituted aromatic heterocyclic group having 5 to 50 ring forming atoms, "a" to "c" and "p" to "r" each represent an integer of 0 to 3, and $Ar^3$ and $Ar^4$, $Ar^5$ and $Ar^6$, or $Ar^7$ and $Ar^8$ may be linked to each other to form a saturated or unsaturated ring. Specific examples of the substituted or unsubstituted aromatic hydrocarbon group having 6 to 50 ring forming carbon atoms, and the substituted or unsubstituted aromatic heterocyclic group having 5 to 50 ring forming atoms include the same groups as those given above.

[Chem. 40]

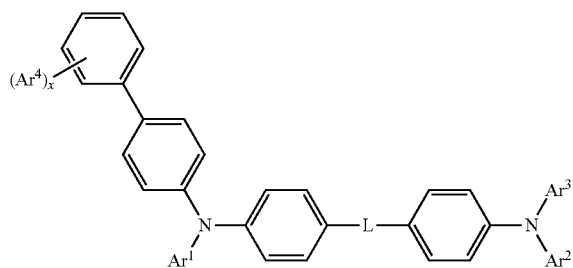

(12)

Ar¹ to Ar⁴ in the general formula (12) each represent a substituted or unsubstituted aromatic hydrocarbon group having 6 to 50 ring forming carbon atoms, or an aromatic heterocyclic group having 5 to 50 ring forming atoms. L represents a linking group, and represents a single bond, a substituted or unsubstituted aromatic hydrocarbon group having 6 to 50 ring forming carbon atoms, or an aromatic heterocyclic group having 5 to 50 ring forming atoms. "x" represents an integer of 0 to 5. Ar² and Ar³ may be linked to each other to form a saturated or unsaturated ring. Herein, specific examples of the aromatic hydrocarbon group having 6 to 50 ring forming carbon atoms and the aromatic heterocyclic group having 5 to 50 ring forming atoms include the same examples as those described above.

Specific examples of the compounds include: triazole derivatives (see, for example, U.S. Pat. No. 3,112,197); oxadiazole derivatives (see, for example, U.S. Pat. No. 3,189,447); imidazole derivatives (see, for example, JP-B-37-16096); polyarylalkane derivatives (see, for example, U.S. Pat. No. 3,615,402, U.S. Pat. No. 3,820,989, U.S. Pat. No. 3,542,544, JP-B-45-555, JP-B-51-10983, JP-A-51-93224, JP-A-55-17105, JP-A-56-4148, JP-A-55-108667, JP-A-55-156953, and JP-A-56-36656); pyrazoline derivatives and pyrazolone derivatives (see, for example, U.S. Pat. No. 3,180,729, U.S. Pat. No. 4,278,746, JP-A-55-88064, JP-A-55-88065, JP-A-49-105537, JP-A-55-51086, JP-A-56-80051, JP-A-56-88141, JP-A-57-45545, JP-A-54-112637, and JP-A-55-74546); phenylenediamine derivatives (see, for example, U.S. Pat. No. 3,615,404, JP-B-51-10105, JP-B-46-3712, JP-B-47-25336, and JP-A-54-119925); arylamine derivatives (see, for example, U.S. Pat. No. 3,567,450, U.S. Pat. No. 3,240,597, U.S. Pat. No. 3,658,520,U.S. Pat. No. 4,232,103,U.S. Pat. No. 4,175,961,U.S. Pat. No. 4,012,376, JP-B-49-35702, JP-B-39-27577, JP-A-55-144250, JP-A-56-119132, JP-A-56-22437, and DE 1,110,518); amino-substituted chalcone derivatives (see, for example, U.S. Pat. No. 3,526,501); oxazole derivatives (those disclosed in, for example, U.S. Pat. No. 3,257,203); styrylanthracene derivatives (see, for example, JP-A-56-46234); fluorenone derivatives (see, for example, JP-A-54-110837); hydrazone derivatives (see, for example, U.S. Pat. No. 3,717,462, JP-A-54-59143, JP-A-55-52063, JP-A-55-52064, JP-A-55-46760, JP-A-57-11350, JP-A-57-148749, and JP-A-02-311591); stilbene derivatives (see, for example, JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749, and JP-A-60-175052); silazane derivatives (U.S. Pat. No. 4,950, 950); polysilane-based copolymers (JP-A-02-204996); aniline-based copolymers (JP-A-02-282263); and conductive high molecular oligomers (in particular, thiophene oligomer).

As a material for the hole injecting layer, the materials described above can be used. However, porphyrin compounds (those disclosed in, for example, JP-A-63-295695), and aromatic tertiary amine compounds and styrylamine compounds (see, for example, U.S. Pat. No. 4,127,412, JP-A-53-27033, JP-A-54-58445, JP-A-55-79450, JP-A-55-144250, JP-A-56-119132, JP-A-61-295558, JP-A-61-98353, and JP-A-63-295695) are preferably used. The aromatic tertiary amine compounds are particularly preferably used.

Further examples include a compound having two fused aromatic rings in the molecule, such as 4,4'-bis(N-(1-naphthyl)-N-phenylamino)biphenyl (hereinafter abbreviated as NPD), as disclosed in U.S. Pat. No. 5,061,569, and a compound in which three triphenylamine units are bonded together in a star-burst shape, such as 4,4',4"-tris(N-(3-methylphenyl)-N-phenylamino)triphenylamine (hereinafter abbreviated as MTDATA), as disclosed in JP-A-04-308688. In addition to the compounds described above, a nitrogen-containing heterocyclic derivative represented by the following general formula (13), as disclosed in JP-B-3571977, can also be used.

[Chem. 41]

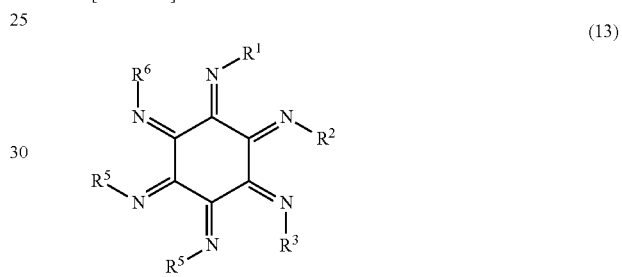

(13)

$R^1$, $R^2$, $R^3$, $R^4$, $R^5$, and $R^6$ in the general formula (13) each represent a substituted or unsubstituted alkyl group, a substituted or unsubstituted aromatic group, a substituted or unsubstituted aralkyl group, or a substituted or unsubstituted heterocyclic group, provided that $R^1$, $R^2$, $R^3$, $R^4$, $R^5$, and $R^6$ may be identical to or different from each other. $R^1$ and $R^2$, $R^3$ and $R^4$, and $R^5$ and $R^6$, or $R^1$ and $R^6$, $R^2$ and $R^3$, and $R^4$ and $R^5$ may each form a fused ring.

In addition, a compound represented by the following general formula (14), as described in US 2004-0113547, can also be used.

[Chem. 42]

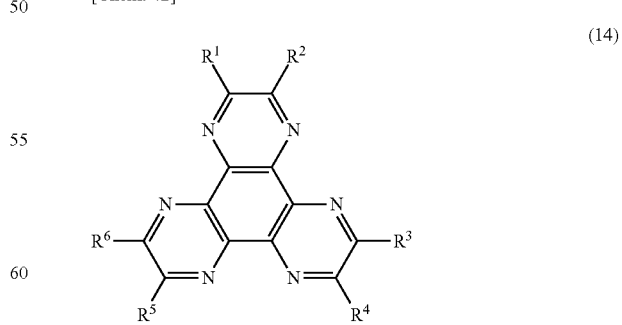

(14)

$R^1$ to $R^6$ in the general formula (14) each represent a substituent, or preferably an electrophilic group such as a cyano group, a nitro group, a sulfonyl group, a carbonyl group, a trifluoromethyl group, or a halogen.

An inorganic compound such as p-type Si or p-type SiC can also be used as a material for the hole injecting layer.

The hole injecting layer and the hole transporting layer can each be formed by forming a thin layer from the compounds described above in accordance with a known method such as a vacuum vapor deposition method, a spin coating method, a casting method, or an LB method. The thickness of each of the hole injecting layer and the hole transporting layer is not particularly limited. In general, the thickness is 5 nm to 5 μm. The hole injecting layer and the hole transporting layer may be formed of a single layer containing one kind of or two or more kinds of the materials described above, or may be a laminate as long as the materials are incorporated in the hole transporting zone.

Further, an organic semiconductor layer is a layer for helping the injection of holes and electrons into the light emitting layer. As the organic semiconductor layer, a layer having a conductivity of $10^{-10}$ S/cm or more is suitable. As the material for the organic semiconductor layer, the following can be used: an oligomer containing thiophene; and conductive oligomers such as an oligomer containing an arylamine and conductive dendrimers such as a dendrimer containing an arylamine, which are disclosed in JP-A-08-193191.

Subsequently, the electron injecting layer and the transporting layer are layers which help injection of electrons into the light emitting layer, transport the electrons to the light emitting region, and exhibit a great mobility of electrons. In addition, the adhesion improving layer is an electron injecting layer including a material exhibiting particularly improved adhesion with the cathode. In addition, it is known that, in an organic EL device, emitted light is reflected by an electrode (cathode in this case), so emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. However, when the thickness is particularly large, an electron mobility is preferably at least $10^{-5}$ cm$^2$/Vs or more upon application of an electric field of $10^4$ to $10^6$ V/cm in order to avoid an increase in voltage. A metal complex of 8-hydroxyquinoline or of a derivative of 8-hydroxyquinoline, or an oxadiazole derivative is suitable as the material to be used for the electron injecting layer. Specific examples of the above-mentioned metal complex of 8-hydroxyquinoline or of the derivative of 8-hydroxyquinoline, which can be used as the electron injecting material, include metal chelate oxynoid compounds each containing a chelate of oxine (generally 8-quinolinol or 8-hydroxyquinoline) such as tris(8-quinolinol)aluminum.

On the other hand, examples of the oxadiazole derivative include electron transfer compounds represented by the following general formula (15).

[Chem. 43]

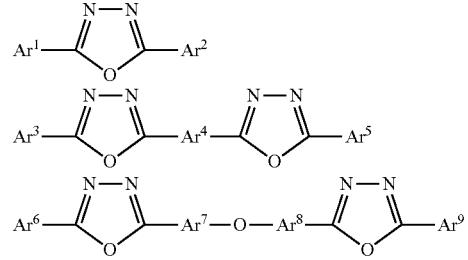

(15)

$Ar^1$, $Ar^2$, $Ar^3$, $Ar^5$, $Ar^6$ and $Ar^9$ in the general formula (15) each represent a substituted or unsubstituted aryl group and may be identical to or different from each other. Further, $Ar^4$, $Ar^7$, and $Ar^8$ each represent a substituted or unsubstituted arylene group and may be identical to or different from each other.

Herein, examples of the aryl group include a phenyl group, a biphenyl group, an anthranyl group, a perylenyl group, and a pyrenyl group. Further, examples of the arylene group include a phenylene group, a naphthylene group, a biphenylene group, an anthranylene group, a perylenylene group, and a pyrenylene group. In addition, examples of the substituent include alkyl groups each having 1 to 10 carbon atoms, alkoxy groups each having 1 to 10 carbon atoms, and a cyano group. As the electron transfer compound, compounds which can form thin films are preferred.

Specific examples of the electron transfer compounds described above include the following (16).

[Chem. 44]

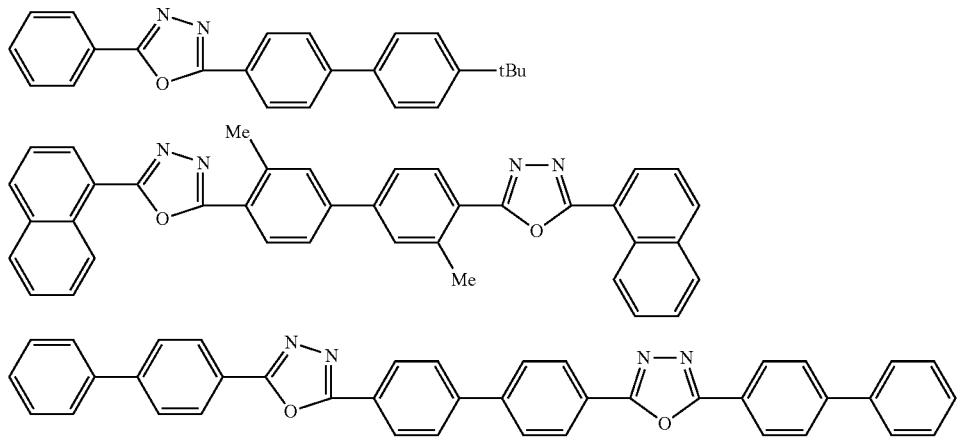

(16)

-continued

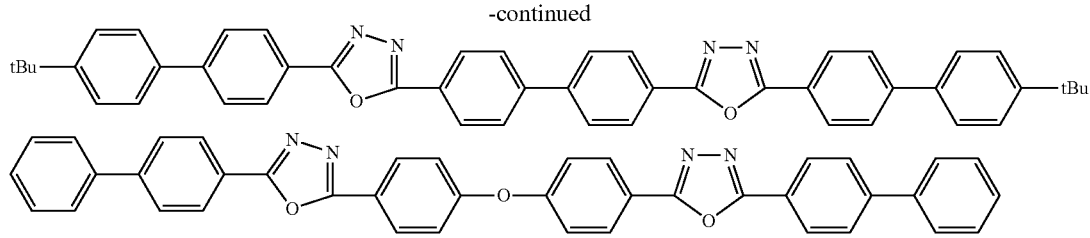

Further, materials represented by the following general formulae (17) to (20) can be used as materials used for the electron injecting layer and electron transporting layer.

[Chem. 45]

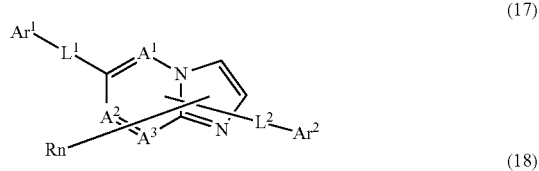

$A^1$ to $A^3$ in the general formulae (17) and (18) each independently represent a nitrogen atom or a carbon atom.

$Ar^1$ in the nitrogen-containing heterocyclic derivative represented by each of the general formulae (17) and (18) represents a substituted or unsubstituted aryl group having 6 to 60 ring forming carbon atoms, or a substituted or unsubstituted heteroaryl group having 3 to 60 ring forming atoms, $Ar^2$ represents a hydrogen atom, a substituted or unsubstituted aryl group having 6 to 60 ring forming carbon atoms, a substituted or unsubstituted heteroaryl group having 3 to 60 ring forming atoms, a substituted or unsubstituted alkyl group having 1 to 20 carbon atoms, or a substituted or unsubstituted alkoxy group having 1 to 20 carbon atoms, or a divalent group of any one of those groups, provided that one of $Ar^1$ and $Ar^2$ represents a substituted or unsubstituted fused ring group having 10 to 60 ring forming carbon atoms or a substituted or unsubstituted monohetero fused ring group having 3 to 60 ring forming carbon atoms.

$L^1$, $L^2$, and L each independently represent a single bond, a substituted or unsubstituted arylene group having 6 to 60 ring forming carbon atoms, a substituted or unsubstituted heteroarylene group having 3 to 60 ring forming carbon atoms, or a substituted or unsubstituted fluorenylene group.

R represents a hydrogen atom, a substituted or unsubstituted aryl group having 6 to 60 ring forming carbon atoms, a substituted or unsubstituted heteroaryl group having 3 to 60 ring forming atoms, a substituted or unsubstituted alkyl group having 1 to 20 carbon atoms, or a substituted or unsubstituted alkoxy group having 1 to 20 carbon atoms, and n represents an integer of 0 to 5, and, when n represents 2 or more, multiple R's may be identical to or different from each other, and multiple R groups adjacent to each other may be bonded to each other to form a carbocyclic aliphatic ring or a carbocyclic aromatic ring.

HAr-L-Ar$^1$—Ar$^2$ (19)

HAr in the nitrogen-containing heterocyclic derivative represented by the general formula (19) represents a nitrogen-containing heterocyclic ring which has 3 to 40 ring forming atoms and may have a substituent, L represents a single bond, an arylene group which has 6 to 60 ring forming carbon atoms and may have a substituent, a heteroarylene group which has 3 to 60 ring forming carbon atoms and may have a substituent, or a fluorenylene group which may have a substituent, $Ar^1$ represents a divalent aromatic hydrocarbon group which has 6 to 60 ring forming carbon atoms and may have a substituent, and $Ar^2$ represents an aryl group which has 6 to 60 ring forming carbon atoms and may have a substituent, or a heteroaryl group which has 3 to 60 ring forming atoms and may have a substituent.

[Chem. 46]

X and Y in the silacyclopentadiene derivative represented by the general formula (20) each independently represent a saturated or unsaturated hydrocarbon group having 1 to 6 carbon atoms, an alkoxy group, an alkenyloxy group, an alkynyloxy group, a hydroxy group, a substituted or unsubstituted aryl group, or a substituted or unsubstituted heterocycle, or X and Y are bonded to each other to form a structure as a saturated or unsaturated ring; and $R_1$ to $R_4$ each independently represent hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or, when two or more of $R_1$ to $R_4$ are adjacent to each other, a structure in which substituted or unsubstituted rings are fused is formed.

[Chem. 47]

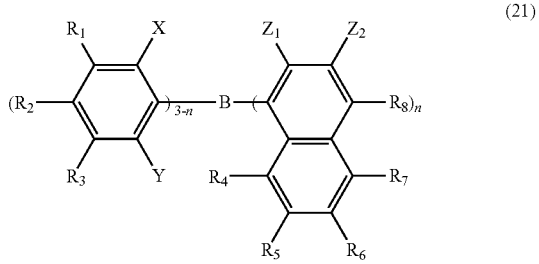

R₁ to R₈ and Z₂ in the borane derivative represented by the general formula (21) each independently represent a hydrogen atom, a saturated or unsaturated hydrocarbon group, an aromatic hydrocarbon group, a heterocyclic group, a substituted amino group, a substituted boryl group, an alkoxy group, or an aryloxy group; X, Y, and Z₁ each independently represent a saturated or unsaturated hydrocarbon group, an aromatic hydrocarbon group, a heterocyclic group, a substituted amino group, an alkoxy group, or an aryloxy group; substituents of Z₁ and Z₂ may be bonded to each other to form a fused ring; and "n" represents an integer of 1 to 3, and, when "n" represents 2 or more, Z's may be different from each other, provided that the case where n represents 1, X, Y, and R₂ each represent a methyl group, R₈ represents a hydrogen atom or a substituted boryl group and the case where n represents 3 and Z₁'s each represent a methyl group are excluded.

[Chem. 48]

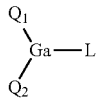

(22)

Q¹ and Q² in the metal complex represented by the general formula (22) each independently represent a ligand represented by the following general formula (K); and L represents a halogen atom, a substituted or unsubstituted alkyl group, a substituted or unsubstituted cycloalkyl group, a substituted or unsubstituted aryl group, a substituted or unsubstituted heterocyclic group, —OR¹ (where R¹ represents a hydrogen atom, a substituted or unsubstituted alkyl group, a substituted or unsubstituted cycloalkyl group, a substituted or unsubstituted aryl group, or a substituted or unsubstituted heterocyclic group), or a ligand represented by —O—Ga—Q³ (Q⁴) (where Q³ and Q⁴ are identical to Q¹ and Q², respectively).

[Chem. 49]

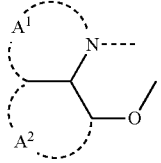

(23)

Rings A¹ and A² in the metal complex represented by the above-mentioned general formula (23) are six-membered aryl ring structures which are fused with each other and each of which may have a substituent.

The metal complex behaves strongly as an n-type semiconductor, and has a significant electron injecting ability. Further, generation energy upon formation of the complex is low. As a result, the metal and the ligand of the formed metal complex are bonded to each other so strongly that the fluorescent quantum efficiency of the complex as a light emitting material improves.

Specific examples of a substituent in the rings A¹ and A² each of which form a ligand in the general formula (22) include: a halogen atom such as chlorine, bromine, iodine, or fluorine; a substituted or unsubstituted alkyl group such as a methyl group, an ethyl group, a propyl group, a butyl group, an s-butyl group, a t-butyl group, a pentyl group, a hexyl group, a heptyl group, an octyl group, a stearyl group, or trichloromethyl group; a substituted or unsubstituted aryl group such as a phenyl group, a naphthyl group, a 3-methylphenyl group, a 3-methoxyphenyl group, a 3-fluorophenyl group, a 3-trichloromethylphenyl group, a 3-trifluoromethylphenyl group, or a 3-nitrophenyl group; a substituted or unsubstituted alkoxy group such as a methoxy group, an n-butoxy group, a t-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group, or a 6-(perfluoroethyl)hexyloxy group; a substituted or unsubstituted aryloxy group such as a phenoxy group, a p-nitrophenoxy group, a p-t-butylphenoxy group, a 3-fluorophenoxy group, a pentafluorophenyl group, or a 3-trifluoromethylphenoxy group; a substituted or unsubstituted alkylthio group such as a methylthio group, an ethylthio group, a t-butylthio group, a hexylthio group, an octylthio group, or a trifluoromethylthio group; a substituted or unsubstituted arylthio group such as a phenylthio group, a p-nitrophenylthio group, a p-t-butylphenylthio group, a 3-fluorophenylthio group, a pentafluorophenylthio group, or a 3-trifluoromethylphenylthio group; a cyano group; a nitro group; an amino group; a mono-substituted or di-substituted amino group such as a methylamino group, a diethylamino group, an ethylamino group, a diethylamino group, a dipropylamino group, a dibutylamino group, or a diphenylamino group; an acylamino group such as a bis(acetoxymethyl) amino group, a bis(acetoxyethyl)amino group, a bis(acetoxypropyl)amino group, or a bis(acetoxybutyl)amino group; a hydroxyl group; a siloxy group; an acyl group; a carbamoyl group such as a methylcarbamoyl group, a dimethylcarbamoyl group, an ethylcarbamoyl group, a diethylcarbamoyl group, a propylcarbamoyl group, a butylcarbamoyl group, or a phenylcarbamoyl group; a carboxylic acid group; a sulfonic acid group; an imide group; a cycloalkyl group such as a cyclopentane group or a cyclohexyl group; an aryl group such as a phenyl group, a naphthyl group, a biphenyl group, an anthranyl group, a phenanthryl group, a fluorenyl group, or a pyrenyl group; and a heterocyclic group such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a triathinyl group, a carbazolyl group, a furanyl group, a thiophenyl group, anoxazolyl group, anoxadiazolyl group, abenzoxazolyl group, a thiazolyl group, a thiadiazolyl group, a benzothiazolyl group, a triazolyl group, an imidazolyl group, a benzoimidazolyl group, or a puranyl group. In addition, the above-mentioned substituents may be bonded to each other to further form a six-membered aryl ring or a heterocycle.

A preferred embodiment of the organic EL device of the present invention includes a device including a reducing dopant in the region of electron transport or in the interfacial region of the cathode and the organic layer. Herein, the reducing dopant is defined as a substance which can reduce a compound having an electron transporting property. Thus, various compounds can be used as the reducing dopant as long as the compounds have a certain reducing property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, carbonates of alkali metals, carbonates of alkaline earth metals, organic complexes of alkali metals, organic complexes of alkaline earth metals, and organic complexes of rare earth metals can be suitably used.

In addition, more specifically, preferred examples of the reducing dopant particularly preferably include substances having a work function of 2.9 eV or less, examples of which include at least one alkali metal selected from the group consisting of Na (work function: 2.36 eV), K (work function: 2.28 eV), Rb (work function: 2.16 eV), and Cs (work function: 1.95 eV) and at least one alkaline earth metal selected from the group consisting of Ca (work function: 2.9 eV), Sr (work function: 2.0 to 2.5 eV), and Ba (work function: 2.52 eV) Of those, at least one alkali metal selected from the group consisting of K, Rb, and Cs is more preferred, Rb and Cs are still more preferred, and Cs is most preferred as the reducing dopant. Those alkali metals have particularly high reducing ability, and the emission luminance and the life time of the organic EL device can be increased by addition of a relatively small amount of any of the alkali metals into the electron injecting region. As the reducing dopant having a work function of 2.9 eV or less, a combination of two or more kinds of the alkali metals is also preferred. In particular, a combination containing Cs such as the combination of Cs and Na, Cs and K, Cs and Rb, or Cs, Na, and K is preferred. The reducing ability can be efficiently exhibited by the combination containing Cs. The emission luminance and the life time of the organic EL device can be increased by adding the combination into the electron injecting region.

The present invention may further include an electron injecting layer which is formed of an insulating material or a semiconductor and disposed between the cathode and the organic layer. In this case, leak of electric current can be effectively prevented, and the electron injecting property can be improved. As the insulating material, at least one metal compound selected from the group consisting of alkali metal chalcogenides, alkaline earth metal chalcogenides, halides of alkali metals, and halides of alkaline earth metals is preferably used. It is preferred that the electron injecting layer be formed of the alkali metal chalcogenide or the like because the electron injecting property can be further improved. Specifically, preferred examples of the alkali metal chalcogenide include $Li_2O$, $K_2O$, $Na_2S$, $Na_2Se$, and $Na_2O$. Preferred examples of the alkaline earth metal chalcogenide include CaO, BaO, SrO, BeO, BaS, and CaSe. In addition, preferred examples of the halide of an alkali metal include LiF, NaF, KF, CsF, LiCl, KCl, and NaCl. In addition, preferred examples of the halide of an alkaline earth metal include fluorides such as $CaF_2$, $BaF_2$, $SrF_2$, $MgF_2$, and $BeF_2$ and halides other than the fluorides.

In addition, examples of the semiconductor forming the electron injecting layer include oxides, nitrides, and oxide nitrides containing at least one element selected from Ba, Ca, Sr, Yb, Al, Ga, In, Li, Na, Cd, Mg, Si, Ta, Sb, and Zn used alone or in combination of two or more kinds. In addition, it is preferred that the inorganic compound forming the electron injecting layer form a crystallite or amorphous insulating thin film. When the electron injecting layer is formed of the insulating thin film described above, a more uniform thin film can be formed, and defects of pixels such as dark spots can be decreased. It should be noted that examples of the inorganic compound include the alkali metal chalcogenides, alkaline earth metal chalcogenides, halides of alkali metals, and halides of alkaline earth metals described above.

Subsequently, as the cathode, a cathode using an electrode material such as a metal, an alloy, a conductive compound, or a mixture of those materials which has a small work function (4 eV or less) is used. Specific examples of the electrode material include sodium, a sodium-potassium alloy, magnesium, lithium, cesium, a magnesium-silver alloy, aluminum/aluminum oxide, $Al/Li_2O$, Al/LiO, Al/LiF, an aluminum-lithium alloy, indium, and rare earth metals. The cathode can be prepared by forming a thin film of the electrode material by a method such as vapor deposition or sputtering. Herein, when the light emitted from the light emitting layer is obtained through the cathode, it is preferred that the cathode have a transmittance of the emitted light of more than 10%. It is also preferred that the sheet resistivity of the cathode be several hundred $\Omega/\square$ or less. Further, the thickness of the cathode is, in general, in the range of 10 nm to 1 μm or preferably in the range of 50 to 200 nm.

Further, defects in pixels are, in general, easily formed in organic EL devices due to leak or short circuit because an electric field is applied to ultra-thin films. To prevent the formation of the defects, a layer of a thin film having an insulating property may be inserted between the pair of electrodes.

Examples of a material used for the insulating layer include aluminum oxide, lithiumfluoride, lithiumoxide, cesiumfluoride, cesiumoxide, magnesiumoxide, magnesiumfluoride, calciumoxide, calciumfluoride, aluminum nitride, titanium oxide, silicon oxide, germanium oxide, silicon nitride, boron nitride, molybdenum oxide, ruthenium oxide, and vanadium oxide. A mixture or laminate of the materials may also be used.

Subsequently, the organic EL device of the present invention is produced by forming the anode, the light emitting layer, the hole injecting layer as required, and the electron injecting layer as required, and finally forming the cathode from, for example, the above-mentioned materials according to, for example, the above-mentioned methods. Alternatively, the organic EL device can be produced by initially forming the cathode and finally forming the anode, in other words, by forming the electrodes and the layers in the order inverse to that described above.

Hereinafter, an embodiment of preparation of an organic EL device having a structure in which an anode, a hole injecting layer, a light emitting layer, an electron injecting layer, and a cathode are disposed successively on a light-transmissive substrate is described.

First, on a suitable light-transmissive substrate, a thin film made of a material for the anode is formed in accordance with the vapor deposition method or the sputtering method so that the thickness of the formed thin film is 1 μm or less or preferably in the range of 10 to 200 nm. The formed thin film is used as the anode. Then, a hole injecting layer is formed on the anode. The hole injecting layer can be formed in accordance with the vacuum vapor deposition method, the spin coating method, the casting method, or the LB method, as described above. The vacuum vapor deposition method is preferred because a uniform film can be easily obtained and the possibility of formation of pin holes is small. When the hole injecting layer is formed in accordance with the vacuum vapor deposition method, in general, it is preferred that the conditions be suitably selected from the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C.; and the thickness of the film: 5 nm to 5 μm although the conditions of the vacuum vapor deposition are different depending on the compound to be used (i.e., material for the hole injecting layer) and the crystal structure and the recombination structure of the target hole injecting layer.

Then, the light emitting layer is formed on the hole injecting layer formed above. The light emitting layer can be formed by forming the light emitting material according to the present invention into a thin film by a method such as the vacuum vapor deposition method, the sputtering method, the spin coating method, or the casting method. The vacuum vapor deposition method is preferred because a uniform film can be easily obtained and the possibility of formation of pin holes is small. When the light emitting layer is formed in accordance with the vacuum vapor deposition method, in general, the conditions of the vacuum vapor deposition method can be selected in the same ranges as the conditions described for the vacuum vapor deposition when forming the hole injecting layer, although the conditions are different depending on the compound to be used. The thickness of the film is preferably in the range of 10 to 40 nm.

Subsequently, the electron injecting layer is formed on the light emitting layer formed above. Also in this case, similarly to the hole injecting layer and the light emitting layer, it is preferred that the electron injecting layer be formed in accordance with the vacuum vapor deposition method because a uniform film must be obtained. The conditions of the vapor deposition can be selected in the same ranges as the conditions described for the vacuum vapor deposition of the hole injecting layer and the light emitting layer. Then, the cathode is laminated in the last step, and an organic EL device can be obtained. The cathode is formed of a metal and can be formed in accordance with the vacuum vapor deposition method or the sputtering method. It is preferred that the vacuum vapor deposition method be used in order to prevent formation of damages on the lower organic layers during the formation of the film. In the above-mentioned preparation of the organic EL device, it is preferred that the above-mentioned layers from the anode to the cathode be formed successively while the preparation system is kept in a vacuum after being evacuated once.

A method of forming each layer of the organic EL device of the present invention is not particularly limited. A forming method based on, for example, a conventionally known vacuum deposition method or spin coating method can be employed. The organic thin film layers containing the compound represented by the general formula (1-1) or (1-2) used in the organic EL device of the present invention can each be formed by a known method based on a vacuum deposition method, a molecular beam epitaxy method (MBE method), or an application method involving the use of a solution prepared by dissolving the compound in a solvent such as a dipping method, a spin coating method, a casting method, a bar coating method, or a roll coating method.

The thickness of each organic layer of the organic EL device of the present invention, which is not particularly limited, preferably ranges from several nanometers to one micrometer in ordinary cases in order that a defect such as a pinhole may be prevented and efficiency may be improved.

It should be noted that, when applying a direct voltage to the organic EL device, light emission can be observed in the condition that the polarity of the anode is positive (+), the polarity of the cathode is negative (−) and a voltage of 5 to 40 V is applied. In addition, when the polarity is reversed, no electric current is observed and no light is emitted at all. Further, when an alternating voltage is applied to the organic EL device, a uniform light emission is observed only in the condition that the polarity of the anode is positive and the polarity of the cathode is negative. When an alternating voltage is applied to the organic EL device, any type of wave shape may be used.

EXAMPLES

Hereinafter, the present invention is described more specifically by way of examples. However, the present invention is not limited to the examples.

Synthesis Examples and Examples of Anthracene Derivatives Each Having a Phenanthryl Group when $L^1$ does not Represent a Single Bond, and Comparative Examples Synthesis of Compound 1

[Chem. 50]

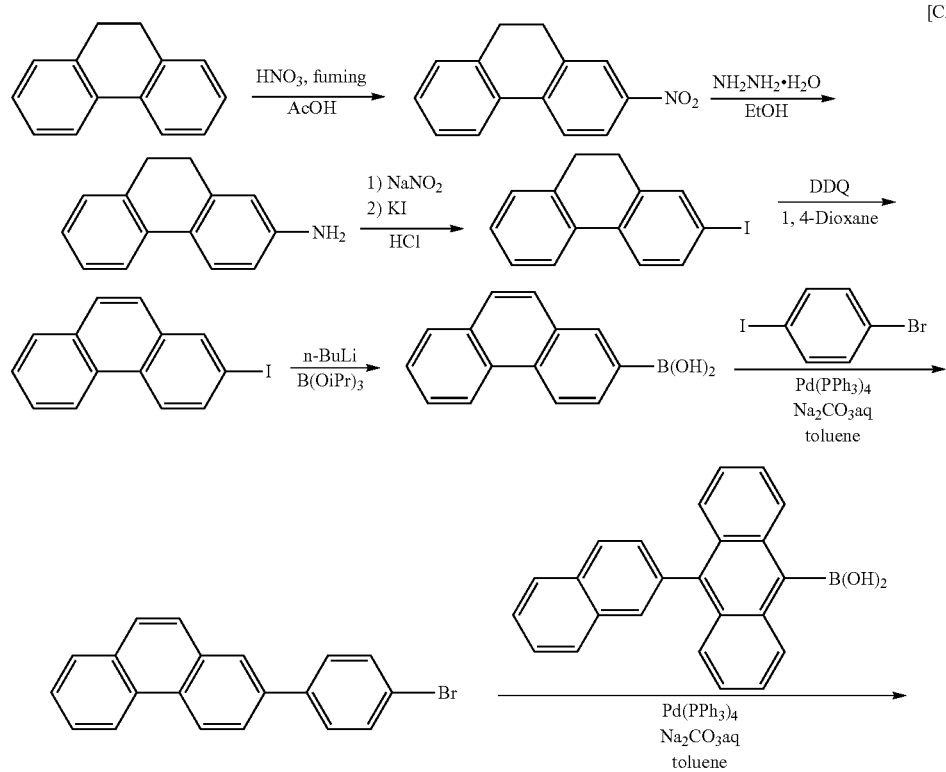

-continued

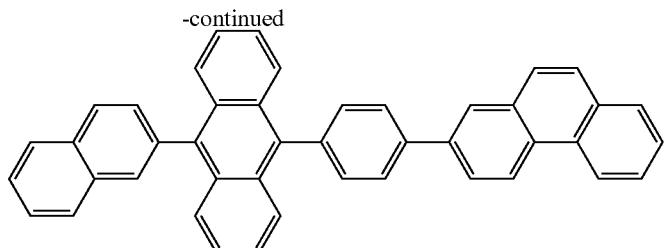

(1-1) Synthesis of 2-nitro-9,10-dihydrophenanthrene

First, 300 g of 9,10-dihydrophenanthrene were dissolved in 2 L of acetic acid, and then 450 mL of fuming nitric acid (d=1.50) were dropped to the mixture. The reaction solution was stirred at room temperature for 7 hours. The reaction solution was poured into 5 L of water, and then the precipitated crystal was separated by filtration and recovered. The resultant crystal was washed with water and methanol, and was then dried under reduced pressure. Thus, 280 g of an orange crystal were obtained (in 74% yield).

(1-2) Synthesis of 2-amino-9,10-dihydrophenanthrene

First, 280 g of 2-nitro-9,10-dihydrophenanthrene, 2.0 g of palladium carbon, and 2.5 L of ethanol were loaded, and then 140 mL of hydrazine monohydrate were added to the mixture. The reaction solution was stirred for 4 hours under heating reflux. After having been cooled to room temperature, the reaction solution was poured into 5 L of water. Then, the mixture was extracted with 3 L of toluene. After the water layer had been removed, the organic layer was dried with magnesium sulfate. After magnesium sulfate had been separated by filtration, the solvent was removed by distillation under reduced pressure. The residue was purified by silica gel column chromatography. Thus, 220 g of a pale yellow solid were obtained (in 89% yield).

(1-3) Synthesis of 2-iodo-9,10-dihydrophenanthrene

Under an argon atmosphere, 220 g of 2-amino-9,10-dihydrophenanthrene, 3 L of 3N HCl, and 2 L of acetic acid were added, and then the mixture was stirred for 3 hours under heat. After having been cooled to room temperature, the mixture was cooled with ice, and then an aqueous solution of 91 g of sodium nitrite was dropped to the mixture. After the resultant mixture had been stirred for 1 hour under ice cooling, an aqueous solution of 660 g of potassium iodide was added to the mixture. Subsequently, 2 L of dichloromethane were added to the mixture, and then the whole was stirred at room temperature for 3 hours. After that, the mixture was extracted with dichloromethane. The organic layer was repeatedly washed with an aqueous solution of potassium carbonate, and was then dried with magnesium sulfate. After that, the solvent was removed by distillation under reduced pressure. The residue was purified by silica gel column chromatography. Thus, 210 g of a pale yellow solid were obtained (in 62% yield).

(1-4) Synthesis of 2-iodophenanthrene

Under an argon atmosphere, 125 g of 2-iodo-9,10-dihydrophenanthrene, 98 g of 2,3-dichloro-5,6-dicyano-p-benzoquinone, and 1.2 L of 1,4-dioxane were added, and then the mixture was stirred for 24 hours under heating reflux. After having been cooled to room temperature, the reaction solution was concentrated. The residue was purified by silica gel column chromatography, and was then washed with methanol. Thus, 98 g of a white crystal were obtained (in 68% yield).

(1-5) Synthesis of phenanthrene-2-boronic acid

Under an argon atmosphere, 98 g of 2-iodophenanthrene and 3 L of dehydrated ether were loaded, and then the reaction solution was cooled to −60° C. After that, 210 mL of a 1.6-M solution of n-butyllithium in hexane were added to the reaction solution. The reaction solution was stirred for 1 hour while its temperature was increased to 0° C. The reaction solution was cooled to −60° C. again, and then a solution of 151 g of triisopropyl borate in 100 mL of dehydrated ether was dropped to the reaction solution. The reaction solution was continuously stirred for 5 hours while its temperature was increased to room temperature. Subsequently, 1 L of a 10% aqueous solution of hydrochloric acid was added to the reaction solution, and then the mixture was stirred for 1 hour. The water layer was removed, and the organic layer was washed with water and a saturated salt solution, and was then dried with magnesium sulfate. After magnesium sulfate had been separated by filtration, the organic layer was concentrated. The resultant solid was washed with hexane and toluene. Thus, 42 g of phenanthrene-2-boronic acid as a target were obtained (in 58% yield).

(1-6) Synthesis of 2-(4-bromophenyl)phenanthrene

Under an argon atmosphere, 22.2 g of phenanthrene-2-boronic acid, 28.3 g of 4-bromoiodobenzene, 2.31 g of tetrakis(triphenyl phosphine) palladium(0), 400 mL of toluene, and 200 mL of a 2-M aqueous solution of sodium carbonate were loaded, and then the mixture was stirred for 8 hours under reflux. After having been cooled to room temperature, the reaction solution was extracted with toluene. The water layer was removed, and the organic layer was sequentially washed with water and a saturated salt solution, and was then dried with magnesium sulfate. After magnesium sulfate had been separated by filtration, the organic layer was concentrated. The residue was purified by silica gel column chromatography. Thus, 30.3 g of 10-(3-bromophenyl)benzo[c]phenanthrene were obtained (91%).

(1-7) Synthesis of Compound 1

Under an argon atmosphere, 3.33 g of 2-(4-bromophenyl)phenanthrene, 4.18 g of 10-(2-naphthyl)anthracene-9-boronic acid synthesized by a known method, 0.231 g of tetrakis(triphenylphosphine)palladium(0), 40 mL of toluene, and 20 mL of a 2-M aqueous solution of sodium carbonate were loaded, and then the mixture was stirred for 8 hours under reflux. After having been cooled to room temperature, the reaction solution was extracted with toluene. The water layer was removed, and the organic layer was sequentially washed with water and a saturated salt solution, and was then dried with magnesium sulfate. After magnesium sulfate had been separated by filtration, the organic layer was concentrated. The residue was purified by silica gel column chromatography. Thus, 4.56 g of a pale yellow crystal were obtained. Mass spectral analysis confirmed that the crystal was a target product and had a ratio m/e of 556 with respect to its molecular weight, i.e., 556.22.

Synthesis of Compound 2

[Cem. 51]

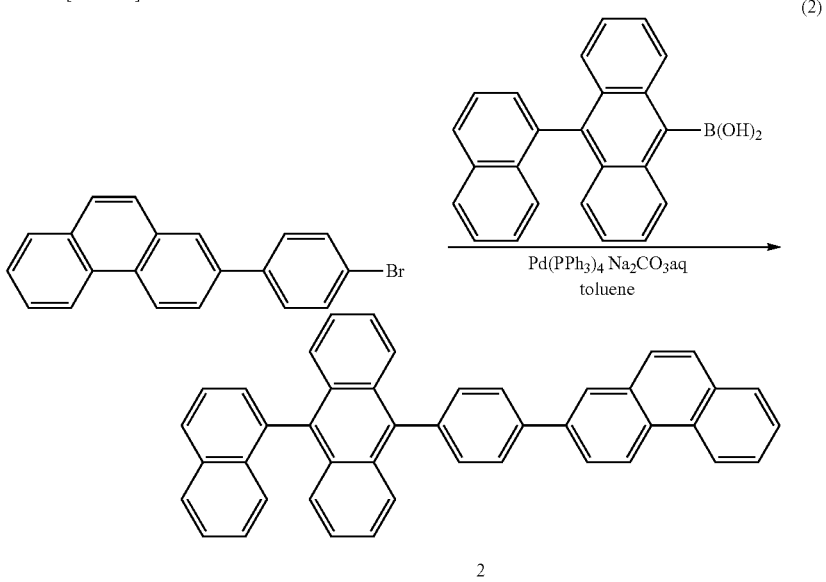

(2)

2

Synthesis of Compound 2

Synthesis was performed in the same manner as in the synthesis of Compound 1 except that 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 3

[Chem. 52]

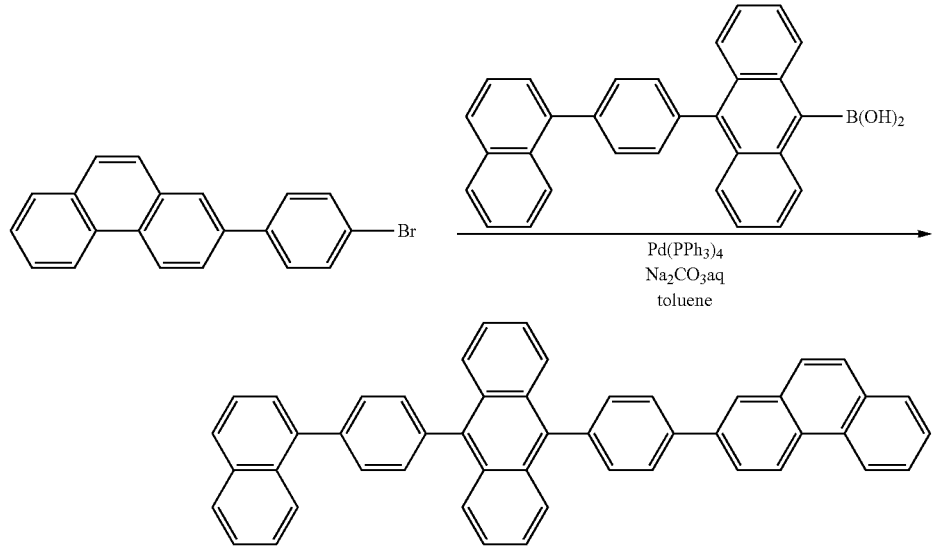

(3)

3

Synthesis of Compound 3

Synthesis was performed in the same manner as in the synthesis of Compound 1 except that 10-[4-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 4

[Chem. 53]

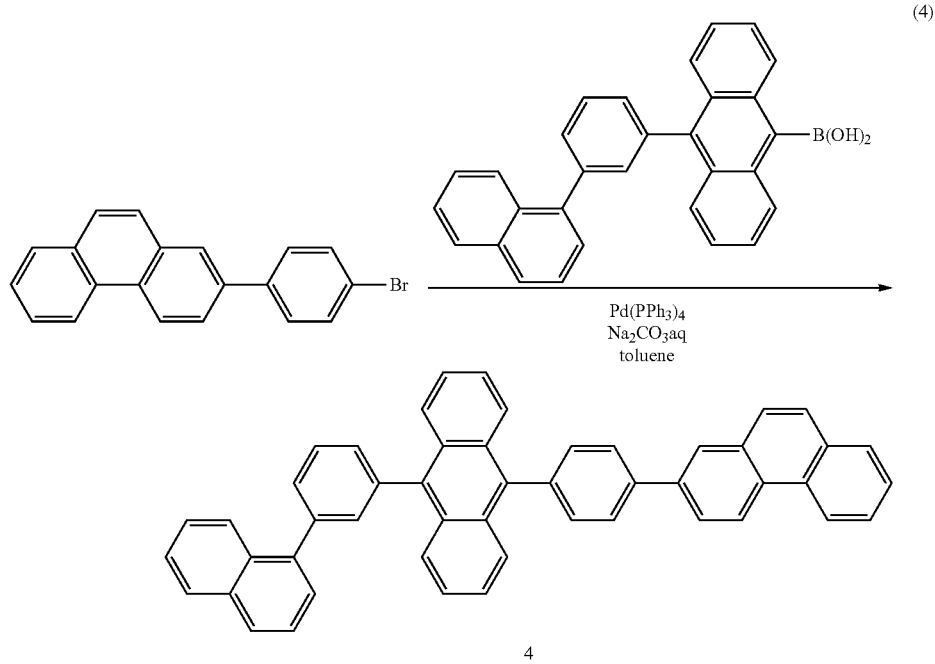

(4)

4

Synthesis of Compound 4

Synthesis was performed in the same manner as in the synthesis of Compound 1 except that 10-[3-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 5

[Chem. 54]

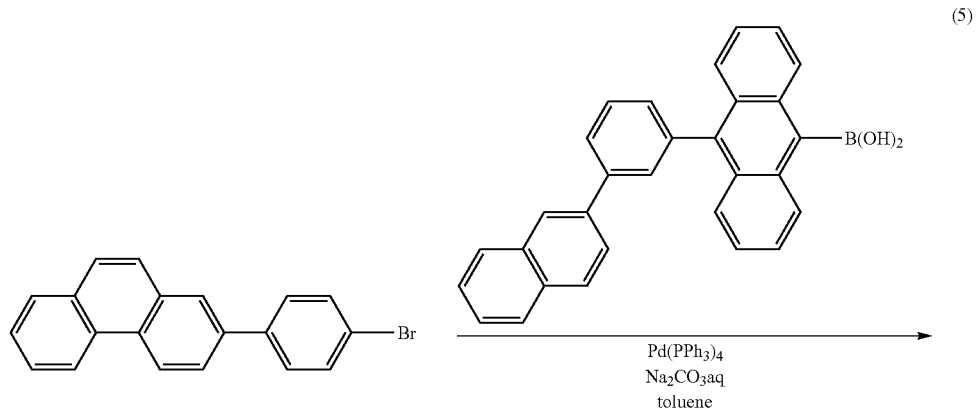

(5)

-continued

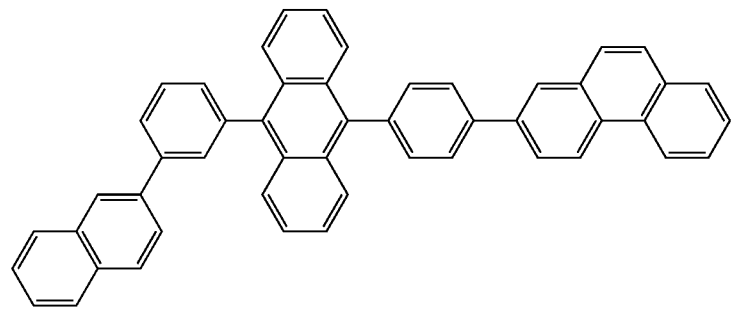

5

Synthesis of Compound 5

Synthesis was performed in the same manner as in the synthesis of Compound 1 except that 10-[3-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 6

[Chem. 55]

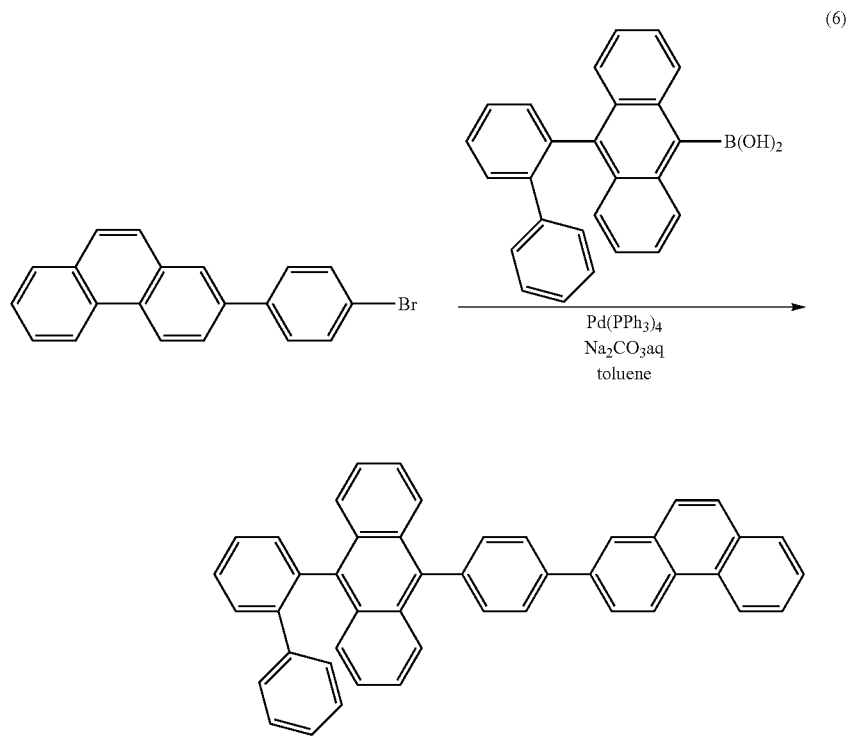

6

Synthesis of Compound 6

Synthesis was performed in the same manner as in the synthesis of Compound 1 except that 10-(2-biphenyl)anthracene-9-boronic acid synthesized by a known method was used instead of 10-(2-naphthyl)anthracene-9-boronic acid. Mass spectral analysis confirmed that the resultant was a target product and had a ratio m/e of 582 with respect to its molecular weight, i.e., 582.23.

Synthesis of Compound 7

[Chem. 56]

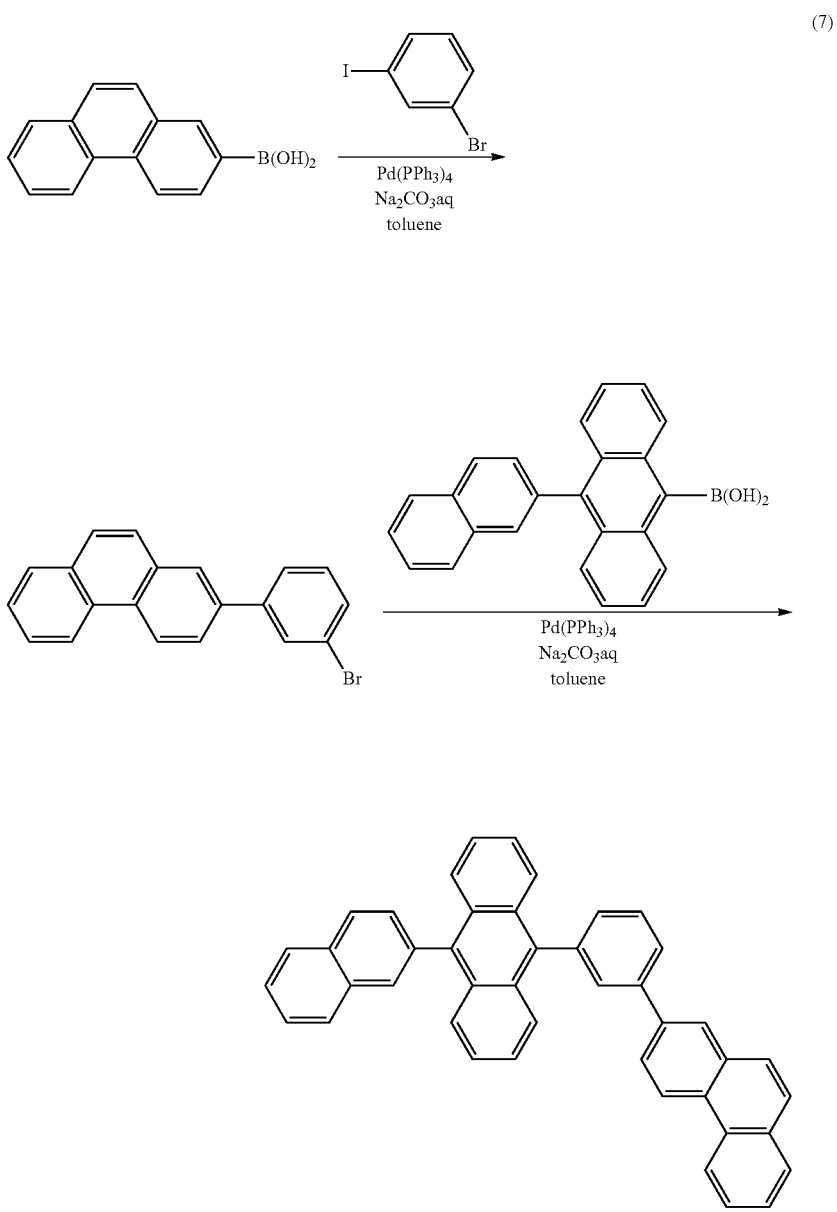

(7)

Synthesis of Compound 7

(7-1) Synthesis of 2-(3-bromophenyl)phenanthrene

Synthesis was performed in the same manner as in the synthesis of 2-(4-bromophenyl)phenanthrene except that 3-bromoiodobenzene was used instead of 4-bromoiodobenzene.

(7-2) Synthesis of Compound 7

Synthesis was performed in the same manner as in the synthesis of Compound 1 except that 2-(3-bromophenyl)phenanthrene was used instead of 2-(4-bromophenyl)phenanthrene. Mass spectral analysis confirmed that the resultant was a target product and had a ratio m/e of 556 with respect to its molecular weight, i.e., 556.22.

Synthesis of Compound 8

[Chem. 57]

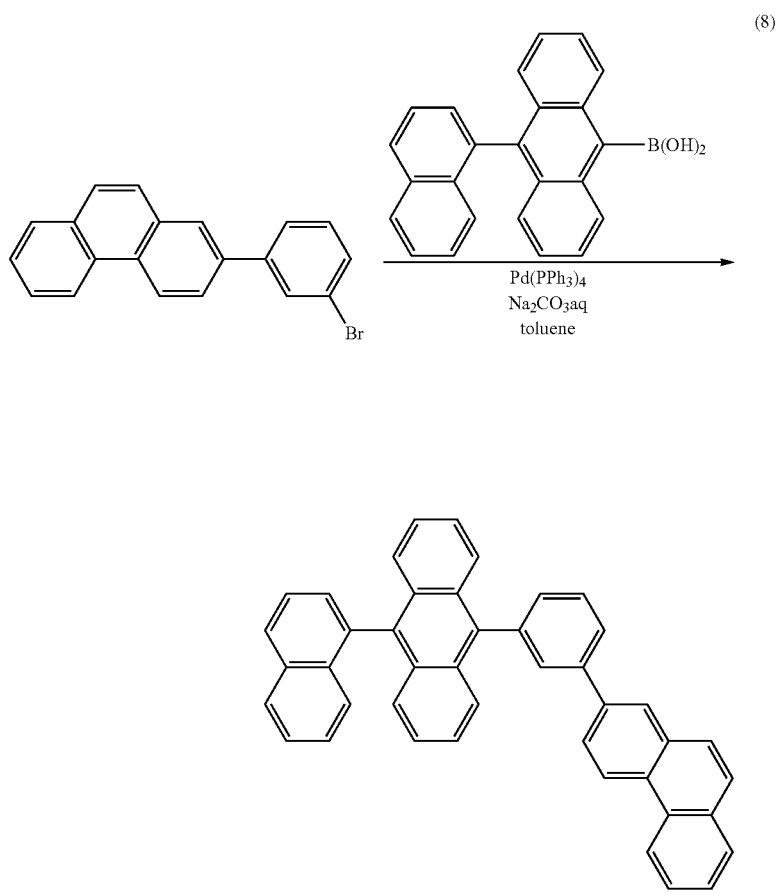

Synthesis of Compound 8

Synthesis was performed in the same manner as in the synthesis of Compound 1 except that: 2-(3-bromophenyl) phenanthrene was used instead of 2-(4-bromophenyl) phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 9

[Chem. 58]

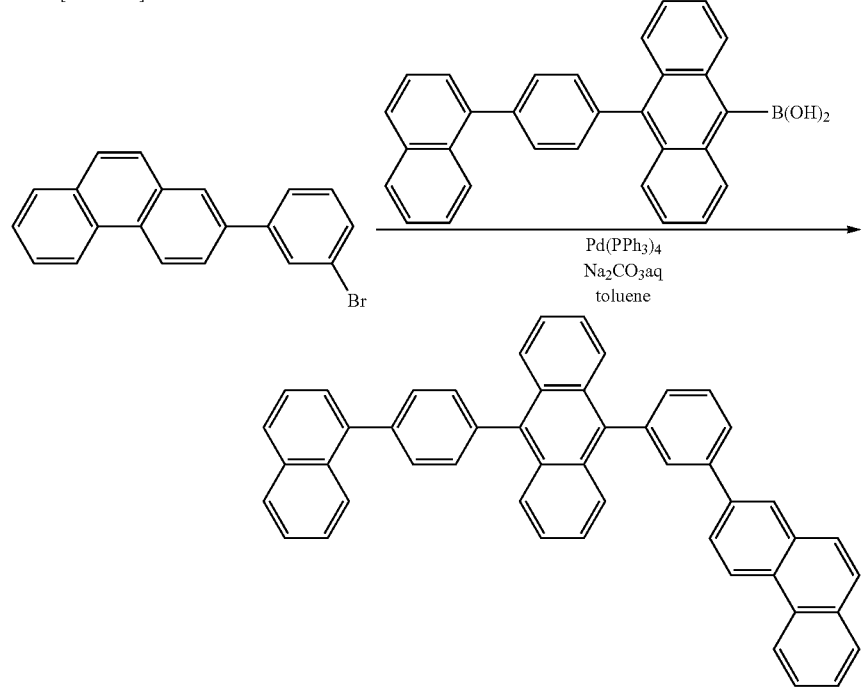

(9)

9

Synthesis of Compound 9

Synthesis was performed in the same manner as in the synthesis of Compound 1 except that: 2-(3-bromophenyl) phenanthrene was used instead of 2-(4-bromophenyl) phenanthrene; and 10-[4-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 10

[Chem. 59]

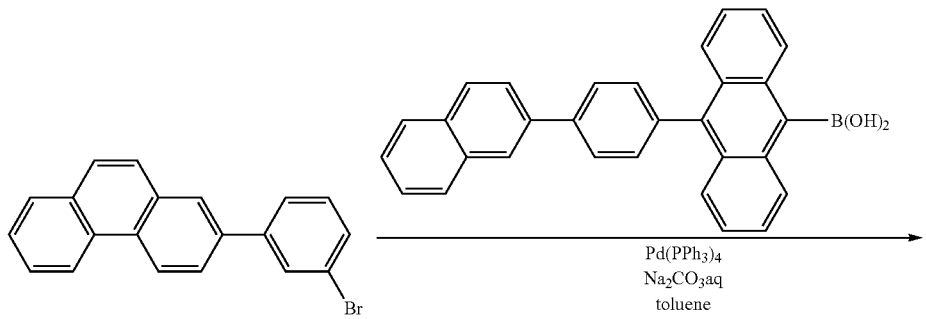

(10)

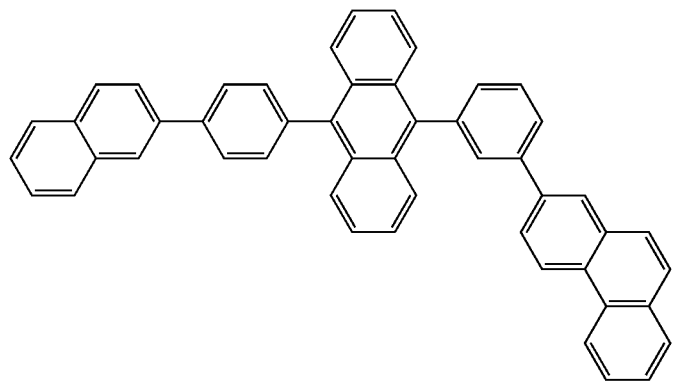

10

Synthesis of Compound 10

Synthesis was performed in the same manner as in the synthesis of Compound 1 except that: 2-(3-bromophenyl)phenanthrene was used instead of 2-(4-bromophenyl)phenanthrene; and 10-[4-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 11

[Chem. 60]

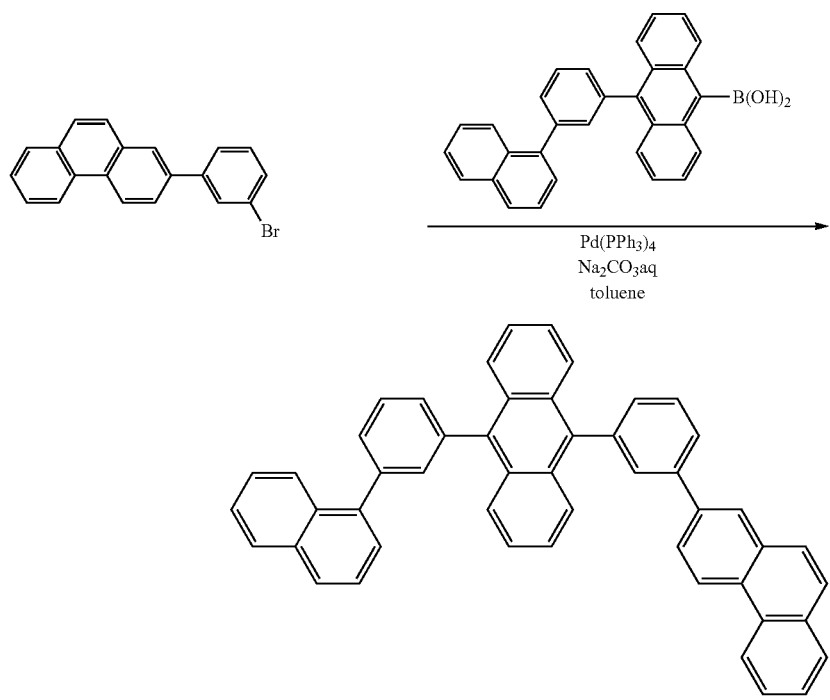

11

Synthesis of Compound 11

Synthesis was performed in the same manner as in the synthesis of Compound 1 except that: 2-(3-bromophenyl)phenanthrene was used instead of 2-(4-bromophenyl)phenanthrene; and 10-[3-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.26.

Synthesis of Compound 12

[Chem. 61]

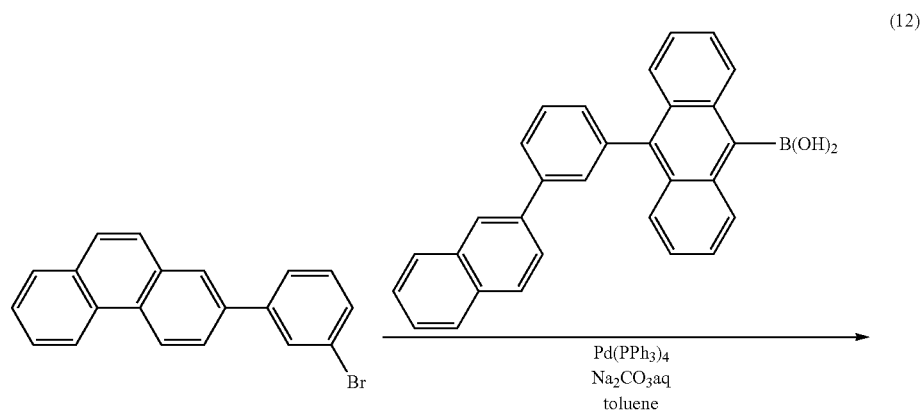

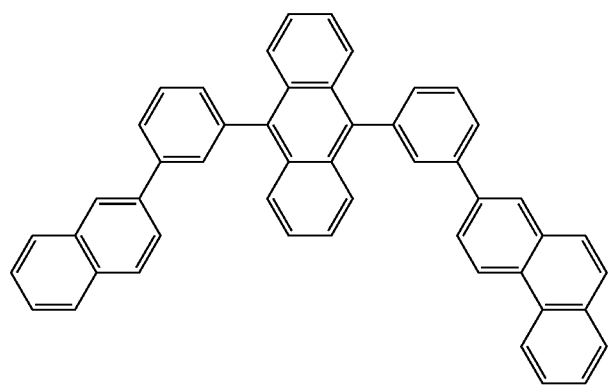

Synthesis of Compound 12

Synthesis was performed in the same manner as in the synthesis of Compound 1 except that: 2-(3-bromophenyl)phenanthrene was used instead of 2-(4-bromophenyl)phenanthrene; and 10-[3-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 13

[Chem. 62]

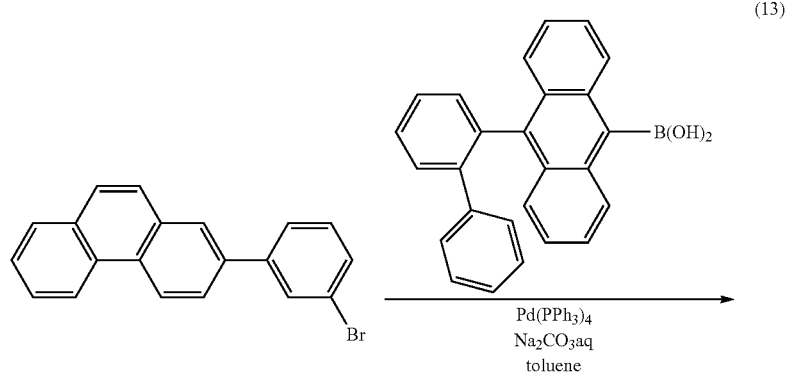

(13)

13

Synthesis of Compound 13

Synthesis was performed in the same manner as in the synthesis of Compound 1 except that: 2-(3-bromophenyl)phenanthrene was used instead of 2-(4-bromophenyl)phenanthrene; and 10-(2-biphenyl) anthracene-9-boronic acid synthesized by a known method was used instead of 10-(2-naphthyl)anthracene-9-boronic acid. Mass spectral analysis confirmed that the resultant was a target product and had a ratio m/e of 582 with respect to its molecular weight, i.e., 582.23.

Synthesis of Compound 14

[Chem. 63]

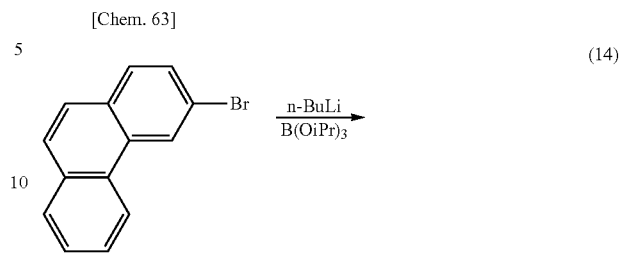

(14)

-continued

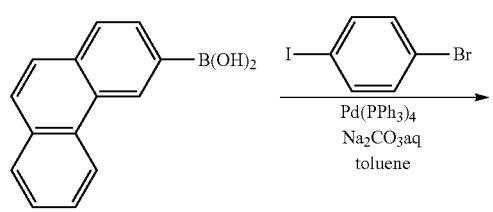

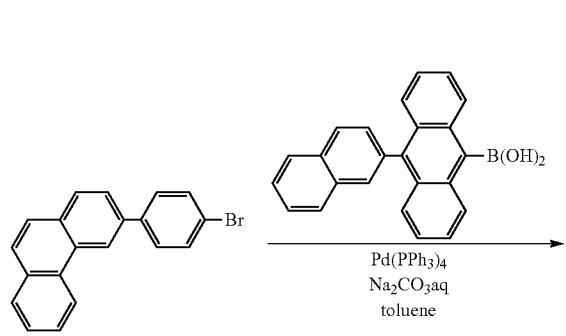

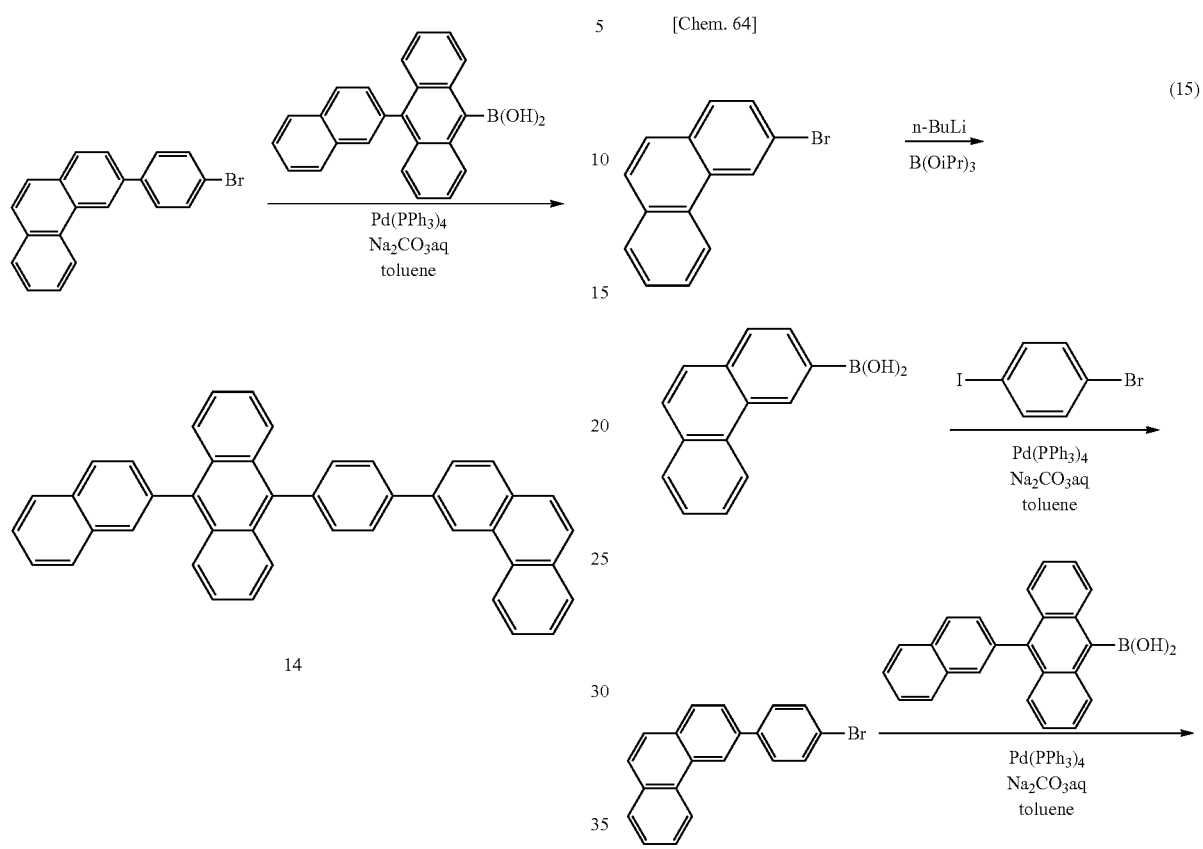

Synthesis of Compound 14

(8-1) Synthesis of phenanthrene-3-boronic acid

Synthesis was performed in the same manner as in the synthesis of phenanthrene-2-boronic acid except that commercially available 3-bromophenanthrene was used instead of 2-iodophenanthrene.

(8-2) Synthesis of 3-(4-bromophenyl)phenanthrene

Synthesis was performed in the same manner as in the synthesis of 2-(4-bromophenyl)phenanthrene except that phenanthrene-3-boronic acid was used instead of phenanthrene-2-boronic acid.

(8-3) Synthesis of Compound 14

Synthesis was performed in the same manner as in the synthesis of Compound 1 except that 3-(4-bromophenyl)phenanthrene was used instead of 2-(4-bromophenyl)phenanthrene. Mass spectral analysis confirmed that the resultant was a target product and had a ratio m/e of 556 with respect to its molecular weight, i.e., 556.22.

Synthesis of Compound 15

[Chem. 64]

(15)

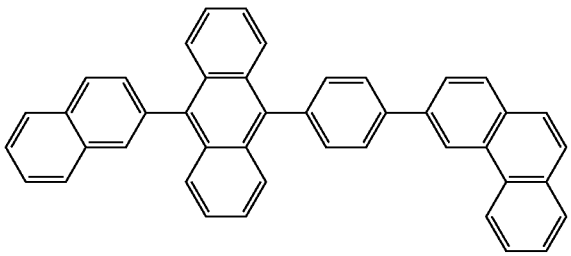

Synthesis of Compound 15

Synthesis was performed in the same manner as in the synthesis of Compound 1 except that: 3-(4-bromophenyl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 16

[Chem. 65]

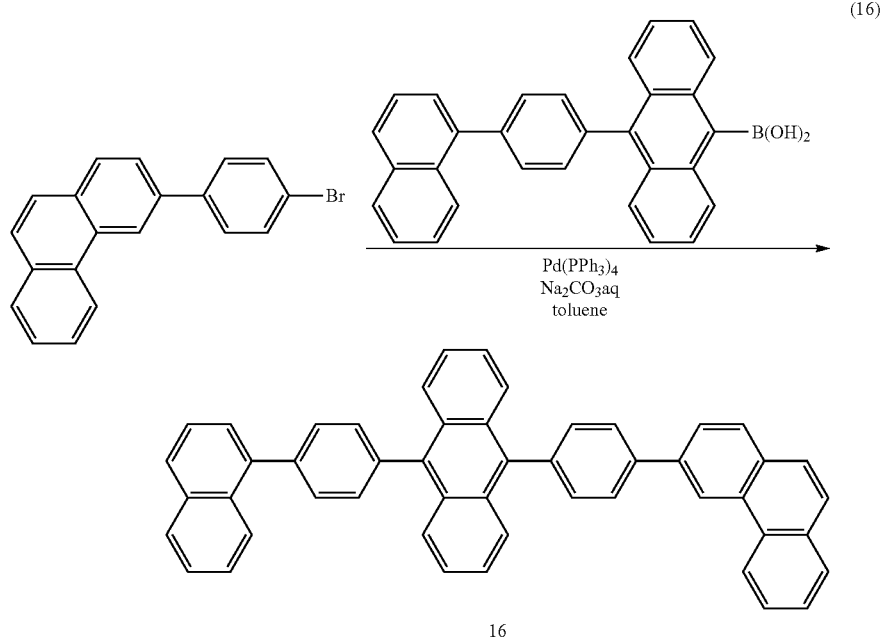

Synthesis of Compound 16

Synthesis was performed in the same manner as in the synthesis of Compound 1 except that: 3-(4-bromophenyl)phenanthrene was used instead of 2-(4-bromophenyl)phenanthrene; and 10-[4-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 17

[Chem. 66]

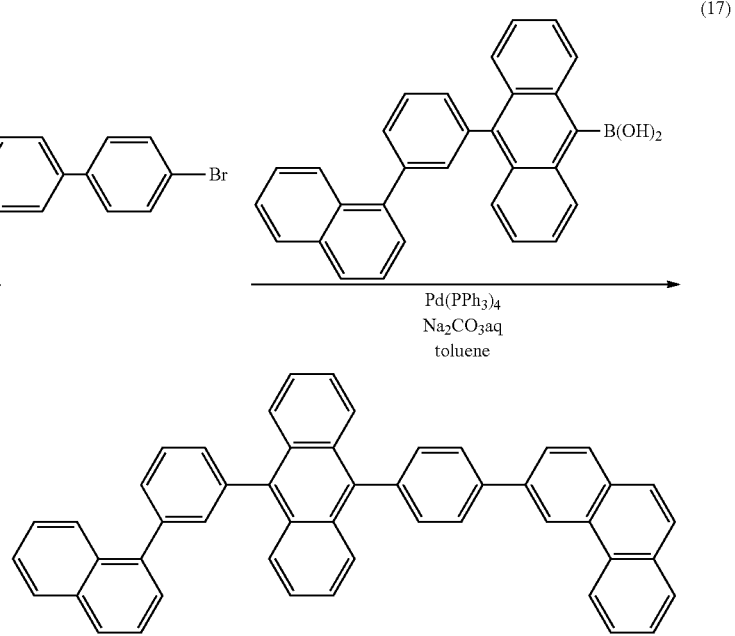

Synthesis of Compound 17

Synthesis was performed in the same manner as in the synthesis of Compound 1 except that: 3-(4-bromophenyl) phenanthrene was used instead of 2-(4-bromophenyl) phenanthrene; and 10-[3-(1-naphthyl) phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 18

[Chem. 67]

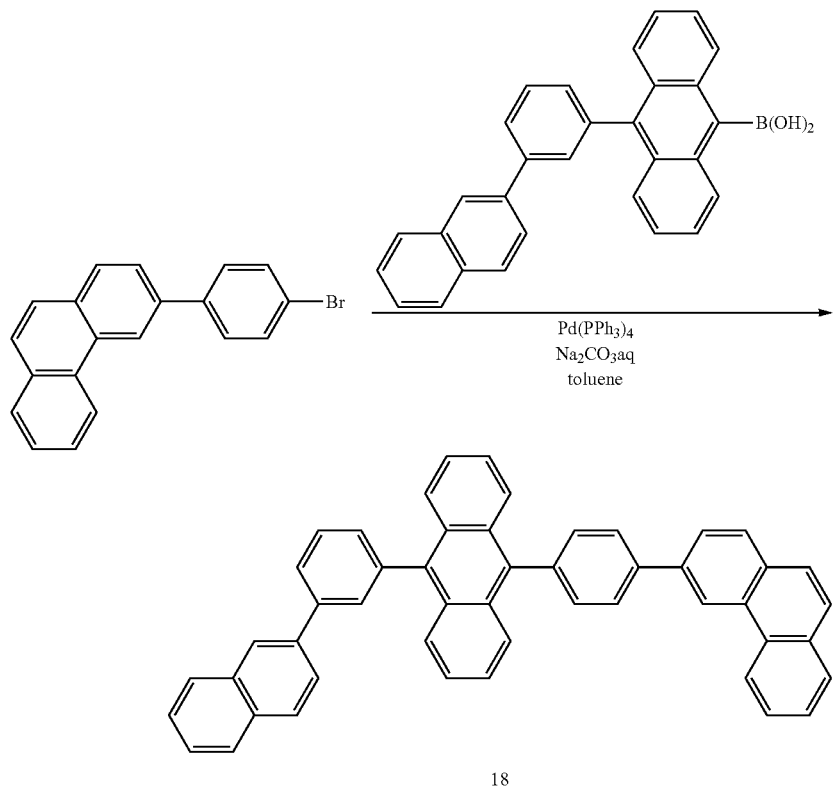

18

Synthesis of Compound 18

Synthesis was performed in the same manner as in the synthesis of Compound 1 except that: 3-(4-bromophenyl) phenanthrene was used instead of 2-(4-bromophenyl) phenanthrene; and 10-[3-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 19

[Chem. 68]

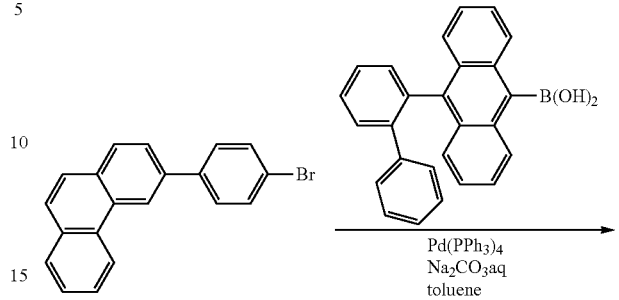

(19)

-continued

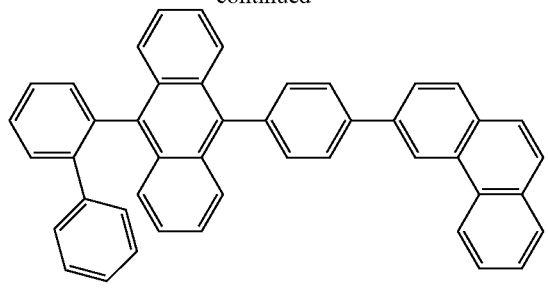

19

Synthesis of Compound 19

Synthesis was performed in the same manner as in the synthesis of Compound 1 except that: 3-(4-bromophenyl)phenanthrene was used instead of 2-(4-bromophenyl)phenanthrene; and 10-(2-biphenyl)anthracene-9-boronic acid synthesized by a known method was used instead of 10-(2-naphthyl)anthracene-9-boronic acid. Mass spectral analysis confirmed that the resultant was a target product and had a ratio m/e of 582 with respect to its molecular weight, i.e., 582.23.

Synthesis of Compound 20

[Chem. 69]

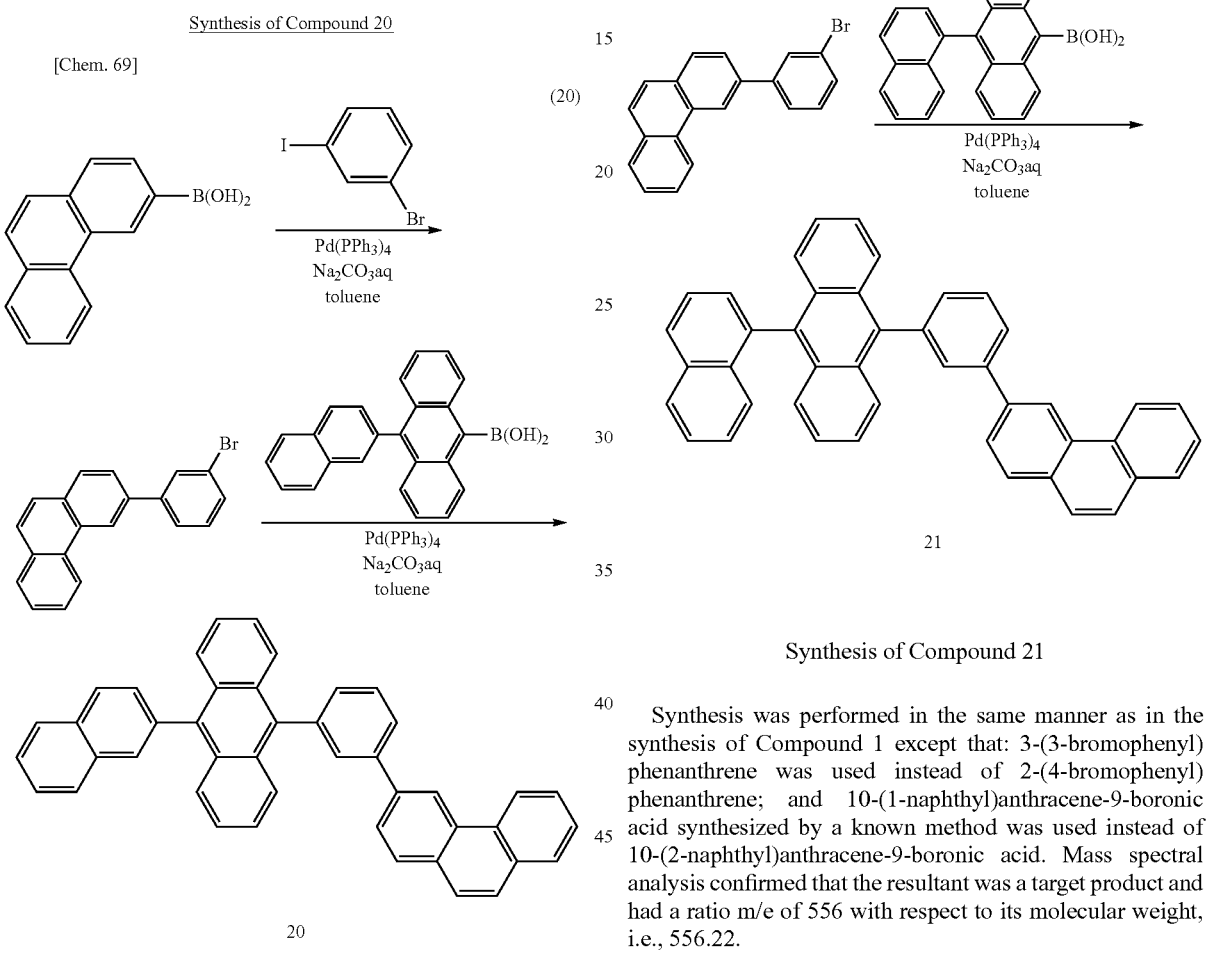

20

Synthesis of Compound 20

(9-1) Synthesis of 3-(3-bromophenyl)phenanthrene

Synthesis was performed in the same manner as in the synthesis of 2-(4-bromophenyl)phenanthrene except that: phenanthrene-3-boronic acid was used instead of phenanthrene-2-boronic acid; and 3-bromoiodobenzene was used instead of 4-bromoiodobenzene.

(9-2) Synthesis of Compound 20

Synthesis was performed in the same manner as in the synthesis of Compound 1 except that: 3-(3-bromophenyl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 21

[Chem. 70]

21

Synthesis of Compound 21

Synthesis was performed in the same manner as in the synthesis of Compound 1 except that: 3-(3-bromophenyl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 22

[Chem. 71]

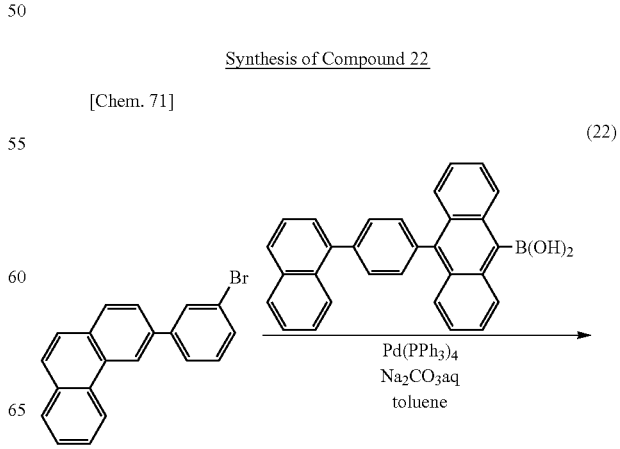

-continued

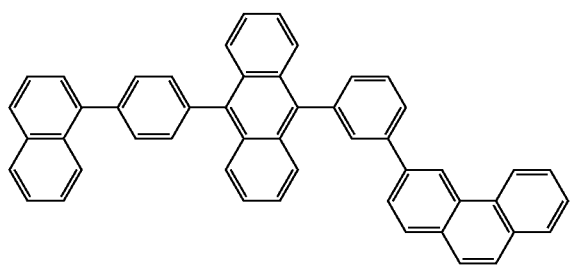

22

Synthesis of Compound 22

Synthesis was performed in the same manner as in the synthesis of Compound 1 except that: 3-(3-bromophenyl)phenanthrene was used instead of 2-(4-bromophenyl)phenanthrene; and 10-[4-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 23

[Chem. 72]

Synthesis of Compound 23

Synthesis was performed in the same manner as in the synthesis of Compound 1 except that: 3-(3-bromophenyl)phenanthrene was used instead of 2-(4-bromophenyl)phenanthrene; and 10-[4-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 24

[Chem. 73]

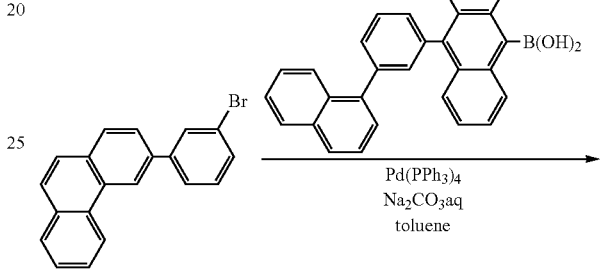

(24)

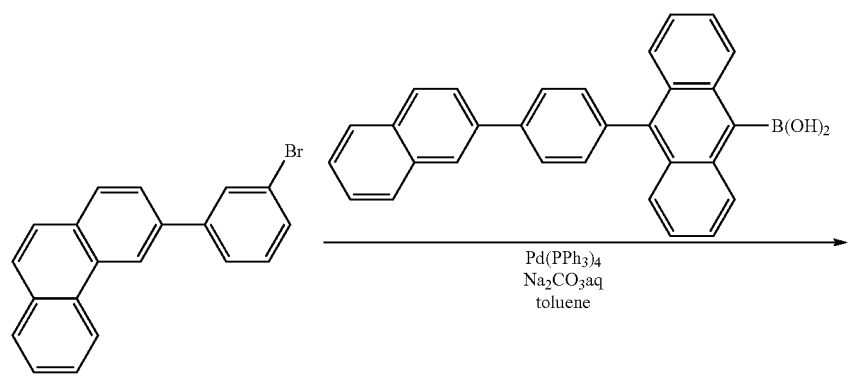

(23)

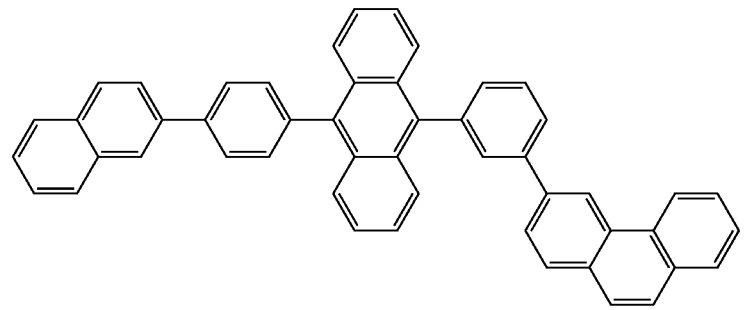

23

-continued

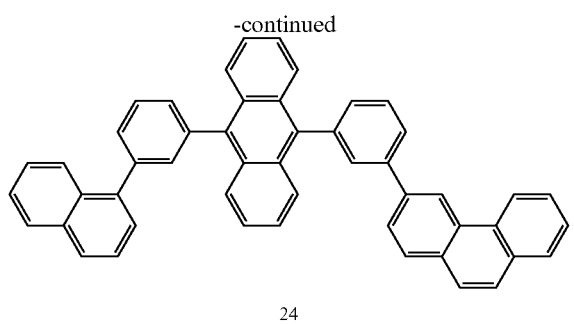

24

Synthesis of Compound 24

Synthesis was performed in the same manner as in the synthesis of Compound 1 except that: 3-(3-bromophenyl)phenanthrene was used instead of 2-(4-bromophenyl)phenanthrene; and 10-[3-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound of 25

[Chem. 74]

(25)

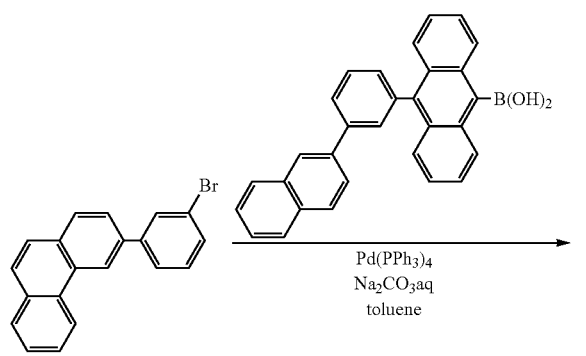

25

Synthesis of Compound 25

Synthesis was performed in the same manner as in the synthesis of Compound 1 except that: 3-(3-bromophenyl)phenanthrene was used instead of 2-(4-bromophenyl)phenanthrene; and 10-[3-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 26

[Chem. 75]

(26)

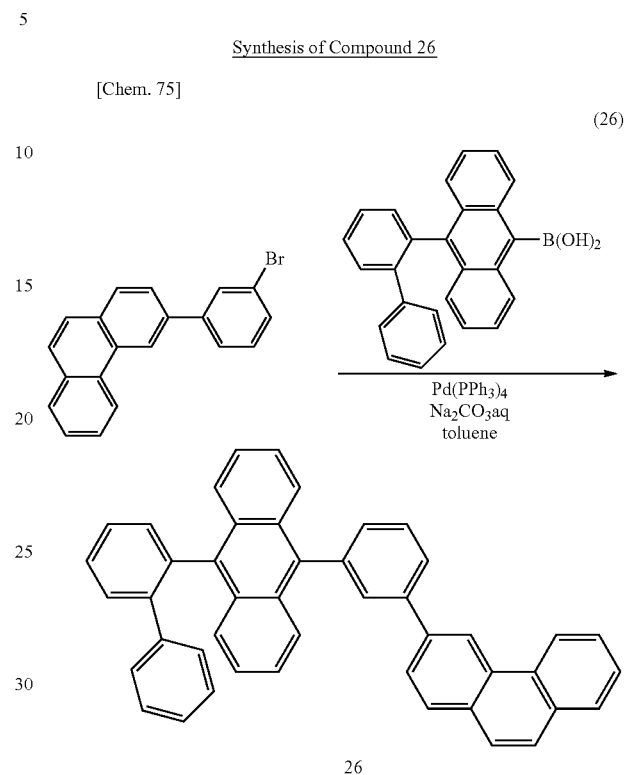

26

Synthesis of Compound 26

Synthesis was performed in the same manner as in the synthesis of Compound 1 except that: 3-(3-bromophenyl)phenanthrene was used instead of 2-(4-bromophenyl)phenanthrene; and 10-(2-biphenyl)anthracene-9-boronic acid synthesized by a known method was used instead of 10-(2-naphthyl)anthracene-9-boronic acid. Mass spectral analysis confirmed that the resultant was a target product and had a ratio m/e of 582 with respect to its molecular weight, i.e., 582.23.

Synthesis of Compound 27

[Chem. 76]

(27)

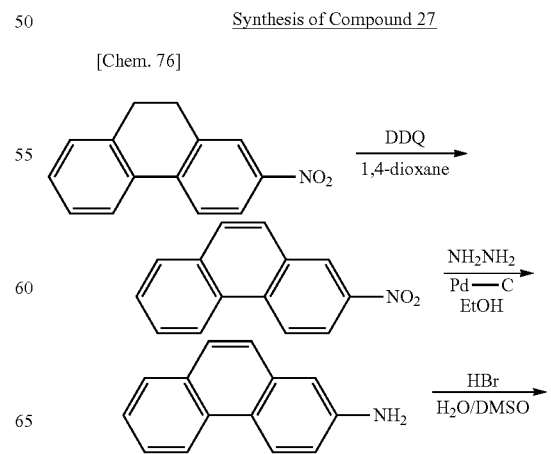

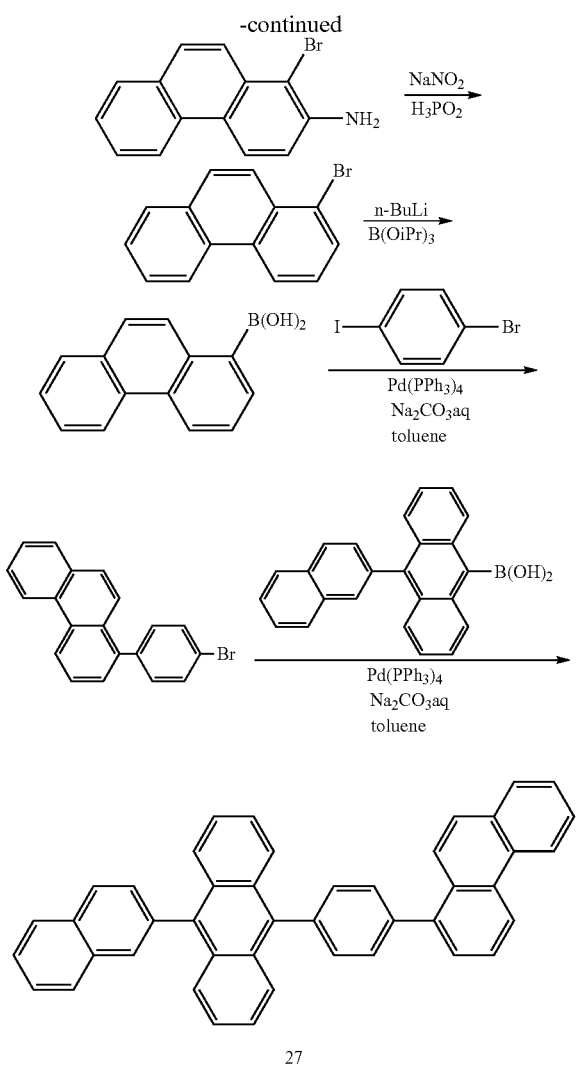

Synthesis of Compound 27

(10-1) Synthesis of 2-nitrophenanthrene

Under an argon atmosphere, 225 g of 2-nitro-9,10-dihydrophenanthrene, 227 g of 2,3-dichloro-5,6-dicyano-p-benzoquinone, and 2.4 L of 1,4-dioxane were added, and then the mixture was stirred for 24 hours under heating reflux. After having been cooled to room temperature, the reaction solution was concentrated. The residue was purified by silica gel column chromatography, and was then washed with methanol. Thus, 134 g of a white crystal were obtained (in 60% yield).

(10-2) Synthesis of 2-aminophenanthrene

First, 134 g of 2-nitrophenanthrene, 1.00 g of palladium carbon, and 1.2 L of ethanol were loaded, and then 70 mL of hydrazine monohydrate were added to the mixture. The reaction solution was stirred for 4 hours under heating ref lux. After having been cooled to room temperature, the reaction solution was poured into 3 L of water. Then, the mixture was extracted with 2 L of toluene. After the water layer had been removed, the organic layer was dried with magnesium sulfate. After magnesium sulfate had been separated by filtration, the solvent was removed by distillation under reduced pressure. The residue was purified by silica gel column chromatography. Thus, 100 g of a pale yellow solid were obtained (in 86% yield).

(10-3) Synthesis of 2-amino-1-bromophenanthrene

First, 100 g of 2-aminophenanthrene were dissolved in 750 mL of N,N-dimethyl sulfoxide, and then 83 g of 48% hydrobromic acid were dropped to the solution over 4 hours while the solution was stirred at room temperature. The mixture was continuously stirred at room temperature for 20 hours, and was then stirred at 100° C. for 1 hour under heat. After having been cooled to room temperature, the reaction solution was poured into 3 L of water. After the mixed solution had been neutralized with ammonia water, the crystal was obtained through separation by filtration. The resultant solid was recrystallized with ethanol and water. Thus, 126 g of a colorless crystal were obtained (in 90% yield).

(10-4) Synthesis of 1-bromophenanthrene

First, 120 g of 2-amino-1-bromophenanthrene were dissolved in 750 mL of THF, and then 4.5 L of concentrated hydrochloric acid and 1.5 L of water were added to the solution. The reaction solution was cooled with ice, and then a solution of 45 g of sodium nitrite in 230 mL of water was dropped to the solution. After the mixture had been stirred for 1 hour under ice cooling, 2.25 L of a 50% aqueous solution of phosphinic acid were added to the mixture. The reaction solution was stirred for 30 minutes under ice cooling, and was then continuously stirred at room temperature for 17 hours. Subsequently, 10 L of water were added to the solution, and a solid was obtained through separation by filtration. The resultant solid was purified by silica gel column chromatography. Thus, 75 g of 1-bromophenanthrene were obtained (in 66% yield).

(10-5) Synthesis of phenanthrene-1-boronic acid

Synthesis was performed in the same manner as in the synthesis of phenanthrene-2-boronic acid except that 1-bromophenanthrene was used instead of 2-iodophenanthrene.

(10-6) Synthesis of 1-(4-bromophenyl)phenanthrene

Synthesis was performed in the same manner as in the synthesis of 2-(4-bromophenyl)phenanthrene except that phenanthrene-1-boronic acid was used instead of phenanthrene-2-boronic acid.

(10-7) Synthesis of Compound 27

Synthesis was performed in the same manner as in the synthesis of Compound 1 except that 1-(4-bromophenyl) phenanthrene was used instead of 2-(4-bromophenyl) phenanthrene. Mass spectral analysis confirmed that the resultant was a target product and had a ratio m/e of 556 with respect to its molecular weight, i.e., 556.22.

Synthesis of Compound 28

[Chem. 77]

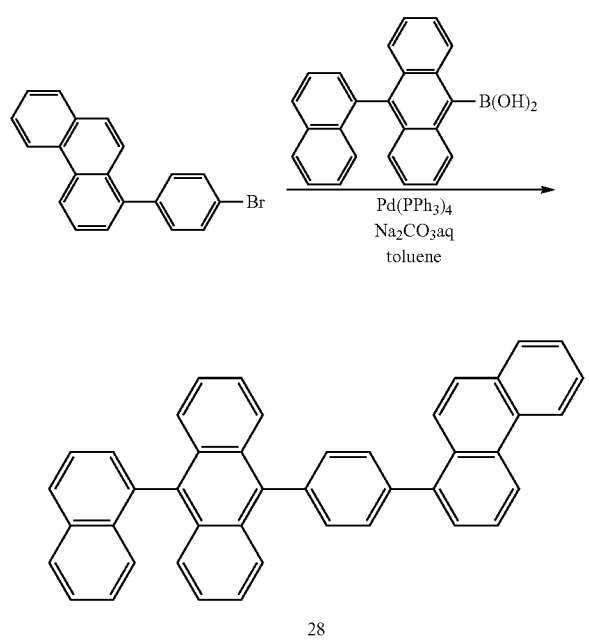

Synthesis of Compound 28

Synthesis was performed in the same manner as in the synthesis of Compound 1 except that: 1-(4-bromophenyl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 29

[Chem. 78]

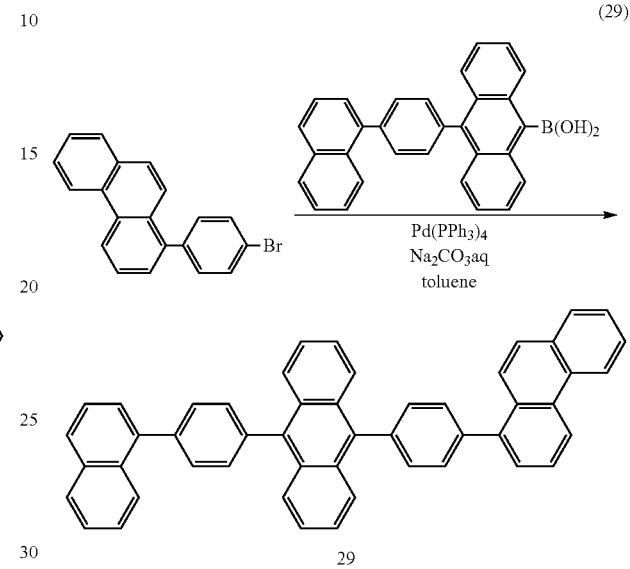

Synthesis of Compound 29

Synthesis was performed in the same manner as in the synthesis of Compound 1 except that: 1-(4-bromophenyl)phenanthrene was used instead of 2-(4-bromophenyl)phenanthrene; and 10-[4-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 30

[Chem. 79]

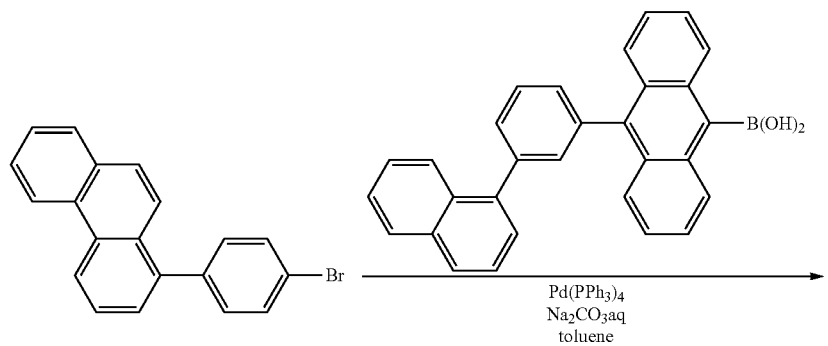

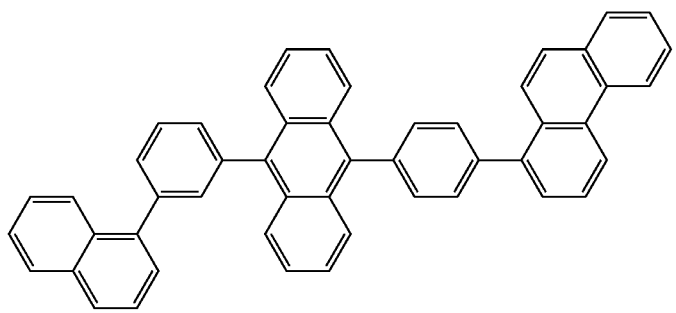

30

Synthesis of Compound 30

Synthesis was performed in the same manner as in the synthesis of Compound 1 except that: 1-(4-bromophenyl)phenanthrene was used instead of 2-(4-bromophenyl)phenanthrene; and 10-[3-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

[Chem. 80]

Synthesis of Compound 31

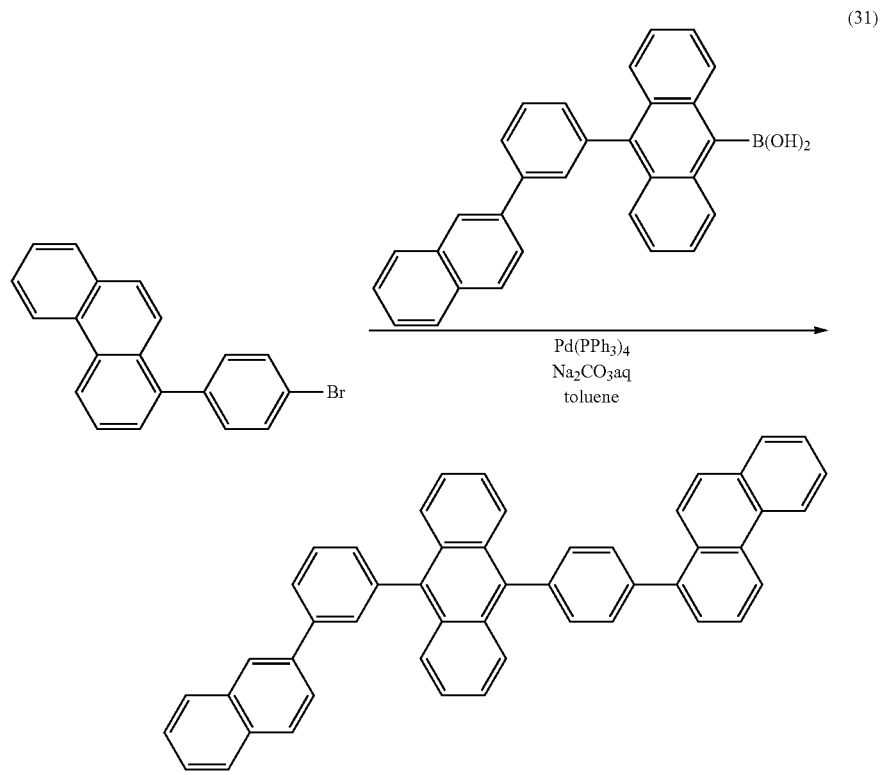

Synthesis of Compound 31

Synthesis was performed in the same manner as in the synthesis of Compound 1 except that: 1-(4-bromophenyl)phenanthrene was used instead of 2-(4-bromophenyl)phenanthrene; and 10-[3-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 32

[Chem. 81]

(32)

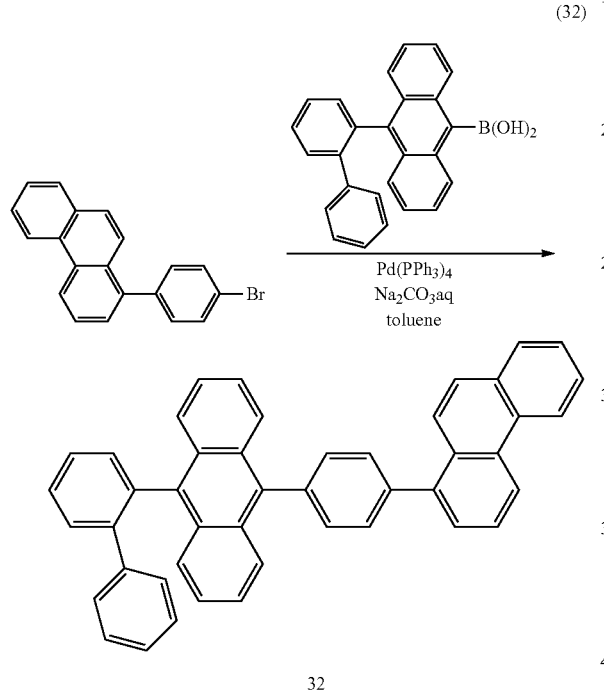

32

Synthesis of Compound 32

Synthesis was performed in the same manner as in the synthesis of Compound 1 except that: 1-(4-bromophenyl)phenanthrene was used instead of 2-(4-bromophenyl)phenanthrene; and 10-(2-biphenyl)anthracene-9-boronic acid synthesized by a known method was used instead of 10-(2-naphthyl)anthracene-9-boronic acid. Mass spectral analysis confirmed that the resultant was a target product and had a ratio m/e of 582 with respect to its molecular weight, i.e., 582.23.

Synthesis of Compound 33

[Chem. 82]

(33)

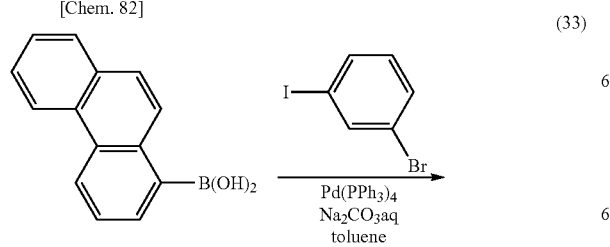

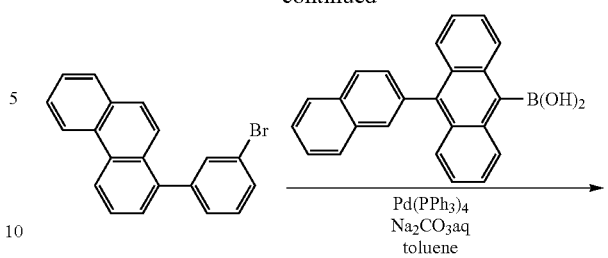

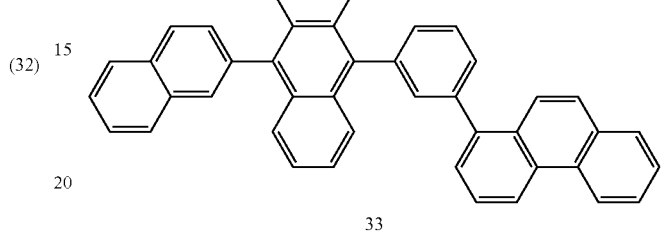

33

Synthesis of Compound 33

(33-1) Synthesis of 3-(3-bromophenyl)phenanthrene

Synthesis was performed in the same manner as in the synthesis of 2-(4-bromophenyl)phenanthrene except that: phenanthrene-1-boronic acid was used instead of phenanthrene-2-boronic acid; and 3-bromoiodobenzene was used instead of 4-bromoiodobenzene.

(33-2) Synthesis of Compound 33

Synthesis was performed in the same manner as in the synthesis of Compound 1 except that: 1-(3-bromophenyl)phenanthrene was used instead of 2-(4-bromophenyl)phenanthrene; and 10-(1-naphthyl) anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 34

[Chem. 83]

(34)

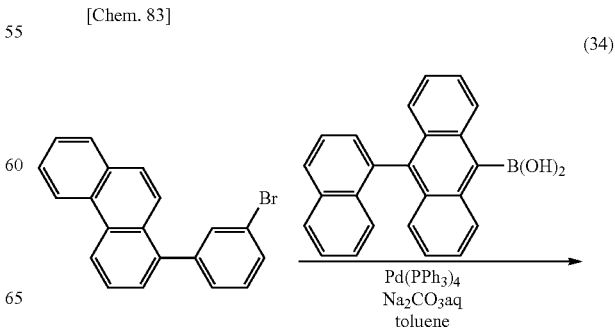

-continued

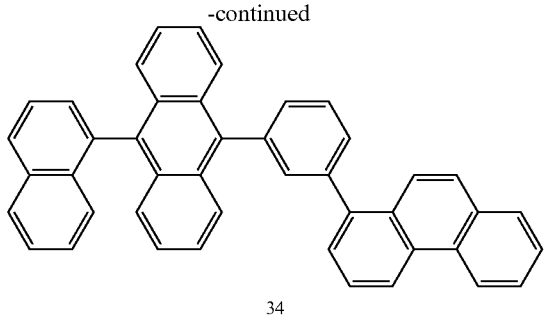

34

Synthesis of Compound 34

Synthesis was performed in the same manner as in the synthesis of Compound 1 except that: 1-(3-bromophenyl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 35

[Chem. 84]

(35)

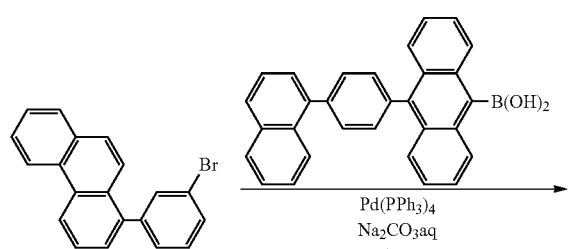

-continued

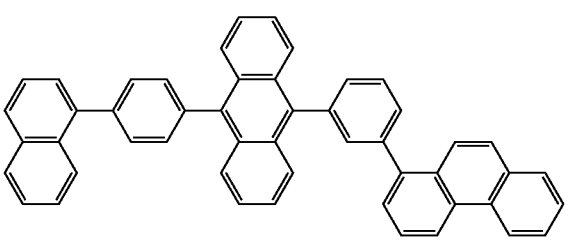

35

Synthesis of Compound 35

Synthesis was performed in the same manner as in the synthesis of Compound 1 except that: 1-(3-bromophenyl)phenanthrene was used instead of 2-(4-bromophenyl)phenanthrene; and 10-[4-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 36

[Chem. 85]

(36)

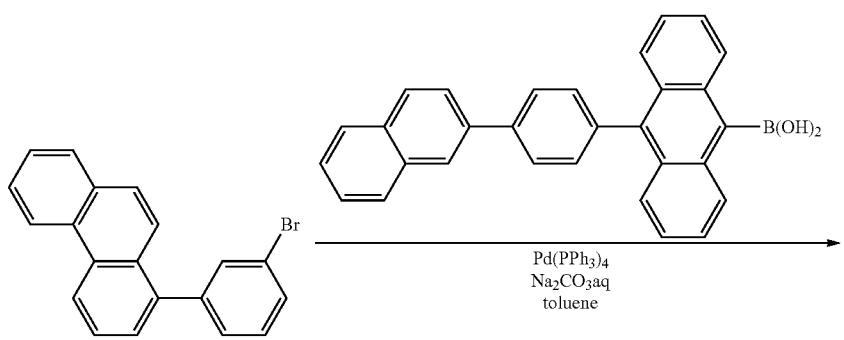

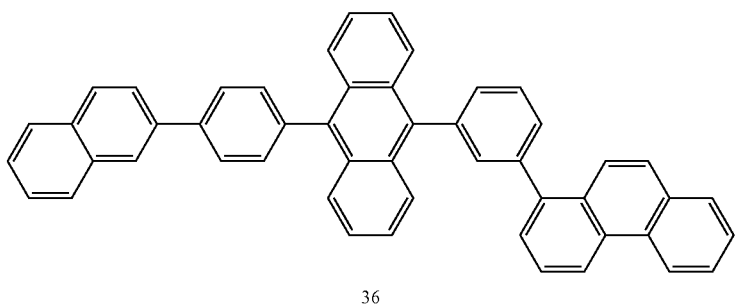

36

Synthesis of Compound 36

Synthesis was performed in the same manner as in the synthesis of Compound 1 except that: 1-(3-bromophenyl)phenanthrene was used instead of 2-(4-bromophenyl)phenanthrene; and 10-[4-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 37

Synthesis was performed in the same manner as in the synthesis of Compound 1 except that: 1-(3-bromophenyl)phenanthrene was used instead of 2-(4-bromophenyl)phenanthrene; and 10-[3-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 37

[Chem. 86]

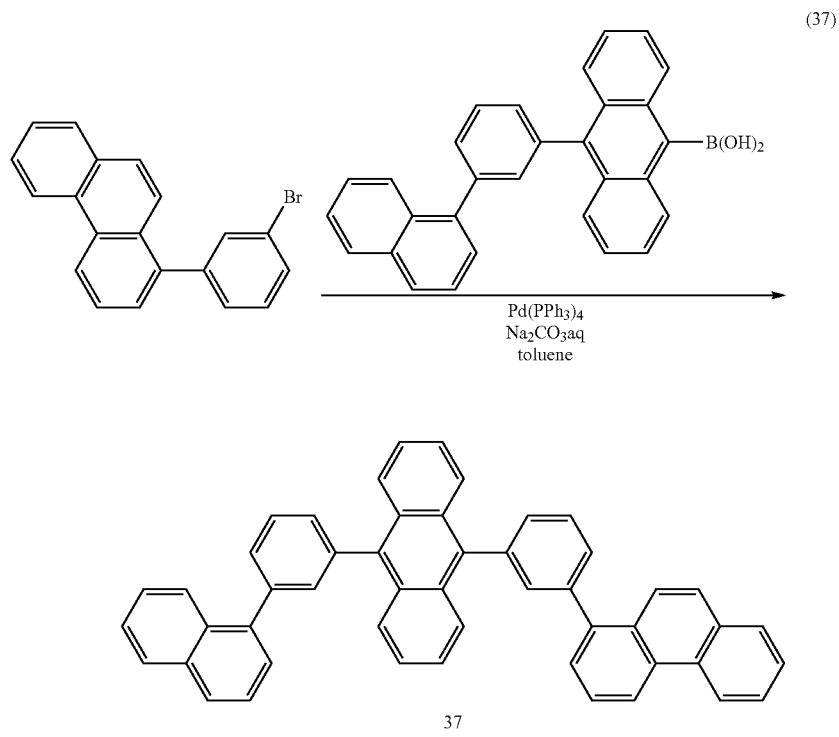

(37)

37

Synthesis of Compound 38

[Chem. 87]

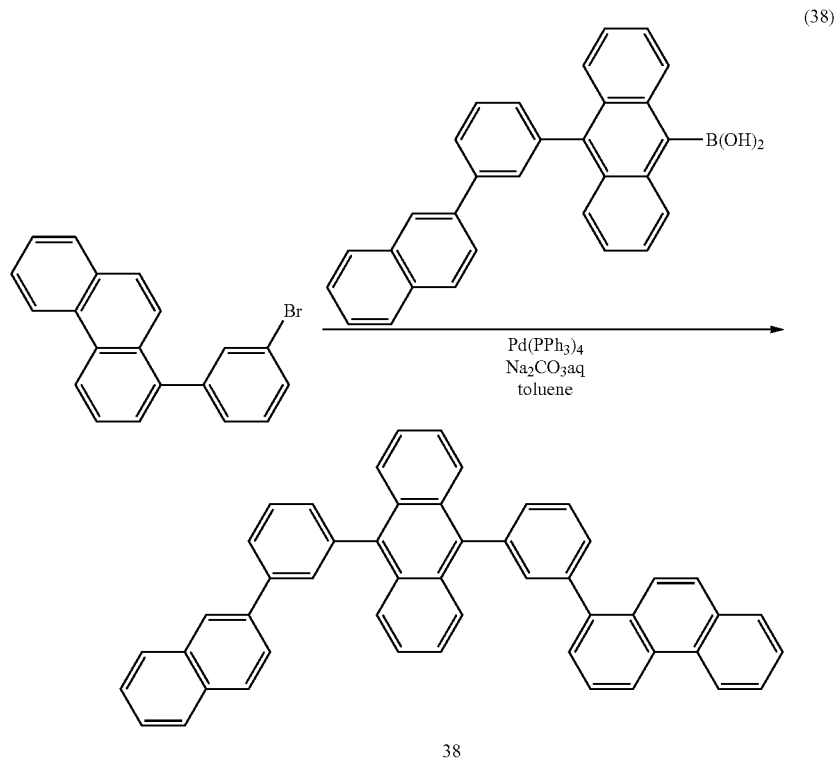

Synthesis of Compound 38

Synthesis was performed in the same manner as in the synthesis of Compound 1 except that: 1-(3-bromophenyl) phenanthrene was used instead of 2-(4-bromophenyl) phenanthrene; and 10-[3-(2-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 632 with respect to its molecular weight, i.e., 632.25.

Synthesis of Compound 39

[Chem. 88]

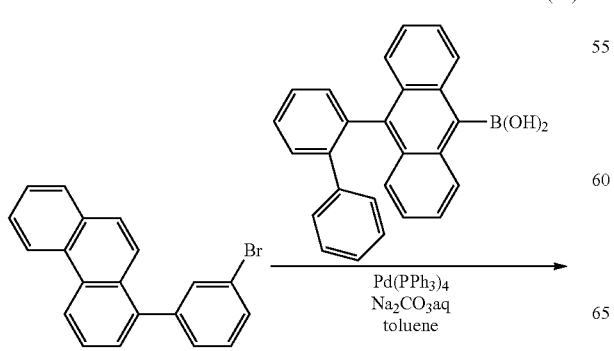

-continued

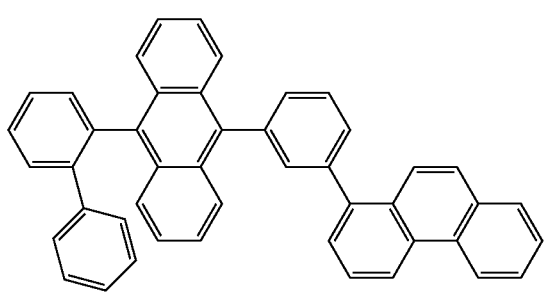

Synthesis of Compound 39

Synthesis was performed in the same manner as in the synthesis of Compound 1 except that: 1-(3-bromophenyl) phenanthrene was used instead of 2-(4-bromophenyl) phenanthrene; and 10-(2-biphenyl) anthracene-9-boronic acid synthesized by a known method was used instead of 10-(2-naphthyl)anthracene-9-boronic acid. Mass spectral analysis confirmed that the resultant was a target product and had a ratio m/e of 582 with respect to its molecular weight, i.e., 582.23.

Synthesis of Compound 40

[Chem. 89]

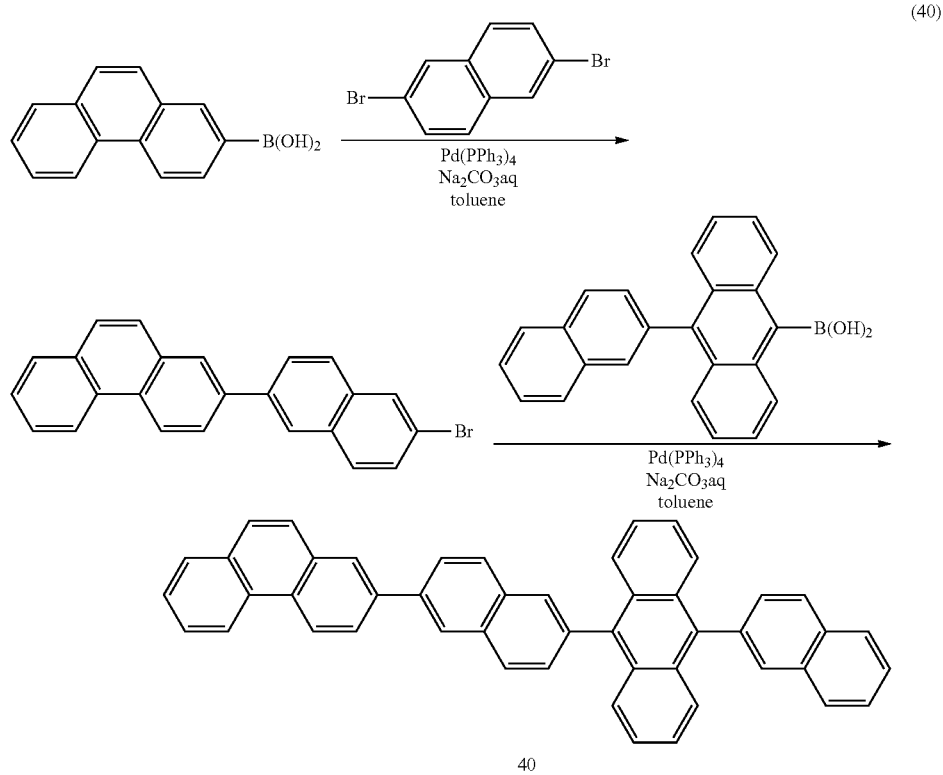

Synthesis of Compound 40

(40-1) Synthesis of 2-(6-bromonaphthalene-2-yl)phenanthrene

Synthesis was performed in the same manner as in the synthesis of 2-(4-bromophenyl)phenanthrene except that 2,6-dibromo naphthalene was used instead of 4-bromoiodobenzene.

(40-2) Synthesis of Compound 40

Synthesis was performed in the same manner as in the synthesis of Compound 1 except that 2-(6-bromonaphthalene-2-yl)phenanthrene was used instead of 2-(4-bromophenyl)phenanthrene. Mass spectral analysis confirmed that the resultant was a target product and had a ratio m/e of 606 with respect to its molecular weight, i.e., 606.23.

Synthesis of Compound 41

[Chem. 90]

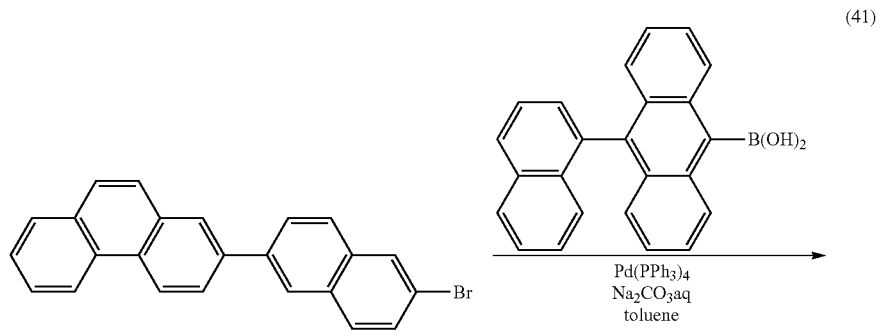

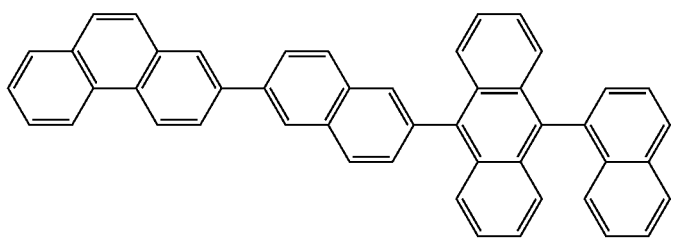

41

Synthesis of Compound 41

Synthesis was performed in the same manner as in the synthesis of Compound 1 except that: 2-(6-bromonaphthalene-2-yl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 606 with respect to its molecular weight, i.e., 606.23.

Synthesis of Compound 42

[Chem. 91]

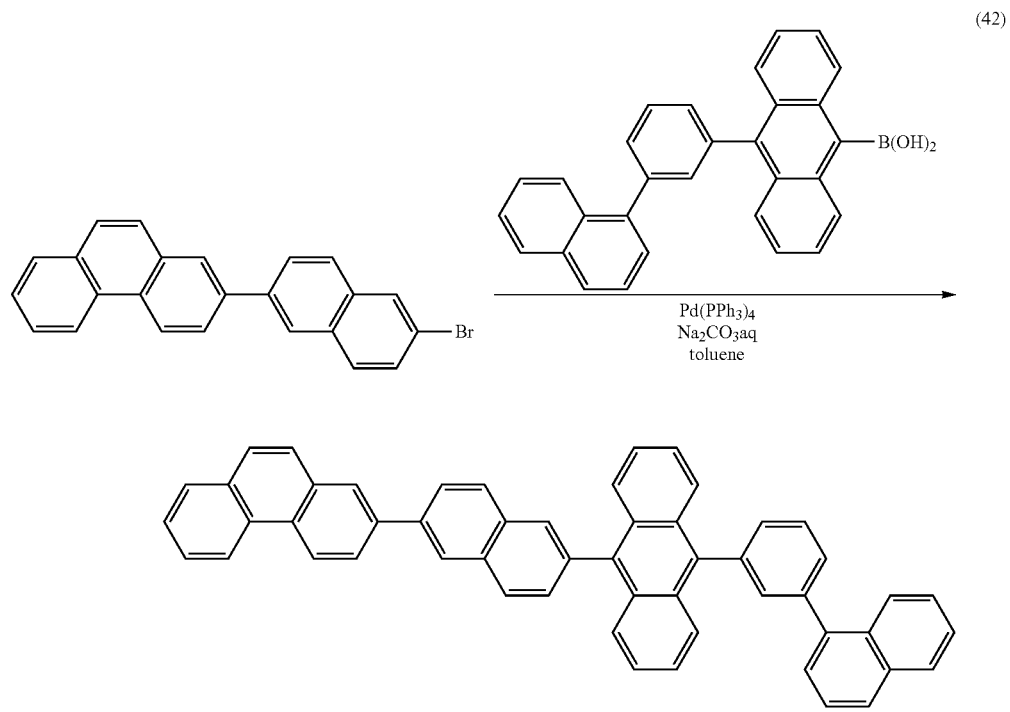

(42)

42

Synthesis of Compound 42

Synthesis was performed in the same manner as in the synthesis of Compound 1 except that: 2-(6-bromonaphtha-lene-2-yl)phenanthrene was used instead of 2-(4-bromophe-nyl)phenanthrene; and 10-[3-(1-naphthyl)phenyl]an-thracene-9-boronic acid synthesized by a known method was used instead of 10-(2-naphthyl)anthracene-9-boronic acid. Mass spectral analysis confirmed that the resultant was a target product and had a ratio m/e of 682 with respect to its molecular weight, i.e., 682.27.

Synthesis of Compound 43

[Chem. 92]

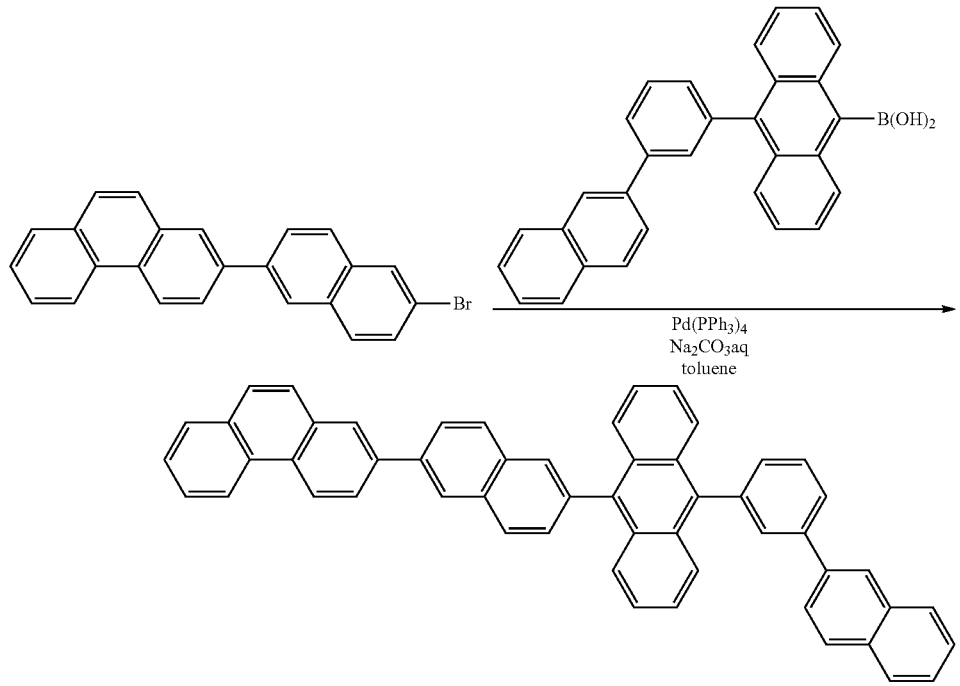

Synthesis of Compound 43

Synthesis was performed in the same manner as in the synthesis of Compound 1 except that: 2-(6-bromonaphtha-lene-2-yl)phenanthrene was used instead of 2-(4-bromophe-nyl)phenanthrene; and 10-[3-(2-naphthyl)phenyl]an-thracene-9-boronic acid synthesized by a known method was used instead of 10-(2-naphthyl)anthracene-9-boronic acid. Mass spectral analysis confirmed that the resultant was a target product and had a ratio m/e of 682 with respect to its molecular weight, i.e., 682.27.

Synthesis of Compound 44

[Chem. 93]

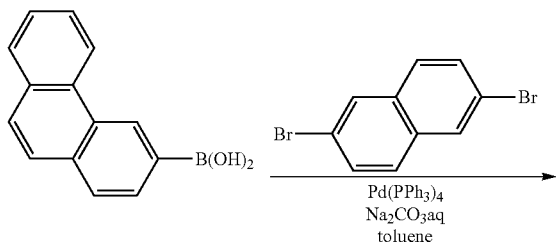

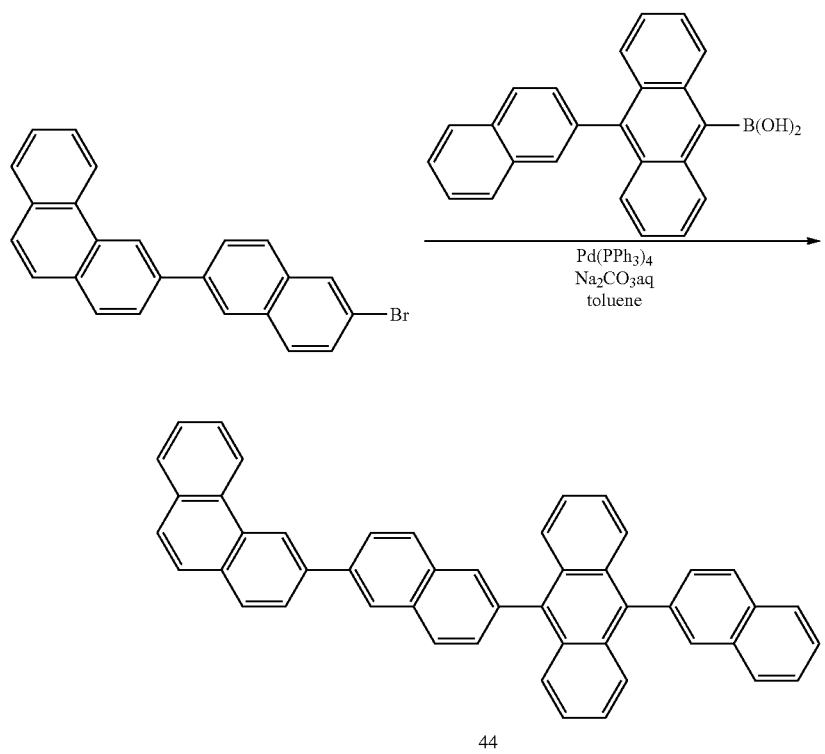

Synthesis of Compound 44

(44-1) Synthesis of 3-(6-bromonaphthalene-2-yl)phenanthrene

Synthesis was performed in the same manner as in the synthesis of 2-(4-bromophenyl)phenanthrene except that: phenanthrene-3-boronic acid was used instead of phenanthrene-2-boronic acid; and 2,6-dibromonaphthalene was used instead of 4-bromoiodobenzene.

(44-2) Synthesis of Compound 44

Synthesis was performed in the same manner as in the synthesis of Compound 1 except that: 3-(6-bromonaphthalene-2-yl)phenanthrene was used instead of 2-(4-bromophenyl)phenanthrene. Mass spectral analysis confirmed that the resultant was a target product and had a ratio m/e of 606 with respect to its molecular weight, i.e., 606.23.

[Chem. 94]

Synthesis of Compound 45

(45)

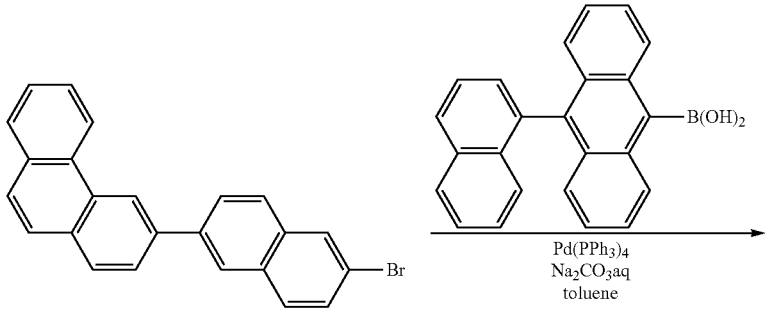

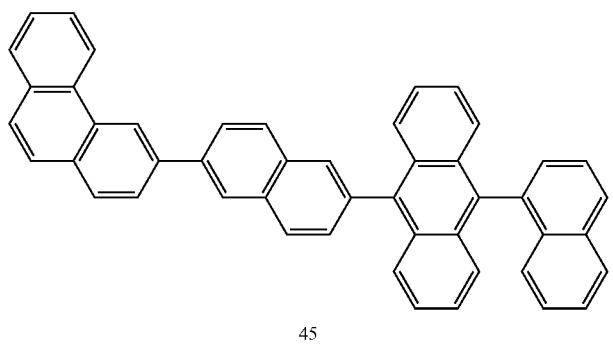

45

Synthesis of Compound 45

Synthesis was performed in the same manner as in the synthesis of Compound 1 except that: 3-(6-bromonaphthalene-2-yl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 606 with respect to its molecular weight, i.e., 606.23.

Synthesis of Compound 46

[Chem. 95]

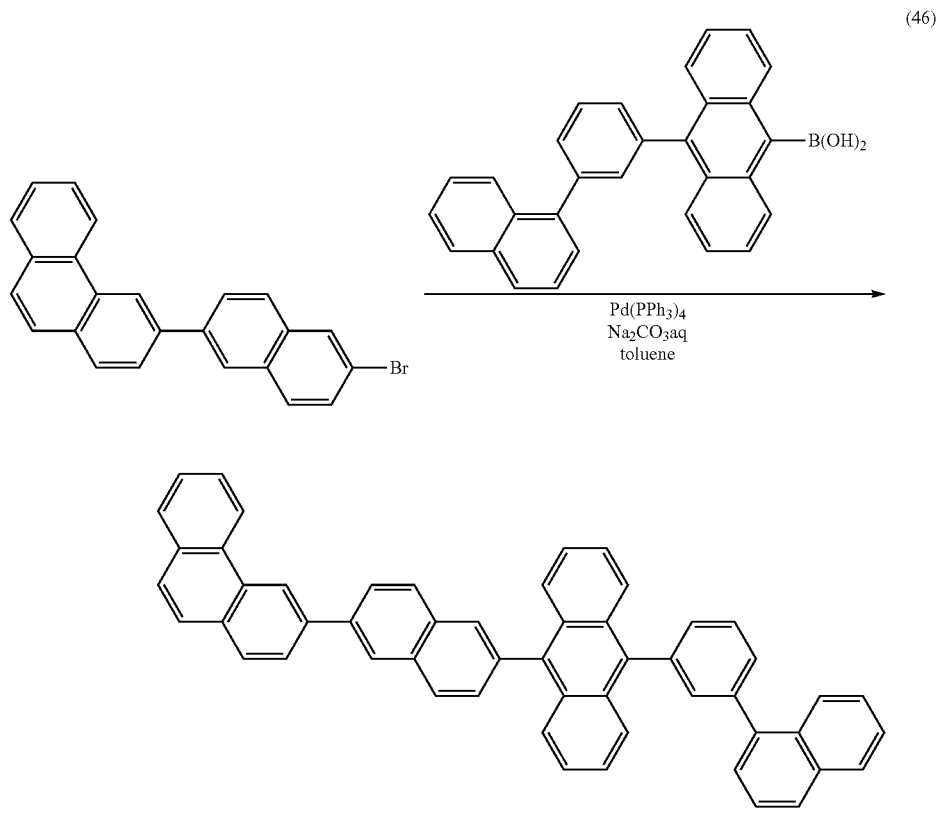

46

Synthesis of Compound 46

Synthesis was performed in the same manner as in the synthesis of Compound 1 except that: 3-(6-bromonaphtha-lene-2-yl)phenanthrene was used instead of 2-(4-bromophe-nyl)phenanthrene; and 10-[3-(1-naphthyl)phenyl]an-thracene-9-boronic acid synthesized by a known method was used instead of 10-(2-naphthyl)anthracene-9-boronic acid. Mass spectral analysis confirmed that the resultant was a target product and had a ratio m/e of 682 with respect to its molecular weight, i.e., 682.27.

Synthesis of Compound 47

[Chem. 96]

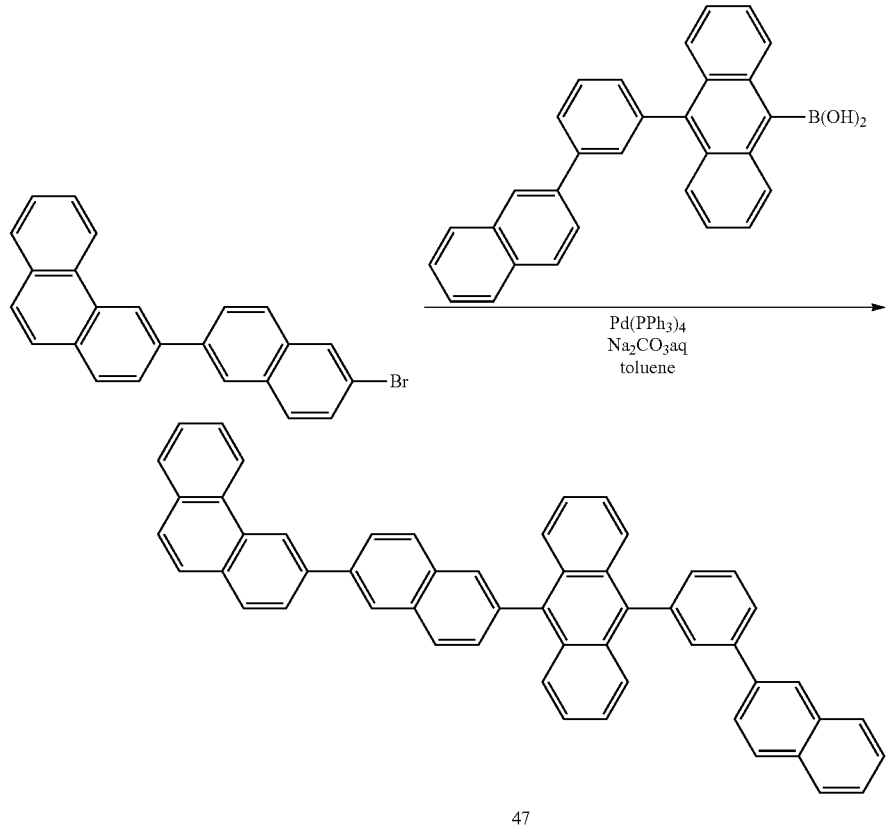

Synthesis of Compound 47

Synthesis was performed in the same manner as in the synthesis of Compound 1 except that: 3-(6-bromonaphtha-lene-2-yl)phenanthrene was used instead of 2-(4-bromophe-nyl)phenanthrene; and 10-[3-(2-naphthyl)phenyl]an-thracene-9-boronic acid synthesized by a known method was used instead of 10-(2-naphthyl)anthracene-9-boronic acid. Mass spectral analysis confirmed that the resultant was a target product and had a ratio m/e of 682 with respect to its molecular weight, i.e., 682.27.

Synthesis of Compound 48

[Chem. 97]

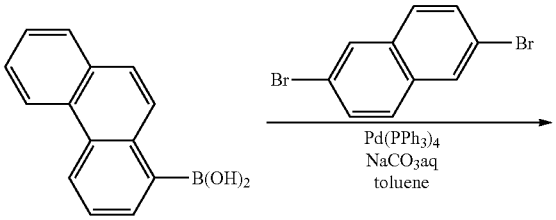

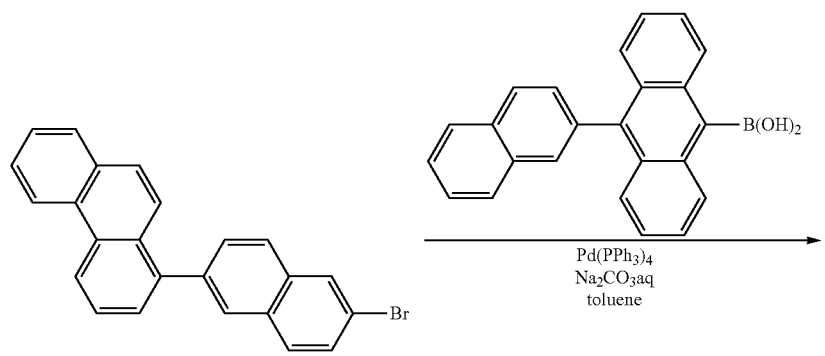

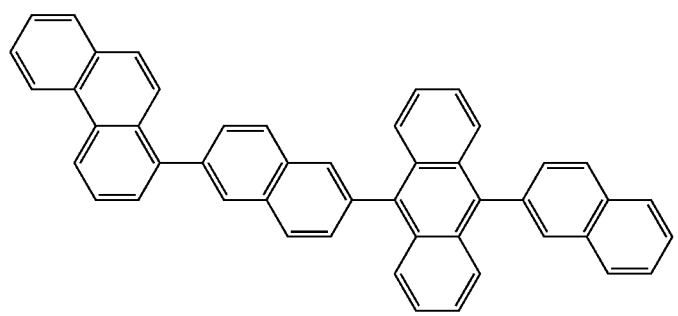

48

Synthesis of Compound 48

(48-1) Synthesis of 1-(6-bromonaphthalene-2-yl)phenanthrene

Synthesis was performed in the same manner as in the synthesis of 2-(4-bromophenyl)phenanthrene except that: phenanthrene-1-boronic acid was used instead of phenanthrene-2-boronic acid; and 2,6-dibromonaphthalene was used instead of 4-bromoiodobenzene.

[Chem. 98]

(48-2) Synthesis of Compound 48

Synthesis was performed in the same manner as in the synthesis of Compound 1 except that: 1-(6-bromonaphthalene-2-yl)phenanthrene was used instead of 2-(4-bromophenyl)phenanthrene. Mass spectral analysis confirmed that the resultant was a target product and had a ratio m/e of 606 with respect to its molecular weight, i.e., 606.23.

Synthesis of Compound 49

(49)

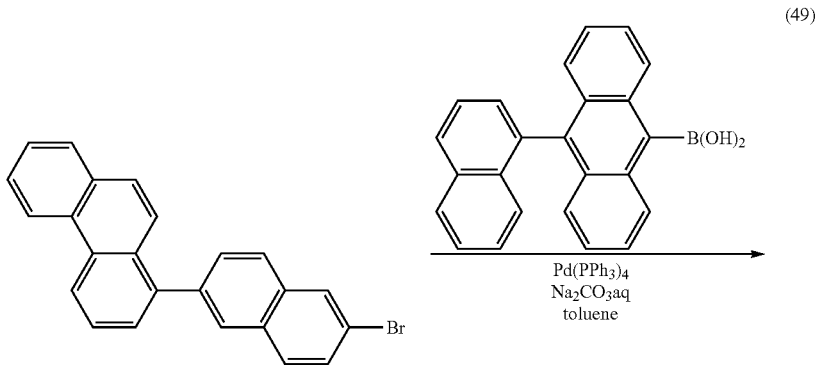

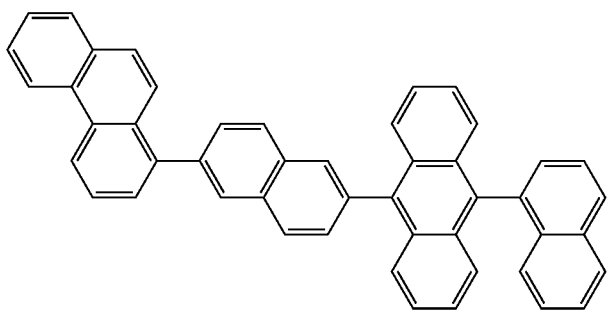

49

Synthesis of Compound 49

Synthesis was performed in the same manner as in the synthesis of Compound 1 except that: 1-(6-bromonaphthalene-2-yl)phenanthrene was used instead of 2-(4-bromophenyl)phenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 606 with respect to its molecular weight, i.e., 606.23.

[Chem. 99]

Synthesis of Compound 50

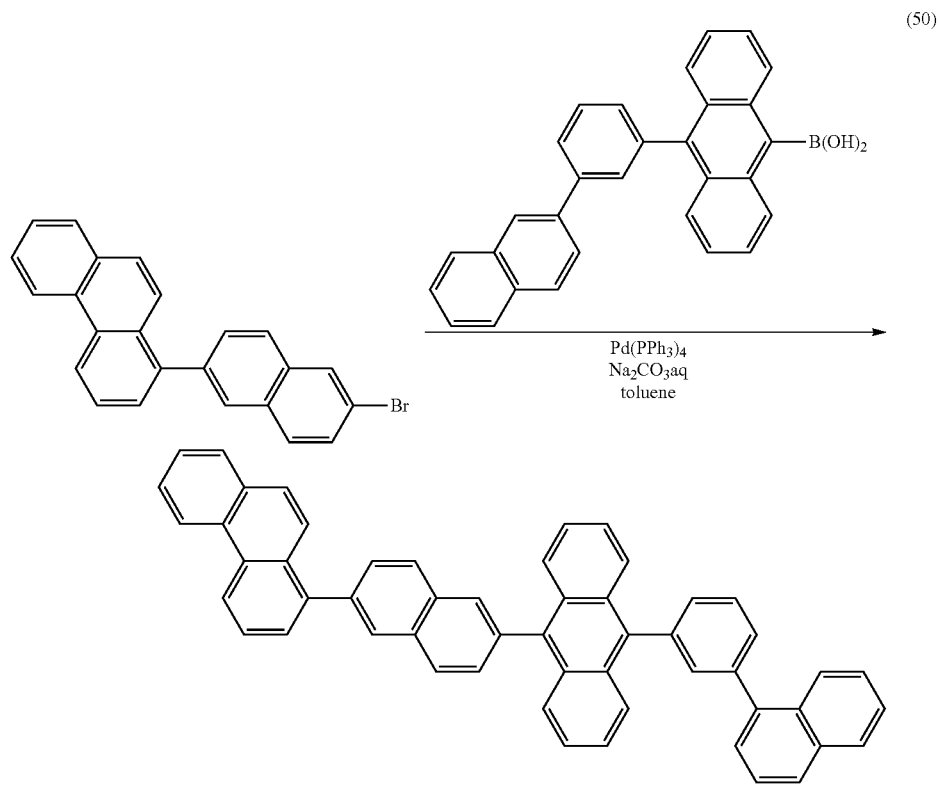

50

Synthesis of Compound 50

Synthesis was performed in the same manner as in the synthesis of Compound 1 except that: 1-(6-bromonaphthalene-2-yl)phenanthrene was used instead of 2-(4-bromophenyl)phenanthrene; and 10-[3-(1-naphthyl)phenyl]anthracene-9-boronic acid synthesized by a known method was used instead of 10-(2-naphthyl)anthracene-9-boronic acid. Mass spectral analysis confirmed that the resultant was a target product and had a ratio m/e of 682 with respect to its molecular weight, i.e., 682.27.

Synthesis of Compound 51

[Chem. 100]

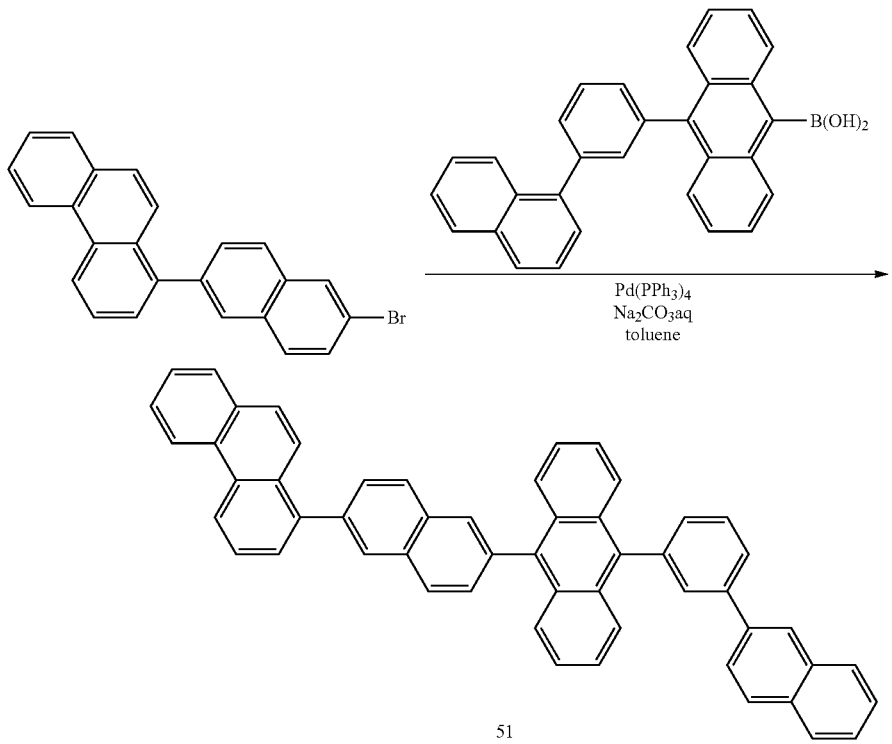

Synthesis of Compound 52

[Chem. 101]

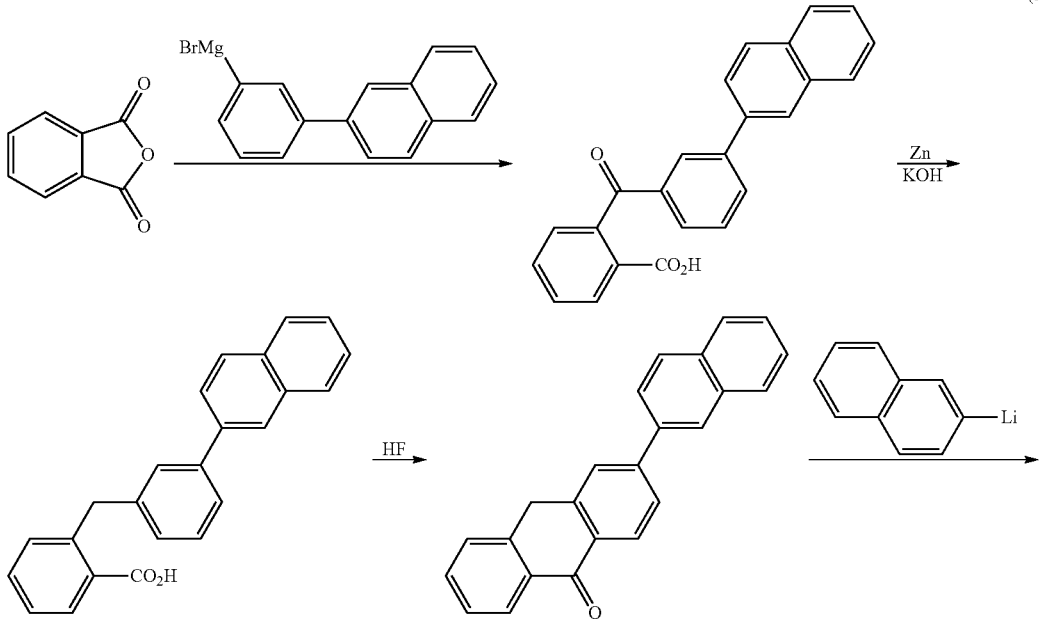

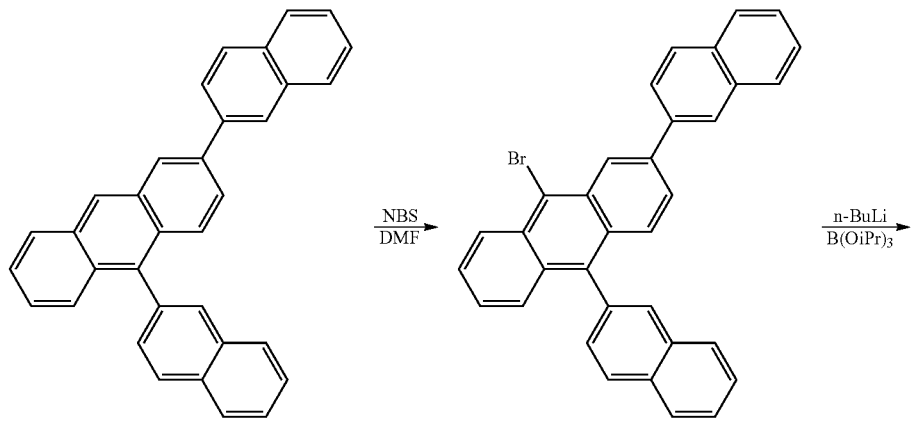

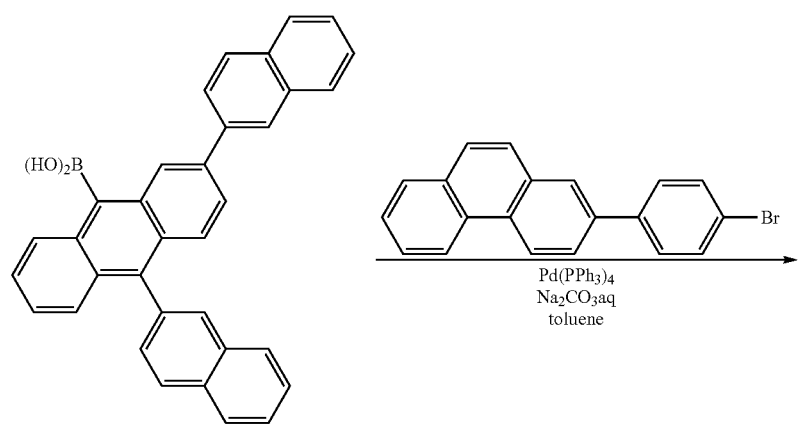

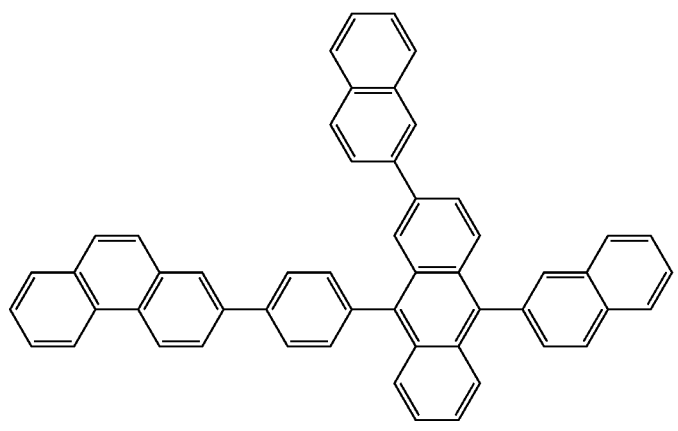

52

Synthesis of Compound 51

Synthesis was performed in the same manner as in the synthesis of Compound 1 except that: 1-(6-bromonaphtha-lene-2-yl)phenanthrene was used instead of 2-(4-bromophe-nyl)phenanthrene; and 10-[3-(2-naphthyl)phenyl]an-thracene-9-boronic acid synthesized by a known method was used instead of 10-(2-naphthyl)anthracene-9-boronic acid. Mass spectral analysis confirmed that the resultant was a target product and had a ratio m/e of 682 with respect to its molecular weight, i.e., 682.27.

Synthesis of Compound 52

(52-1) Synthesis of 2-[3-(2-naphthyl)benzoyl]benzoic acid

Under an argon atmosphere, 132 g of magnesium were dispersed in 500 mL of ether. A solution of 142 g of 2-(3-bromophenyl)naphthalene in 500 mL of ether was added to the dispersion, and then the mixture was stirred at room temperature for 1 hour. A solution of 74 g of phthalic anhydride in 150 mL of benzene was added to the mixture, and then the resultant reaction solution was stirred for 3 hours under reflux. After having been cooled to room temperature, the reaction solution was poured into ice water, and then 1 L of 10% hydrochloric acid was added to the mixture. The organic layer was separated and extracted with an aqueous solution of potassium carbonate. The alkaline extract was acidified, and then the resultant solid was washed with boiling water. The resultant crude product was recrystallized with acetic acid. Thus, 121 g of 2-(3-phenylbenzoyl)benzoic acid were obtained (in 69% yield).

(52-2) Synthesis of 2-[3-(2-naphthyl)benzyl]benzoic acid

First, 121 g of 2-[3-(2-naphthyl)benzoyl]benzoic acid were dissolved in 10 L of a 1N sodium hydroxide solution, and then a zinc powder activated with an aqueous solution of copper sulfate was added to the solution. The reaction solution was stirred for 50 hours under ref lux. After having been cooled to room temperature, the reaction solution was filtrated. The filtrate was acidified, and then the resultant solid was washed with boiling water. Thus, 110 g of 2-[3-(2-naphthyl)benzyl]benzoic acid were obtained (in 90% yield)

(52-3) Synthesis of 2-(2-naphthyl)-10-anthrone

First, 11.7 g of 2-[3-(2-naphthyl)benzyl]benzoic acid were added to 250 mL of liquid hydrogen fluoride, and then the mixture was stirred until hydrogen fluoride evaporated. The residue was dissolved in chloroform, and then the solution was sequentially washed with water, an aqueous solution of ammonium hydroxide, and water. After the chloroform solution had been dried with magnesium sulfate, the solvent was removed by distillation under reduced pressure. The residue was crystallized with methanol, and was then recrystallized with cyclohexane and acetone. Thus, 6.76 g of 2-phenyl-10-anthrone were obtained (in 61% yield).

(52-4) Synthesis of 2,10-di(2-naphthyl)anthracene

Under an argon atmosphere, a solution of 4.81 g of 2-bromonaphthalene in 30 mL of THF was cooled to −78° C. Subsequently, 25 mL of a 1.6-M solution of n-butyllithium in hexane were dropped to the solution, and then the mixture was stirred at −78° C. for 1 hour. A solution of 6.76 g of 2-(2-naphthyl)-10-anthrone in 20 mL of THF was added to the mixture, and then the resultant reaction solution was stirred for 5 hours at 50° C. under heat. After the reaction solution had been cooled to room temperature, 100 mL of 10% hydrochloric acid were added to the solution. After the water layer had been removed, the organic layer was washed with water and a saturated salt solution. Then, the organic layer was dried with magnesium sulfate. The solvent was removed by distillation under reduced pressure, and then the residue was purified by silica gel column chromatography. Thus, 2.90 g of 2,10-di(2-naphthyl)anthracene were obtained (in 32% yield).

(52-5) Synthesis of 9-bromo-2,10-di(2-naphthyl)anthracene

First, 2.90 g of 2-phenyl-10-(6-phenylnaphthalen-2-yl) anthracene were dissolved in 30 mL of DMF, and then a solution of 1.32 g of N-bromosuccinimide in 10 mL of DMF was added to the solution. The mixture was stirred at 60° C. for 5 hours under heat. After having been cooled to room temperature, the reaction solution was poured into 100 mL of water. The precipitated crystal was separated by filtration, and was then sequentially washed with methanol, water, and methanol. After that, the crystal was purified by silica gel column chromatography. Thus, 3.09 g of 9-bromo-2,10-di(2-naphthyl)anthracene were obtained (in 90% yield).

(52-6) Synthesis of 2,10-di(2-naphthyl)anthracene-9-boronic acid

Under an argon atmosphere, 10.2 g of 9-bromo-2,10-di(2-naphthyl)anthracene, 100 mL of dehydrated ether, and 100 mL of dehydrated toluene were loaded, and then the reaction solution was cooled to −60° C. After that, 14 mL of a 1.6-M solution of n-butyllithium in hexane were added to the reaction solution. The reaction solution was stirred for 1 hour while its temperature was increased to 0° C. The reaction solution was cooled to −60° C. again, and then a solution of 11.3 g of triisopropyl borate in 10 mL of dehydrated ether was dropped to the reaction solution. The reaction solution was continuously stirred for 5 hours while its temperature was increased to room temperature. Subsequently, 1 L of a 10% aqueous solution of hydrochloric acid was added to the reaction solution, and then the mixture was stirred for 1 hour. The water layer was removed, and the organic layer was washed with water and a saturated salt solution, and was then dried with magnesium sulfate. After magnesium sulfate had been separated by filtration, the organic layer was concentrated. The resultant solid was washed with hexane and toluene. Thus, 5.69 g of 2,10-di(2-naphthyl)anthracene-9-boronic acid as a target were obtained (in 60% yield).

(52-7) Synthesis of Compound 52

Under an argon atmosphere, 5.21 g of 2,10-di(2-naphthyl) anthracene-9-boronic acid, 3.33 g of 2-(4-bromophenyl) phenanthrene, 0.231 g of tetrakis(triphenylphosphine)palladium(0), 40 mL of toluene, and 20 mL of a 2-M aqueous solution of sodium carbonate were loaded, and then the mixture was stirred for 8 hours under reflux. After the mixture had been cooled to room temperature, the precipitated crystal was separated by filtration. The resultant crystal was washed with methanol, water, and methanol, and was then recrystallized with toluene. Thus, 5.59 g of a pale yellow crystal were obtained. Mass spectral analysis confirmed that the crystal was a target product and had a ratio m/e of 682 with respect to its molecular weight, i.e., 682.27.

Synthesis of Compound 53
[Chem. 102]
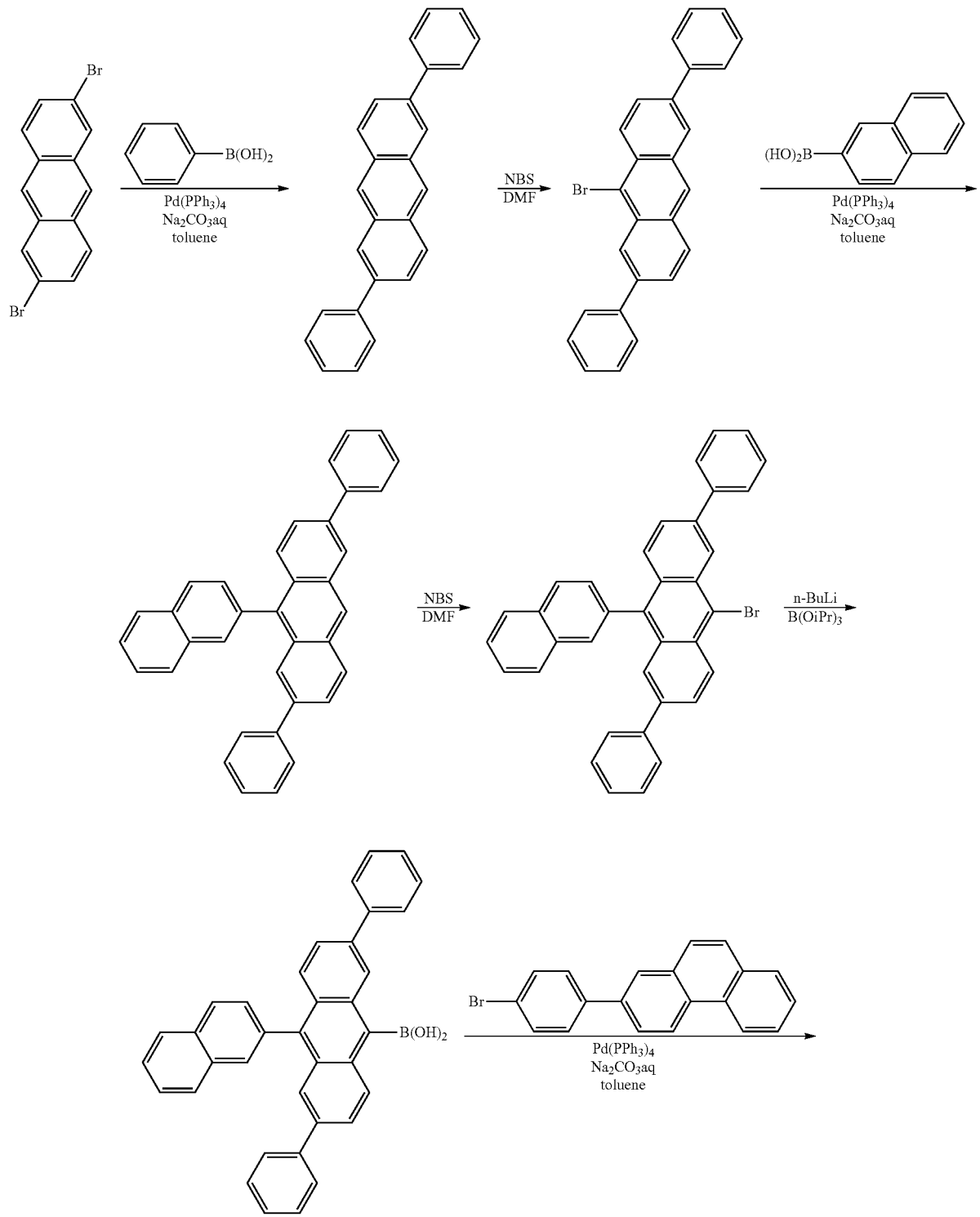
(53)

-continued

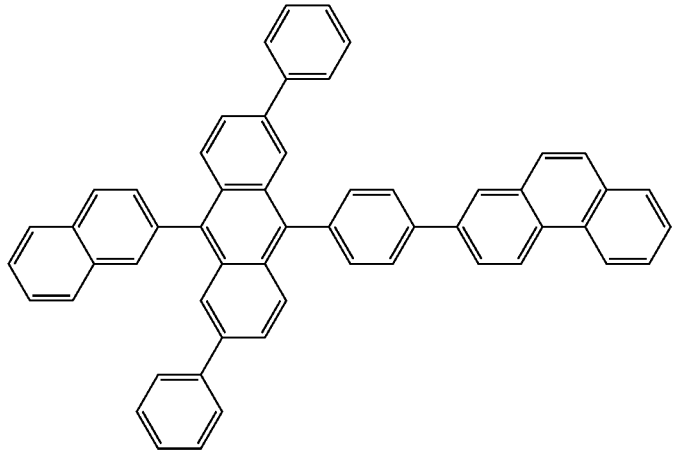

53

Synthesis of Compound 53

(53-1) Synthesis of 2,6-diphenylanthracene

Under an argon atmosphere, 29.0 g of phenylboronic acid, 25.7 g of 2,6-dibromoanthracene, 4.62 g of tetrakis(triphenyl phosphine) palladium (0), 800 mL of toluene, and 400 mL of a 2-M aqueous solution of sodium carbonate were loaded, and then the mixture was stirred for 8 hours under reflux. After the mixture had been cooled to room temperature, the precipitated crystal was taken by filtration. The resultant solid was repeatedly recrystallized with toluene and hexane and washed. Thus, 25.0 g of 2-phenylanthracene were obtained (in 75% yield).

(53-2) Synthesis of 9-bromo-2,6-diphenylanthracene

First, 33.0 g of 2,6-diphenylanthracene were dissolved in 200 mL of N,N-dimethylformamide under heat, and then a solution of 18.0 g of N-bromosuccinimide in 20 mL of N,N-dimethylformamide was added to the solution. The mixture was stirred at 60° C. for 6 hours under heat. After having been cooled to room temperature, the reaction solution was poured into 1 L of water. The resultant solid was sequentially washed with methanol, water, and methanol. After that, the solid was repeatedly recrystallized with toluene and hexane and washed. Thus, 33.5 g of 9-bromo-2,6-diphenylanthracene were obtained (in 82% yield).

(53-3) Synthesis of 2,6-diphenyl-9-(2-naphthyl)anthracene

Under an argon atmosphere, 20.5 g of 9-bromo-2,6-diphenyl anthracene, 9.37 g of naphthalene-2-boronic acid, 1.16 g of tetrakis(triphenylphosphine)palladium(0), 200 mL of toluene, and 100 mL of a 2-M aqueous solution of sodium carbonate were loaded, and then the mixture was stirred for 8 hours under reflux. After the mixture had been cooled to room temperature, the precipitated crystal was separated by filtration. The resultant crystal was washed with methanol, water, and methanol, and was then recrystallized with toluene. Thus, 17.1 g of a yellow crystal were obtained (in 75% yield).

(53-4) Synthesis of 9-bromo-2,6-diphenyl-10-(2-naphthyl)anthracene

First, 9.09 g of 2,6-diphenyl-9-(2-naphthyl)anthracene were dissolved in 100 mL of N,N-dimethylformamide under heat, and then a solution of 3.91 g of N-bromosuccinimide in 10 mL of N,N-dimethylformamide was added to the solution. The mixture was stirred at 60° C. for 6 hours under heat. After having been cooled to room temperature, the reaction solution was poured into 500 mL of water. The resultant solid was sequentially washed with methanol, water, and methanol. After that, the solid was repeatedly recrystallized with toluene and hexane and washed. Thus, 8.55 g of 9-bromo-2,6-diphenyl-10-(2-naphthyl)anthracene were obtained (in 80% yield).

(53-5) Synthesis of 2,6-diphenyl-10-(2-naphthyl)anthracene-9-boronic acid

Under an argon atmosphere, 10.7 g of 9-bromo-2,6-diphenyl-10-(2-naphthyl)anthracene, 100 mL of dehydrated ether, and 100 mL of dehydrated toluene were loaded, and then the reaction solution was cooled to −60° C. After that, 14 mL of a 1.6-M solution of n-butyllithium in hexane were added to the reaction solution. The reaction solution was stirred for 1 hour while its temperature was increased to 0° C. The reaction solution was cooled to −60° C. again, and then a solution of 11.3 g of triisopropyl borate in 10 mL of dehydrated ether was dropped to the reaction solution. The reaction solution was continuously stirred for 5 hours while its temperature was increased to room temperature. Subsequently, 1 L of a 10% aqueous solution of hydrochloric acid was added to the reaction solution, and then the mixture was stirred for 1 hour. The water layer was removed, and the organic layer was washed with water and a saturated salt solution, and was then dried with magnesium sulfate. After magnesium sulfate had been separated by filtration, the organic layer was concentrated. The resultant solid was washed with hexane and toluene. Thus, 6.00 g of 2,6-diphenyl-10-(2-naphthyl)anthracene-9-boronic acid as a target were obtained (in 60% yield).

(53-6) Synthesis of Compound 53

Under an argon atmosphere, 5.00 g of 2,6-diphenyl-10-(2-naphthyl)anthracene-9-boronic acid, 3.33 g of 2-(4-bromophenyl)phenanthrene, 0.231 g of tetrakis(triphenylphosphine) palladium(0), 40 mL of toluene, and 20 mL of a 2-M aqueous solution of sodium carbonate were loaded, and then the mixture was stirred for 8 hours under reflux. After the mixture had been cooled to room temperature, the precipitated crystal was separated by filtration. The resultant crystal was washed with methanol, water, and methanol, and was then recrystallized with toluene. Thus, 5.66 g of a pale yellow crystal were obtained. Mass spectral analysis confirmed that the crystal was a target product and had a ratio m/e of 708 with respect to its molecular weight, i.e., 708.28.

Synthesis of Compound 54

[Chem. 103]

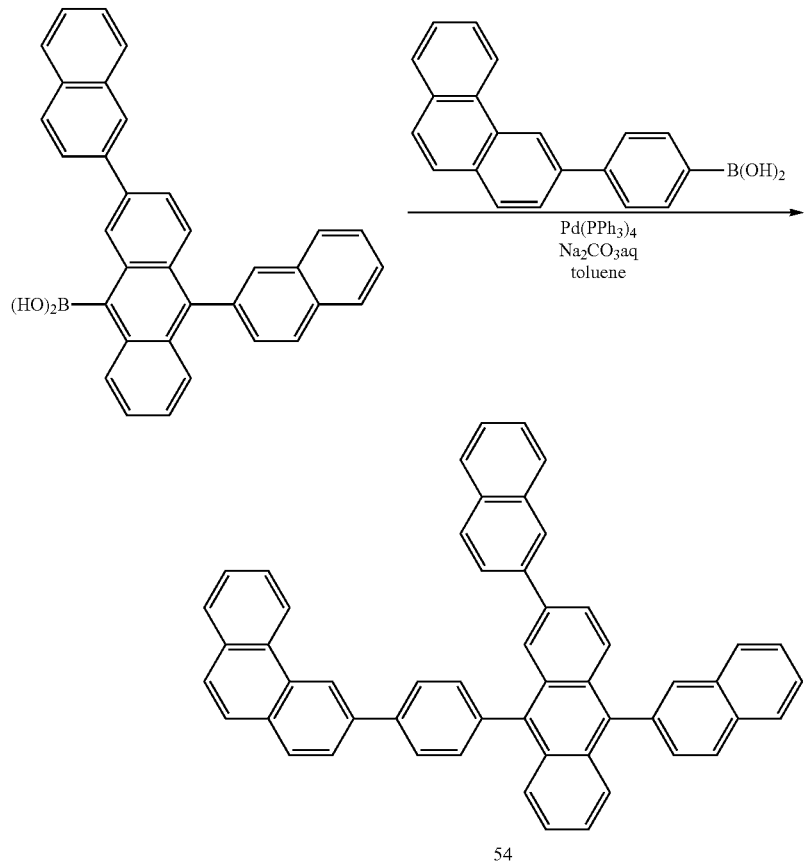

(54)

54

Synthesis of Compound 54

Synthesis was performed in the same manner as in the synthesis of Compound 52 except that 3-(4-bromophenyl) phenanthrene was used instead of 2-(4-bromophenyl) phenanthrene. Mass spectral analysis confirmed that the resultant was a target product and had a ratio m/e of 682 with respect to its molecular weight, i.e., 682.27.

Synthesis of Compound 55

[Chem. 104]

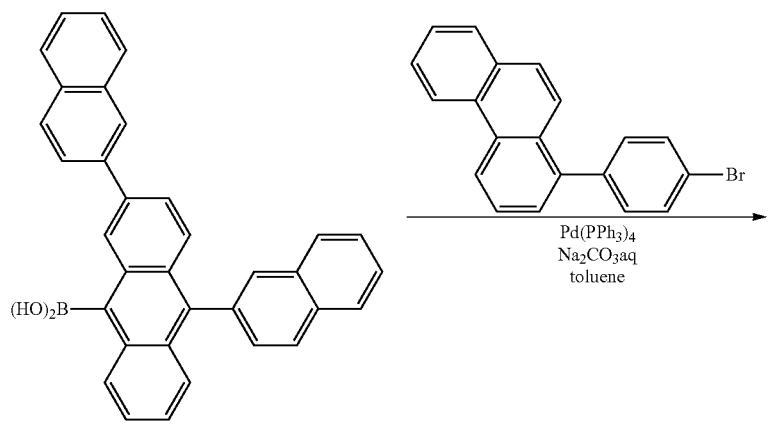

(55)

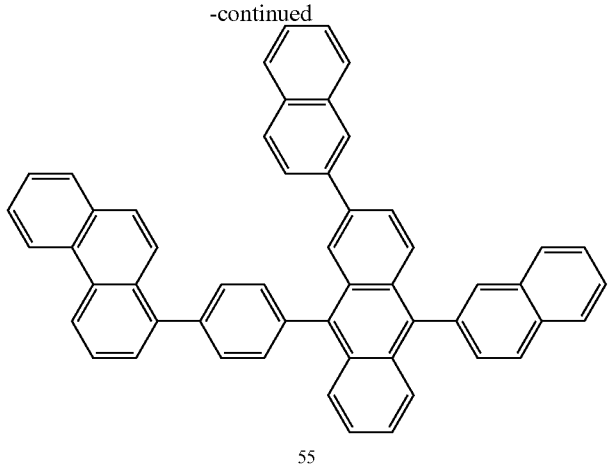
55
Synthesis of Compound 55
Synthesis was performed in the same manner as in the synthesis of Compound 52 except that 1-(4-bromophenyl) phenanthrene was used instead of 2-(4-bromophenyl) phenanthrene. Mass spectral analysis confirmed that the resultant was a target product and had a ratio m/e of 682 with respect to its molecular weight, i.e., 682.27.
Synthesis of Compound 56
[Chem. 105]
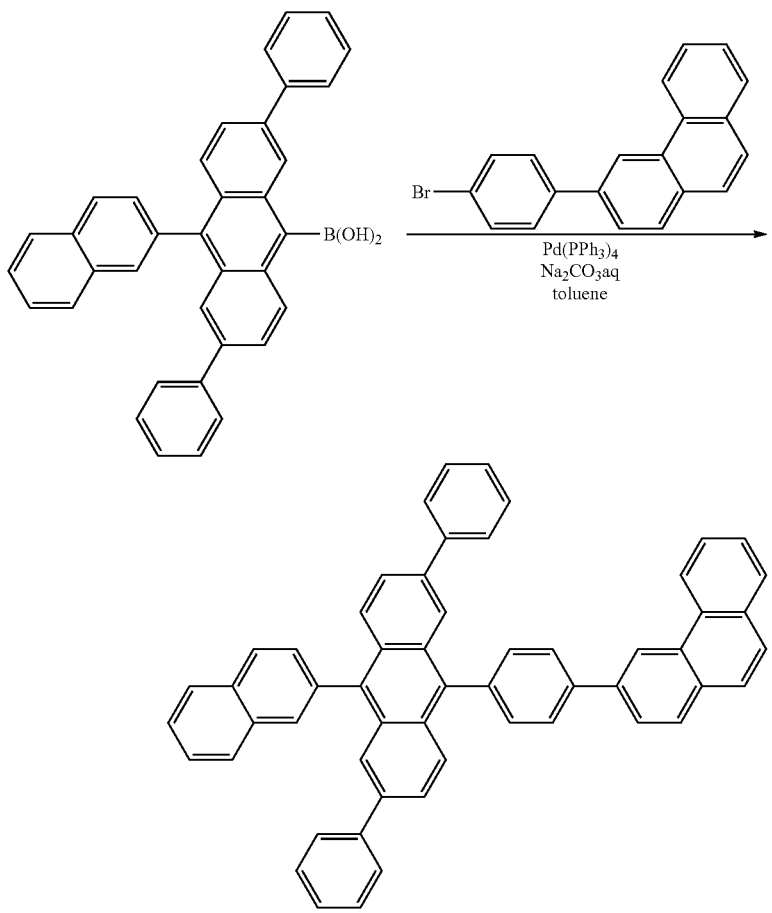
56

Synthesis of Compound 56

Synthesis was performed in the same manner as in the synthesis of Compound 52 except that 3-(4-bromophenyl) phenanthrene was used instead of 2-(4-bromophenyl) phenanthrene. Mass spectral analysis confirmed that the resultant was a target product and had a ratio m/e of 708 with respect to its molecular weight, i.e., 708.28.

Synthesis of Compound 57

[Chem. 106]

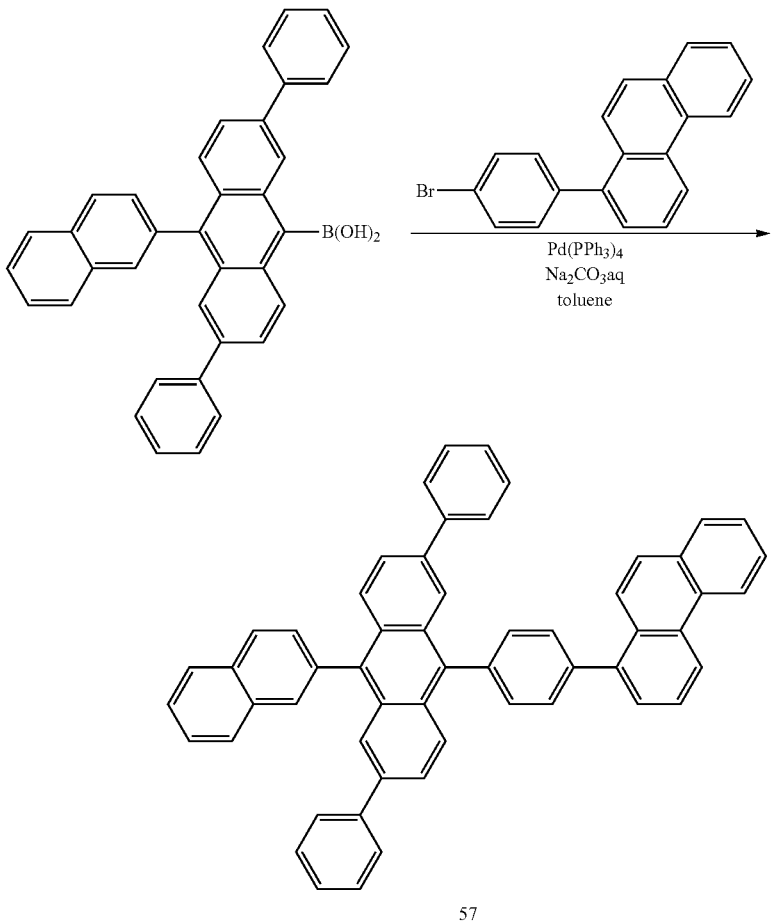

Synthesis of Compound 57

Synthesis was performed in the same manner as in the synthesis of Compound 52 except that 1-(4-bromophenyl) phenanthrene was used instead of 2-(4-bromophenyl) phenanthrene. Mass spectral analysis confirmed that the resultant was a target product and had a ratio m/e of 708 with respect to its molecular weight, i.e., 708.28.

Synthesis of Compound 58

[Chem. 107]

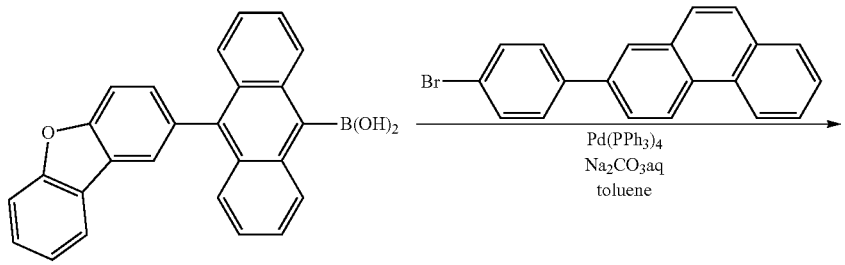

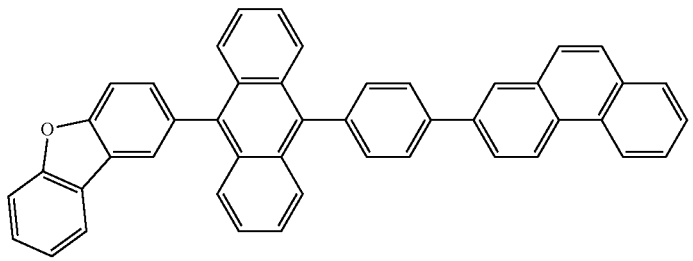

58

Synthesis of Compound 58

Synthesis was performed in the same manner as in the synthesis of Compound 1 except that 10-(2-dibenzofuranyl)anthracene-9-boronic acid synthesized by a known method was used instead of 10-(2-naphthyl)anthracene-9-boronic acid. Mass spectral analysis confirmed that the resultant was a target product and had a ratio m/e of 596 with respect to its molecular weight, i.e., 596.21.

Synthesis of Compound 59

[Chem. 108]

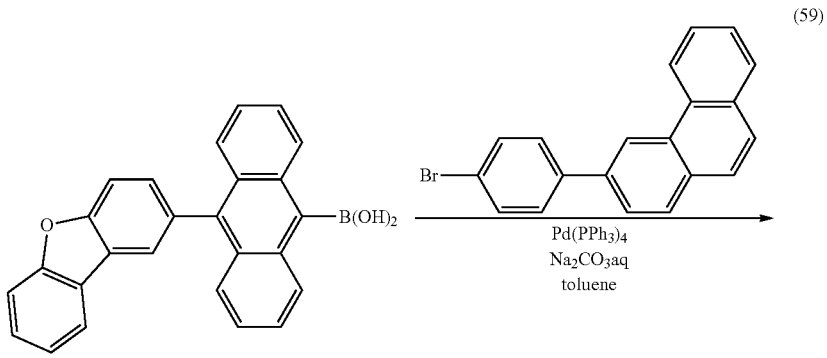

(59)

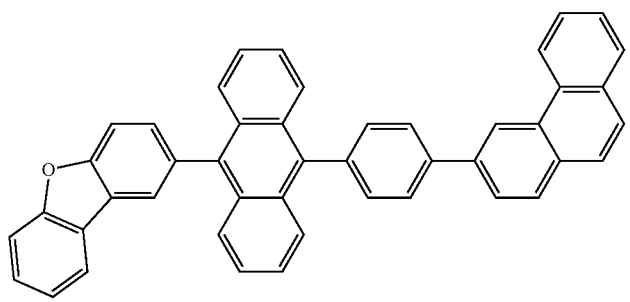

59

Synthesis of Compound 59

Synthesis was performed in the same manner as in the synthesis of Compound 1 except that: 10-(2-dibenzofuranyl)anthracene-9-boronic acid synthesized by a known method was used instead of 10-(2-naphthyl)anthracene-9-boronic acid; and 3-(4-bromophenyl)phenanthrene was used instead of 2-(4-bromophenyl)phenanthrene. Mass spectral analysis confirmed that the resultant was a target product and had a ratio m/e of 596 with respect to its molecular weight, i.e., 596.21.

Synthesis of Compound 60

[Chem. 109]

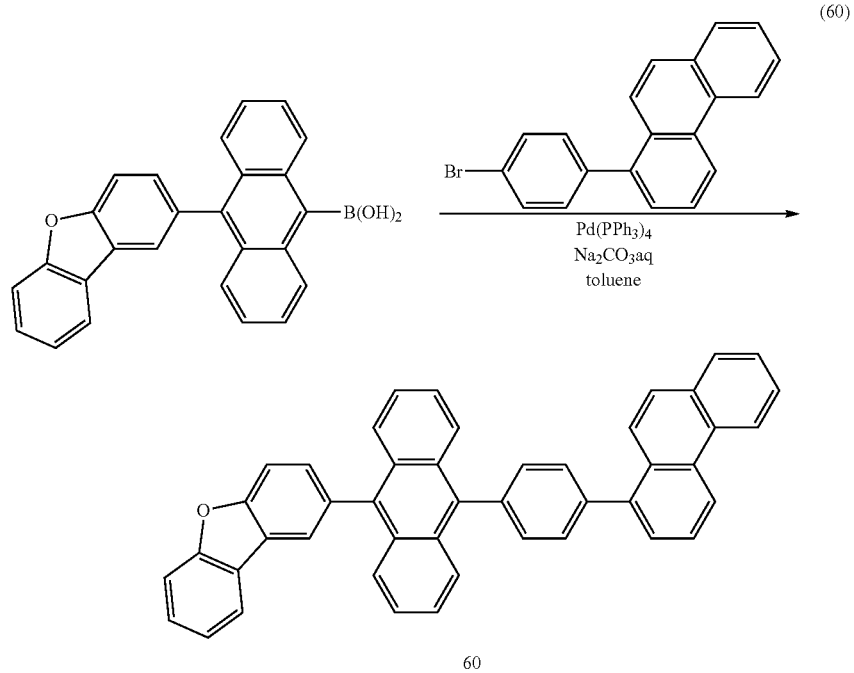

(60)

Synthesis of Compound 60

Synthesis was performed in the same manner as in the synthesis of Compound 1 except that: 10-(2-dibenzofuranyl)anthracene-9-boronic acid synthesized by a known method was used instead of 10-(2-naphthyl)anthracene-9-boronic acid; and 3-(4-bromophenyl)phenanthrene was used instead of 1-(4-bromophenyl)phenanthrene. Mass spectral analysis confirmed that the resultant was a target product and had a ratio m/e of 596 with respect to its molecular weight, i.e., 596.21.

Example 1

A glass substrate (manufactured by GEOMATEC Corporation) with an ITO transparent electrode (anode) measuring 25 mm wide by 75 mm long by 1.1 mm thick was subjected to ultrasonic cleaning in isopropyl alcohol for 5 minutes. After that, the substrate was subjected to UV/ozone cleaning for 30 minutes. The glass substrate with the transparent electrode line after the cleaning was mounted on the substrate holder of a vacuum deposition apparatus. First, the compound A-1 was formed into a film having a thickness of 60 nm on the surface on the side where the transparent electrode line was formed so as to cover the transparent electrode. After forming the film formed of A-1, A-2 was formed into a film having a thickness of 20 nm on the film formed of A-1.

Further, Compound 1 of the present invention and Compound D-1 shown below were formed into a film having a thickness of 40 nm at a thickness ratio of 40:2 on the A-2 film so as to serve as a blue light emitting layer.

Alq having the following structure was formed into a film having a thickness of 20 nm by vapor deposition on the film so as to serve as an electron transporting layer. After that, LiF was formed into a film having a thickness of 1 nm. Metal Al was deposited from the vapor onto the LiF film so that a metal cathode having a thickness of 150 nm might be formed. Thus, an organic EL device was formed. Hosts and dopants except Compounds 1 to 95 used in Examples 1 to 101 and Comparative Examples 1 to 15 are collectively shown below.

[Chem. 110]

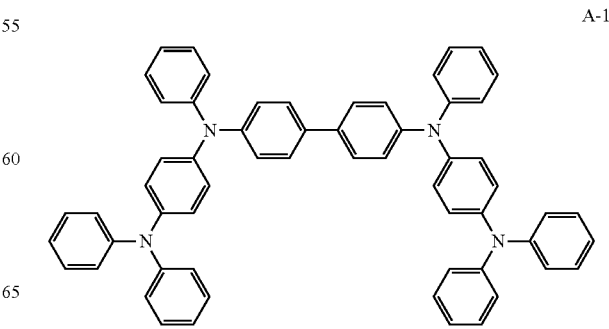

A-1

A-2
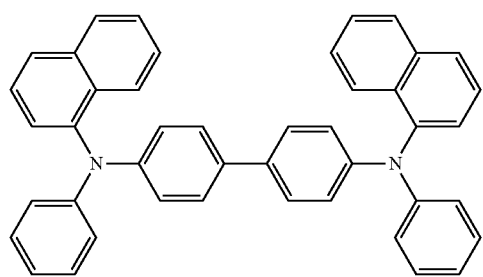
D-1
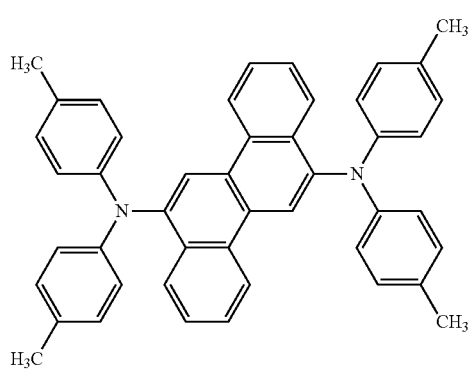
D-2
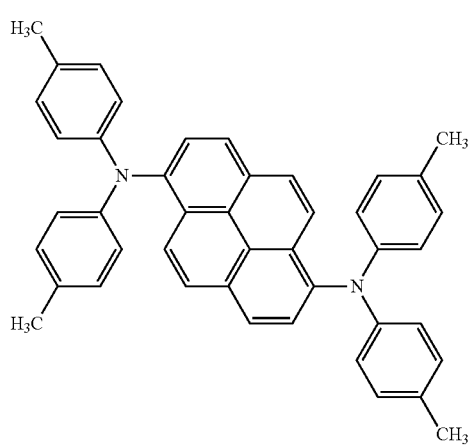
D-3
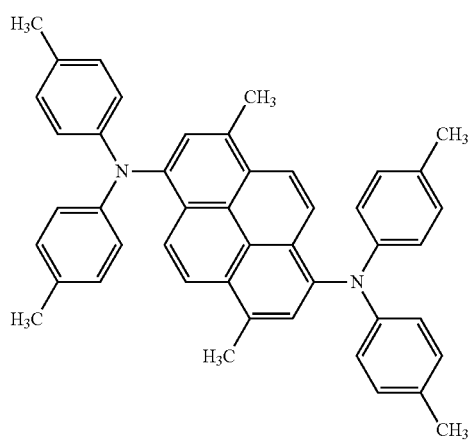
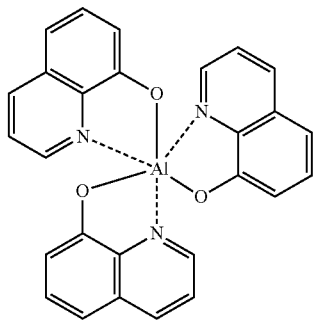
Alq
[Chem. 111]
(A)
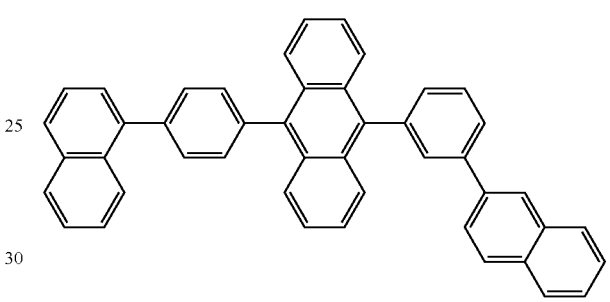
(B)
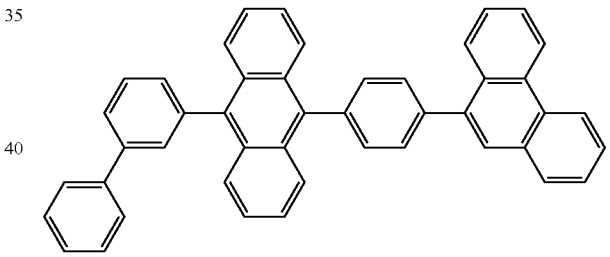
(C)
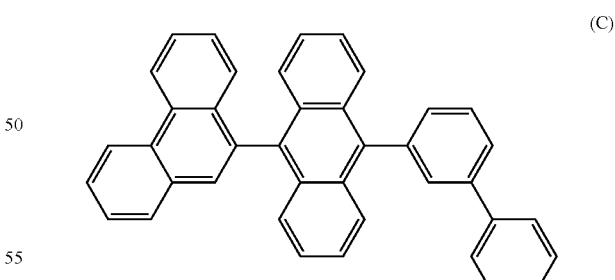
(D)
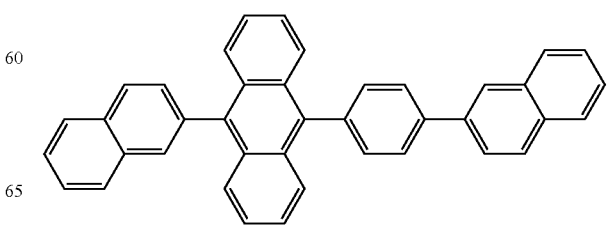

-continued (E)
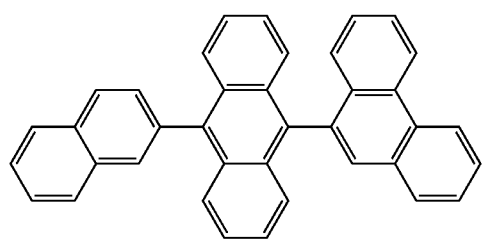

(F)
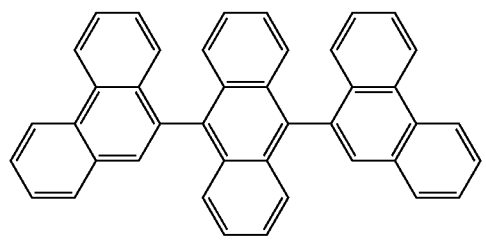

(G)
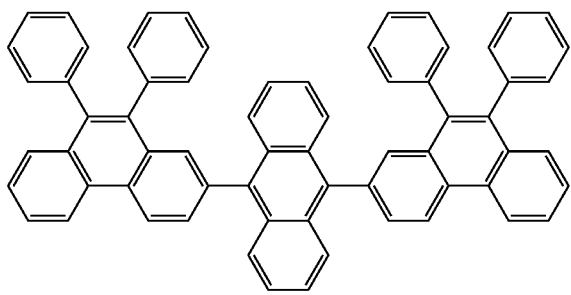

(H)
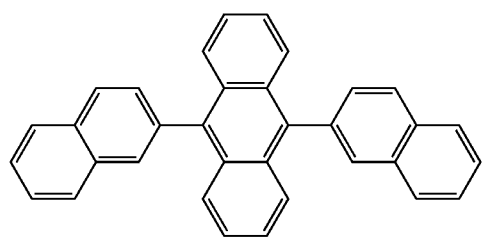

(I)
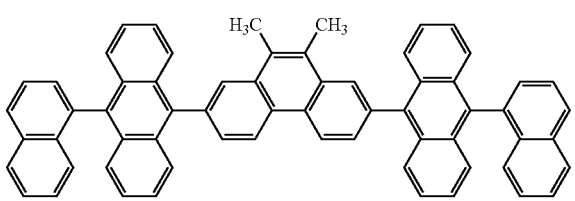

(J)
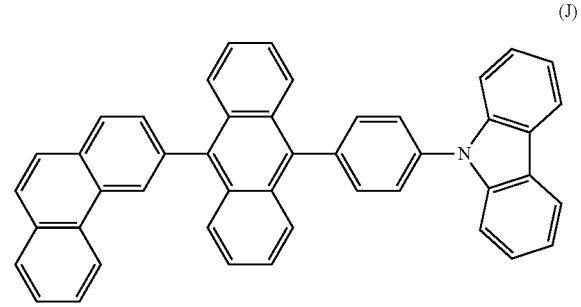

Examples 2 to 56

Organic EL devices were each produced in the same manner as in Example 1 except that a compound shown in Table 1 was used instead of Compound 1. In addition, some of the organic EL devices were each produced in the same manner as in Example 1 except that a compound shown in Table 1 was used instead of D-1.

TABLE 1

| | Host | Dopant | Current efficiency | Lifetime |
|---|---|---|---|---|
| Example No. | | | | |
| 1 | Compound 1 | D-1 | 7.1 | 9000 |
| 2 | Compound 2 | D-1 | 7.1 | 9000 |
| 3 | Compound 3 | D-1 | 7.5 | 9000 |
| 4 | Compound 4 | D-1 | 7.5 | 9000 |
| 5 | Compound 5 | D-1 | 7.5 | 9000 |
| 6 | Compound 6 | D-1 | 7.5 | 9000 |
| 7 | Compound 7 | D-1 | 7.1 | 9000 |
| 8 | Compound 8 | D-1 | 7.1 | 9000 |
| 9 | Compound 9 | D-1 | 7.5 | 9000 |
| 10 | Compound 10 | D-1 | 7.5 | 9000 |
| 11 | Compound 11 | D-1 | 7.5 | 9000 |
| 12 | Compound 12 | D-1 | 7.5 | 9000 |
| 13 | Compound 13 | D-1 | 7.5 | 9000 |
| 14 | Compound 14 | D-1 | 7.2 | 8000 |
| 15 | Compound 15 | D-1 | 7.2 | 8000 |
| 16 | Compound 16 | D-1 | 7.6 | 9000 |
| 17 | Compound 17 | D-1 | 7.6 | 9000 |
| 18 | Compound 18 | D-1 | 7.6 | 9000 |
| 19 | Compound 19 | D-1 | 7.6 | 9000 |
| 20 | Compound 20 | D-1 | 7.2 | 9000 |
| 21 | Compound 21 | D-1 | 7.2 | 9000 |
| 22 | Compound 22 | D-1 | 7.6 | 9000 |
| 23 | Compound 23 | D-1 | 7.6 | 9000 |
| 24 | Compound 24 | D-1 | 7.6 | 9000 |
| 25 | Compound 25 | D-1 | 7.6 | 9000 |
| 26 | Compound 26 | D-1 | 7.6 | 9000 |
| 27 | Compound 27 | D-1 | 7.2 | 8000 |
| 28 | Compound 28 | D-1 | 7.2 | 8000 |
| 29 | Compound 29 | D-1 | 7.6 | 8000 |
| 30 | Compound 30 | D-1 | 7.6 | 8000 |
| 31 | Compound 31 | D-1 | 7.6 | 8000 |
| 32 | Compound 32 | D-1 | 7.6 | 8000 |
| 33 | Compound 33 | D-1 | 7.2 | 8000 |
| 34 | Compound 34 | D-1 | 7.2 | 8000 |
| 35 | Compound 35 | D-1 | 7.6 | 8000 |
| 36 | Compound 36 | D-1 | 7.6 | 8000 |
| 37 | Compound 37 | D-1 | 7.6 | 8000 |
| 38 | Compound 38 | D-1 | 7.6 | 8000 |
| 39 | Compound 39 | D-1 | 7.6 | 8000 |
| 40 | Compound 40 | D-1 | 7.2 | 8000 |
| 41 | Compound 41 | D-1 | 7.2 | 8000 |
| 42 | Compound 42 | D-1 | 7.2 | 8000 |
| 43 | Compound 43 | D-1 | 7.2 | 8000 |
| 44 | Compound 44 | D-1 | 7.2 | 8000 |
| 45 | Compound 45 | D-1 | 7.2 | 8000 |
| 46 | Compound 46 | D-1 | 7.2 | 8000 |
| 47 | Compound 47 | D-1 | 7.2 | 8000 |
| 48 | Compound 48 | D-1 | 7.2 | 8000 |
| 49 | Compound 49 | D-1 | 7.2 | 8000 |
| 50 | Compound 50 | D-1 | 7.2 | 8000 |
| 51 | Compound 51 | D-1 | 7.2 | 8000 |
| 52 | Compound 4 | D-2 | 7.6 | 10,000 |
| 53 | Compound 11 | D-2 | 7.6 | 10,000 |
| 54 | Compound 14 | D-2 | 7.6 | 10,000 |
| 55 | Compound 18 | D-2 | 7.6 | 10,000 |
| 56 | Compound 31 | D-2 | 7.6 | 10,000 |
| Comparative Example No. | | | | |
| 1 | Compound (A) | D-1 | 6.5 | 5000 |
| 2 | Compound (B) | D-1 | 6.5 | 5000 |
| 3 | Compound (C) | D-1 | 6.0 | 4000 |
| 4 | Compound (D) | D-1 | 6.0 | 5000 |

Comparative Example 1

An organic EL device was produced in the same manner as in Example 1 except that Compound (A) shown above was used instead of Compound 1.

Comparative Example 2

An organic EL device was produced in the same manner as in Example 1 except that Compound (B) shown above was used instead of Compound 1.

Comparative Example 3

An organic EL device was produced in the same manner as in Example 1 except that Compound (C) shown above was used instead of Compound 1.

Comparative Example 4

An organic EL device was produced in the same manner as in Example 1 except that Compound (D) shown above was used instead of Compound 1.

Table 1 above collectively shows performances measured by using the organic EL devices obtained in Examples 1 to 56 and Comparative Examples 1 to 4.

(1) Initial performance: Each device was evaluated for its current efficiency (cd/A) at a current density of 10 mA/cm$^2$.

(2) Lifetime: Each device was driven with a constant current at an initial luminance of 1000 cd/cm$^2$, and was evaluated for the half lifetime of its luminance.

In Table 1, the current efficiency is shown in a cd/m$^2$ unit, and the lifetime is shown in an hour unit. The same holds true for Tables 2 and 3 below.

Synthesis Examples and Examples of Anthracene Derivatives Each Having a Phenanthryl Group and Each Represented by the General Formula (1-1) when L Represents a Single Bond and Ar$^1$ Represents a Group Except a Group Represented by the General Formula (2), and Comparative Examples Synthesis of Compound 61

Compound 1 in the Following Formulae

Synthesis of Compound 61 (1 in the following formulae)

[Chem. 112]

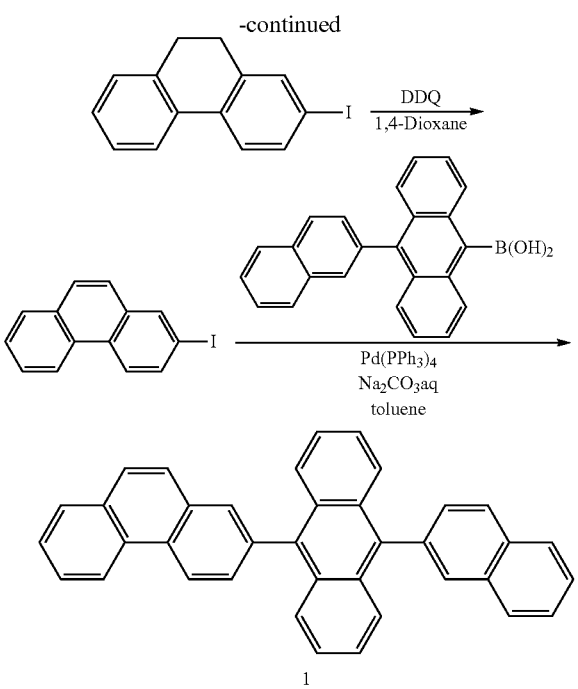

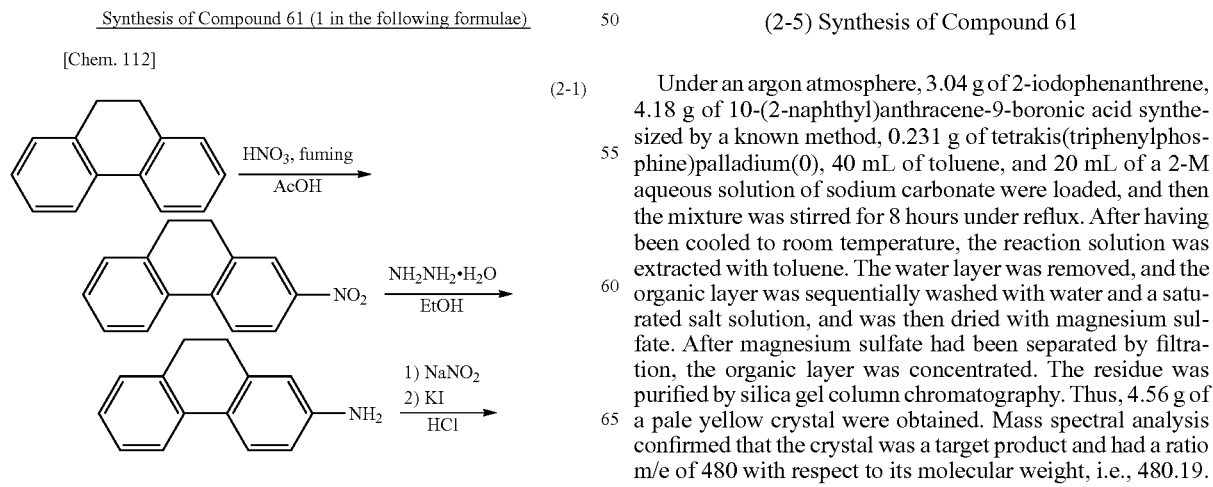

(2-1) Synthesis of 2-nitro-9,10-dihydrophenanthrene

Synthesis was performed as described in the section (1-1).

(2-2) Synthesis of 2-amino-9,10-dihydrophenanthrene

Synthesis was performed as described in the section (1-2).

(2-3) Synthesis of 2-iodo-9,10-dihydrophenanthrene

Synthesis was performed as described in the section (1-3).

(2-4) Synthesis of 2-iodophenanthrene

Synthesis was performed as described in the section (1-4).

(2-5) Synthesis of Compound 61

Under an argon atmosphere, 3.04 g of 2-iodophenanthrene, 4.18 g of 10-(2-naphthyl)anthracene-9-boronic acid synthesized by a known method, 0.231 g of tetrakis(triphenylphosphine)palladium(0), 40 mL of toluene, and 20 mL of a 2-M aqueous solution of sodium carbonate were loaded, and then the mixture was stirred for 8 hours under reflux. After having been cooled to room temperature, the reaction solution was extracted with toluene. The water layer was removed, and the organic layer was sequentially washed with water and a saturated salt solution, and was then dried with magnesium sulfate. After magnesium sulfate had been separated by filtration, the organic layer was concentrated. The residue was purified by silica gel column chromatography. Thus, 4.56 g of a pale yellow crystal were obtained. Mass spectral analysis confirmed that the crystal was a target product and had a ratio m/e of 480 with respect to its molecular weight, i.e., 480.19.

Synthesis of Compound 62

Compound 2 in the Following Formulae

Synthesis of Compound 62 (2 in the following formulae)

[Chem. 113]

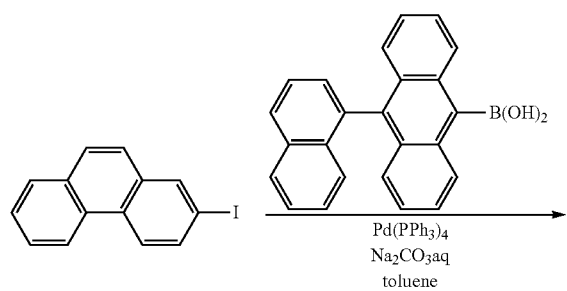

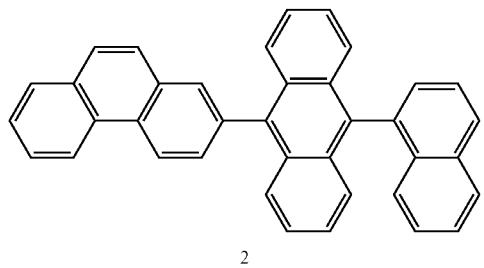

Synthesis was performed in the same manner as in the synthesis of Compound 61 except that 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 480 with respect to its molecular weight, i.e., 480.19.

Synthesis of Compound 63

Compound 3 in the Following Formulae

Synthesis of Compound 63 (3 in the following formulae)

[Chem. 114]

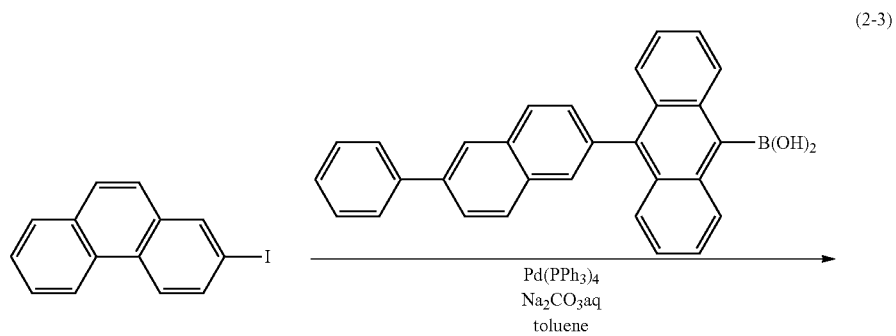

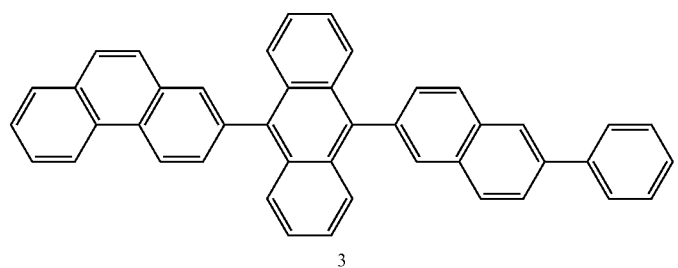

Synthesis was performed in the same manner as in the synthesis of Compound 61 except that 10-(6-phenylnaphthalen-2-yl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 64

Compound 4 in the Following Formulae

Synthesis of Compound 64 (4 in the following formulae)

[Chem. 115]

(2-4)

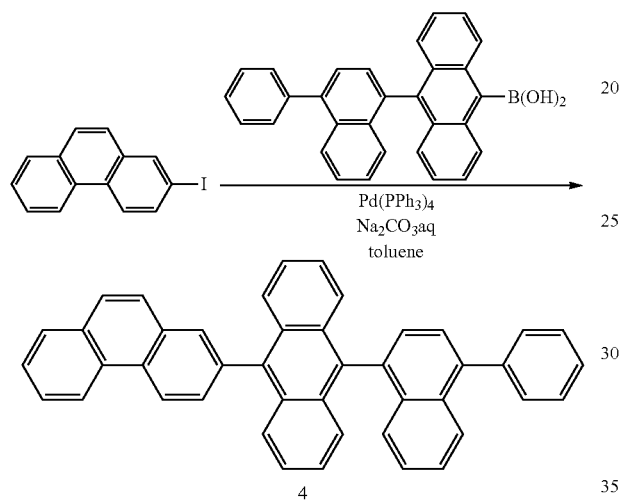

4

Synthesis was performed in the same manner as in the synthesis of Compound 61 except that 10-(4-phenylnaphthalen-1-yl) anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 65

Compound 5 in the Following Formulae

Synthesis of Compound 65 (5 in the following formulae)

[Chem. 116]

(2-5)

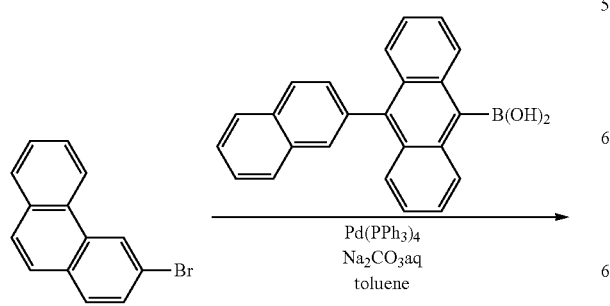

-continued

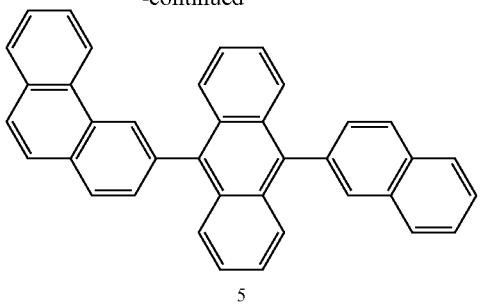

5

Synthesis was performed in the same manner as in the synthesis of Compound 61 except that commercially available 3-bromophenanthrene was used instead of 2-iodophenanthrene. Mass spectral analysis confirmed that the resultant was a target product and had a ratio m/e of 480 with respect to its molecular weight, i.e., 480.19.

Synthesis of Compound 66

Compound 6 in the Following Formulae

Synthesis of Compound 66 (6 in the following formulae)

[Chem. 117]

(2-6)

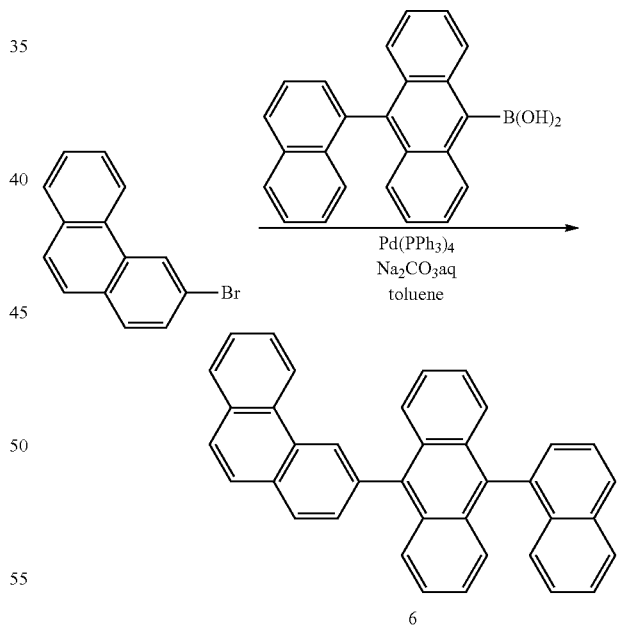

6

Synthesis was performed in the same manner as in the synthesis of Compound 61 except that: commercially available 3-bromophenanthrene was used instead of 2-iodophenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 480 with respect to its molecular weight, i.e., 480.19.

Synthesis of Compound 67

Compound 7 in the Following Formulae

Synthesis of Compound 67 (7 in the following formulae)

[Chem. 118]

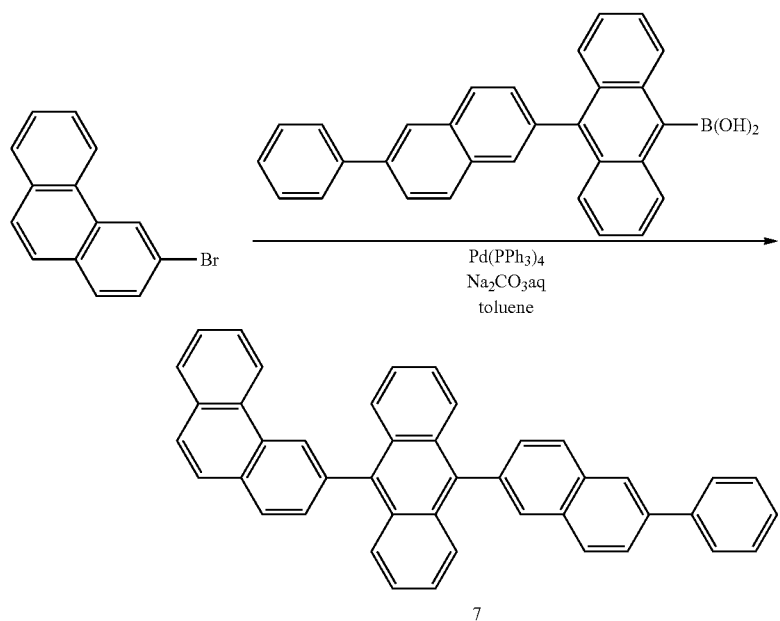

(2-7)

Synthesis was performed in the same manner as in the synthesis of Compound 61 except that: commercially available 3-bromophenanthrene was used instead of 2-iodophenanthrene; and 10-(6-phenylnaphthalen-2-yl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 68

Compound 8 in the Following Formulae

Synthesis of Compound 68 (8 in the following formulae)

[Chem. 119]

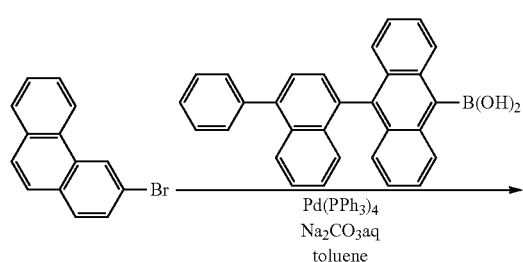

(2-8)

-continued

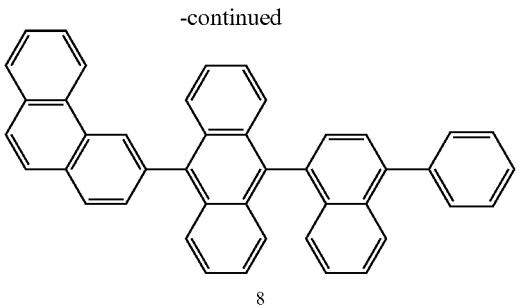

8

Synthesis was performed in the same manner as in the synthesis of Compound 61 except that: commercially available 3-bromophenanthrene was used instead of 2-iodophenanthrene; and 10-(4-phenylnaphthalen-1-yl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 69

Compound 9 in the Following Formulae

Synthesis of Compound 69 (9 in the following formulae)

[Chem. 120]

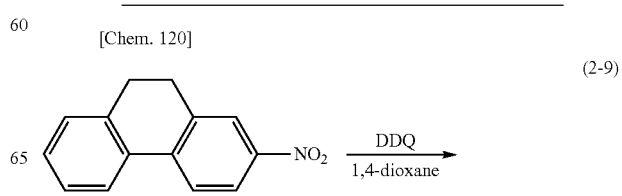

(2-9)

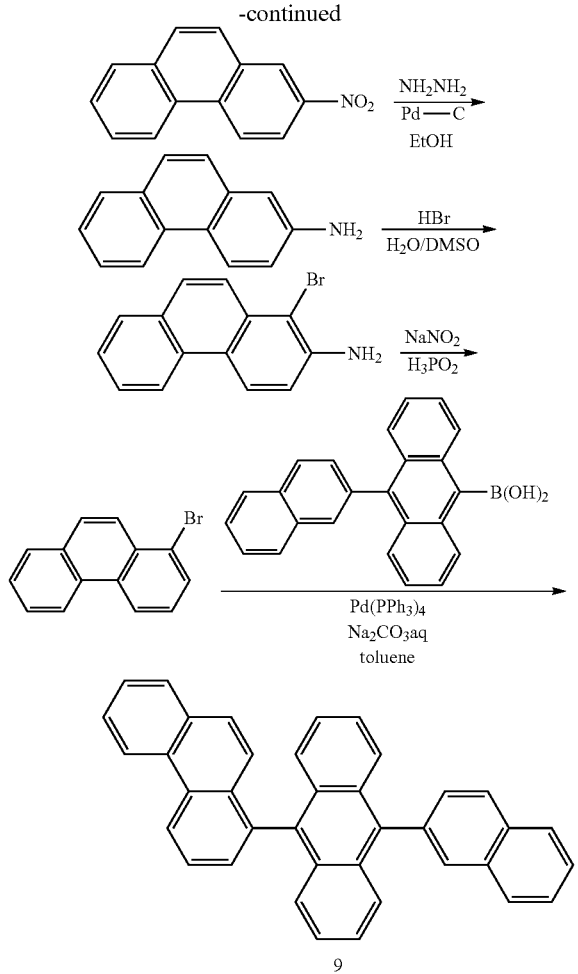

(9-1) Synthesis of 2-nitrophenanthrene

Under an argon atmosphere, 225 g of 2-nitro-9,10-dihydrophenanthrene, 227 g of 2,3-dichloro-5,6-dicyano-p-benzoquinone, and 2.4 L of 1,4-dioxane were added, and then the mixture was stirred for 24 hours under heating ref lux. After having been cooled to room temperature, the reaction solution was concentrated. The residue was purified by silica gel column chromatography, and was then washed with methanol. Thus, 134 g of a white crystal were obtained (in 60% yield).

(9-2) Synthesis of 2-aminophenanthrene

First, 134 g of 2-nitrophenanthrene, 1.00 g of palladium carbon, and 1.2 L of ethanol were loaded, and then 70 mL of hydrazine monohydrate were added to the mixture. The reaction solution was stirred for 4 hours under heating reflux. After having been cooled to room temperature, the reaction solution was poured into 3 L of water. Then, the mixture was extracted with 2 L of toluene. After the water layer had been removed, the organic layer was dried with magnesium sulfate. After magnesium sulfate had been separated by filtration, the solvent was removed by distillation under reduced pressure. The residue was purified by silica gel column chromatography. Thus, 100 g of a pale yellow solid were obtained (in 86% yield).

(9-3) Synthesis of 2-amino-1-bromophenanthrene

First, 100 g of 2-aminophenanthrene were dissolved in 750 mL of N,N-dimethyl sulfoxide, and then 83 g of 48% hydrobromic acid were dropped to the solution over 4 hours while the solution was stirred at room temperature. The mixture was continuously stirred at room temperature for 20 hours, and was then stirred at 100° C. for 1 hour under heat. After having been cooled to room temperature, the reaction solution was poured into 3 L of water. After the mixed solution had been neutralized with ammonia water, the crystal was obtained through separation by filtration. The resultant solid was recrystallized with ethanol and water. Thus, 126 g of a colorless crystal were obtained (in 90% yield).

(9-4) Synthesis of 1-bromophenanthrene

First, 120 g of 2-amino-1-bromophenanthrene were dissolved in 750 mL of THF, and then 4.5 L of concentrated hydrochloric acid and 1.5 L of water were added to the solution. The reaction solution was cooled with ice, and then a solution of 45 g of sodium nitrite in 230 mL of water was dropped to the solution. After the mixture had been stirred for 1 hour under ice cooling, 2.25 L of a 50% aqueous solution of phosphinic acid were added to the mixture. The reaction solution was stirred for 30 minutes under ice cooling, and was then continuously stirred at room temperature for 17 hours. Subsequently, 10 L of water were added to the solution, and a solid was obtained through separation by filtration. The resultant solid was purified by silica gel column chromatography. Thus, 75 g of 1-bromophenanthrene were obtained (in 66% yield).

(9-5) Synthesis of Compound 69

Synthesis was performed in the same manner as in the synthesis of Compound 1 except that 1-bromophenanthrene was used instead of 2-iodophenanthrene. Mass spectral analysis confirmed that the resultant was a target product and had a ratio m/e of 480 with respect to its molecular weight, i.e., 480.19.

Synthesis of Compound 70

Compound 10 in the Following Formulae

Synthesis of Compound 70 (10 in the following formulae)

[Chem. 121]

(2-10)

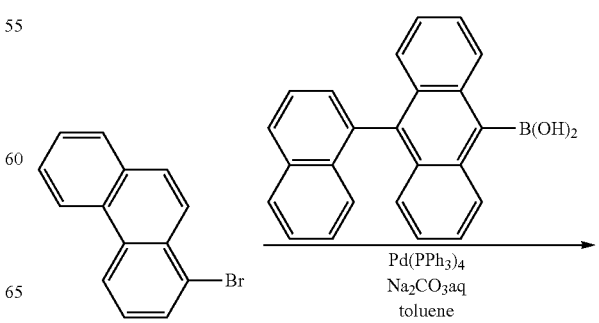

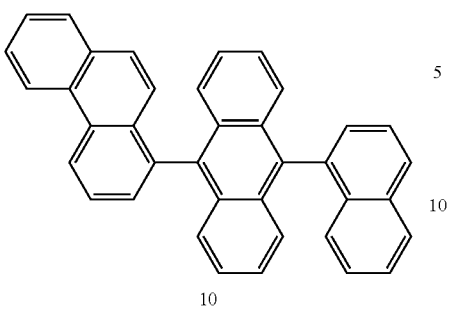

10

Synthesis was performed in the same manner as in the synthesis of Compound 61 except that: 1-bromophenanthrene was used instead of 2-iodophenanthrene; and 10-(1-naphthyl)anthracene-9-boronic acid synthesized by a known method was used instead of 10-(2-naphthyl)anthracene-9-boronic acid. Mass spectral analysis confirmed that the resultant was a target product and had a ratio m/e of 480 with respect to its molecular weight, i.e., 480.19.

Synthesis of Compound 71

Compound 11 in the Following Formulae

Synthesis of Compound 71 (11 in the following formulae)

[Chem. 122]

Synthesis was performed in the same manner as in the synthesis of Compound 61 except that: 1-bromophenanthrene was used instead of 2-iodophenanthrene; and 10-(6-phenylnaphthalen-2-yl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 72

Compound 12 in the Following Formulae

Synthesis of Compound 72 (12 in the following formulae)

[Chem. 123]

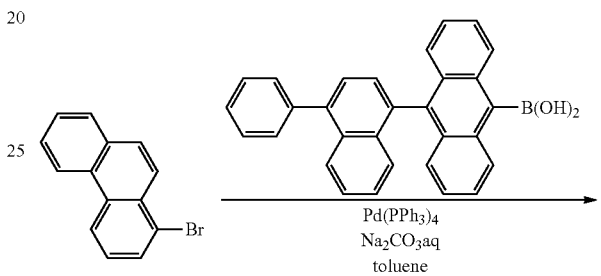

(2-12)

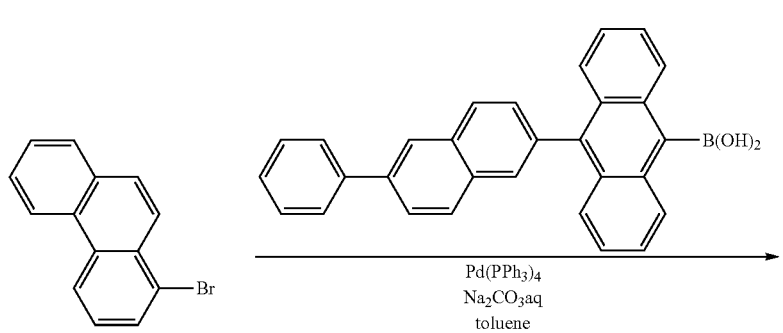

(2-11)

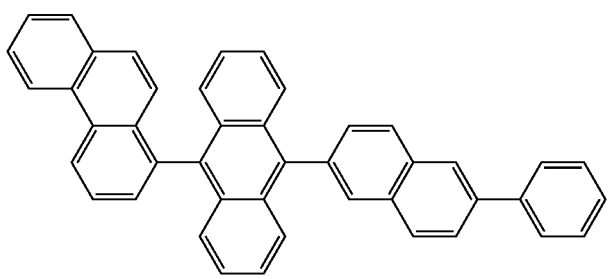

11

-continued

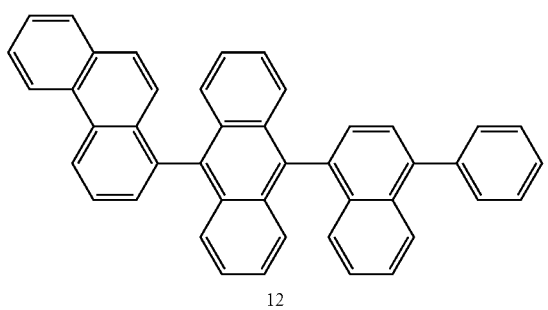

12

Synthesis was performed in the same manner as in the synthesis of Compound 61 except that: 1-bromophenanthrene was used instead of 2-iodophenanthrene; and 10-(4-phenylnaphthalen-1-yl)anthracene-9-boronic acid synthesized by a known method was used instead of 10-(2-naphthyl)anthracene-9-boronic acid. Mass spectral analysis confirmed that the resultant was a target product and had a ratio m/e of 556 with respect to its molecular weight, i.e., 556.22.

Synthesis of Compound 73

Compound 13 in the Following Formulae

Synthesis of Compound 73 (13 in the following formulae)

[Chem. 124]

(2-13)

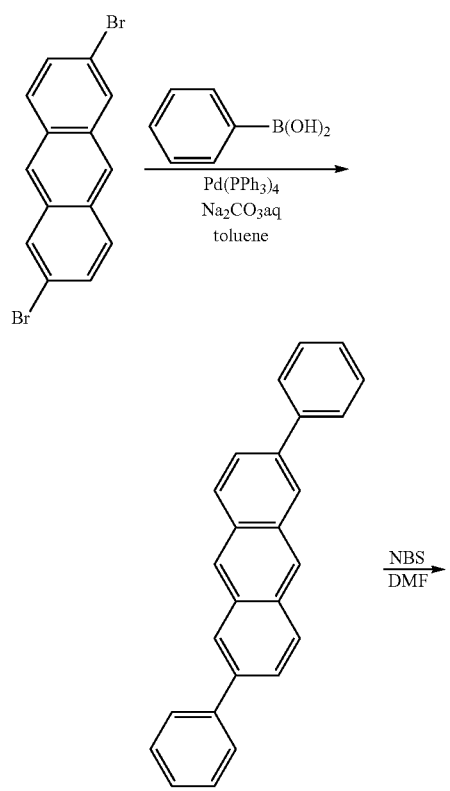

-continued

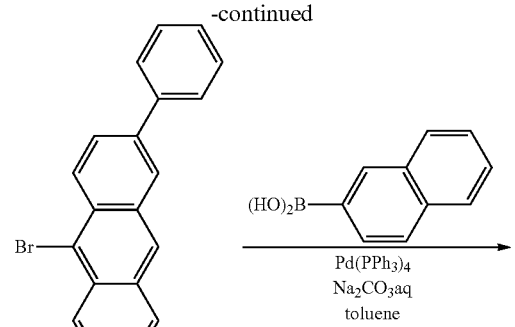

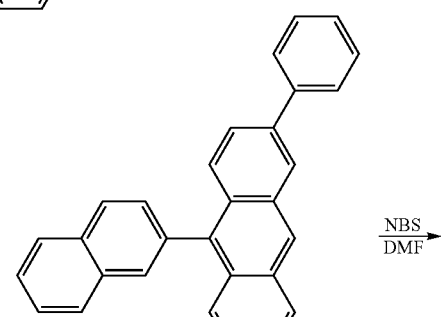

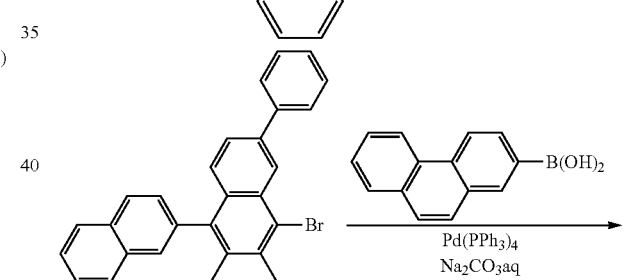

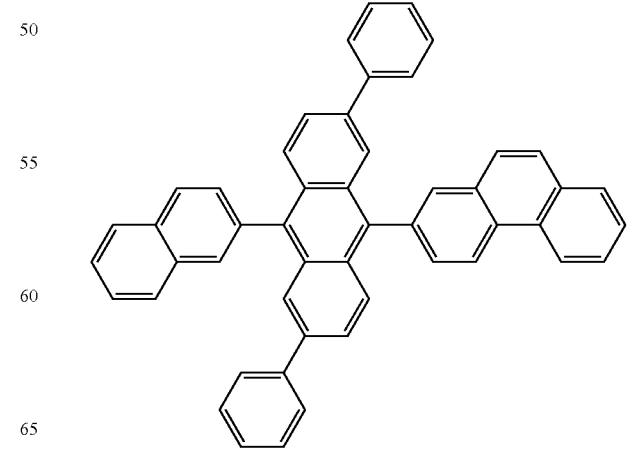

13

(13-1) Synthesis of 2,6-diphenylanthracene

Under an argon atmosphere, 29.0 g of phenylboronic acid, 25.7 g of 2,6-dibromoanthracene, 4.62 g of tetrakis(triphenylphosphine) palladium(0), 800 mL of toluene, and 400 mL of a 2-M aqueous solution of sodium carbonate were loaded, and then the mixture was stirred for 8 hours under ref lux. After the mixture had been cooled to room temperature, the precipitated crystal was taken by filtration. The resultant solid was repeatedly recrystallized with toluene and hexane and washed. Thus, 25.0 g of 2-phenylanthracene were obtained (in 75% yield).

(13-2) Synthesis of 9-bromo-2,6-diphenylanthracene

First, 33.0 g of 2,6-diphenylanthracene were dissolved in 200 mL of N,N-dimethylformamide under heat, and then a solution of 18.0 g of N-bromosuccinimide in 20 mL of N,N-dimethylformamide was added to the solution. The mixture was stirred at 60° C. for 6 hours under heat. After having been cooled to room temperature, the reaction solution was poured into 1 L of water. The resultant solid was sequentially washed with methanol, water, and methanol. After that, the solid was repeatedly recrystallized with toluene and hexane and washed. Thus, 33.5 g of 9-bromo-2,6-diphenylanthracene were obtained (in 82% yield).

(13-3) Synthesis of 2,6-diphenyl-9-(2-naphthyl)anthracene

Under an argon atmosphere, 20.5 g of 9-bromo-2,6-diphenylanthracene, 9.37 g of naphthalene-2-boronic acid, 1.16 g of tetrakis(triphenylphosphine)palladium(0), 200 mL of toluene, and 100 mL of a 2-M aqueous solution of sodium carbonate were loaded, and then the mixture was stirred for 8 hours under reflux. After the mixture had been cooled to room temperature, the precipitated crystal was separated by filtration. The resultant crystal was washed with methanol, water, and methanol, and was then recrystallized with toluene. Thus, 17.1 g of a yellow crystal were obtained (in 75% yield).

(13-4) Synthesis of 9-bromo-2,6-diphenyl-10-(2-naphthyl)anthracene

First, 9.09 g of 2,6-diphenyl-9-(2-naphthyl)anthracene were dissolved in 100 mL of N,N-dimethylformamide under heat, and then a solution of 3.91 g of N-bromosuccinimide in 10 mL of N,N-dimethylformamide was added to the solution. The mixture was stirred at 60° C. for 6 hours under heat. After having been cooled to room temperature, the reaction solution was poured into 500 mL of water. The resultant solid was sequentially washed with methanol, water, and methanol. After that, the solid was repeatedly recrystallized with toluene and hexane and washed. Thus, 8.55 g of 9-bromo-2,6-diphenyl-10-(2-naphthyl)anthracene were obtained (in 80% yield).

(13-5) Synthesis of Compound 73

Under an argon atmosphere, 5.35 g of 9-bromo-2,6-diphenyl-10-(2-naphthyl)anthracene, 2.44 g of 2-phenanthryl boronic acid, 0.231 g of tetrakis(triphenylphosphine)palladium(0), 40 mL of toluene, and 20 mL of a 2-M aqueous solution of sodium carbonate were loaded, and then the mixture was stirred for 8 hours under reflux. After the mixture had been cooled to room temperature, the precipitated crystal was separated by filtration. The resultant crystal was washed with methanol, water, and methanol, and was then recrystallized with toluene. Thus, 4.74 g of a pale yellow crystal were obtained. Mass spectral analysis confirmed that the crystal was a target product and had a ratio m/e of 632 with respect to its molecular weight, i.e., 632.25.

Synthesis of Compound 74

Compound 14 in the Following Formulae

Synthesis of Compound 74 (14 in the following formulae)

[Chem. 125]

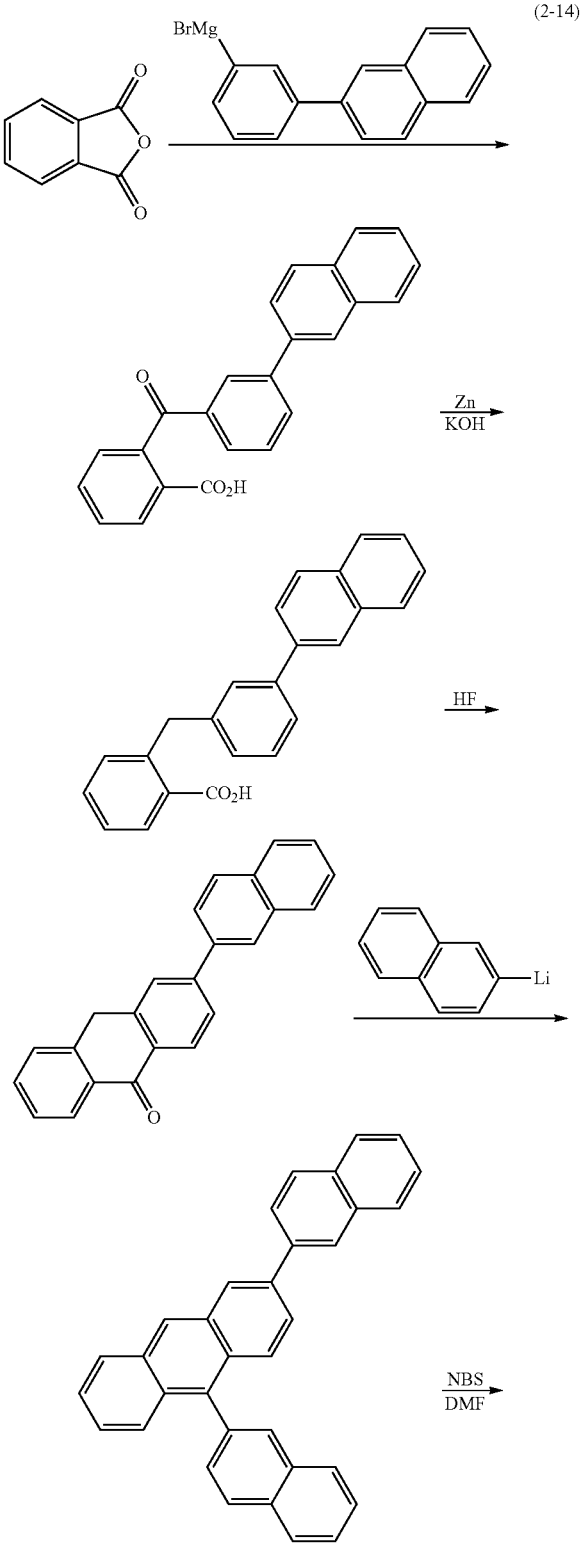

(2-14)

-continued

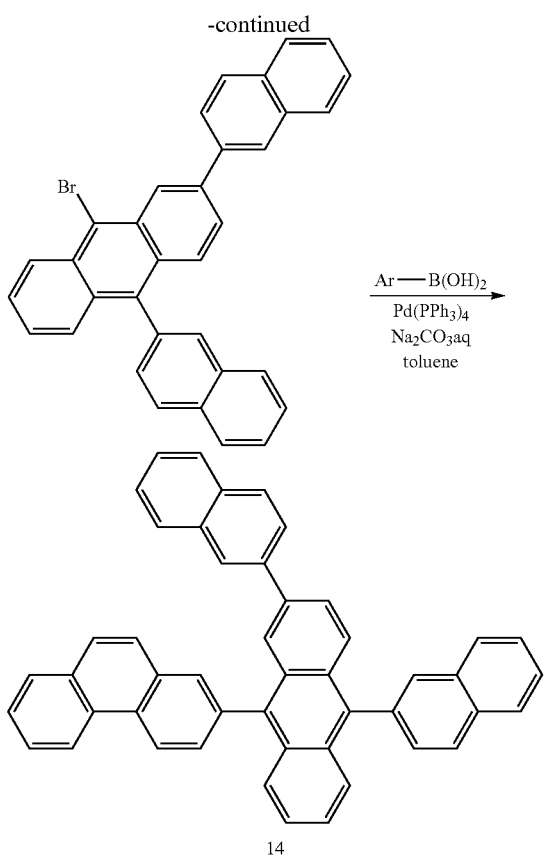

14

(14-1) Synthesis of 2-[3-(2-naphthyl)benzoyl]benzoic acid

Under an argon atmosphere, 132 g of magnesium were dispersed in 500 mL of ether. A solution of 142 g of 2-(3-bromophenyl) naphthalene in 500 mL of ether was added to the dispersion, and then the mixture was stirred at room temperature for 1 hour. A solution of 74 g of phthalic anhydride in 150 mL of benzene was added to the mixture, and then the resultant reaction solution was stirred for 3 hours under reflux. After having been cooled to room temperature, the reaction solution was poured into ice water, and then 1 L of 10% hydrochloric acid was added to the mixture. The organic layer was separated and extracted with an aqueous solution of potassium carbonate. The alkaline extract was acidified, and then the resultant solid was washed with boiling water. The resultant crude product was recrystallized with acetic acid. Thus, 121 g of 2-(3-phenylbenzoyl)benzoic acid were obtained (in 69% yield).

(14-2) Synthesis of 2-[3-(2-naphthyl)benzyl]benzoic acid

First, 121 g of 2-[3-(2-naphthyl)benzoyl]benzoic acid were dissolved in 10 L of a 1N sodium hydroxide solution, and then a zinc powder activated with an aqueous solution of copper sulfate was added to the solution. The reaction solution was stirred for 50 hours under reflux. After having been cooled to room temperature, the reaction solution was filtrated. The filtrate was acidified, and then the resultant solid was washed with boiling water. Thus, 110 g of 2-[3-(2-naphthyl)benzyl]benzoic acid were obtained (in 90% yield).

(14-3) Synthesis of 2-(2-naphthyl)-10-anthrone

First, 11.7 g of 2-[3-(2-naphthyl)benzyl]benzoic acid were added to 250 mL of liquid hydrogen fluoride, and then the mixture was stirred until hydrogen fluoride evaporated. The residue was dissolved in chloroform, and then the solution was sequentially washed with water, an aqueous solution of ammonium hydroxide, and water. After the chloroform solution had been dried with magnesium sulfate, the solvent was removed by distillation under reduced pressure. The residue was crystallized with methanol, and was then recrystallized with cyclohexane and acetone. Thus, 6.76 g of 2-phenyl-10-anthrone were obtained (in 61% yield).

(14-4) Synthesis of 2,10-di(2-naphthyl)anthracene

Under an argon atmosphere, a solution of 4.81 g of 2-bromonaphthalene in 30 mL of THF was cooled to −78° C. Subsequently, 25 mL of a 1.6-M solution of n-butyllithium in hexane were dropped to the solution, and then the mixture was stirred at −78° C. for 1 hour. A solution of 6.76 g of 2-(2-naphthyl)-10-anthrone in 20 mL of THF was added to the mixture, and then the resultant reaction solution was stirred for 5 hours at 50° C. under heat. After the reaction solution had been cooled to room temperature, 100 mL of 10% hydrochloric acid were added to the solution. After the water layer had been removed, the organic layer was washed with water and a saturated salt solution. Then, the organic layer was dried with magnesium sulfate. The solvent was removed by distillation under reduced pressure, and then the residue was purified by silica gel column chromatography. Thus, 2.90 g of 2,10-di(2-naphthyl)anthracene were obtained (in 32% yield).

(14-5) Synthesis of 9-bromo-2,10-di(2-naphthyl)anthracene

First, 2.90 g of 2-phenyl-10-(6-phenylnaphthalen-2-yl) anthracene were dissolved in 30 mL of DMF, and then a solution of 1.32 g of N-bromosuccinimide in 10 mL of DMF was added to the solution. The mixture was stirred at 60° C. for 5 hours under heat. After having been cooled to room temperature, the reaction solution was poured into 100 mL of water. The precipitated crystal was separated by filtration, and was then sequentially washed with methanol, water, and methanol. After that, the crystal was purified by silica gel column chromatography. Thus, 3.09 g of 9-bromo-2,10-di(2-naphthyl)anthracene were obtained (in 90% yield).

(14-6) Synthesis of Compound 74

Under an argon atmosphere, 5.08 g of 9-bromo-2,10-di(2-naphthyl)anthracene, 2.44 g of 2-phenanthryl boronic acid, 0.231 g of tetrakis(triphenylphosphine)palladium(0), 40 mL of toluene, and 20 mL of a 2-M aqueous solution of sodium carbonate were loaded, and then the mixture was stirred for 8 hours under reflux. After the mixture had been cooled to room temperature, the precipitated crystal was separated by filtration. The resultant crystal was washed with methanol, water, and methanol, and was then recrystallized with toluene. Thus, 4.97 g of a pale yellow crystal were obtained. Mass spectral analysis confirmed that the crystal was a target product and had a ratio m/e of 606 with respect to its molecular weight, i.e., 606.23.

Example 57

An organic EL device was formed in the same manner as in Example 1 except that Compound 61 was used.

Examples 58 to 72

Organic EL devices were each produced in the same manner as in Example 57 except that a host and a dopant were changed as shown in Table 2. Then, the devices were each evaluated in the same manner as that described above.

Comparative Example 5

An organic EL device was produced in the same manner as in Example 57 except that Compound (E) shown above was used instead of Compound 61.

Comparative Example 6

An organic EL device was produced in the same manner as in Example 57 except that Compound (F) shown above was used instead of Compound 61.

Comparative Example 7

An organic EL device was produced in the same manner as in Example 57 except that Compound (G) shown above was used instead of Compound 61.

Comparative Example 8

An organic EL device was produced in the same manner as in Example 57 except that Compound (H) shown above was used instead of Compound 61.

Comparative Example 9

An organic EL device was produced in the same manner as in Example 57 except that Compound (I) shown above was used instead of Compound 61.

Comparative Example 10

An organic EL device was produced in the same manner as in Example 57 except that Compound (C) shown above was used instead of Compound 61.

Table 2 shows the results obtained in Examples 57 to 72 and Comparative Examples 5 to 10 described above.

[Table 2]

TABLE 2

| | Host | Dopant | Current efficiency | Lifetime |
|---|---|---|---|---|
| Example No. | | | | |
| 57 | Compound 61 | D-1 | 7.5 | 9000 |
| 58 | Compound 62 | D-1 | 7.5 | 9000 |
| 59 | Compound 63 | D-1 | 7.5 | 9000 |
| 60 | Compound 64 | D-1 | 7.5 | 9000 |
| 61 | Compound 65 | D-1 | 7.3 | 9000 |
| 62 | Compound 66 | D-1 | 7.3 | 9000 |
| 63 | Compound 67 | D-1 | 7.3 | 9000 |
| 64 | Compound 68 | D-1 | 7.3 | 9000 |
| 65 | Compound 69 | D-1 | 7.2 | 9000 |
| 66 | Compound 70 | D-1 | 7.2 | 9000 |
| 67 | Compound 71 | D-1 | 7.2 | 9000 |
| 68 | Compound 72 | D-1 | 7.2 | 9000 |
| 69 | Compound 61 | D-2 | 7.6 | 10,000 |
| 70 | Compound 66 | D-2 | 7.6 | 10,000 |
| 71 | Compound 70 | D-2 | 7.6 | 10,000 |
| 72 | Compound 73 | D-2 | 7.6 | 10,000 |
| Comparative Example No. | | | | |
| 5 | Compound (E) | D-1 | 6.5 | 4000 |
| 6 | Compound (F) | D-1 | 6.5 | 4000 |
| 7 | Compound (G) | D-1 | 6.0 | 2000 |
| 8 | Compound (H) | D-1 | 6.0 | 2000 |
| 9 | Compound (I) | D-1 | 6.0 | 1000 |
| 10 | Compound (C) | D-1 | 6.0 | 5000 |

Synthesis Examples and Examples of Anthracene Derivatives Each Having a Phenanthryl Group and Each Represented by the General Formula (1-1) when $Ar^1$ Represents a Group Represented by the General Formula (2), and Comparative Examples Synthesis of Compound 75

Compound 1 in the Following Formulae

[Chem. 126]

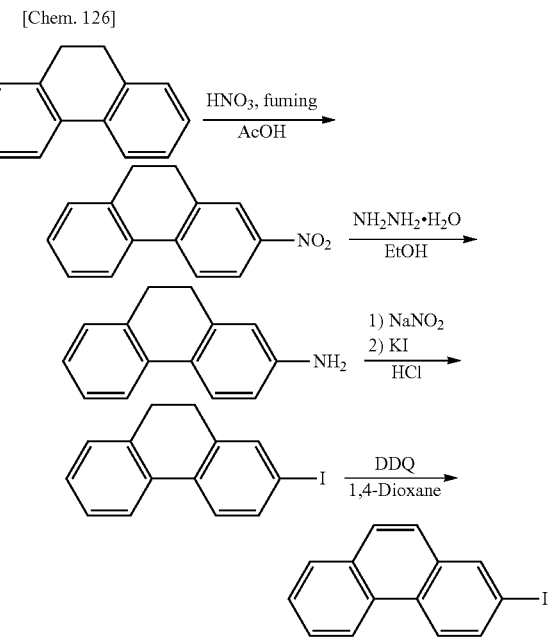

(3-1) Synthesis of 2-nitro-9,10-dihydrophenanthrene

Synthesis was performed as described in the section (1-1).

(3-2) Synthesis of 2-amino-9,10-dihydrophenanthrene

Synthesis was performed as described in the section (1-2).

(3-3) Synthesis of 2-iodo-9,10-dihydrophenanthrene

Synthesis was performed as described in the section (1-3).

(3-4) Synthesis of 2-iodophenanthrene

Synthesis was performed as described in the section (1-4).

(3-5) Synthesis of Compound 75

[Chem. 127]

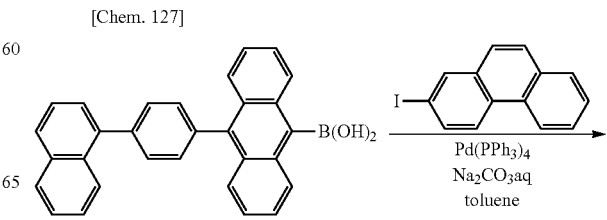

-continued

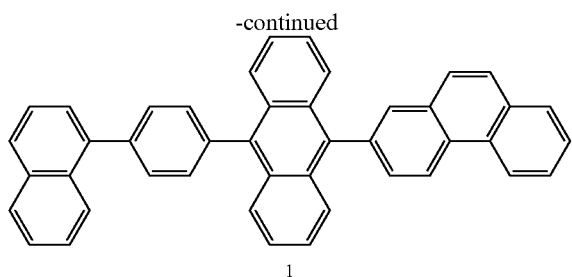

1

Under an argon atmosphere, 3.04 g of 2-iodophenanthrene synthesized by the above-mentioned method, 4.66 g of 10-[4-(1-naphthyl)phenyl]anthracene-9-boronic acid synthesized by a known method, 0.231 g of tetrakis(triphenylphosphine)palladium(0), 40 mL of toluene, and 20 mL of a 2-M aqueous solution of sodium carbonate were loaded, and then the mixture was stirred for 8 hours under reflux. After the mixture had been cooled to room temperature, the precipitated crystal was separated by filtration. The resultant crystal was repeatedly recrystallized with toluene and hexane. Thus, 4.45 g of a pale yellow crystal were obtained. Mass spectral analysis confirmed that the crystal was a target product and had a ratio m/e of 556 with respect to its molecular weight, i.e., 556.22.

Synthesis of Compound 76

Compound 2 in the Following Formulae

[Chem. 128]

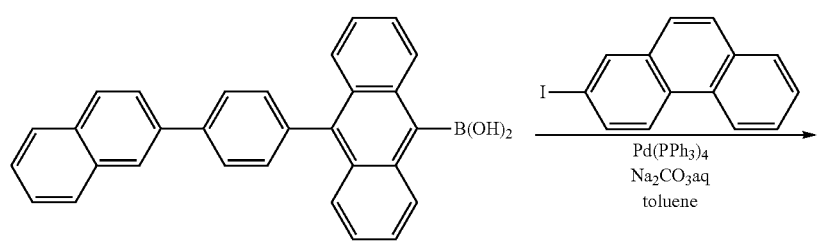

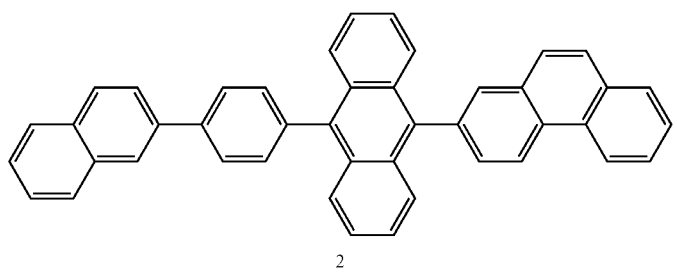

2

Synthesis was performed in the same manner as in the synthesis of Compound 75 except that 10-[4-(2-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 77

Compound 3 in the Following Formulae

[Chem. 129]

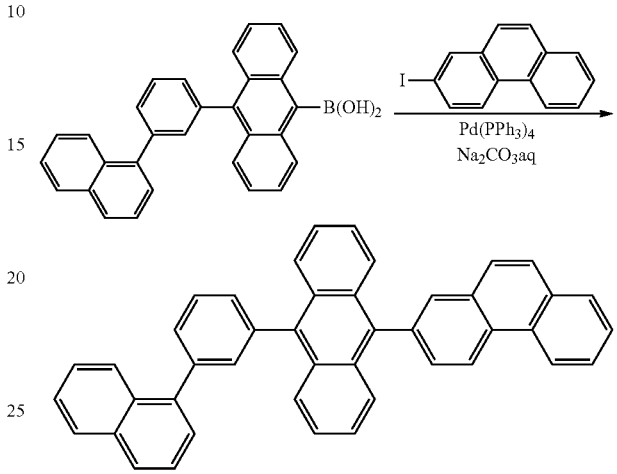

3

Synthesis was performed in the same manner as in the synthesis of Compound 75 except that 10-[3-(1-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 78

Compound 4 in the Following Formulae

[Chem. 130]

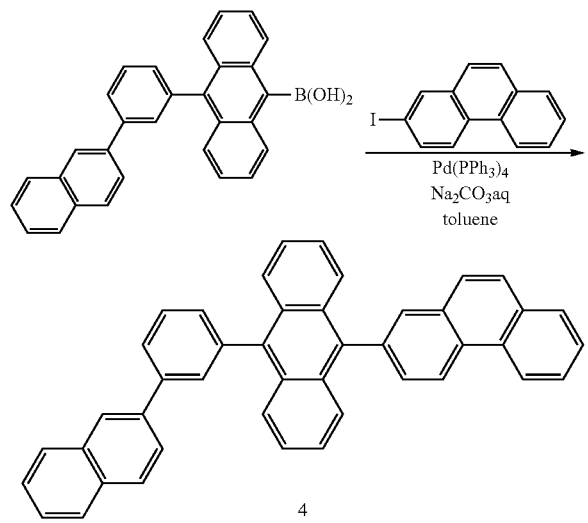

4

Synthesis was performed in the same manner as in the synthesis of Compound 75 except that 10-[3-(2-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 79

Compound 5 in the Following Formulae

Synthesis was performed in the same manner as in the synthesis of Compound 75 except that 10-(4-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Synthesis of Compound 80

Compound 6 in the Following Formulae

[Chem. 132]

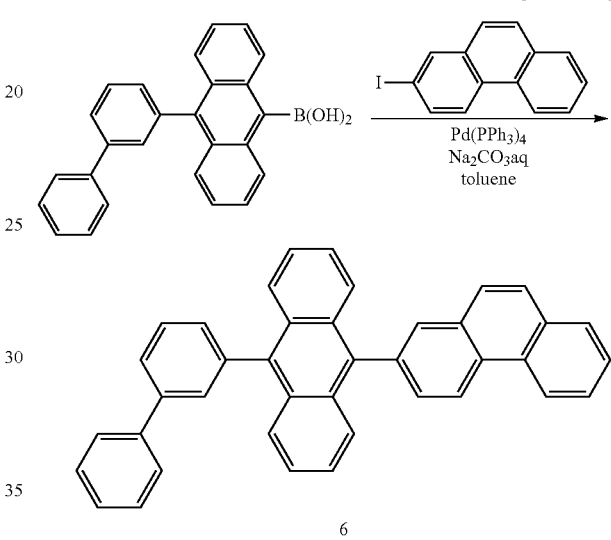

6

Synthesis was performed in the same manner as in the synthesis of Compound 75 except that 10-(3-biphenyl)anthracene-9-boronic acid synthesized by a known method was used instead of 10-[4-(1-naphthyl)phenyl]anthracene. Mass

[Chem. 131]

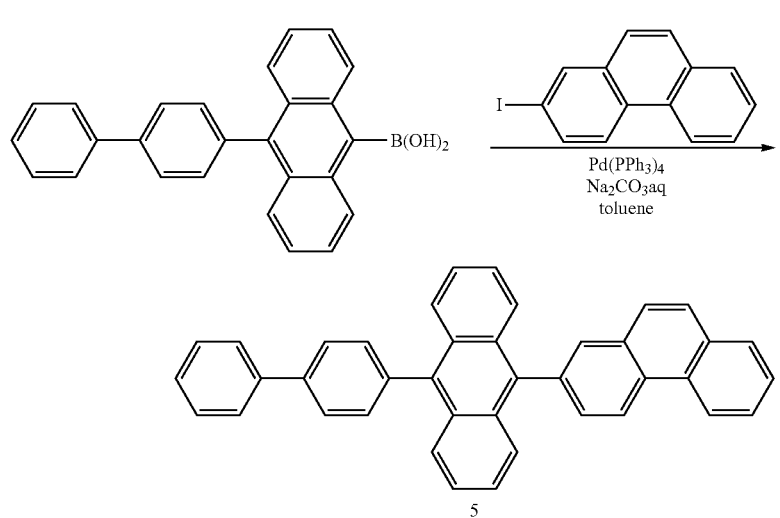

5 spectral analysis confirmed that the resultant was a target product and had a ratio m/e of 506 with respect to its molecular weight, i.e., 506.20.

Synthesis of Compound 81

Compound 7 in the Following Formulae

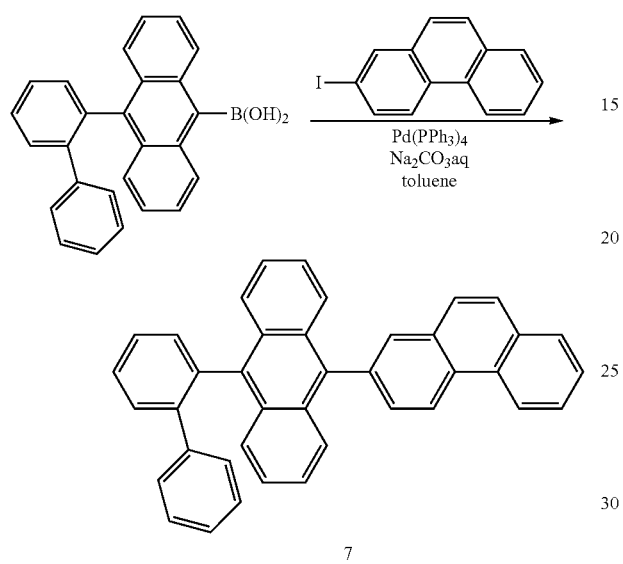

[Chem. 133]

Synthesis was performed in the same manner as in the synthesis of Compound 75 except that 10-(2-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Synthesis of Compound 82

Compound 8 in the Following Formulae

[Chem. 134]

Synthesis was performed in the same manner as in the synthesis of Compound 75 except that commercially available 3-bromophenanthrene was used instead of 2-iodophenanthrene. Mass spectral analysis confirmed that the resultant was a target product and had a ratio m/e of 556 with respect to its molecular weight, i.e., 556.22.

Synthesis of Compound 83

Compound 9 in the Following Formulae

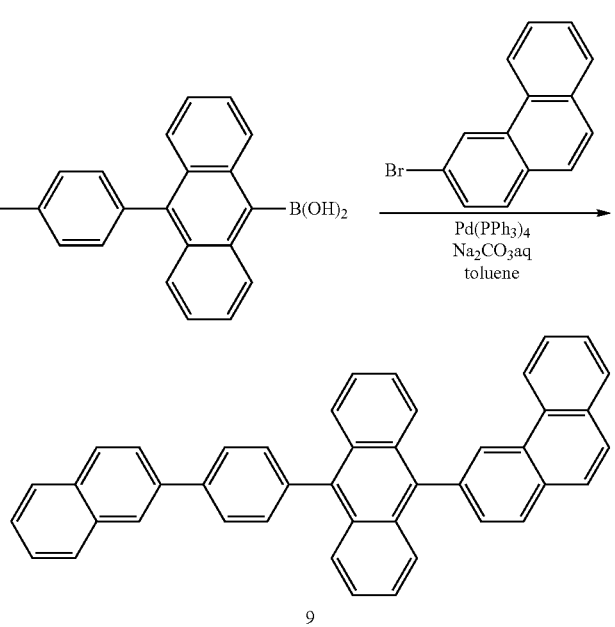

[Chem. 135]

Synthesis was performed in the same manner as in the synthesis of Compound 75 except that: commercially available 3-bromophenanthrene was used instead of 2-iodophenanthrene; and 10-[4-(2-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 84

Compound 10 in the Following Formulae

[Chem. 136]

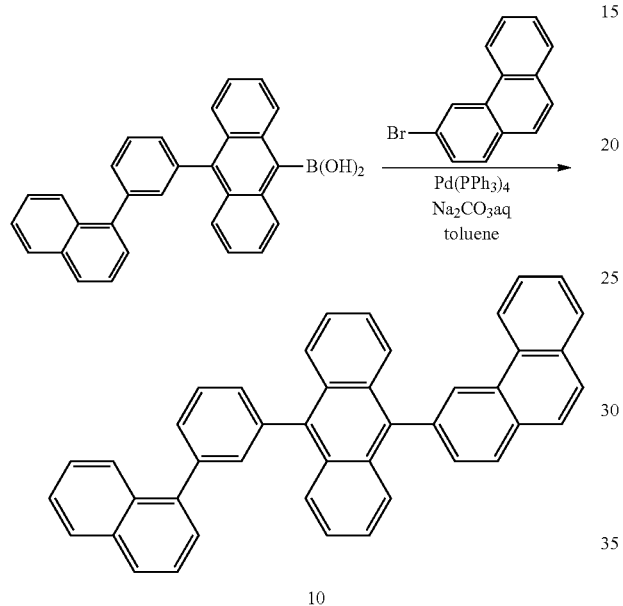

10

Synthesis was performed in the same manner as in the synthesis of Compound 75 except that: commercially available 3-bromophenanthrene was used instead of 2-iodophenanthrene; and 10-[3-(1-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 85

Compound 11 in the Following Formulae

[Chem. 137]

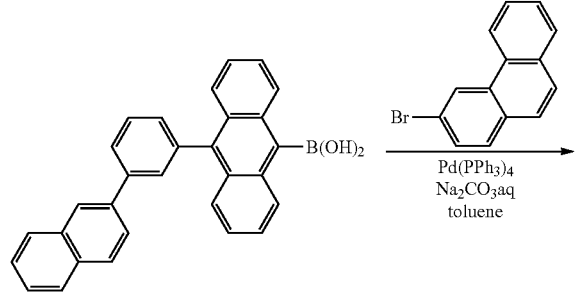

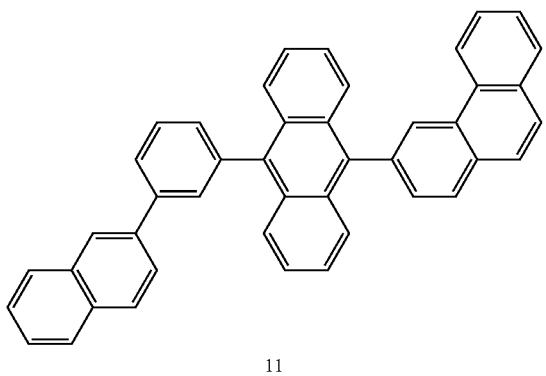

11

Synthesis was performed in the same manner as in the synthesis of Compound 75 except that: commercially available 3-bromophenanthrene was used instead of 2-iodophenanthrene; and 10-[3-(2-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 86

Compound 12 in the Following Formulae

[Chem. 138]

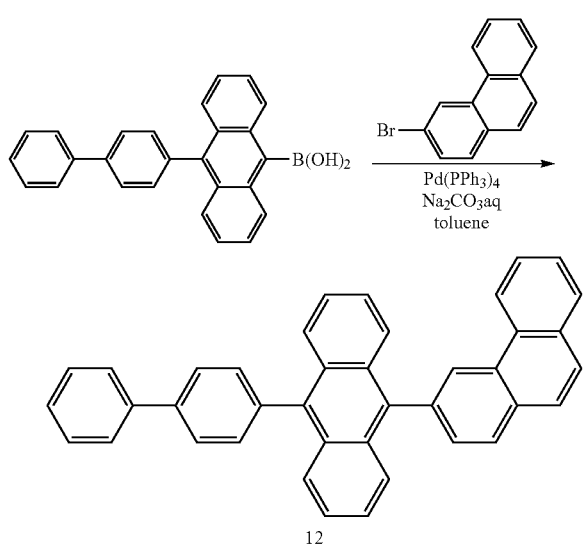

12

Synthesis was performed in the same manner as in the synthesis of Compound 75 except that: commercially available 3-bromophenanthrene was used instead of 2-iodophenanthrene; and 10-(4-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

243

Synthesis of Compound 87

Compound 13 in the Following Formulae

[Chem. 139]

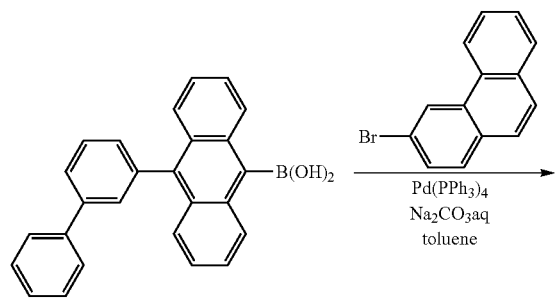

13

Synthesis was performed in the same manner as in the synthesis of Compound 75 except that: commercially available 3-bromophenanthrene was used instead of 2-iodophenanthrene; and 10-(3-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Synthesis of Compound 88

Compound 14 in the Following Formulae

[Chem. 140]

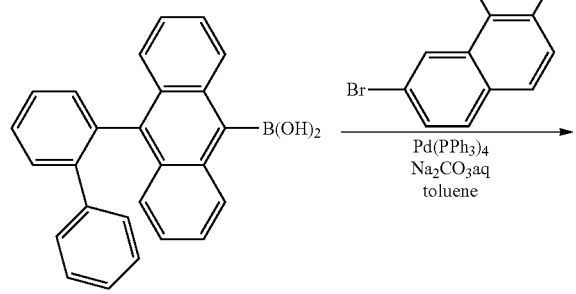

244

-continued

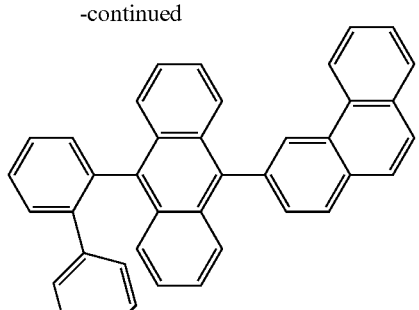

14

Synthesis was performed in the same manner as in the synthesis of Compound 75 except that: commercially available 3-bromophenanthrene was used instead of 2-iodophenanthrene; and 10-(2-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Synthesis of Compound 89

[Chem. 141]

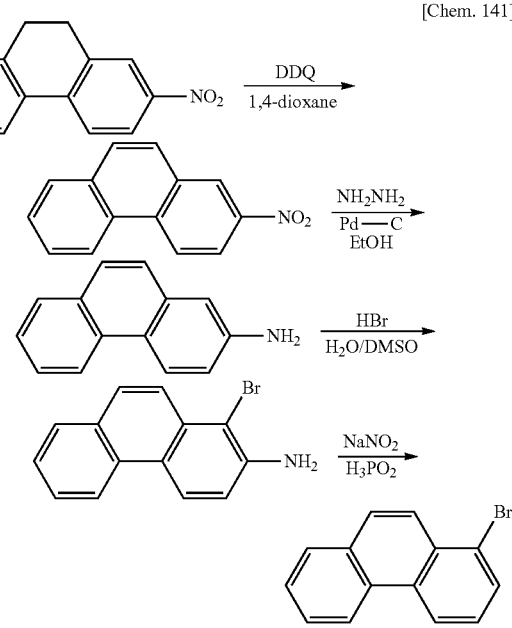

(89-1) Synthesis of 2-nitrophenanthrene

Under an argon atmosphere, 22.5 g of 2-nitro-9,10-dihydrophenanthrene, 22.7 g of 2,3-dichloro-5,6-dicyano-p-benzoquinone, and 240 mL of 1,4-dioxane were added, and then the mixture was stirred for 24 hours under heating reflux. After having been cooled to room temperature, the reaction solution was concentrated. The residue was purified by silica gel column chromatography, and was then washed with methanol. Thus, 13.4 g of a white crystal were obtained (in 60% yield).

(89-2) Synthesis of 2-aminophenanthrene

First, 13.4 g of 2-nitrophenanthrene, 0.10 g of palladium carbon, and 120 mL of ethanol were loaded, and then 7 mL of hydrazine monohydrate were added to the mixture. The reaction solution was stirred for 4 hours under heating reflux. After having been cooled to room temperature, the reaction solution was poured into 300 mL of water. Then, the mixture was extracted with 200 mL of toluene. After the water layer had been removed, the organic layer was dried with magnesium sulfate. After magnesium sulfate had been separated by filtration, the solvent was removed by distillation under reduced pressure. The residue was purified by silica gel column chromatography. Thus, 10.0 g of a pale yellow solid were obtained (in 86% yield).

(89-3) Synthesis of 2-amino-1-bromophenanthrene

First, 10.0 g of 2-aminophenanthrene were dissolved in 75 mL of N,N-dimethyl sulfoxide, and then 8.3 g of 48% hydrobromic acid were dropped to the solution over 4 hours while the solution was stirred at room temperature. The mixture was continuously stirred at room temperature for 20 hours, and was then stirred at 100° C. for 1 hour under heat. After having been cooled to room temperature, the reaction solution was poured into 300 mL of water. After the mixed solution had been neutralized with ammonia water, the crystal was separated by filtration. The resultant solid was recrystallized with ethanol and water. Thus, 12.6 g of a colorless crystal were obtained (in 90% yield).

(89-4) Synthesis of 1-bromophenanthrene

First, 12.0 g of 2-amino-1-bromophenanthrene were dissolved in 75 mL of THF, and then 450 mL of concentrated hydrochloric acid and 150 mL of water were added to the solution. The reaction solution was cooled with ice, and then a solution of 4.5 g of sodium nitrite in 23 mL of water was dropped to the solution. After the mixture had been stirred for 1 hour under ice cooling, 225 mL of a 50% aqueous solution of phosphinic acid were added to the mixture. The reaction solution was stirred for 30 minutes under ice cooling, and was then continuously stirred at room temperature for 17 hours. Subsequently, 1 L of water were added to the solution, and a solid was separated by filtration. The resultant solid was purified by silica gel column chromatography. Thus, 7.5 g of 1-bromophenanthrene were obtained (in 66% yield).

(89-5) Synthesis of Compound 89

Compound 15 in the Following Formulae

[Chem. 142]

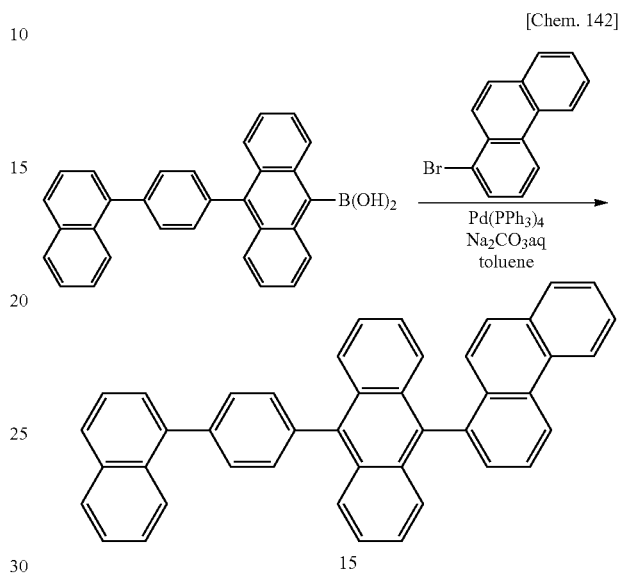

Synthesis was performed in the same manner as in the synthesis of Compound 75 except that: 1-bromophenanthrene was used instead of 2-iodophenanthrene; and 10-[4-(1-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 90

Compound 16 in the Following Formulae

[Chem. 143]

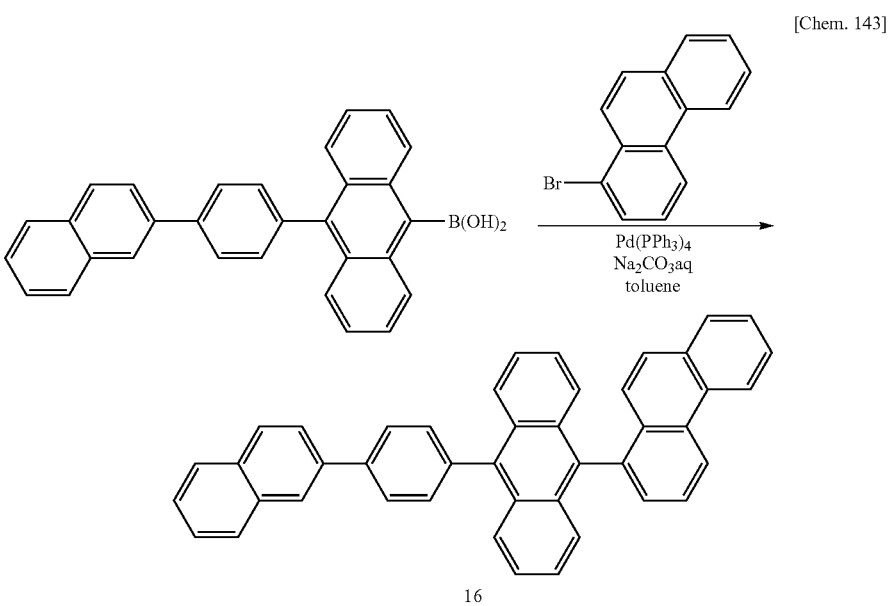

Synthesis was performed in the same manner as in the synthesis of Compound 75 except that: 1-bromophenanthrene was used instead of 2-iodophenanthrene; and 10-[4-(2-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 91

Compound 17 in the Following Formulae

[Chem. 144]

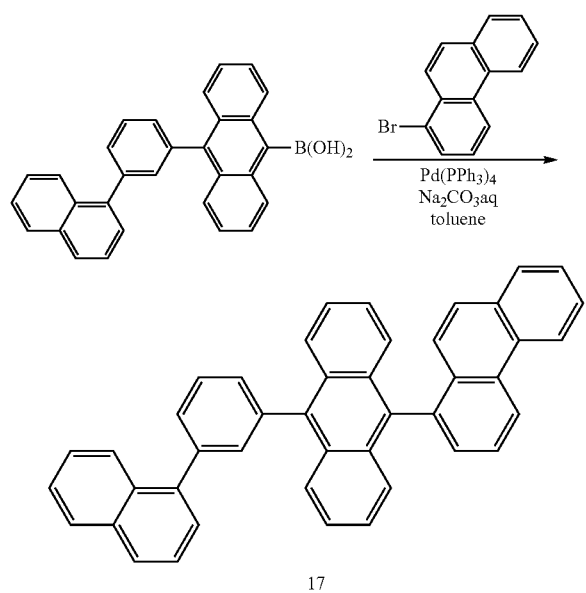

17

Synthesis was performed in the same manner as in the synthesis of Compound 75 except that: 1-bromophenanthrene was used instead of 2-iodophenanthrene; and 10-[3-(1-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 92

Compound 18 in the Following Formulae

[Chem. 145]

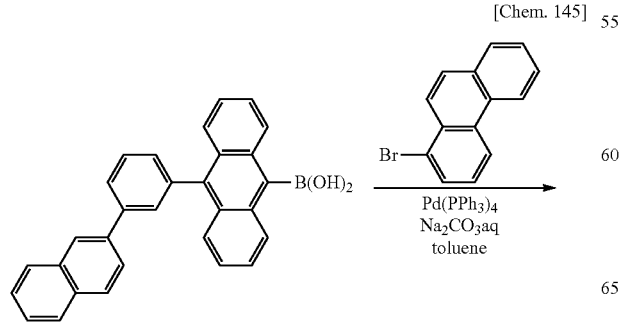

-continued

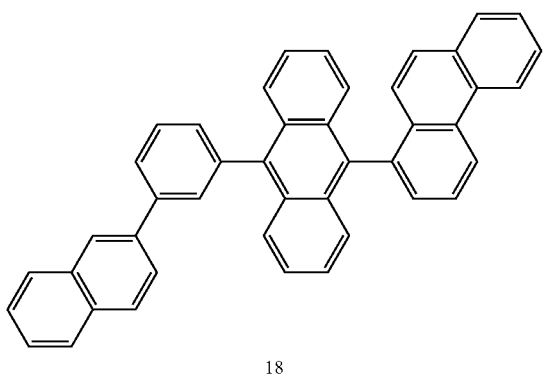

18

Synthesis was performed in the same manner as in the synthesis of Compound 75 except that: 1-bromophenanthrene was used instead of 2-iodophenanthrene; and 10-[3-(2-naphthyl)phenyl]anthracene-9-boronic acid synthesized by a known method was used instead of 10-[4-(1-naphthyl)phenyl]anthracene. Mass spectral analysis confirmed that the resultant was a target product and had a ratio m/e of 556 with respect to its molecular weight, i.e., 556.22.

Synthesis of Compound 93

Compound 19 in the Following Formulae

[Chem. 146]

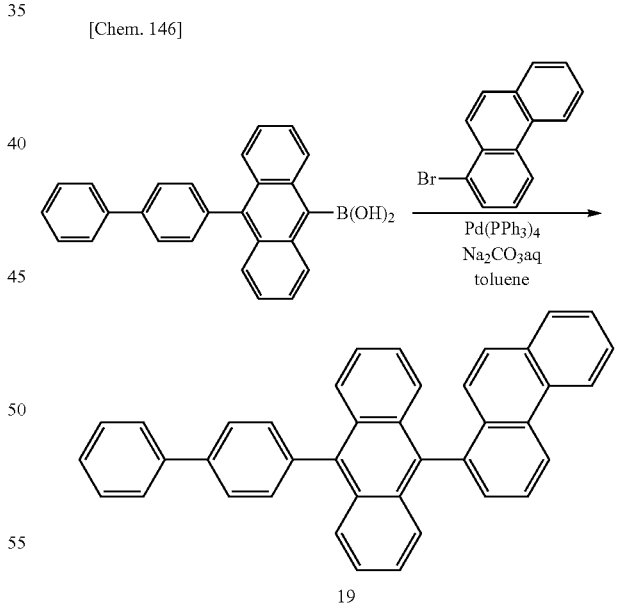

19

Synthesis was performed in the same manner as in the synthesis of Compound 75 except that: 1-bromophenanthrene was used instead of 2-iodophenanthrene; and 10-(4-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Synthesis of Compound 94

Compound 20 in the Following Formulae

[Chem. 147]

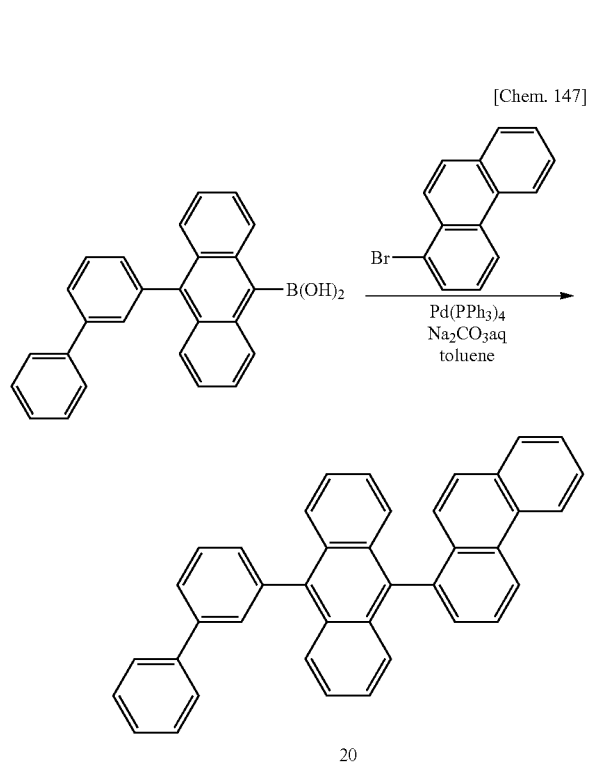

Synthesis was performed in the same manner as in the synthesis of Compound 75 except that: 1-bromophenanthrene was used instead of 2-iodophenanthrene; and 10-(3-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Synthesis of Compound 95

Compound 21 in the Following Formulae

[Chem. 148]

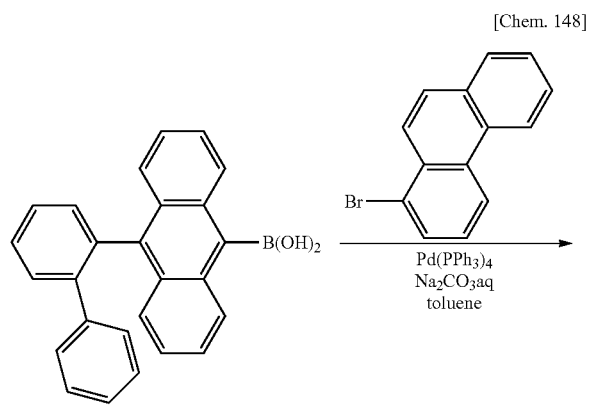

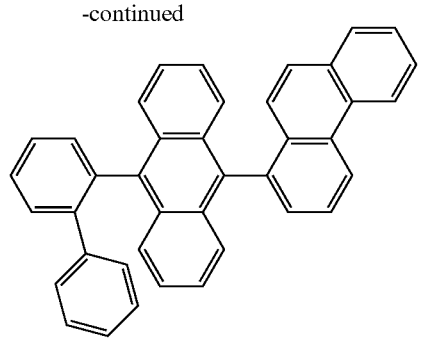

Synthesis was performed in the same manner as in the synthesis of Compound 75 except that: 1-bromophenanthrene was used instead of 2-iodophenanthrene; and 10-(2-biphenyl)anthracene-9-boronic acid synthesized by a known method was used instead of 10-[4-(1-naphthyl)phenyl]anthracene. Mass spectral analysis confirmed that the resultant was a target product and had a ratio m/e of 506 with respect to its molecular weight, i.e., 506.20.

Example 73

An organic EL device was formed in the same manner as in Example 1 except that Compound 75 was used.

Example 74 to Example 101

An organic EL device was produced in the same manner as in Example 73 except that the Compound of Table 3 shown below was used instead of Compound 75. Further, the organic EL device was produced in the same manner except that the Compound of Table 3 shown below was used instead of D-1.

Comparative Example 11

An organic EL device was produced in the same manner as in Example 73 except that Compound (C) shown above was used instead of Compound 75.

Comparative Example 12

An organic EL device was produced in the same manner as in Example 73 except that Compound (F) shown above was used instead of Compound 75.

Comparative Example 13

An organic EL device was produced in the same manner as in Example 73 except that Compound (D) shown above was used instead of Compound 75.

Comparative Example 14

An organic EL device was produced in the same manner as in Example 73 except that Compound (I) shown above was used instead of Compound 75.

Comparative Example 15

An organic EL device was produced in the same manner as in Example 73 except that Compound (J) shown above was used instead of Compound 75.

(1) Initial performance: Each device was evaluated for its current efficiency (cd/A) at a current density of 10 mA/cm$^2$.

(2) Lifetime: Each device was driven with a constant current at an initial luminance of 1000 cd/cm², and was evaluated for the half lifetime of its luminance.

Table 3 summarizes the results of device evaluation.

TABLE 3

| Example No. | Host | Dopant | Current efficiency | Lifetime |
|---|---|---|---|---|
| 73 | Compound 75 | D-1 | 7.5 | 9000 |
| 74 | Compound 76 | D-1 | 7.5 | 9000 |
| 75 | Compound 77 | D-1 | 7.5 | 9000 |
| 76 | Compound 78 | D-1 | 7.5 | 9000 |
| 77 | Compound 79 | D-1 | 7.5 | 9000 |
| 78 | Compound 80 | D-1 | 7.5 | 9000 |
| 79 | Compound 81 | D-1 | 7.5 | 9000 |
| 80 | Compound 82 | D-1 | 7.3 | 10,000 |
| 81 | Compound 83 | D-1 | 7.3 | 10,000 |
| 82 | Compound 84 | D-1 | 7.3 | 10,000 |
| 83 | Compound 85 | D-1 | 7.3 | 10,000 |
| 84 | Compound 86 | D-1 | 7.3 | 10,000 |
| 85 | Compound 87 | D-1 | 7.3 | 10,000 |
| 86 | Compound 88 | D-1 | 7.3 | 10,000 |
| 87 | Compound 89 | D-1 | 7.1 | 10,000 |
| 88 | Compound 90 | D-1 | 7.1 | 10,000 |
| 89 | Compound 91 | D-1 | 7.1 | 10,000 |
| 90 | Compound 92 | D-1 | 7.1 | 10,000 |
| 91 | Compound 93 | D-1 | 7.1 | 10,000 |
| 92 | Compound 94 | D-1 | 7.1 | 10,000 |
| 93 | Compound 95 | D-1 | 7.1 | 10,000 |
| 94 | Compound 81 | D-2 | 7.3 | 11,000 |
| 95 | Compound 86 | D-2 | 7.3 | 11,000 |
| 96 | Compound 89 | D-2 | 7.3 | 11,000 |
| 97 | Compound 94 | D-2 | 7.3 | 11,000 |
| 98 | Compound 81 | D-3 | 7.5 | 12,000 |
| 99 | Compound 86 | D-3 | 7.5 | 12,000 |
| 100 | Compound 89 | D-3 | 7.5 | 12,000 |
| 101 | Compound 94 | D-3 | 7.5 | 12,000 |
| Comparative Example 11 | Compound (C) | D-1 | 6.0 | 4000 |
| Comparative Example 12 | Compound (F) | D-1 | 6.0 | 3000 |
| Comparative Example 13 | Compound (D) | D-1 | 6.0 | 5000 |
| Comparative Example 14 | Compound (I) | D-1 | 6.0 | 1000 |
| Comparative Example 15 | Compound (J) | D-1 | 5.2 | 500 |

INDUSTRIAL APPLICABILITY

As described hereinabove in detail, an organic EL device using the anthracene derivative having a phenanthryl group of the present invention has high luminous efficiency and a long lifetime. Further, the device emits blue light with high luminous efficiency and high color purity, and is excellent in film formability. Accordingly, the device is useful as a light source such as a flat emitter for a wall-hung television or a backlight for a display.

The invention claimed is:

1. An organic electroluminescence device comprising one or more organic thin film layers comprising a light emitting layer between a cathode and an anode,
   wherein the light emitting layer comprises a host material that consists of an anthracene derivative comprising a phenanthryl group, the anthracene derivative being represented by formula (1-2):

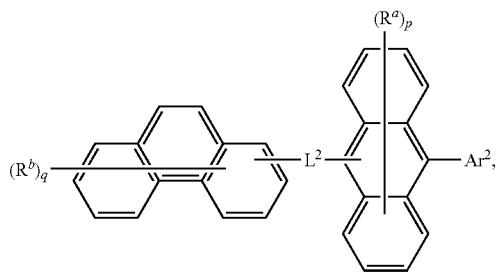

(1-2)

wherein:
the phenanthryl group in formula (1-2) is one of a substituted or unsubstituted 1-phenanthryl group, a substituted or unsubstituted 2-phenanthryl group, a substituted or unsubstituted 3-phenanthryl group, and a substituted or unsubstituted 4-phenanthryl group;
$L^2$ represents a substituted or unsubstituted arylene group having 6 to 50 ring-forming carbon atoms, or a divalent heterocyclic group having 5 to 50 ring-forming atoms;
$Ar^2$ represents a substituted or unsubstituted aryl group having 6 to 50 ring-forming carbon atoms, or a heterocyclic group having 5 to 50 ring-forming atoms;
substituents $R^a$ and $R^b$ each independently represent a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring-forming carbon atoms, a substituted or unsubstituted aryl group having 6 to 50 ring-forming carbon atoms, a substituted or unsubstituted heteroaryl group having 5 to 50 ring-forming atoms, a substituted or unsubstituted alkylsilyl group having 1 to 30 carbon atoms, a substituted or unsubstituted arylsilyl group having 6 to 50 ring-forming carbon atoms, a substituted or unsubstituted alkylgermanium group having 1 to 50 carbon atoms, or a substituted or unsubstituted arylgermanium group having 6 to 50 ring-forming carbon atoms, and the substituent $R^b$ represents a group except a substituted or unsubstituted anthracenyl group;
"p" represents an integer of 0 to 8;
"q" represents an integer of 0 to 9; and
when "p" represents 2 to 8 or "q" represents 2 to 9, a plurality of $R^a$'s or a plurality of $R^b$'s are identical to or different from each other.

2. The organic electroluminescence device according to claim 1, wherein $L^2$ is represented by formula (3):

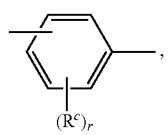

(3)

wherein:
a substituent $R^c$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring-forming carbon atoms, a substituted or unsubstituted aryl group having 5 to 50 ring-forming carbon atoms, a substituted or unsubstituted heteroaryl group having 5 to 50 ring-forming atoms, a substituted or unsubstituted alkylsilyl group having 1 to 30 carbon atoms, a substituted or unsubstituted arylsilyl group having 6 to 50 ring-forming carbon atoms, a substituted or unsubstituted alkylgermanium group having 1 to 50 carbon atoms, or a substituted or unsubstituted arylgermanium group having 6 to 50 ring-forming carbon atoms; and "r" represents an integer of 0 to 4, and when "r" represents 2 to 4, a plurality of $R^c$'s are identical to or different from each other.

3. The organic electroluminescence device according to claim 1, wherein $L^2$ represents a substituted or unsubstituted fused aromatic ring group having 10 to 50 ring-forming carbon atoms.

4. The organic electroluminescence device according to claim 1, wherein $Ar^2$ represents a substituted or unsubstituted fused aromatic ring having 10 to 50 ring-forming carbon atoms.

5. The organic electroluminescence device according to claim 1, wherein $L^2$ is represented by formula (3):

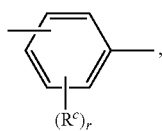

(3)

and $Ar^2$ is represented by formula (4):

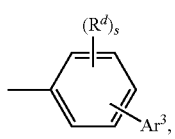

(4)

wherein:
$Ar^3$ represents a substituted or unsubstituted aryl group having 6 to 50 ring-forming carbon atoms, or a heterocyclic group having 5 to 50 ring-forming atoms;
a substituent $R^c$ or $R^d$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxyl group having 1 to 20 carbon atoms, a substituted or unsubstituted aryloxy group having 6 to 20 ring-forming carbon atoms, a substituted or unsubstituted aryl group having 6 to 50 ring-forming carbon atoms, a substituted or unsubstituted heteroaryl group having 5 to 50 ring-forming atoms, a substituted or unsubstituted alkylsilyl group having 1 to 30 carbon atoms, a substituted or unsubstituted arylsilyl group having 6 to 50 ring-forming carbon atoms, a substituted or unsubstituted alkylgermanium group having 1 to 50 carbon atoms, or a substituted or unsubstituted arylgermanium group having 6 to 50 ring-forming carbon atoms; and "r" and "s" each represent an integer of 0 to 4, and when "r" and/or "s" each represent/represents 2 to 4, a plurality of $R^c$'s and/or a plurality of $R^d$'s are identical to or different from each other.

6. The organic electroluminescence device according to claim 1, wherein "q" represents 0.

7. The organic electroluminescence device according to claim 1, wherein the light emitting layer further comprises at least one of a fluorescent dopant and a phosphorescent dopant.

8. The organic electroluminescence device according to claim 7, wherein the fluorescent dopant comprises an arylamine compound.

9. The organic electroluminescence device according to claim 7, wherein the fluorescent dopant comprises a styrylamine compound.

10. The organic electroluminescence device according to claim 7, wherein the fluorescent dopant comprises a fused ring amine derivative represented by formula (5):

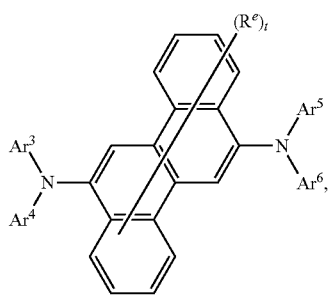

(5)

wherein:
$R^e$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxy group having 1 to 20 carbon atoms, a substituted or unsubstituted aryloxy group having 6 to 20 ring-forming carbon atoms, a substituted or unsubstituted aryl group having 6 to 50 ring-forming carbon atoms, a substituted or unsubstituted alkylsilyl group having 1 to 30 carbon atoms, a substituted or unsubstituted arylsilyl group having 6 to 50 ring-forming carbon atoms, a substituted or unsubstituted alkylgermanium group having 1 to 50 carbon atoms, or a substituted or unsubstituted arylgermanium group having 6 to 50 ring-forming carbon atoms;

"t" represents an integer of 0 to 10; and $Ar^3$ to $Ar^6$ each represent a substituted or unsubstituted aryl group having 6 to 20 ring-forming carbon atoms, or a substituted or unsubstituted heteroaryl group having 5 to 20 ring-forming atoms.

11. The organic electroluminescence device according to claim 7, wherein the fluorescent dopant comprises a fused ring amine derivative represented by formula (6):

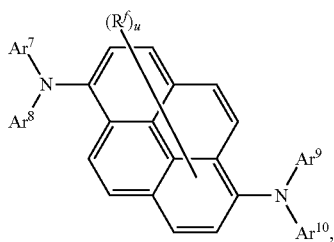

(6)

wherein:
a substituent $R^f$ represents a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 7 to 20 carbon atoms, a substituted or unsubstituted cycloalkyl group having 3 to 20 carbon atoms, a substituted or unsubstituted alkoxy group having 1 to 20 carbon atoms, a substituted or unsubstituted aryloxy group having 6 to 20 ring-forming carbon atoms, a substituted or unsubstituted aryl group having 6 to 50 ring-forming carbon atoms, a substituted or unsubstituted alkylsilyl group having 1 to 30 carbon atoms, a substituted or unsubstituted arylsilyl group having 6 to 50 ring-forming carbon atoms, a substituted or unsubstituted alkylgermanium group having 1 to 50 carbon atoms, or a substituted or unsubstituted arylgermanium group having 6 to 50 ring-forming carbon atoms;
"u" represents an integer of 0 to 8; and
$Ar^7$ to $Ar^{10}$ each represent a substituted or unsubstituted aryl group having 6 to 20 ring-forming carbon atoms, or a substituted or unsubstituted heteroaryl group having 5 to 20 ring-forming atoms.

12. The organic electroluminescence device according to claim 1, wherein $L^2$ is a phenyl group and $Ar^2$ is a naphthyl group.

13. The organic electroluminescence device according to claim 1, wherein $L^2$ is a phenyl group and $Ar^2$ is a naphthyl-substituted phenyl group.

14. The organic electroluminescence device according to claim 1, wherein $L^2$ represents a substituted or unsubstituted arylene group selected from the group consisting of a phenylene group, a naphthylene group, a biphenylene group, a terphenylene group, an anthranylene group, a pentacenylene group, a perylenylene group, a picenylene group, a pyrenylene group and a pentaphenylene group, or a substituted or unsubstituted divalent heterocyclic group selected from the group consisting of a pyridinylene group, a pyrazinylene group, a pyrimidinylene group, a pyridazinylene group, a triazinylene group, an indolinylene group, a quinolinylene group, an acridinylene group, a pyrrolidinylene group, a dioxanylene group, a piperidinylene group, a morpholidinylene group, a piperazinylene group, a triathinylene group, a carbazolylene group, a furanylene group, a thiophenylene group, an oxazolylene group, an oxadiazolylene group, a benzoxazolylene group, a thiazolylene group, a thindiazolylene group, a benzothiazolylene group, a triazolylene group, an imidazolylene group, a benzimidazolylene group, a furanylene group, a dibenzofuranylene group and a benzofuranylene group.

15. The organic electroluminescence device according to claim 1, wherein $L^2$ represents a substituted or unsubstituted arylene group selected from the group consisting of a phenylene group, a naphthylene group, a biphenylene group, a terphenylene group, an anthranylene group, a pentacenylene group, a perylenylene group, a picenylene group, a pyrenylene group and a pentaphenylene group.

16. The organic electroluminescence device according to claim 1, wherein $Ar^2$ represents a substituted or unsubstituted aryl group selected from the group consisting of a phenyl group, a naphthyl group, a phenanthryl group, a chrysenyl group, a benzophenanthryl group, a triphenylenyl group, a benzanthranyl group, a benzochrysenyl group, a biphenyl group, a naphthacenyl group, a terphenyl group, an anthranyl group, a pentacenyl group, a picenyl group and a pentaphenyl group, or a substituted or unsubstituted heterocyclic group selected from the group consisting of a pyridinylene group, a pyrazinylene group, a pyrimidinylene group, a pyridazinylene group, a triazinylene group, an indolinylene group, a quinolinylene group, an acridinylene group, a pyrrolidinylene group, a dioxanylene group, a piperidinylene group, a morpholidinylene group, a piperazinylene group, a triathinylene group, a carbazolylene group, a furanylene group, a thiophenylene group, an oxazolylene group, an oxadiazolylene group, a benzoxazolylene group, a thiazolylene group, a thiadiazolylene group, a benzothiazolylene group, a triazolylene group, an imidazolylene group, a benzimidazolylene group, a furanylene group, a benzofuranylene group and a dibenzofuranylene group.

17. The organic electroluminescence device according to claim 1, wherein $L^2$ represents a substituted or unsubstituted arylene group selected from the group consisting of a phenylene group, a naphthylene group, a biphenylene group, a terphenylene group, an anthranylene group, a pentacenylene group, a perylenylene group, a picenylene group, a pyrenylene group, a pentaphenylene group, or a substituted or unsubstituted divalent heterocyclic group selected from the group consisting of a pyridinylene group, a pyrazinylene group, a pyrimidinylene group, a pyridazinylene group, a triazinylene group, an indolinylene group, a quinolinylene group, an acridinylene group, a pyrrolidinylene group, a dioxanylene group, a piperidinylene group, a morpholidinylene group, a piperazinylene group, a triathinylene group, a carbazolylene group, a furanylene group, a thiophenylene group, an oxazolylene group, an oxadiazolylene group, a benzoxazolylene group, a thiazolylene group, a thiadiazolylene group, a benzothiazolylene group, a triazolylene group, an imidazolylene group, a benzimidazolylene group, a furanylene group and a dibenzofuranylene group, and $Ar^2$ represents a substituted or unsubstituted aryl group selected from the group consisting of a phenyl group, a naphthyl group, a phenanthryl group, a chrysenyl group, a benzophenanthryl group, a triphenylenyl group, a benzanthranyl group, a benzochrysenyl group, a biphenyl group, a naphthacenyl group, a terphenyl group, an anthranyl group, a pentacenyl group, a picenyl group a pentaphenyl group, or a substituted or unsubstituted heterocyclic group selected from the group consisting of a pyridinylene group, a pyrazinylene group, a pyrimidinylene group, a pyridazinylene group, a triazinylene group, an indolinylene group, a quinolinylene group, an acridinylene group, a pyrrolidinylene group, a dioxanylene group, a piperidinylene group, a morpholidinylene group, a piperazinylene group, a triathinylene group, a carbazolylene group, a furanylene group, a thiophenylene group, an oxazolylene group, an oxadiazolylene group, a benzoxazolylene group, a thiazolylene group, a thiadiazolylene group, a benzothiazolylene group, a triazolylene group, an imidazolylene group, a benzimidazolylene group, a furanylene group, a benzofuranylene group and a dibenzofuranylene group.

18. The organic electroluminescence device according to claim 1, wherein $L^2$ represents a substituted or unsubstituted group selected from the group consisting of a phenylene group a naphthylene group, a biphenylene group, a terphenylene group and an anthranylene group, and $Ar^2$ represents a substituted or unsubstituted group selected from the group consisting of a phenyl group, a naphthyl group, a biphenyl group, a naphthacenyl group, a terphenyl group, an anthranyl group, a carbazolylene group, a benzoxazolylene group, a benzothiazolylene group, a benzimidazolylene group, a benzofuranylene group, furanylene group and a dibenzofuranylene group.

19. The organic electroluminescence device according to claim 1, wherein $R^a$ and $R^b$ each independently represents a substituted or unsubstituted alkyl group selected from the group consisting of an ethyl group, a methyl group, an i-propyl group, an n-propyl group, an s-butyl group, a t-butyl group, a pentyl group, a hexyl group, a cyclopentyl group, and a cyclohexyl group; a substituted or unsubstituted alkenyl group selected from the group consisting of a vinyl group, an allyl group, a 1-butenyl group, a 2-butenyl group, a 3-butenyl group, a 1,3-butadienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group; a substituted or unsubstituted aryl group selected from the group consisting of a phenyl group, a naphthyl group, a phenanthryl group, a chrysenyl group, a benzophenanthryl group, a triphenylenyl group, a benzanthranyl group, a benzochrysenyl group, a biphenyl group, a naphthacenyl group, a terphenyl group, an anthranyl group, a pentacenyl group, a picenyl group and a pentaphenyl group; a substituted or unsubstituted heteroaryl group selected from the group consisting of a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 2-isoquinolyl group, a 3-isoquinolyl group, a 4-isoquinolyl group, a 5-isoquinolyl group, a 8-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrohn-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2 yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin*5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9*yl group, a 2,8-phenanthrolin-10 71 group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxaminyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group; a substituted or unsubstituted alkylsilyl group selected from the group consisting of a trimethylsilyl group, a triethylsilyl group, a t-butyldimethylsilyl group, a vinyldimethylsilyl group, and a propyldimethylsilyl group; or a substituted or unsubstituted arylsilyl group selected from the group consisting of a triphenylsilyl group, a phenyldimethylsilyl group, a t-butyldiphenylsilyl group, a tritolylsilyl group, a trixylylsilyl group, and a trinaphthylsilyl group.

20. The organic electroluminescence device according to claim 1, wherein $R^a$ and $R^b$ represent a substituted or unsubstituted alkyl group selected from the group consisting of an ethyl group, a methyl group, an i-propyl group, an n-propyl group, an s-butyl group, a t-butyl group, a pentyl group, a hexyl group, a cyclopentyl group, and a cyclohexyl group, or a substituted or unsubstituted aryl group selected from the group consisting of a phenyl group, a naphthyl group, a phenanthryl group, a chrysenyl group, a benzophenanthryl group, a triphenylenyl group, a benzanthranyl group, a benzochrysenyl group, a biphenyl group, a naphthacenyl group, a terphenyl group, an anthranyl group, a pentacenyl group, a picenyl group and a pentaphenyl group.

21. The organic electroluminescence device according to claim 1, wherein $R^b$ represents a substituted or unsubstituted alkyl group selected from the group consisting of an ethyl group, a methyl group, an i-propyl group, an n-propyl group, an s-butyl group, a t-butyl group, a pentyl group, a hexyl group, a cyclopentyl group, and a cyclohexyl group, or
  a substituted or unsubstituted aryl group selected from the group consisting of a phenyl group, a phenanthryl group, a chrysenyl group, a benzophenanthryl group, a triphenylenyl group, a benzanthranyl group, a benzochrysenyl group, a biphenyl group, a naphthacenyl group, a terphenyl group, an anthranyl group, a pentacenyl group, a picenyl group and a pentaphenyl group.

* * * * *